United States Patent
Howe et al.

(10) Patent No.: US 11,939,588 B2
(45) Date of Patent: Mar. 26, 2024

(54) ELEVATED RESISTANCE TO INSECTS AND PLANT PATHOGENS WITHOUT COMPROMISING SEED PRODUCTION

(71) Applicant: Board of Trustees of Michigan State University, East Lansing, MI (US)

(72) Inventors: Gregg A. Howe, East Lansing, MI (US); Qiang Guo, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 17/071,555

(22) Filed: Oct. 15, 2020

(65) Prior Publication Data
US 2021/0115464 A1   Apr. 22, 2021

Related U.S. Application Data

(60) Provisional application No. 62/916,609, filed on Oct. 17, 2019.

(51) Int. Cl.
 *C12N 15/82*   (2006.01)

(52) U.S. Cl.
 CPC ..... *C12N 15/8279* (2013.01); *C12N 15/8286* (2013.01)

(58) Field of Classification Search
 CPC ................................................ C12N 15/8279
 USPC ...................................................... 800/279
 See application file for complete search history.

(56) References Cited

FOREIGN PATENT DOCUMENTS

WO   WO-2018/039590 A1   3/2018

OTHER PUBLICATIONS

Campos et al. Nature Communication, 7:12570, pp. 1-10) (Year: 2016).*
Further in view of Zhu et al. The Plant Cell, 26:4149-4170 (Year: 2014).*
"European Application Serial No. 20202431.1, Extended European Search Report dated Mar. 26, 2021", 10 pgs.
Guo, Qiang, et al., "JAZ repressors of metabolic defense promote growth and reproductive fitness in *Arabidopsis*", Proc. Natl. Acad. Sci. USA, 115(45), E10768-E10777.
Guo, Qiang, et al., "Resolution of growth-defense conflict: mechanistic insights from jasmonate signaling", Current Opinion in Plant Biology, vol. 44, (Mar. 16, 2018), 72-81.
Kong, Lingyao, et al., "Suppression of wheat TaCDK8/TaWIN1 interaction negatively affects germination of *Blumeria graminis* f.sp. *triticiby* interfering with very-long-chain aldehyde biosynthesis", Plant Molecular Biology, 96(1), (2018), 165-178.
Leone, Melisa, et al., "To grow or defend? Low red far-red ratios reduce jasmonate sensitivity in *Arabidopsis* seedlings by promoting DELLA degradation and increasing JAZ10 stability", New Phytologist, vol. 204, (2014), 355-367.
Zhai, Qingzhe, et al., "The plant Mediator complex and its role in jasmonate signaling", Journal of Experimental Botany, 70(13), (May 14, 2019), 3415-3424.
"European Application Serial No. 20202431.1, Communication Pursuant to Article 94(3) EPC dated Jun. 9, 22", 5 pgs.
"European Application Serial No. 20202431.1, Response filed Oct. 27, 2021 to Extended European Search Report dated Mar. 26, 2021", 17 pgs.
"European Application Serial No. 20202431.1, Response filed Oct. 19, 2022 to Communication Pursuant to Article 94(3) EPC dated Jun. 9, 2022", 20 pgs.

* cited by examiner

*Primary Examiner* — Li Zheng

(74) *Attorney, Agent, or Firm* — Schwegman Lundberg & Woessner, P.A.

(57) ABSTRACT

Described herein are modified plants, plant cells, and plant seeds that have at least one mutant loss-of-function JAZ gene and at least one loss-of-function cdk8 gene. Such plants are highly resistant to pests and environmental stress and have restored growth and increased seed yield compared to plant lines with a jazD genetic background.

22 Claims, 36 Drawing Sheets
Specification includes a Sequence Listing.

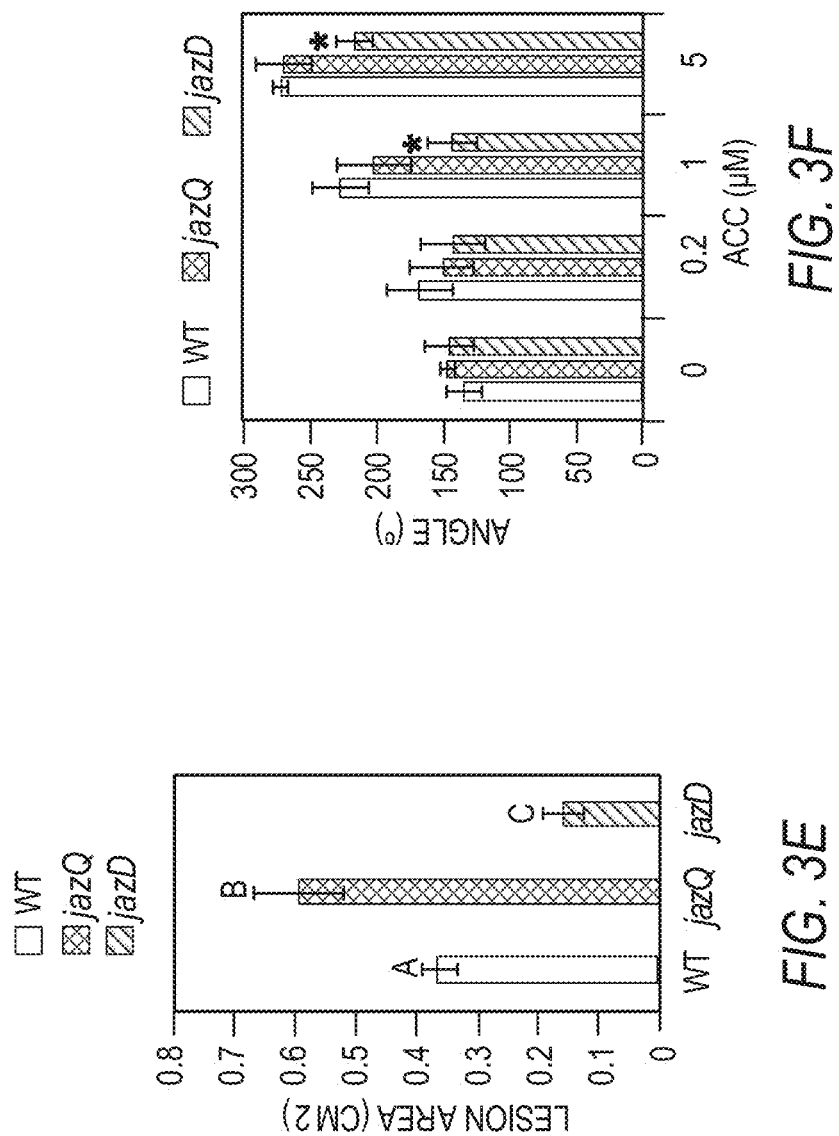

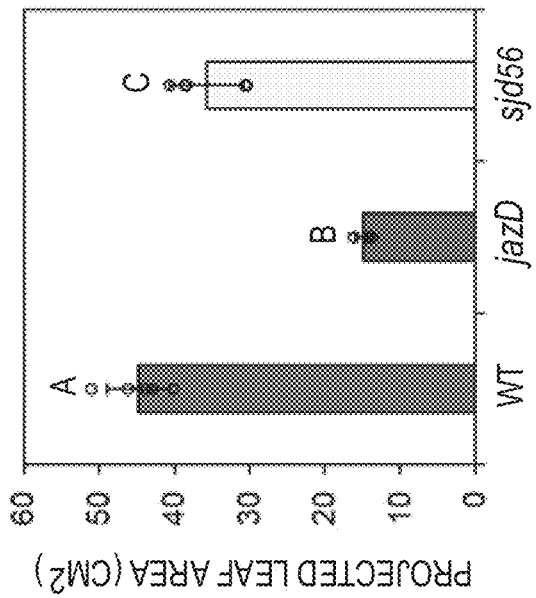
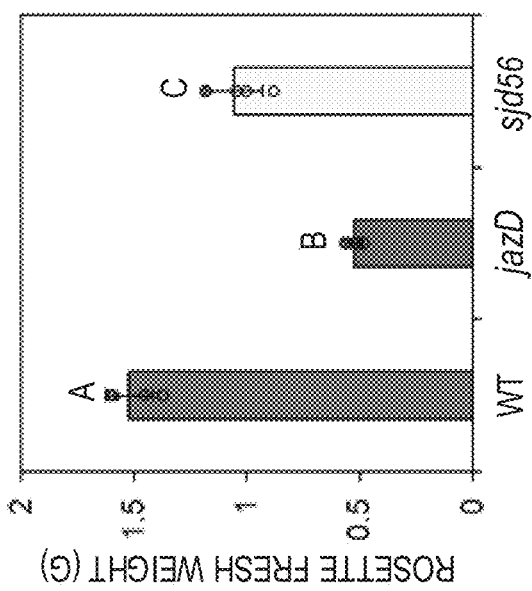
FIG. 8A
FIG. 8B

SEQUENCE LISTING

```
<160> NUMBER OF SEQ ID NOS: 121

<210> SEQ ID NO 1
<211> LENGTH: 187
<212> TYPE: PRT
<213> ORGANISM: Arabidopsis thaliana

<400> SEQUENCE: 1

Met Ser Leu Phe Pro Cys Glu Ala Ser Asn Met Asp Ser Met Val Gln
1               5                   10                  15

Asp Val Lys Pro Thr Asn Leu Phe Pro Arg Gln Pro Ser Phe Ser Ser
                20                  25                  30

Ser Ser Ser Ser Leu Pro Lys Glu Asp Val Leu Lys Met Thr Gln Thr
            35                  40                  45

Thr Arg Ser Val Lys Pro Glu Ser Gln Thr Ala Pro Leu Thr Ile Phe
    50                  55                  60

Tyr Ala Gly Gln Val Ile Val Phe Asn Asp Phe Ser Ala Glu Lys Ala
65                  70                  75                  80

Lys Glu Val Ile Asn Leu Ala Ser Lys Gly Thr Ala Asn Ser Leu Ala
                85                  90                  95

Lys Asn Gln Thr Asp Ile Arg Ser Asn Ile Ala Thr Ile Ala Asn Gln
            100                 105                 110

Val Pro His Pro Arg Lys Thr Thr Thr Gln Glu Pro Ile Gln Ser Ser
    115                 120                 125

Pro Thr Pro Leu Thr Glu Leu Pro Ile Ala Arg Arg Ala Ser Leu His
130                 135                 140

Arg Phe Leu Glu Lys Arg Lys Asp Arg Val Thr Ser Lys Ala Pro Tyr
145                 150                 155                 160

Gln Leu Cys Asp Pro Ala Lys Ala Ser Ser Asn Pro Gln Thr Thr Gly
                165                 170                 175

Asn Met Ser Trp Leu Gly Leu Ala Ala Glu Ile
            180                 185

<210> SEQ ID NO 2
<211> LENGTH: 1527
<212> TYPE: DNA
<213> ORGANISM: Arabidopsis thaliana

<400> SEQUENCE: 2
atattggagg taggaagaag aactctgcaa ccaaaccaac caaccccaaa gccaaacaaa        60
gttttataga gaccttccat ttctccctct cgtgacaaac gcaatttgca gagaagcaac      120
agcaacaaca agaagaagaa gaaaaagatt tgagattact ttgtatcgat ttagctattc      180
```

```
gagaaactct tgccgtttga aagttttaat tgttaaagat gtcgagttct atggaatgtt    240
ctgagttcgt cggtagccgg agatttactg ggaagaagcc tagcttctca cagacgtgta    300
gtcgattgag tcagtatcta aaagagaacg gtagctttgg agatctgagc ttaggaatgg    360
catgcaagcc tgatgtcaat ggtaagaaac cttctctttc tcctagatcc acttcttttt    420
tcgttttctc tgttttttat ttcttgaatc ttgatcttga aaacttttca agaaaatttt    480
gaatcgattt caaagaaatt agggagagtt agtttgctaa attttgacat agaaaatgat    540
tggagagagt tctaactttt ggatcatata tatttgcagg aactttaggc aactcacgtc    600
agccgacaac aaccatgagt ttattcccct tgtgaagctt caacatggat tccatggttc    660
aagatgttaa accgacgaat ctgtttccta ggcaaccaag cttttcttcc tcatcttcct    720
ctcttccaaa ggaagatgtt ttgaaaatga cacagactac cagatctgtg aaaccagagt    780
ctcaaactgc accattgact atattctacg ccgggcaagt gattgtattc aatgactttt    840
ctgctgagaa agccaagaa gtgatcaact ggcgagcaa aggcaccgct aatagcttag    900
ccaagaatca aaccgatatc agaagcaaca tcgctactat cgcaaaccaa gttcctcatc    960
caagaaaaac cacaacacaa gagccaatcc aatcctcccc aacaccattg acagaacttc    1020
ctattgctag aagagcttca cttcaccggt tcttggagaa gagaaaggac agagttacgt    1080
caaaggcacc ataccaatta tgcgatccag ccaaagcgtc ttcaaaccct caaaccacag    1140
gcaacatgtc gtggctcggt ttagcagctg aaatatgaat gctaaccacc ctcaagccgt    1200
accaagaaat tcttttgacg acgttgcttc aagacaagat ataaaagctc ctatcttcat    1260
gcttttgat ttaagataca aactactcaa tgattaggaa acttcatata tttgtatgta    1320
ttgattagtg atcaattatt gttagtattc gttatagtct gttttctac tagttattgt    1380
cgcctgtcta aatccccttg ctatgggtta tctcaaaatt agtttcgtat gtaactaatt    1440
ttgtaagaac aataattttt gttgacgaac catactatca aatactctaa attatatctt    1500
gataaatcta cctatcaggt aagtagg                                       1527
```

<210> SEQ ID NO 3
<211> LENGTH: 249
<212> TYPE: PRT
<213> ORGANISM: Arabidopsis thaliana

<400> SEQUENCE: 3

```
Met Ser Ser Phe Ser Ala Glu Cys Trp Asp Phe Ser Gly Arg Lys Pro
1               5                   10                  15

Ser Phe Ser Gln Thr Cys Thr Arg Leu Ser Arg Tyr Leu Lys Glu Lys
            20                  25                  30

Gly Ser Phe Gly Asp Leu Ser Leu Gly Met Thr Cys Lys Pro Asp Val
        35                  40                  45

Asn Gly Gly Ser Arg Gln Pro Thr Met Met Asn Leu Phe Pro Cys Glu
    50                  55                  60

Ala Ser Gly Met Asp Ser Ala Gly Gln Glu Asp Ile Lys Pro Lys
65                  70                  75                  80

Thr Met Phe Pro Arg Gln Ser Ser Phe Ser Ser Ser Ser Gly
                85                  90                  95

Thr Lys Glu Asp Val Gln Met Ile Lys Glu Thr Lys Ser Val Lys
            100                 105                 110

Pro Glu Ser Gln Ser Ala Pro Leu Thr Ile Phe Tyr Gly Gly Arg Val
        115                 120                 125

Met Val Phe Asp Asp Phe Ser Ala Glu Lys Ala Lys Glu Val Ile Asp
```

```
                130                 135                 140
Leu Ala Asn Lys Gly Ser Ala Lys Ser Phe Thr Cys Phe Thr Ala Glu
145                 150                 155                 160

Val Asn Asn His Ser Ala Tyr Ser Gln Lys Glu Ile Ala Ser Ser
                165                 170                 175

Pro Asn Pro Val Cys Ser Pro Ala Lys Thr Ala Ala Gln Glu Pro Ile
            180                 185                 190

Gln Pro Asn Pro Ala Ser Leu Ala Cys Glu Leu Pro Ile Ala Arg Arg
        195                 200                 205

Ala Ser Leu His Arg Phe Leu Glu Lys Arg Lys Asp Arg Ile Thr Ser
    210                 215                 220

Lys Ala Pro Tyr Gln Ile Asp Gly Ser Ala Glu Ala Ser Ser Lys Pro
225                 230                 235                 240

Thr Asn Pro Ala Trp Leu Ser Ser Arg
                245
```

<210> SEQ ID NO 4
<211> LENGTH: 1282
<212> TYPE: DNA
<213> ORGANISM: Arabidopsis thaliana

<400> SEQUENCE: 4

```
gcaaccagcg aaaaaaaagt aataaagagg tcctccattt cttcctcgtg acaaaacgca      60
cttggcagag aaagataaac aagaaccta  agttttttta taagattcga gaaaattcaa     120
caactcagga aggaagatcc ttttgctcca atttctcaat cgaaacgatt tcaatttcgg     180
tttcaacgat gtcgagtttt tctgccgagt gttgggactt ctctggtcgt aaaccgagct     240
tttcacaaac atgtactcga ttgagtcgtt acctgaagga aagggtagt  tttggagatc     300
tgagcttagg gatgacatgc aagcccgacg ttaatggagg ttcacgtcag cctacaatga     360
tgaatctgtt ccccttgtga agcttcaggaa tggattcttc tgctggtcaa gaagacatta    420
aaccgaagac tatgtttccg agacaatcaa gcttttcttc ttcctcttcc tctgggacca    480
agaagatgt  acagatgatc aaagagacta ctaaatctgt gaagccagag tctcaatctg    540
ctccgttgac tatattctac ggtggtcgag ttatggtgtt tgatgatttt tctgctgaga    600
aagctaaaga agtcattgat ttggctaaca aggaagtgc  caaaagcttc acatgtttca    660
cagctgaagt aaacaataac catagtgctt attctcaaaa agagattgct tctagcccaa    720
atcctgtttg tagtcctgca aaaaccgcag cacaagagcc aattcagcct aacccggcct    780
ctttagcctg cgaactcccg attgcaagaa gagcttcact tcatcggttc cttgagaaga    840
ggaaggatag gatcacatca aaggcaccat accaaataga cggttcagct gaagcgtctt    900
ccaagcctac taacccagct tggctcagtt cacggtaaac ttcgagcctg tccgacccag    960
aaggcacaac ttgagagacc ttcttgtaag attcttctga tgctccatcg ttacaaatat   1020
caagctgctc ctctgttcat tttttctata gattaatttc accctagta gttttgtttg   1080
tttaactccc ccgaaaactc attatatttg tatgaaatca atatcaatag tgttcaatgt   1140
ttgcttctgg ggtttaagtt ttagccagtg tgtataaccc tttcctctgc cgatctcaac   1200
attagcttgc aactttgtta agaaacatca cttgtgtttt tgtgttgatg gccattaata   1260
taatccaagt ttatttaatc cg                                             1282
```

<210> SEQ ID NO 5
<211> LENGTH: 352
<212> TYPE: PRT

<213> ORGANISM: Arabidopsis thaliana

<400> SEQUENCE: 5

Met Glu Arg Asp Phe Leu Gly Leu Gly Ser Lys Asn Ser Pro Ile Thr
1               5                   10                  15

Val Lys Glu Glu Thr Ser Glu Ser Ser Arg Asp Ser Ala Pro Asn Arg
            20                  25                  30

Gly Met Asn Trp Ser Phe Ser Asn Lys Val Ser Ala Ser Ser Ser Gln
        35                  40                  45

Phe Leu Ser Phe Arg Pro Thr Gln Glu Asp Arg His Arg Lys Ser Gly
    50                  55                  60

Asn Tyr His Leu Pro His Ser Gly Ser Phe Met Pro Ser Ser Val Ala
65                  70                  75                  80

Asp Val Tyr Asp Ser Thr Arg Lys Ala Pro Tyr Ser Ser Val Gln Gly
                85                  90                  95

Val Arg Met Phe Pro Asn Ser Asn Gln His Glu Glu Thr Asn Ala Val
            100                 105                 110

Ser Met Ser Met Pro Gly Phe Gln Ser His His Tyr Ala Pro Gly Gly
        115                 120                 125

Arg Ser Phe Met Asn Asn Asn Asn Ser Gln Pro Leu Val Gly Val
    130                 135                 140

Pro Ile Met Ala Pro Pro Ile Ser Ile Leu Pro Pro Gly Ser Ile
145                 150                 155                 160

Val Gly Thr Thr Asp Ile Arg Ser Ser Ser Lys Pro Ile Gly Ser Pro
                165                 170                 175

Ala Gln Leu Thr Ile Phe Tyr Ala Gly Ser Val Cys Val Tyr Asp Asp
            180                 185                 190

Ile Ser Pro Glu Lys Ala Lys Ala Ile Met Leu Leu Ala Gly Asn Gly
        195                 200                 205

Ser Ser Met Pro Gln Val Phe Ser Pro Pro Gln Thr His Gln Gln Val
    210                 215                 220

Val His His Thr Arg Ala Ser Val Asp Ser Ser Ala Met Pro Pro Ser
225                 230                 235                 240

Phe Met Pro Thr Ile Ser Tyr Leu Ser Pro Glu Ala Gly Ser Ser Thr
                245                 250                 255

Asn Gly Leu Gly Ala Thr Lys Ala Thr Arg Gly Leu Thr Ser Thr Tyr
            260                 265                 270

His Asn Asn Gln Ala Asn Gly Ser Asn Ile Asn Cys Pro Val Pro Val
        275                 280                 285

Ser Cys Ser Thr Asn Val Met Ala Pro Thr Val Ala Leu Pro Leu Ala
    290                 295                 300

Arg Lys Ala Ser Leu Ala Arg Phe Leu Glu Lys Arg Lys Glu Arg Val
305                 310                 315                 320

Thr Ser Val Ser Pro Tyr Cys Leu Asp Lys Lys Ser Ser Thr Asp Cys
                325                 330                 335

Arg Arg Ser Met Ser Glu Cys Ile Ser Ser Leu Ser Ser Ala Thr
            340                 345                 350

<210> SEQ ID NO 6
<211> LENGTH: 3253
<212> TYPE: DNA
<213> ORGANISM: Arabidopsis thaliana

<400> SEQUENCE: 6
gcgatttgtt aataaaacta gaaattgcgg tgaattaact tcattccacg ttttttcatt    60

```
ttctccctca aaagtctctg ttttttttcc tttttccggc gaagctctat ttagcttgat      120
tccggcgttt aacacgcgtt ttaatcgaaa cagacatttg agatcgaatt aattttgtag      180
cgggctgtgt ctttattata gatggagaga gattttctcg ggttgggttc gaaaaattct      240
ccgatcactg tcaaggagga aaccagcgaa agctctagag attcaggtta tttattactc      300
ttctcaattt ttctgattct gattgttttt aaatcgtaga tttgtttgat tgattaggag      360
ttattaggac tacttgtagt atggaatttg tttttggata gctgatttta tggcttgctc      420
gggaactgga attgtcagtt tgttgcttgg agcagaacat tgtcctttgc ttttctcggg      480
agatgtagaa tttggatttg gaaaaactag tgttcttttc caaagccttg tcttaaacat      540
gctttcggtc ggagaaatta acgagaacta atctcaagct tctaacataa ttaaactcgg      600
taaacttttt tttactagag taaattttt tgttttgttt gaagagtctt ataattgaga      660
aatactttat tagtttatac taaaaaaaaa acgaatacgt aaaatgttgg aaaagagggg      720
atgtatagag actgatacaa aaatgataaa atagagacgg ttggtagtag gtagaaagat      780
taaatatact caaaagagtg agttggatta gtttataaga tgattaactt cttgattgtg      840
tgagttggat tagtttatga gattattaaa atattgattg tgtatttgtg ttgtgtgttg      900
attaagcgga acttgcgtta gaatattgtt caaggtacaa tgtggaaata atagttttct      960
caccacgagg aatataatta tttcaacttt gttttcttat cagccaaaac gtgccacacc     1020
ataaaagtag tgcatcaaca tgtggtgtgg tgtggtgggg ttaaagtttg aatctctctt     1080
taatttaaac tattaaaaca aacttaaatt attggagttt cgtacaatga ctttcaatca     1140
aatgttttag aattagacac ggttttcgaa agtggttttc cctcgttgaa tttgtcaaca     1200
gtatcagatt ctacattgtt ggttactaat cttttccttg aagtaggtgt tgaattaatc     1260
ctctgttgtt tatgtaagga gatctcgaga catttatggt taacagttaa cactacatgt     1320
ttgactttaa actgattatc ttttattctt tttcttttgt agctcccaac agaggaatga     1380
actggtcttt ctcaaacaaa gtatcagctt cttcttctca gtttctatcc ttcaggccaa     1440
ctcaagaaga tagacataga aagtctggaa attatcatct tcctcactct ggttccttca     1500
tgccatcatc agtagctgat gtttatgatt caacccgcaa agctccttac agttctgtac     1560
aggtatttgt catcaaaacc tatgttaacc aagaccttg tgtttttttt atccttcgca     1620
agatagcttt aaaagtgagc cctgttttat gagcatatag taattggttt tgagtctagt     1680
ttagcacaag ttcatggcaa ttagtttgtg gatctaatct tggtttaata ctgattcatt     1740
ttaagtgtaa gctaagcttc tcatttttga taagttagtt catacaatgc ctcacaccta     1800
ctttatggct tgttactctc agggagtgag gatgttccct aattccaatc aacacgaaga     1860
aactaacgca gtttccatgt cgatgccggg tttccagtct catcattatg caccaggagg     1920
aagaagcttc atgaacaata acaataactc acaacctttg gtaggagttc ctatcatggc     1980
acctccaatt tcaatccttc ctcctccagg ttccattgta gggactactg atattaggta     2040
cccactagtc atcatatcat acagaaactc tttctacatt ttcatagttg actaaagact     2100
tattttttgtc agatcttctt ccaagccaat aggttcacct gcgcagttga cgatctttta     2160
tgccggttca gttgtgttt acgatgacat atctcctgaa aaggtatctc aatcattttc     2220
ttccatatat gcatctcttt tactcgtaag gtatggtact catttgcttt ctttcatttc     2280
tcaggcaaag gcgataatgt tgctagctgg gaacggttcc tctatgcctc aagtcttttc     2340
gccgcctcaa actcatcaac aagtggtcca tcatactcgt gcctctgtcg attcttcagc     2400
```

-continued

```
tatgcctcct agcttcatgc ctacaatatc ttatcttagc cctgaagctg gaagtagcac    2460
aaacggactc ggagccacaa aagcgacaag aggcttgacg tcaacatatc acaacaacca    2520
agctaatgga tccaatatta actgcccagt accagtttct tgttctacca atgtaatggc    2580
tccaacaggt aaaaacaaa gtcagagacc tgatactaca ttcgccatct aacttactag    2640
tattttcatg gatgtaactt cattctcgtt ctgtttctta tgcagtggca ttacctctgg    2700
ctcgcaaagc atccctggct aggtttttag agaaacgcaa agaaaggtac gcaacacttc    2760
tttagaatac accattcaat agtttcttgg gctaactctc tttctcgctg tgggtttctc    2820
agggtcacga gcgtatcccc atattgctta gacaagaagt catcgacaga ttgtcgcaga    2880
tcaatgtctg aatgcattag ttcttctctc agctctgcaa cctaatttca tctacagtaa    2940
gaaggttgct ttagaccact ccacatccat atttgcattt caatggcggt cttttcaatg    3000
tctcagttaa ttttcctca ctcgccacac tgagtttctc cttagcttta tatatacgat    3060
agtgtatact ttgtttacat gttttttggt ggaatggaac ttatgagagc atatcagata    3120
tgtacttggg aaaattagta gaaactgttt gtttctttt ttaactct gttcttttgt    3180 atatatcact gaagctcgca tatgtataat tcatgtaatg gaattgcatc gcttctgttt    3240
ccctaagtta ttt                                                       3253
```

<210> SEQ ID NO 7
<211> LENGTH: 310
<212> TYPE: PRT
<213> ORGANISM: Arabidopsis thaliana

<400> SEQUENCE: 7

```
Met Glu Arg Asp Phe Leu Gly Leu Gly Ser Lys Leu Ser Pro Ile Thr
1               5                   10                  15

Val Lys Glu Glu Thr Asn Glu Asp Ser Ala Pro Ser Arg Gly Met Met
            20                  25                  30

Asp Trp Ser Phe Ser Ser Lys Val Gly Ser Gly Pro Gln Phe Leu Ser
        35                  40                  45

Phe Gly Thr Ser Gln Gln Glu Thr Arg Val Asn Thr Val Asn Asp His
    50                  55                  60

Leu Leu Ser Ser Ala Ala Met Asp Gln Asn Gln Arg Thr Tyr Phe Ser
65                  70                  75                  80

Ser Leu Gln Glu Asp Arg Val Phe Pro Gly Ser Ser Gln Gln Asp Gln
                85                  90                  95

Thr Thr Ile Thr Val Ser Met Ser Glu Pro Asn Tyr Ile Asn Ser Phe
            100                 105                 110

Ile Asn His Gln His Leu Gly Gly Ser Pro Ile Met Ala Pro Pro Val
        115                 120                 125

Ser Val Phe Pro Ala Pro Thr Thr Ile Arg Ser Ser Lys Pro Leu
    130                 135                 140

Pro Pro Gln Leu Thr Ile Phe Tyr Ala Gly Ser Val Leu Val Tyr Gln
145                 150                 155                 160

Asp Ile Ala Pro Glu Lys Ala Gln Ala Ile Met Leu Leu Ala Gly Asn
                165                 170                 175

Gly Pro His Ala Lys Pro Val Ser Gln Pro Lys Pro Gln Lys Leu Val
            180                 185                 190

His His Ser Leu Pro Thr Thr Asp Pro Pro Thr Met Pro Pro Ser Phe
        195                 200                 205

Leu Pro Ser Ile Ser Tyr Ile Val Ser Glu Thr Arg Ser Ser Gly Ser
    210                 215                 220
```

```
Asn Gly Val Thr Gly Leu Gly Pro Thr Lys Thr Lys Ala Ser Leu Ala
225                 230                 235                 240

Ser Thr Arg Asn Asn Gln Thr Ala Ala Phe Ser Met Ala Pro Thr Val
            245                 250                 255

Gly Leu Pro Gln Thr Arg Lys Ala Ser Leu Ala Arg Phe Leu Glu Lys
        260                 265                 270

Arg Lys Glu Arg Val Ile Asn Val Ser Pro Tyr Tyr Val Asp Asn Lys
    275                 280                 285

Ser Ser Ile Asp Cys Arg Thr Leu Met Ser Glu Cys Val Ser Cys Pro
    290                 295                 300

Pro Ala His His Leu His
305             310

<210> SEQ ID NO 8
<211> LENGTH: 3187
<212> TYPE: DNA
<213> ORGANISM: Arabidopsis thaliana

<400> SEQUENCE: 8
attagaggaa tcataaatcg gcggtgtgtg taacttcaac tcacgttttt catttctctc      60
caaagtcctt caattgttac taattctctc tgatctctca tttcttctct tctccggtga    120
catttttttt ctcccccgcg aaagctaaac cgttttgta ttctcaacga ttgataagcc     180
tgatggagag agattttctc gggctgggat caaagttatc tccgataact gtgaaggagg    240
aaactaacga agattcaggt aattcatctt caacatcttc cattatgatc tgatgattgt    300 gttttcatc tcactttttt tgtttctat ttttgtaatc tctttttttg tttattgttc      360
aagtacatat atattgtttt tctagcttga ttgggagtcc tactgtctgg ttttttcttg    420
aacaagaaat ttttcttcg ttttctcggg aagagaaaaa ataaattagg gtttcttttt    480
tcttgatata tatttaagaa attaggtttt agtactatag acagaaattt agctactcga    540
atttgtttga cgtagccgat gaaaaacac gttttgggac tcgatagtta gaaaattcat    600
acgttcacga tctactttg aagttttttt cattaaatat tttttgcaaa ctacaaatgt    660
acaagtatac aactatacaa gcaaacacca aacttgttga cgttagtaat taacaagtg    720 ttagtattat ctttgaaaaa taatattcag agaacaaact tgattttcta ggtgactagg    780
tgatgcatgt ttctaaagct gttggtaatg ttgagtgttt tcaaaataat ttcgtttttt    840
tcttcaaaca gccgacaccg acagaacaaa aatgctatat ttttttttgtt gcttacaaaa    900 ttgatcaatt ggtttcaata caatagtatc ttctttagaa aagattgttt ttttcaaagc    960
cggattgaat attgagaatt agaacattgg ctggttattc ttttgaaaa gtttatgcca    1020 tttttaagg tttattaagc aacttgaatt ctatcagtat tatttaaaaa cgaagacgtg    1080
aaatgttggg aaaagaatgc gttatatagc gaccggctga cgattagaga tttaacaaca    1140
aatgcaagtt gaattatata aaagcaagat tgattgtgac ttgattaagt tttatttcta    1200
tccaagtaga ctcattgatt aagttaggat catgttgggt attaaattta gatcaagtta    1260
caatttggat gaataattta cttacccacg aggaatttaa tagttagttc ttgtcttttt    1320
atattccgaa acgtgccatt tcttgaaagt atttgtatga tcactatttt ccccagtgtg    1380
tttggcttta tgcagatttg ttcattgttg atgaatctaa tgttaagagt cgtccacttt    1440
agcatagcta gatctgagtg tttcctagtt tgataaaatc taaagacatt tgctcatgtt    1500
tcagccccaa gtagaggtat gatggattgg tcattctcaa gcaaagtcgg ttctggtcct    1560
```

```
cagtttctttt cttttgggac atcccaacaa gaaacgcgtg taaacacagt caatgatcat    1620
ttgctttctt ctgctgcaat ggatcaaaac cagagaactt acttcagctc actacaggtt    1680
aggctatttc ttgaaaagaa aaaagtagt gataaagtgt gatttagtga ccttgtaaga    1740
aagcttggca attggtttag tttcttctgg tctcaaaatt gatacaaaat gatctcagga    1800
agacagagtg ttcccaggtt ccagtcagca agaccaaaca accatcacag tctccatgtc    1860
cgaaccaaac tacatcaaca gtttcataaa ccaccaacat ttaggaggat ctcctatcat    1920
ggcacctcca gtttcagtat ttcctgctcc aaccactatt aggcatgcac tgcattctat    1980
cttcttctgt ttaacatcag atacagaacc tctttacttc tatagttgac tcgagctcct    2040
ttatgttcat ctccagatct tcttcaaaac cacttccccc tcagttgaca atcttttatg    2100
ccggttcagt attagtttac caagacatag ctcctgaaaa ggtaaccaaa tttccttcaa    2160
tatgtgttac attacagtcc aagctatcca ctgactaagt attcaatcaa agaaataagt    2220
ttcacgtata gacatgctga agttatagaa agttactaac ctggtttcaa catacagtat    2280
gttaatgatt catagatatg ataaatcttt gtccttactt cttcatttat tttgtattca    2340
taggcccaag ctatcatgtt gctagccgga aatggacctc atgctaaacc ggtttcacaa    2400
cctaaacctc aaaaactggt tcatcactct cttccaacca ctgatcctcc aactatgcct    2460
cctagtttcc tgccttccat ctcttacatt gtctctgaaa ccagaagtag tggatccaac    2520
ggggttactg gacttggacc aacaaaaaca aaggcgagtt tagcatccac gcgcaacaac    2580
caaactgctg ccttctctat ggctccaaca ggttataaat gaagtcttaa ctcctattaa    2640
tgttttgtca tcaaacttct atcttaggtt tagtttgtta taaccaaaaa atcttgctat    2700
gatttaatac agtgggttta ccacaaacac gcaaagcatc cttggctcgg ttcttagaga    2760
aacgcaaaga aaggtactga gctacaagat tattcactta ttcacaatat caaaacacag    2820
gtttgctgta tattggcttc gttttcttgc agggtcatta acgtatcacc ttattacgta    2880
gacaacaagt catcaataga ctgtagaaca ctgatgtctg aatgtgtaag ctgtcctcca    2940
gctcatcatc tgcactaaaa ccaatttaga cccctcattg ttctaaaggc ttttctttt    3000 ttctctggct ctgtatccta tagactatag tatagttgtt atagcttttg tttattcaga    3060
ttttagtaca ctgggcttgt aaaagcaagt tatttatata tatcctataa atttaatttg    3120
gatactgtat gttttgtctt tactcttgca tgtgtataaa aaacataaaa gtaagactat    3180
tcaagct                                                               3187
```

<210> SEQ ID NO 9
<211> LENGTH: 274
<212> TYPE: PRT
<213> ORGANISM: Arabidopsis thaliana

<400> SEQUENCE: 9

Met Ser Ser Ser Asn Glu Asn Ala Lys Ala Gln Ala Pro Glu Lys Ser
1               5                   10                  15

Asp Phe Thr Arg Arg Cys Ser Leu Leu Ser Arg Tyr Leu Lys Glu Lys
            20                  25                  30

Gly Ser Phe Gly Asn Ile Asp Leu Gly Leu Tyr Arg Lys Pro Asp Ser
        35                  40                  45

Ser Leu Ala Leu Pro Gly Lys Phe Asp Pro Pro Gly Lys Gln Asn Ala
    50                  55                  60

Met His Lys Ala Gly His Ser Lys Gly Glu Pro Ser Thr Ser Ser Gly
65                  70                  75                  80

Gly Lys Val Lys Asp Val Ala Asp Leu Ser Glu Ser Gln Pro Gly Ser
            85                  90                  95

Ser Gln Leu Thr Ile Phe Phe Gly Gly Lys Val Leu Val Tyr Asn Glu
        100                 105                 110

Phe Pro Val Asp Lys Ala Lys Glu Ile Met Glu Val Ala Lys Gln Ala
        115                 120                 125

Lys Pro Val Thr Glu Ile Asn Ile Gln Thr Pro Ile Asn Asp Glu Asn
        130                 135                 140

Asn Asn Asn Lys Ser Ser Met Val Leu Pro Asp Leu Asn Glu Pro Thr
145                 150                 155                 160

Asp Asn Asn His Leu Thr Lys Glu Gln Gln Gln Gln Glu Gln Asn
                165                 170                 175

Gln Ile Val Glu Arg Ile Ala Arg Arg Ala Ser Leu His Arg Phe Phe
        180                 185                 190

Ala Lys Arg Lys Asp Arg Ala Val Ala Arg Ala Pro Tyr Gln Val Asn
        195                 200                 205

Gln Asn Ala Gly His His Arg Tyr Pro Pro Lys Pro Glu Ile Val Thr
        210                 215                 220

Gly Gln Pro Leu Glu Ala Gly Gln Ser Ser Gln Arg Pro Pro Asp Asn
225                 230                 235                 240

Ala Ile Gly Gln Thr Met Ala His Ile Lys Ser Asp Gly Asp Lys Asp
                245                 250                 255

Asp Ile Met Lys Ile Glu Glu Gly Gln Ser Ser Lys Asp Leu Asp Leu
        260                 265                 270

Arg Leu

<210> SEQ ID NO 10
<211> LENGTH: 1765
<212> TYPE: DNA
<213> ORGANISM: Arabidopsis thaliana

<400> SEQUENCE: 10

```
taatcatgga tgaaaattcc tttcttcaca ctagatatag ttctttaact agttaaaaat      60
gcatgcgatg gaatattact aaatatgata taatctcatg ctttatgta agatttgttt     120
tttggttttt ttggttgttg ttaataaatt tattattgag aagtttaatt ctattttggt     180
cacaatatat tgaaatattt ttaagaaact aaaaagttcc tatttatttt tgttttcatt     240
aatttatgag aggctattaa agtcacagaa acttattggg tgaatgagtt tataaacaca     300
tgagctattg agctagtagc ctcttgtact cttccatttt acgcgcaatc cacgcaccaa     360
caaaagaaa agaaagaag agataaagaa tatctttaaa agtaagtgt ggagaattct       420
ttcttctcaa taacaacaa catgtcgtcg agcaatgaaa atgctaaggc acaagcgccg     480
gagaaatctg actttacccg agatgtagt ttgctcagcc gttacttgaa ggagaagggt      540
agtttcggaa acattgatct tggcttatac cgaaacccg attccagtct cgcgttgccc      600
ggaaaattcg atccaccagg gaaacaaaat gcgatgcata aggcagggca ttccaaaggc     660
gaaccctcta cctcatcagg aggcaaagtc aaagatgttg ctgacctcag tgaatcacag     720
ccaggaagtt cgcagctgac catattcttc ggagggaaag ttttagtata taatgagttc     780
cccgtagaca aagctaaaga gattatggaa gtagcaaaac aagccaagcc tgtgactgag     840
attaacattc agacaccaat caatgacgaa acaacaacaa acaagagcag catggttctt     900
cctgatctca tgagcctac tgataataat cacctaacaa aggaacaaca acagcaacaa      960
gaacaaaatc agatcgtgga acgtatagca cgtagagctt ccctccatcg attctttgct    1020
```

-continued

```
aaacggaaag acagagctgt ggctagggct ccgtaccaag ttaaccaaaa cgcaggtcat   1080
catcgttatc ctcccaagcc agagattgta accggtcaac cactagaggc aggacagtcg   1140
tcacaaagac cgccggataa cgccattggt caaaccatgg cccatatcaa atcagacggt   1200
gataaagatg atattatgaa gattgaagaa ggccaaagtt cgaaagatct cgatctaagg   1260
ctatagtaat atttgctaaa tttcttgtag gaactgagtt tttagattaa cgtttcgatt   1320
tttctgactt atctaagtga ttttattttg ctttgtacta cagtatgtaa tcttattcta   1380
acttgaatat tcattcataa acacaataga cgatagtaaa gttatattat aattagttaa   1440
ctacgtacaa cacttgggag ttaaattaca taacgttaag cgagaaatag caaattagac   1500
aagaggaaga atatttagga gttgtgaatt gatctgactg caataacatg aagaggaatc   1560
tgactgcaat cgtaatgcgg gtaaagatgg ttgaaagtga tcagagctcc tttctaattt   1620
atttagggtg taatttatga aaatgattat tattggagtg tatatcaagt tttcactaaa   1680
ctcaggggtg tttattgtaa ttagttgtca ggttcaagtt cattgaaggc gtgtctgatt   1740
tggacagtga ttgggcctga gccat                                          1765
```

<210> SEQ ID NO 11
<211> LENGTH: 269
<212> TYPE: PRT
<213> ORGANISM: Arabidopsis thaliana

<400> SEQUENCE: 11

```
Met Ser Thr Gly Gln Ala Pro Glu Lys Ser Asn Phe Ser Gln Arg Cys
1               5                   10                  15

Ser Leu Leu Ser Arg Tyr Leu Lys Glu Lys Gly Ser Phe Gly Asn Ile
            20                  25                  30

Asn Met Gly Leu Ala Arg Lys Ser Asp Leu Glu Leu Ala Gly Lys Phe
        35                  40                  45

Asp Leu Lys Gly Gln Gln Asn Val Ile Lys Lys Val Glu Thr Ser Glu
    50                  55                  60

Thr Arg Pro Phe Lys Leu Ile Gln Lys Phe Ser Ile Gly Glu Ala Ser
65                  70                  75                  80

Thr Ser Thr Glu Asp Lys Ala Ile Tyr Ile Asp Leu Ser Glu Pro Ala
                85                  90                  95

Lys Val Ala Pro Glu Ser Gly Asn Ser Gln Leu Thr Ile Phe Phe Gly
            100                 105                 110

Gly Lys Val Met Val Phe Asn Glu Phe Pro Glu Asp Lys Ala Lys Glu
        115                 120                 125

Ile Met Glu Val Ala Lys Glu Ala Asn His Val Ala Val Asp Ser Lys
    130                 135                 140

Asn Ser Gln Ser His Met Asn Leu Asp Lys Ser Asn Val Val Ile Pro
145                 150                 155                 160

Asp Leu Asn Glu Pro Thr Ser Ser Gly Asn Asn Glu Asp Gln Glu Thr
                165                 170                 175

Gly Gln Gln His Gln Val Val Glu Arg Ile Ala Arg Arg Ala Ser Leu
            180                 185                 190

His Arg Phe Phe Ala Lys Arg Lys Asp Arg Ala Val Ala Arg Ala Pro
        195                 200                 205

Tyr Gln Val Asn Gln His Gly Ser His Leu Pro Pro Lys Pro Glu Met
    210                 215                 220

Val Ala Pro Ser Ile Lys Ser Gly Gln Ser Ser Gln His Ile Ala Thr
225                 230                 235                 240
```

Pro Pro Lys Pro Lys Ala His Asn His Met Pro Met Glu Val Asp Lys
                245                 250                 255

Lys Glu Gly Gln Ser Ser Lys Asn Leu Glu Leu Lys Leu
            260                 265

<210> SEQ ID NO 12
<211> LENGTH: 1604
<212> TYPE: DNA
<213> ORGANISM: Arabidopsis thaliana

<400> SEQUENCE: 12

| | | | | | |
|---|---|---|---|---|---|
| aaattaatag | cctataatat | gtttgaccat | aaaagaatt | tcttcttctt | gaaccatcat | 60 |
| aagaaaaatg | tgtgtttagt | ctattgatca | gttttgtgtt | caaaaaaaaa | aaaaaaatgt | 120 |
| ctatcgatca | gttaggtgta | aaaaaaaaag | ttacaaaact | cgtgacaaaa | acattctata | 180 |
| ttggacacac | atcactgtca | cttcagacta | aataaaaaaa | agaacacgt | tatttcgttt | 240 |
| tctttattta | ttcgggagag | gttaaaagcc | acagaaactt | attggctaga | attggttatt | 300 |
| tataacaaca | acacatgagc | aaaaagctca | aaacatctac | atactctttg | gaatcctcga | 360 |
| ttttttgtac | gtgtaaagaa | gtcacacaag | aaaatcttgg | gttgttgtaa | tcttcatcac | 420 |
| actagtatgt | caacgggaca | agcgccggag | aagtccaatt | tttctcagag | atgtagtctg | 480 |
| ctcagccggt | acttgaagga | gaagggaagt | tttgggaata | ttaatatggg | gttggctcga | 540 |
| aaatccgatc | ttgaactcgc | cggaaaattc | gatctcaaag | gacaacaaaa | tgtgattaag | 600 |
| aaggtagaga | cctcagaaac | tagaccgttc | aagttgattc | agaagttttc | tattggtgag | 660 |
| gcctctactt | ctaccgaaga | caaagccata | tatattgatc | tcagtgaacc | ggcaaaagta | 720 |
| gcaccggagt | ctggaaattc | acagttgacc | atattctttg | gaggaaaagt | tatggttttc | 780 |
| aacgagtttc | ctgaagacaa | agctaaggag | ataatggaag | tagctaaaga | agcgaatcat | 840 |
| gttgctgttg | attctaagaa | cagtcagagt | cacatgaatc | ttgacaaaag | caacgtggtg | 900 |
| attcccgatc | ttaacgagcc | aacgagttcc | gggaacaatg | aagatcaaga | aactgggcag | 960 |
| caacatcagg | ttgtggaacg | cattgcaaga | agagcttctc | ttcatcgatt | ctttgctaaa | 1020 |
| cgaaaagaca | gggctgtggc | tagagctcca | tatcaagtga | accaacacgg | tagtcatctt | 1080 |
| cctcccaagc | cagagatggt | tgctccatcg | ataaagtcag | gccaatcgtc | gcaacacatt | 1140 |
| gcaactcctc | caaaaccaaa | ggcccataac | catatgccga | tggaggtgga | caagaaagaa | 1200 |
| ggacaatctt | ccaaaaacct | tgaactcaag | ctttagggcg | tataaaatgc | acgatcgagt | 1260 |
| tcacgtttct | agttttcact | tatttaggat | ttgaacccaa | atacccttt | atattttctt | 1320 |
| ccattacttt | tgaccaattt | aagttattta | tagtactgta | ttacgtagct | agtatttata | 1380 |
| tttcaaaaca | tacatatttt | gatacttgtt | ttttagattc | tttaattaaa | attgtcatct | 1440 |
| ggattaccct | ttatcgaaat | tttttaatca | cctgatataa | tctcaccagt | gatggatttg | 1500 |
| cgttgttagt | aattttcta | agtggcaaaa | gtatattaac | ctataatagg | tttcaaagat | 1560 |
| atacatataa | tgtttctatc | aaagatatta | gtataatatt | ttac | | 1604 |

<210> SEQ ID NO 13
<211> LENGTH: 148
<212> TYPE: PRT
<213> ORGANISM: Arabidopsis thaliana

<400> SEQUENCE: 13

Met Ile Ile Ile Ile Lys Asn Cys Asp Lys Pro Leu Leu Asn Phe Lys
1               5                   10                  15

Glu Met Glu Met Gln Thr Lys Cys Asp Leu Glu Leu Arg Leu Leu Thr
                20                  25                  30

Ser Ser Tyr Asp Ser Asp Phe His Ser Ser Leu Asp Glu Ser Ser Ser
            35                  40                  45

Ser Glu Ile Ser Gln Pro Lys Gln Glu Ser Gln Ile Leu Thr Ile Phe
50                  55                  60

Tyr Asn Gly His Met Cys Val Ser Ser Asp Leu Thr His Leu Glu Ala
65                  70                  75                  80

Asn Ala Ile Leu Ser Leu Ala Ser Arg Asp Val Glu Glu Lys Ser Leu
                85                  90                  95

Ser Leu Arg Ser Ser Asp Gly Ser Asp Pro Pro Thr Ile Pro Asn Asn
            100                 105                 110

Ser Thr Arg Phe His Tyr Gln Lys Ala Ser Met Lys Arg Ser Leu His
        115                 120                 125

Ser Phe Leu Gln Lys Arg Ser Leu Arg Ile Gln Ala Thr Ser Pro Tyr
130                 135                 140

His Arg Tyr Arg
145

<210> SEQ ID NO 14
<211> LENGTH: 823
<212> TYPE: DNA
<213> ORGANISM: Arabidopsis thaliana

<400> SEQUENCE: 14
gttgtgttct gtccaaactc tgttctaatg ccagcttttg tctcgtcttt tctctatcct      60
tatcttccct ctatcttcga tcccaacaca tacacaacac gcacacacac atatataaat     120
caactgactg acacatacaa tcatgatcat catcatcaaa actgcgaca agcctttact     180
caatttcaaa gagatggaga tgcaaacaaa atgcgacttg aacttcgcc ttcttacttc      240
ttcttatgat tctgatttcc atagctcgtt ggacgaatca agcagctctg aaatttcaca     300
accaaagcaa gaatctcaga tattaaccat tttctacaac gggcacatgt gtgtttcttc     360
agatcttacc catcttgagg ctaacgctat actatcgcta gcgagtagag atgtggaaga     420
gaaatcttta tccttgagaa gttcagacgg ttcggatcct ccaacaatcc caaacaattc     480
gactcgattt cattatcaaa aggcctctat gaagagatct cttcacagtt tcttcagaa      540
acgaagtctt cggattcaag caacttcccc ttaccaccgt taccgatagc actatctatt     600
tgatttcatt tttgtgattc tcttcaattt ttttttttact gtaacataat aatccaattg    660
tcttgaattc ttttctgtg tgtttggatg gattacagac cttaattagg tagagtatta      720
aagtttcata atttccagta acttgtgttt agagttcaag aggttgacaa aatttatcaa     780
cggtctccta aaatgggtaa accgagaaac ttttatacga aaa                       823

<210> SEQ ID NO 15
<211> LENGTH: 267
<212> TYPE: PRT
<213> ORGANISM: Arabidopsis thaliana

<400> SEQUENCE: 15

Met Glu Arg Asp Phe Leu Gly Leu Ser Asp Lys Gln Tyr Leu Ser Asn
1               5                   10                  15

Asn Val Lys His Glu Val Asn Asp Asp Ala Val Glu Glu Arg Gly Leu
                20                  25                  30

Ser Thr Lys Ala Ala Arg Glu Trp Gly Lys Ser Lys Val Phe Ala Thr

```
                35                  40                  45
Ser Ser Phe Met Pro Ser Ser Asp Phe Gln Glu Ala Lys Ala Phe Pro
 50                  55                  60

Gly Ala Tyr Gln Trp Gly Ser Val Ser Ala Ala Asn Val Phe Arg Arg
 65                  70                  75                  80

Cys Gln Phe Gly Gly Ala Phe Gln Asn Ala Thr Pro Leu Leu Leu Gly
                 85                  90                  95

Gly Ser Val Pro Leu Pro Thr His Pro Ser Leu Val Pro Arg Val Ala
            100                 105                 110

Ser Ser Gly Ser Ser Pro Gln Leu Thr Ile Phe Tyr Gly Gly Thr Ile
            115                 120                 125

Ser Val Phe Asn Asp Ile Ser Pro Asp Lys Ala Gln Ala Ile Met Leu
    130                 135                 140

Cys Ala Gly Asn Gly Leu Lys Gly Glu Thr Gly Asp Ser Lys Pro Val
145                 150                 155                 160

Arg Glu Ala Glu Arg Met Tyr Gly Lys Gln Ile His Asn Thr Ala Ala
                165                 170                 175

Thr Ser Ser Ser Ser Ala Thr His Thr Asp Asn Phe Ser Arg Cys Arg
            180                 185                 190

Asp Thr Pro Val Ala Ala Thr Asn Ala Met Ser Met Ile Glu Ser Phe
        195                 200                 205

Asn Ala Ala Pro Arg Asn Met Ile Pro Ser Val Pro Gln Ala Arg Lys
    210                 215                 220

Ala Ser Leu Ala Arg Phe Leu Glu Lys Arg Lys Glu Arg Leu Met Ser
225                 230                 235                 240

Ala Met Pro Tyr Lys Lys Met Leu Leu Asp Leu Ser Thr Gly Glu Ser
                245                 250                 255

Ser Gly Met Asn Tyr Ser Ser Thr Ser Pro Thr
            260                 265

<210> SEQ ID NO 16
<211> LENGTH: 2297
<212> TYPE: DNA
<213> ORGANISM: Arabidopsis thaliana

<400> SEQUENCE: 16
gcaaagagtt aaataagcct ctccaaaagt gtgtctgtaa cattaccaaa acgaaacctt     60
ccttgtggat tcccacttct ttcttctgtt ttcttcttcc tcttctttaa attggatgtt    120
ttgggcaaga aacagagaga aacacgttaa tttgagagtt tgtcattgaa tatttggttt    180
gcaatggaaa gagattttct gggtttgagc gacaagcagt atctaagtaa taacgttaag    240
catgaggtta acgatgatgc tgtcgaagaa cgaggtttgt gttcttgtct cgagaatctt    300 ttatttaat gtttcaagaa gagatcagtt ttcacttta acatagccgt ataaagttgt    360
ttatttaaat ataattttc agattccaaa acttgaaaaa aaaagattc cattaaatct    420 tttataaaaa tgagattgga tagattagtc aaattgacga ccataaaaa tgatacttat    480 agggttaagt acgaaggcag ctagagaatg ggggaagtca aaggttttg ctacttcaag    540 tttcatgcct tcttcagatt tccaggttgg ttcatcttaa aatttaactt actctgtatc    600
agtttcagat gttatggcta atctaatggt tctataagct accgcataat catggtcgtc    660
ttttagcatg tgcaagagga gtactcaatt atggtcttga ttaaaaagaa gaatttactt    720
tcaaattatg ttaaacacat caatcacata tttatgagaa aagttgtttt cgtaagagat    780
agccaccgga aaatggtcgg ataaatggcc gaactttatc attttgtgt atgtggccaa    840
```

-continued

```
tcattaacca gggaaaaaaa attgttggat aagtgctagt taagagctgg tagggtcggt    900
cgtctgccag ccgcaaagtt agggaaaaaa taatttaata ttttgtggcg tttggtgttt    960
ggcgtttgga tcacgtttat ttcttggcat ttttctaaat ttagaatgta caaaaaattt   1020
aaagacgttg acgattaaaa tttgaattta acaaattagg aggctaaggc gtttccgggt   1080
gcataccagt ggggatcagt ttctgcggcc aatgttttcc gcagatgcca atttggtggt   1140
gcgtttcaaa acgcgacgcc gcttttacta ggcggttcag ttcctttacc aactcatcct   1200
tctcttgttc cacggtaatt tccatattat gatgcaaaaa cattcaacaa ttttttttgct  1260 cttttcatat tttgatttgg ttatgtgggt tgtggaaac agagtggctt cctccggatc    1320
atctcctcag ctcacaatct tttatggcgg aactataagc gtctttaatg acatatctcc   1380
cgataaggta tatataatca agattcatac aaataacatt tacataacat ttacatgttc   1440
taaaacggac tattcatgat atgtgagtag gctcaagcca tcatgttatg cgccgggaac   1500
ggtttgaaag gtgaaactgg agatagcaaa ccggttcgag aagctgaaag aatgtatgga   1560
aaacaaatcc ataacactgc tgctacctca tcaagctctg ccactcacac tgataatttc   1620
tcaaggtgta gggacacacc cgttgctgcg actaatgcaa tgagcatgat cgaatcattc   1680
aatgcagctc ctcgtaacat gattccttca ggtatgtgtg tctaatatca acatcaaaac   1740
aaaatataat caagattttt gcttcctcaa atcatatgtc taaactcgaa aattgctttt   1800
ttccagtccc tcaagctcgg aaagcatcct tggctcggtt cttggagaag cgcaaagaga   1860
ggtttgattt tgtatttttt ttctttatag aaaattttga ggttttcaa ttgaatctaa    1920 aagaattgat gttgttggtg caggcttatg agtgcaatgc catacaagaa gatgcttctt   1980
gatttgtcga ccggagaatc cagtggaatg aattactctt ctacttctcc tacataaaac   2040
ctacactttt ttttttttt tttacaatgg taatttgtaa ttgtaatcat tagattatga    2100
ttatatagtt accatttata ttcttacgag caggagaaga cgttagggcg tctctgtatt   2160
tgatcattgt ttgtaatgct ttggtctgtt tattgtagga ttacattata actttaagaa   2220
ctaacagata tatgtttgtc atggactcat gtctgtcaag aatttaatat caaataaaat   2280
tcactataat tttttt                                                   2297
```

<210> SEQ ID NO 17
<211> LENGTH: 197
<212> TYPE: PRT
<213> ORGANISM: Arabidopsis thaliana

<400> SEQUENCE: 17

Met Ser Lys Ala Thr Ile Glu Leu Asp Phe Leu Gly Leu Glu Lys Lys
1               5                   10                  15

Gln Thr Asn Asn Ala Pro Lys Pro Lys Phe Gln Lys Phe Leu Asp Arg
            20                  25                  30

Arg Arg Ser Phe Arg Asp Ile Gln Gly Ala Ile Ser Lys Ile Asp Pro
        35                  40                  45

Glu Ile Ile Lys Ser Leu Leu Ala Ser Thr Gly Asn Asn Ser Asp Ser
    50                  55                  60

Ser Ala Lys Ser Arg Ser Val Pro Ser Thr Pro Arg Glu Asp Gln Pro
65                  70                  75                  80

Gln Ile Pro Ile Ser Pro Val His Ala Ser Leu Ala Arg Ser Ser Thr
                85                  90                  95

Glu Leu Val Ser Gly Thr Val Pro Met Thr Ile Phe Tyr Asn Gly Ser
            100                 105                 110

```
Val Ser Val Phe Gln Val Ser Arg Asn Lys Ala Gly Glu Ile Met Lys
        115                 120                 125

Val Ala Asn Glu Ala Ala Ser Lys Lys Asp Glu Ser Ser Met Glu Thr
    130                 135                 140

Asp Leu Ser Val Ile Leu Pro Thr Thr Leu Arg Pro Lys Leu Phe Gly
145                 150                 155                 160

Gln Asn Leu Glu Gly Asp Leu Pro Ile Ala Arg Arg Lys Ser Leu Gln
                165                 170                 175

Arg Phe Leu Glu Lys Arg Lys Glu Arg Leu Val Ser Thr Ser Pro Tyr
            180                 185                 190

Tyr Pro Thr Ser Ala
        195

<210> SEQ ID NO 18
<211> LENGTH: 1927
<212> TYPE: DNA
<213> ORGANISM: Arabidopsis thaliana

<400> SEQUENCE: 18
```

| | | | | | |
|---|---|---|---|---|---|
| aaaaactctc | acatgagaaa | tcagaatccg | ttattattcc | tccatttatt | catctcaaaa | 60 |
| cccatatctc | tctgtcttga | tctctctctc | actttctaat | aagatcaaag | aagatgtcga | 120 |
| aagctaccat | agaactcgat | ttcctcggac | ttgagaagaa | acaaaccaac | aacgctccta | 180 |
| agcctaagtt | ccagaaattt | ctcgatcgcc | gtcgtagttt | ccgaggttcg | tttggttttt | 240 |
| agtcgctctc | tcttttttt | ttcttgcgat | aaatcgaatt | tattcatatg | gaactcctgc | 300 |
| agatattcaa | ggtgcgattt | cgaaaatcga | tccggagatt | atcaaatcgc | tgttagcttc | 360 |
| cactggaaac | aattccgatt | catcggctaa | atctcgttcg | gttccgtcta | ctccgaggga | 420 |
| agatcagcct | cagatcccga | tttctccggt | ccacgcgtct | ctcgccaggt | attttgtct | 480 |
| ttccggtaaa | gttttttttt | tcttctaac | ttttttggcg | ctaccagaaa | agacgaaaaa | 540 |
| atttgaaatt | caaattttca | aaacattcat | tttcctcagg | tctagtaccg | aactcgtttc | 600 |
| gggaactgtt | cctatgacga | ttttctacaa | tggaagtgtt | tcagttttcc | aagtgtctcg | 660 |
| taacaaagct | ggtgaaatta | tgaaggtcgc | taatgaagca | gcatctaaga | aagacgagtc | 720 |
| gtcgatggag | acagatcttt | cggtaattct | tccgaccact | ctaagaccaa | agctctttgg | 780 |
| ccagaatcta | gaaggaggtt | agtataataa | aaataaaaat | cacttagtgc | tggattcttc | 840 |
| tagaatttta | gttacatatt | attgcatgta | gagatctaag | aagagtttgt | tgttagagag | 900 |
| gaattggttg | ctaattagtt | tggaattaga | tatcaaagag | ttaaagacta | tagtttatgt | 960 |
| ctatacgtat | taatatacgt | tattaataaa | agtataaaca | tgttgtttaa | tttctgataa | 1020 |
| gaaactggtt | tatgcgtgtg | tatgcagatc | ttcccatcgc | aaggagaaag | tcactgcaac | 1080 |
| gttttctcga | gaagcgcaag | gagaggtaat | gattcttcaa | caatccaagg | atttttaccc | 1140 |
| ccaaataatt | aaagaaaggt | ttttattttt | ctctctctcg | acctttttt | tactataagt | 1200 |
| tatttaagat | agtaattatg | ggtcctgcct | cttttactct | cacatacaac | ttaagattca | 1260 |
| actagttttg | ttcaacaacg | cacatgctta | tacgtagata | gataatggag | atcagtagta | 1320 |
| atatcggtat | acgtaggtta | ctattgtaat | ggaacttta | aaaagcgcgt | tgactttgag | 1380 |
| tctttgactc | tagttctgtt | tgctacaccg | acaagttata | ttttcaaaa | tgatgagaaa | 1440 |
| acgaggagaa | acaccggaaa | aaaatttgaa | cttttacttt | tatcagacca | tacggccaaa | 1500 |
| gaaagatctg | tatattatat | aagttatcac | aaaacgcggt | ttcacatttt | cttttcgtc | 1560 |

```
ttgttgtgtt tgcagattag tatcaacatc tccttactat ccgacatcgg cctaaacgat    1620
ctctttttag attgggacat ggaccaaatt tgtcttttc aatcggaaga catccatgtt     1680 cgttttgga tttggcttat ttccaatctt cttttgaagc cttcttcgtc gttgctaaat     1740
cgtatactat tcacgacaaa cgttttagg agattacgtt acctactaag attatatata    1800
ttggtttgtt tttaaaaatg tctattatct ttattgtcat tgatagcttg atttaagaag   1860
ctctctctta tcccgtgacc ttctactttt gttttatttt ttagtatatg gtaaagaaaa   1920
ttataac                                                             1927
```

<210> SEQ ID NO 19
<211> LENGTH: 125
<212> TYPE: PRT
<213> ORGANISM: Arabidopsis thaliana

<400> SEQUENCE: 19

```
Met Lys Gly Cys Ser Leu Asp Leu His Leu Ser Pro Met Ala Ser Thr
 1               5                  10                  15

Leu Gln Ser Cys His Gln Asp Ser Thr Val Asn Asp Arg Ser Ser Thr
             20                  25                  30

Ile Arg Ser Lys Glu Ile Asn Ala Phe Tyr Ser Gly Arg Leu Ser Glu
         35                  40                  45

Tyr Asp Leu Val Glu Ile Gln Met Arg Ala Ile Ile Glu Met Ala Ser
     50                  55                  60

Lys Asp Arg Glu Val Thr Ala Leu Glu Leu Val Pro Val Arg Leu Glu
 65                  70                  75                  80

Ser Pro Leu Gly Cys Ser Val Lys Arg Ser Val Lys Arg Phe Leu Glu
                 85                  90                  95

Lys Arg Lys Lys Arg Ser Lys Ser Phe Thr Leu Thr Pro Asn Tyr Thr
            100                 105                 110

Ser Ser Thr Ser Ser Ser Ser Ser Leu His Asn Phe
            115                 120             125
```

<210> SEQ ID NO 20
<211> LENGTH: 834
<212> TYPE: DNA
<213> ORGANISM: Arabidopsis thaliana

<400> SEQUENCE: 20

```
ttgattactt tgatacgaaa atcgaccaaa gtaagaatat ttacctagag aggatcatga     60
agggttgcag cttagatctt cacctatctc caatggcctc tacgcttcaa tcttgtcatc    120
aagattctac agttaatgat cgttcttcaa ccataagatc taaggaaatc aatgcatttt    180
atagtgggag attaagtgag tacgatcttg tagagatcca gatgagagca ataatagaga    240
tggcgagcaa ggatcgtgaa gtaacagcgt tagagttagt gccggtgaga ctggaatcac    300
cgttaggatg ttcggtgaag agatctgtga aaaggttctt ggagaagagg aagaagagaa    360
gcaaatcttt tacacttaca cctaattaca cctcaagtac ttcctcatca tcctcctctc    420
ttcataattt ctaatcataa ttttattatg ttttccttct agttatcaat caaaacaaaa    480
aaatctttgt ttctttcttt tttctttttt ccattatggg tttctatagc tctcatttat    540
ctcttgtaat ttttcccgat actcgacgat gaatttcgag ttttttttt tgatctgttt     600 taaatcaaga cattctagta ccattggagt ctgtataaaa ttcagatcat ttggatcgtt    660 attttttcc taattcatgt atgaagtgtc acacttctcc tacaatgaat tatgaggttg     720
tccgtttatt ccaagttagc tctatgtact ttgacgtaag ctaatgcaac ttgtaaaatg    780
```

```
ttgggaactc ttctattact ttttttcctt tacaaaataa gaaaatgcac gcat          834
```

<210> SEQ ID NO 21
<211> LENGTH: 273
<212> TYPE: PRT
<213> ORGANISM: Brassica rapa

<400> SEQUENCE: 21

Met Ser Ser Pro Met Glu Ser Ser Asp Phe Ala Ala Thr Arg Arg Phe
1               5                   10                  15

Ser Arg Lys Pro Ser Phe Ser Gln Thr Cys Ser Arg Leu Ser Gln Tyr
            20                  25                  30

Leu Lys Glu Asn Gly Ser Phe Gly Asp Leu Ser Leu Gly Met Ala Cys
        35                  40                  45

Lys Pro Glu Val Asn Gly Ile Ser Arg Gln Pro Thr Thr Thr Met Ser
    50                  55                  60

Leu Phe Pro Cys Glu Ala Ser Asn Met Glu Pro Ile Gly Gln Asp Val
65                  70                  75                  80

Lys Pro Lys Asn Leu Phe Pro Arg Gln Pro Ser Phe Ser Ser Ser
                85                  90                  95

Ser Ser Leu Pro Lys Glu Asp Ile Leu Lys Met Thr Gln Ala Thr Ser
            100                 105                 110

Ser Thr Arg Ser Val Lys Pro Glu Pro Gln Thr Ala Pro Leu Thr Ile
        115                 120                 125

Phe Tyr Gly Gly Gln Val Ile Val Phe Asn Asp Phe Ser Ala Glu Lys
    130                 135                 140

Ala Lys Glu Val Met Asp Leu Ala Ser Lys Gly Thr Ala Asn Thr Phe
145                 150                 155                 160

Thr Gly Phe Thr Ser Asn Val Asn Asn Ile Gln Ser Val Tyr Thr
                165                 170                 175

Thr Asn Leu Ala Asn Asn Gln Thr Glu Met Arg Ser Asn Ile Ala Pro
            180                 185                 190

Ile Pro Asn Gln Leu Pro His Leu Met Lys Thr Thr Thr Gln Asn Pro
        195                 200                 205

Val Gln Ser Ser Thr Ala Met Ala Cys Glu Leu Pro Ile Ala Arg
    210                 215                 220

Arg Ala Ser Leu His Arg Phe Leu Ala Lys Arg Lys Asp Arg Val Thr
225                 230                 235                 240

Ser Lys Ala Pro Tyr Gln Leu Asn Asp Pro Ala Lys Ala Ser Ser Lys
                245                 250                 255

Pro Gln Thr Gly Asp Asn Thr Thr Ser Trp Leu Gly Leu Ala Ala Glu
            260                 265                 270

Met

<210> SEQ ID NO 22
<211> LENGTH: 252
<212> TYPE: PRT
<213> ORGANISM: Brassica oleracea

<400> SEQUENCE: 22

Met Ser Ser Ser Met Glu Cys Ser Thr Thr Arg Arg Ser Ser Ser Gly
1               5                   10                  15

Lys Pro Ser Phe Ser Leu Thr Cys Ser Arg Leu Ser Gln Tyr Leu Lys
            20                  25                  30

Glu Asn Gly Ser Phe Gly Asp Leu Ser Leu Gly Met Ser Cys Lys Pro

```
                    35                  40                  45
Asp Thr Asn Gly Met Ser Arg Lys Pro Thr Thr Met Ser Leu Phe
 50                  55                  60

Pro Cys Glu Ala Ser Asn Val Gly Ser Met Ala Ala Gln Asp Val
 65                  70                  75                  80

Lys Pro Lys Asn Leu Phe Pro Arg Gln Pro Ser Phe Ser Ser Ser
                 85                  90                  95

Ser Ser Ile Pro Lys Glu Asp Val Pro Lys Met Thr Gln Thr Thr
            100                 105                 110

Arg Ser Leu Lys Pro Glu Pro Gln Thr Ala Pro Leu Thr Ile Phe Tyr
            115                 120                 125

Gly Gly Gln Val Ile Val Phe Asn Asp Phe Ser Ala Glu Lys Ala Lys
130                 135                 140

Glu Val Met Asn Leu Ala Asn Lys Gly Thr Ala Asn Thr Phe Thr Gly
145                 150                 155                 160

Phe Thr Ser Thr Leu Asn Asn Asn Ile Ala Pro Thr Pro Asn Gln Val
                165                 170                 175

Pro His Leu Met Lys Ala Ala Thr Gln Asp Pro Lys Gln Thr Ser Ser
            180                 185                 190

Ala Ala Met Ala Cys Glu Leu Pro Ile Ala Arg Arg Ala Ser Leu His
            195                 200                 205

Arg Phe Leu Ala Lys Arg Lys Asp Arg Val Thr Ser Lys Ala Pro Tyr
210                 215                 220

Gln Leu Asn Asp Pro Ala Lys Ala Tyr Ser Lys Pro Gln Thr Gly Asn
225                 230                 235                 240

Thr Thr Thr Ser Trp Leu Gly Leu Ala Ala Asp Met
                245                 250

<210> SEQ ID NO 23
<211> LENGTH: 233
<212> TYPE: PRT
<213> ORGANISM: Zea mays

<400> SEQUENCE: 23

Met Ala Ala Ser Ala Arg Pro Gly Glu Arg Ala Thr Ser Phe Ala Val
  1               5                  10                  15

Ala Cys Ser Leu Leu Ser Arg Phe Val Arg Gln Asn Gly Val Ala Ala
                 20                  25                  30

Ala Asp Leu Gly Leu Arg Ile Lys Gly Glu Val Glu Gln Gln Arg Thr
             35                  40                  45

Pro Ala Thr Thr Asn Ser Leu Pro Gly Ala Glu Gly Glu Glu Val Glu
 50                  55                  60

Arg Arg Lys Glu Thr Met Glu Leu Phe Pro Gln Ser Val Gly Phe Ser
 65                  70                  75                  80

Ile Lys Asp Ala Ala Ala Pro Arg Glu Glu Gln Gly Asp Lys Glu Lys
                 85                  90                  95

Pro Lys Gln Leu Thr Ile Phe Tyr Gly Gly Lys Val Leu Val Phe Asp
            100                 105                 110

Asp Phe Pro Ala Asp Lys Ala Lys Asp Leu Met Gln Leu Ala Ser Lys
            115                 120                 125

Gly Ser Pro Val Val Gln Asn Val Ala Leu Pro Gln Pro Ser Ala Ala
            130                 135                 140

Ala Ala Val Thr Thr Asp Lys Ala Val Leu Asp Pro Val Ile Ser Leu
145                 150                 155                 160
```

```
Ala Ala Ala Lys Lys Pro Ala Arg Thr Asn Ala Ser Asp Met Pro Ile
            165                 170                 175

Met Arg Lys Ala Ser Leu His Arg Phe Leu Glu Lys Arg Lys Asp Arg
        180                 185                 190

Leu Asn Ala Lys Thr Pro Tyr Gln Thr Ala Pro Ser Asp Ala Ala Pro
            195                 200                 205

Val Lys Lys Glu Pro Glu Ser Gln Pro Trp Leu Gly Leu Gly Pro Asn
210                 215                 220

Ala Val Asp Ser Ser Leu Asn Leu Ser
225                 230
```

<210> SEQ ID NO 24
<211> LENGTH: 240
<212> TYPE: PRT
<213> ORGANISM: Glycine max

<400> SEQUENCE: 24

```
Met Ser Ser Ser Glu Tyr Leu Val Phe Ser Ser His His Pro Ala
1               5                   10                  15

Asn Ser Pro Ala Glu Lys Ser Thr Phe Ser Gln Thr Cys Ser Leu Leu
            20                  25                  30

Ser Gln Tyr Ile Lys Glu Lys Gly Thr Phe Gly Asp Leu Thr Leu Gly
        35                  40                  45

Met Thr Cys Thr Ala Glu Thr Asn Gly Ser Pro Glu Thr Ser Cys His
50                  55                  60

Ser Ala Thr Thr Met Glu Leu Phe Pro Thr Ile Ile Thr Gln Arg Asn
65                  70                  75                  80

Pro Thr Thr Val Asp Phe Leu Ser Pro Gln Thr Ala Tyr Pro His His
                85                  90                  95

Ser Glu Val Pro Ile Met Val Lys Ser Ser Ala Phe Lys Ser Met Glu
            100                 105                 110

Lys Glu Pro Lys Ala Ala Gln Leu Thr Ile Phe Tyr Ala Gly Gln Val
        115                 120                 125

Val Val Phe Asp Asp Phe Pro Ala Glu Lys Leu Glu Glu Ile Thr Ser
130                 135                 140

Leu Ala Gly Lys Gly Ile Ser Gln Ser Gln Asn Thr Ser Ala Tyr Ala
145                 150                 155                 160

His Thr His Asn Gln Gln Val Asn His Pro Ser Phe Val Pro Asn Ile
                165                 170                 175

Ser Pro Gln Ala Pro Ser Arg Pro Leu Val Cys Asp Leu Pro Ile Ala
            180                 185                 190

Arg Lys Ala Ser Leu His Arg Phe Leu Ser Lys Arg Lys Asp Arg Ile
        195                 200                 205

Ala Ala Lys Ala Pro Tyr Gln Ile Asn Asn Pro Asn Ser Ala Ser Ser
210                 215                 220

Lys Pro Ala Glu Ser Met Ser Trp Leu Gly Leu Gly Ala Gln Ser Thr
225                 230                 235                 240
```

<210> SEQ ID NO 25
<211> LENGTH: 244
<212> TYPE: PRT
<213> ORGANISM: Oryza sativa

<400> SEQUENCE: 25

```
Met Ala Ala Ser Ala Arg Pro Val Gly Val Gly Gly Glu Arg Ala Thr
1               5                   10                  15
```

-continued

```
Ser Phe Ala Met Ala Cys Ser Leu Leu Ser Arg Tyr Val Arg Gln Asn
             20                  25                  30

Gly Ala Ala Ala Glu Leu Gly Leu Gly Ile Arg Gly Glu Gly Glu
         35                  40                  45

Ala Pro Arg Ala Ala Pro Ala Thr Met Ser Leu Leu Pro Gly Glu Ala
 50                  55                  60

Glu Arg Lys Lys Glu Thr Met Glu Leu Phe Pro Gln Ser Ala Gly Phe
 65                  70                  75                  80

Gly Gln Gln Asp Ala Ile Thr Ala Asp Ser Ala Ala Asp Ala Arg Glu
                 85                  90                  95

Gln Glu Pro Glu Lys Arg Gln Leu Thr Ile Phe Tyr Gly Gly Lys Val
            100                 105                 110

Leu Val Phe Asn Asp Phe Pro Ala Asp Lys Ala Lys Gly Leu Met Gln
        115                 120                 125

Leu Ala Ser Lys Gly Ser Pro Val Ala Pro Gln Asn Ala Ala Ala Pro
    130                 135                 140

Ala Pro Ala Ala Val Thr Asp Asn Thr Lys Ala Pro Met Ala Val Pro
145                 150                 155                 160

Ala Pro Val Ser Ser Leu Pro Thr Ala Gln Ala Asp Ala Gln Lys Pro
                165                 170                 175

Ala Arg Ala Asn Ala Ser Asp Met Pro Ile Ala Arg Lys Ala Ser Leu
            180                 185                 190

His Arg Phe Leu Glu Lys Arg Lys Asp Arg Leu Asn Ala Lys Thr Pro
        195                 200                 205

Tyr Gln Ala Ser Pro Ser Asp Ala Thr Pro Val Lys Lys Glu Pro Glu
    210                 215                 220

Ser Gln Pro Trp Leu Gly Leu Gly Pro Asn Ala Val Val Lys Pro Ile
225                 230                 235                 240

Glu Arg Gly Gln

<210> SEQ ID NO 26
<211> LENGTH: 237
<212> TYPE: PRT
<213> ORGANISM: Zea mays

<400> SEQUENCE: 26

Met Ala Ala Ser Ala Arg Pro Gly Glu Arg Ala Thr Ser Phe Ala Val
 1               5                  10                  15

Ala Cys Ser Leu Leu Ser Arg Phe Val Arg Gln Asn Gly Ala Ala Pro
             20                  25                  30

Ala Gln Leu Gly Leu Gly Ile Lys Gly Glu Val Glu Gln Gln Arg Thr
         35                  40                  45

Pro Ala Thr Ile Asn Leu Leu Pro Gly Ala Asp Gly Glu Glu Thr Glu
 50                  55                  60

Arg Arg Lys Glu Thr Met Glu Leu Phe Pro Gln Ser Ala Gly Phe Gly
 65                  70                  75                  80

Val Lys Asp Ala Ala Ala Pro Arg Glu Gln Glu Asn Lys Glu Lys
                 85                  90                  95

Pro Lys Gln Leu Thr Ile Phe Tyr Gly Gly Lys Val Leu Val Phe Asp
            100                 105                 110

Asp Phe Pro Ala Asp Lys Ala Lys Asp Leu Met Gln Leu Ala Ser Lys
        115                 120                 125

Gly Gly Pro Val Val Gln Asn Val Val Leu Pro Gln Pro Ser Ala Pro
    130                 135                 140
```

```
Ala Ala Ala Val Thr Asp Lys Ala Pro Val Pro Val Ile Ser Leu
145                 150                 155                 160

Pro Ala Ala Gln Ala Asp Ala Lys Lys Pro Thr Arg Thr Asn Ala Ser
                165                 170                 175

Asp Met Pro Ile Met Arg Lys Ala Ser Leu His Arg Phe Leu Glu Lys
            180                 185                 190

Arg Lys Asp Arg Leu Asn Ala Asn Ala Pro Tyr Gln Thr Ser Pro Ser
        195                 200                 205

Asp Ala Ala Pro Val Lys Lys Glu Pro Glu Ser Gln Ala Trp Leu Gly
    210                 215                 220

Leu Gly Pro Asn Ala Val Lys Ser Asn Leu Asn Leu Ser
225                 230                 235
```

<210> SEQ ID NO 27
<211> LENGTH: 231
<212> TYPE: PRT
<213> ORGANISM: Triticum aestivum

<400> SEQUENCE: 27

```
Met Ala Ala Ser Ala Arg Gln Gly Glu Arg Ala Thr Ser Phe Ala Met
1               5                   10                  15

Ala Cys Ser Leu Leu Ser Arg Tyr Val Arg Gln Asn Gly Ala Ala Ala
            20                  25                  30

Ala Glu Leu Gly Leu Gly Ile Asn Lys Gly Ala Glu Ala Gln Arg
        35                  40                  45

Ala Ala Asp Thr Lys Ser Pro Leu Pro Gly Ala Glu Gly Glu Ala
    50                  55                  60

Gly Arg Lys Lys Glu Thr Met Glu Leu Phe Pro Gln Ser Ala Gly Leu
65                  70                  75                  80

Gln Asp Ala Ala Ala Pro Asp Ala Thr Arg Glu Glu Asp Lys Ser Gln
                85                  90                  95

Leu Thr Ile Phe Tyr Gly Gly Lys Val Leu Val Phe Asn Asp Phe Pro
            100                 105                 110

Ala Asp Lys Ala Lys Gly Leu Met Gln Leu Ala Gly Lys Gly Ser Pro
        115                 120                 125

Val Val Gln Asn Val Ser Ala Thr Thr Thr Ala Ala Asp Thr Asp Lys
    130                 135                 140

Val Gln Thr Ala Val Leu Ala Pro Ala Ser Ser Leu Pro Thr Gly Pro
145                 150                 155                 160

Val Asp Ala Pro Lys Pro Ala Arg Pro Asn Ala Ser Asp Leu Pro Ile
                165                 170                 175

Ala Arg Lys Ala Ser Leu His Arg Phe Leu Glu Lys Arg Lys Asp Arg
            180                 185                 190

Leu His Ala Lys Ala Pro Tyr Gln Ala Pro Pro Ser Asp Ala Thr Pro
        195                 200                 205

Val Lys Lys Glu Phe Glu Asn Gln Pro Trp Leu Gly Leu Gly Pro Asn
    210                 215                 220

Ala Ala Leu Lys Pro Asn Gln
225                 230
```

<210> SEQ ID NO 28
<211> LENGTH: 242
<212> TYPE: PRT
<213> ORGANISM: Glycine max

<400> SEQUENCE: 28

```
Met Ser Ser Ser Ser Glu Tyr Leu Val Phe Ser Gly His His Pro Ala
1               5                   10                  15

Asn Ser Pro Ala Glu Lys Ser Thr Phe Ser Gln Thr Cys Ser Leu Leu
            20                  25                  30

Ser Gln Tyr Ile Lys Glu Lys Gly Thr Phe Gly Asp Leu Thr Leu Gly
        35                  40                  45

Met Thr Cys Thr Ala Glu Thr Asn Gly Ser Pro Glu Thr Ser Cys His
50                  55                  60

Ser Ala Thr Thr Met Glu Leu Phe Pro Thr Ile Ile Thr Gln Arg Asn
65                  70                  75                  80

Pro Thr Thr Val Asp Phe Leu Ser Pro Gln Thr Ala Tyr Pro His His
                85                  90                  95

Ser Glu Val Pro Ile Met Val Lys Ser Ser Ala Phe Lys Ser Met Glu
            100                 105                 110

Lys Glu Pro Lys Ala Ala Gln Leu Thr Ile Phe Tyr Ala Gly Gln Val
        115                 120                 125

Val Val Phe Asp Asp Phe Pro Ala Glu Lys Leu Glu Glu Ile Thr Ser
130                 135                 140

Leu Ala Gly Lys Gly Ile Ser Gln Ser Gln Asn Thr Ser Ala Tyr Ala
145                 150                 155                 160

His Thr His Asn Gln Gln Val Asn His Pro Ser Phe Val Pro Asn Ile
                165                 170                 175

Ser Pro Gln Ala Pro Ser Arg Pro Leu Val Cys Asp Leu Pro Ile Ala
            180                 185                 190

Arg Lys Ala Ser Leu His Arg Phe Leu Ser Lys Arg Lys Asp Arg Ile
        195                 200                 205

Ala Ala Lys Ala Pro Tyr Gln Ile Asn Asn Pro Asn Ser Ala Ser Ser
210                 215                 220

Lys Pro Ala Glu Ser Met Ser Trp Leu Gly Leu Gly Ala Gln Ser Thr
225                 230                 235                 240

Gln Val

<210> SEQ ID NO 29
<211> LENGTH: 391
<212> TYPE: PRT
<213> ORGANISM: Zea mays

<400> SEQUENCE: 29

Met Glu Arg Asp Phe Leu Ala Ala Ile Gly Lys Glu Gln Gln His Pro
1               5                   10                  15

Arg Lys Glu Lys Ala Gly Gly Ala Glu Gly Ser Ala Tyr Phe Gly
            20                  25                  30

Ala Ala Ala Val Pro Ala Met Asp Trp Ser Phe Ala Ser Lys Pro Cys
        35                  40                  45

Ala Ala Pro Ala Leu Met Ser Phe Arg Ser Ala Arg Glu Glu Pro
50                  55                  60

Ser Phe Pro Gln Phe Ser Ala Leu Asp Gly Thr Lys Asn Thr Ala Pro
65                  70                  75                  80

Arg Met Leu Thr His Gln Arg Ser Phe Gly Pro Asp Ser Thr Gln Tyr
                85                  90                  95

Ala Ala Leu His Arg Ala Gln Asn Gly Ala Arg Val Val Pro Val Ser
            100                 105                 110

Ser Pro Phe Ser Gln Ser Asn Pro Met Phe Arg Val Gln Ser Ser Pro
        115                 120                 125
```

-continued

```
Ser Leu Pro Asn Ser Thr Ala Phe Lys Gln Pro Pro Phe Ala Ile Ser
    130                 135                 140
Asn Ala Val Ala Ser Ser Thr Val Gly Ser Tyr Gly Gly Thr Arg Asp
145                 150                 155                 160
Ala Val Arg Pro Arg Thr Ala Gln Leu Thr Ile Phe Tyr Ala Gly Ser
                165                 170                 175
Val Asn Val Phe Asn Asn Val Ser Ala Glu Lys Ala Gln Glu Leu Met
                180                 185                 190
Phe Leu Ala Ser Arg Gly Ser Ser Ala Pro Val Ala Cys Lys Pro Glu
                195                 200                 205
Ala Pro Pro Thr Leu Ala Pro Ala Lys Val Thr Ala Pro Glu Val Leu
    210                 215                 220
Leu Pro Ala Lys Gln Met Leu Phe Gln Lys Pro Gln His Leu Ser Pro
225                 230                 235                 240
Pro Pro Ser Ser Val Pro Gly Ile Leu Gln Ser Ala Ala Leu Pro Arg
                245                 250                 255
Ser Ala Ser Ser Ser Asn Leu Asp Ser Pro Ala Pro Lys Ser Ser
                260                 265                 270
Val Pro Leu Ala Val Pro Pro Val Ser Gln Ala Pro Pro Ala Thr Leu
    275                 280                 285
Ile Ala Thr Thr Thr Ala Ala Ala Ile Met Pro Arg Ala Val Pro Gln
    290                 295                 300
Ala Arg Lys Ala Ser Leu Ala Arg Phe Leu Glu Lys Arg Lys Glu Arg
305                 310                 315                 320
Val Thr Thr Ala Ala Pro Tyr Pro Ser Ala Lys Ser Pro Leu Glu Ser
                325                 330                 335
Ser Asp Thr Phe Gly Ser Gly Ser Ala Ser Ala Asn Ala Asn Asp Lys
                340                 345                 350
Ser Ser Cys Thr Asp Ile Ala Leu Ser Ser Asn His Glu Glu Ser Leu
                355                 360                 365
Cys Leu Gly Gly Gln Pro Arg Ser Ile Ile Ser Phe Ser Glu Glu Ser
                375                 380
Pro Ser Thr Lys Leu Gln Ile
385                 390

<210> SEQ ID NO 30
<211> LENGTH: 419
<212> TYPE: PRT
<213> ORGANISM: Triticum aestivum

<400> SEQUENCE: 30

Met Glu Arg Asp Phe Leu Gly Thr Ile Gly His Glu Gln Leu Gln Gln
1               5                   10                  15
Gln Gln Gln Gln Gln Arg Gln Arg Ala Ala Ala Glu Asp Ala Ala
                20                  25                  30
Ala Arg Lys Glu Ser Ala Tyr Phe Gly Gly Gly Val Pro Pro Met
                35                  40                  45
Asp Trp Ser Phe Ala Gly Arg Ala Gly Ala Ala Pro Ala Val Met Ser
    50                  55                  60
Phe Arg Ser Ala Pro Arg Glu Glu Gln Arg Gly Glu Leu Ala Tyr Pro
65                  70                  75                  80
Lys Gln Gln Ala Ser Arg Val Leu Thr Pro Gln Arg Ser Phe Gly Ala
                85                  90                  95
Glu Ser His Gly Ser Val Gln Tyr Ala Ala Ala Ala Arg Ala Ala Tyr
                100                 105                 110
```

Gly Gly Gln Pro Pro Gln Gln His Gln His Ala Pro Asn Gly Ala Arg
            115                 120                 125

Val Ile Pro Met Ser Ser Pro Phe Asn Pro Asn Asn Pro Met Phe Arg
            130                 135                 140

Val Gln Ser Ser Pro Asn Leu Pro Asn Gly Val Ala Ala Gly Ser Pro
145                 150                 155                 160

Phe Lys Gln Pro Pro Phe Val Met Asn Ala Val Ala Ala Ser Thr
            165                 170                 175

Val Gly Val Tyr Lys Ser Arg Asp Met Pro Lys Pro Lys Thr Ala Gln
            180                 185                 190

Leu Thr Ile Phe Tyr Ala Gly Ser Val Asn Val Phe Asn Asn Val Ser
            195                 200                 205

Ala Glu Lys Ala Gln Glu Leu Met Phe Leu Ala Ser Arg Gly Ser Leu
            210                 215                 220

Pro Thr Ala Pro Thr Thr Val Thr Arg Ser Pro Asp Ala Thr Phe Phe
225                 230                 235                 240

Thr Pro Ala Lys Leu Ala Ala Pro Glu Ala Ser Pro Ala Lys Gln Met
            245                 250                 255

Leu Ala His Ile Pro Gln Arg Val Ser Pro Pro Leu Pro Ala Ile Ser
            260                 265                 270

Lys Pro Met Ser Ile Met Ser Gln Ala Ala Cys Leu Pro Lys Ser Thr
            275                 280                 285

Ser Ser Ser Asn Thr Asp Ser Ala Val Pro Lys Ser Ser Gly Gln Leu
            290                 295                 300

Val Val Pro Pro Thr Ser Gln Thr Ser Ser Ser Thr His Pro Val Thr
305                 310                 315                 320

Leu Ser Ser Thr Thr Ala Ala Ser Ile Met Pro Arg Ala Val Pro Gln
            325                 330                 335

Ala Arg Lys Ala Ser Leu Ala Arg Phe Leu Glu Lys Arg Lys Glu Arg
            340                 345                 350

Val Thr Thr Thr Ala Pro Tyr Pro Ser Ala Lys Ser Pro Met Glu Ser
            355                 360                 365

Ser Asp Thr Val Gly Ser Ala Asn Asp Asn Asn Ser Lys Ser Ser Ser
            370                 375                 380

Cys Thr Glu Ile Ala Phe Ser Ser Asn His Glu Glu Ser Leu Arg Leu
385                 390                 395                 400

Gly Arg Pro Arg Asn Ile Ser Phe Ser Gly Glu Ser Pro Ser Thr Lys
            405                 410                 415

Leu His Ile

<210> SEQ ID NO 31
<211> LENGTH: 386
<212> TYPE: PRT
<213> ORGANISM: Glycine max

<400> SEQUENCE: 31

Met Glu Arg Glu Phe Phe Gly Leu Ser Ser Lys Asn Gly Ala Trp Thr
1               5                   10                  15

Thr Met Lys Asp Asp Ala Val Asn Lys Ser Arg Asp Gln Val Arg Ser
            20                  25                  30

Ser Gly Met Gln Trp Ser Phe Pro Asn Lys Val Ser Ala Leu Pro Gln
            35                  40                  45

Phe Leu Ser Phe Lys Thr Asn Gln Glu Asp Lys Pro Arg Lys Thr Ile
        50                  55                  60

```
Leu Glu Pro Leu Ala Ser Ser Gly Tyr Met Ala Met Ser Thr Gln Tyr
 65                  70                  75                  80

Ala Phe Asp Ser Asn Gln Lys Ser Phe Leu Gly Leu Thr Asn Arg Asn
                 85                  90                  95

Leu Ser Ile Ser Lys His Ala Ala Gly Asn Lys Gln Gly Met Thr Val
            100                 105                 110

Tyr Pro Leu Gln Cys Cys Asp Ala Gln Ser Glu Glu Ala Arg Ile Phe
                115                 120                 125

Ser Val Ser Asn Gln Ser Asn Gln Val Ser Pro Val Leu Gln Ser Asn
            130                 135                 140

Leu Ala Ser Thr Gly Leu Asn Met Val Asn Ser Val Ile Lys Pro Gln
145                 150                 155                 160

Pro Phe Gly Ser Lys Ser Ser Gly Thr Pro Leu Ser Ile Leu Pro Ser
                165                 170                 175

Ile Gly Ser Ile Val Gly Ser Thr Asp Leu Arg Asn Asn Ser Lys Ser
            180                 185                 190

Ser Thr Met Pro Thr Gln Leu Thr Ile Phe Tyr Ala Gly Ser Val Cys
            195                 200                 205

Val Tyr Asp Asp Ile Ser Pro Glu Lys Ala Lys Ala Ile Met Leu Met
210                 215                 220

Ala Gly Asn Gly Tyr Thr Pro Thr Glu Lys Met Glu Leu Pro Thr Val
225                 230                 235                 240

Lys Leu Gln Pro Ala Ile Ser Ile Pro Ser Lys Asp Asp Gly Phe Met
                245                 250                 255

Ile Ser Gln Ser Tyr Pro Pro Ser Thr Phe Pro Thr Pro Leu Pro Leu
            260                 265                 270

Thr Ser His Val Asn Ser Gln Pro Gly Gly Gly Ser Ser Ser Asn Lys
            275                 280                 285

Glu Ile Ser Ile Ile Arg Gln Val Gly Pro Ser Thr Ala Pro Thr Asn
290                 295                 300

His Leu Glu Ser Pro Ile Ile Gly Ser Ile Gly Ser Ala Ser Lys Glu
305                 310                 315                 320

Lys Ala Gln Pro Val Cys Leu Pro Gln Ala Arg Lys Ala Ser Leu Ala
                325                 330                 335

Arg Phe Leu Glu Lys Arg Lys Gly Arg Met Met Arg Thr Ser Pro Tyr
            340                 345                 350

Leu Tyr Met Ser Lys Lys Ser Pro Glu Cys Ser Ser Ser Gly Ser Asp
            355                 360                 365

Ser Val Ser Phe Ser Leu Asn Phe Ser Gly Ser Cys Ser Leu Pro Ala
            370                 375                 380

Thr Asn
385

<210> SEQ ID NO 32
<211> LENGTH: 416
<212> TYPE: PRT
<213> ORGANISM: Oryza sativa

<400> SEQUENCE: 32

Met Glu Arg Asp Phe Leu Gly Ala Ile Gly Lys Asp Glu Glu Gln Arg
1               5                  10                  15

Arg His Ala Glu Glu Arg Lys Glu Ser Asp Tyr Phe Gly Ala Gly Gly
            20                  25                  30

Gly Ala Ala Ala Ala Ala Met Asp Trp Ser Phe Ala Ser Arg Ala Ala
```

```
                    35                  40                  45
Leu Met Ser Phe Arg Ser Ser Ser Ala Ala Ala Ala Ala Arg
 50                  55                  60

Glu Glu Thr Arg Glu Leu Ala Phe Pro His Phe Ser Ala Leu Asp Gly
 65                  70                  75                  80

Ala Lys Met Gln Gln Ala Ser His Val Leu Ala Arg Gln Lys Ser Phe
                 85                  90                  95

Gly Ala Glu Ser His Gly Ile Pro Gln Tyr Ala Ala Ala Ala Val
            100                 105                 110

His Gly Ala His Arg Gly Gln Pro Pro His Val Leu Asn Gly Ala Arg
            115                 120                 125

Val Ile Pro Ala Ser Ser Pro Phe Asn Pro Asn Pro Met Phe Arg
130                 135                 140

Val Gln Ser Ser Pro Asn Leu Pro Asn Ala Val Gly Ala Gly Gly
145                 150                 155                 160

Ala Phe Lys Gln Pro Pro Phe Ala Met Gly Asn Ala Val Ala Gly Ser
                165                 170                 175

Thr Val Gly Val Tyr Gly Thr Arg Asp Met Pro Lys Ala Lys Ala Ala
            180                 185                 190

Gln Leu Thr Ile Phe Tyr Ala Gly Ser Val Asn Val Phe Asn Asn Val
            195                 200                 205

Ser Pro Glu Lys Ala Gln Glu Leu Met Phe Leu Ala Ser Arg Gly Ser
210                 215                 220

Leu Pro Ser Ala Pro Thr Thr Val Ala Arg Met Pro Glu Ala His Val
225                 230                 235                 240

Phe Pro Pro Ala Lys Val Thr Val Pro Glu Val Ser Pro Thr Lys Pro
                245                 250                 255

Met Met Leu Gln Lys Pro Gln Leu Val Ser Ser Pro Val Pro Ala Ile
            260                 265                 270

Ser Lys Pro Ile Ser Val Val Ser Gln Ala Thr Ser Leu Pro Arg Ser
275                 280                 285

Ala Ser Ser Ser Asn Val Asp Ser Asn Val Thr Lys Ser Ser Gly Pro
290                 295                 300

Leu Val Val Pro Pro Thr Ser Leu Pro Pro Pro Ala Gln Pro Glu Thr
305                 310                 315                 320

Leu Ala Thr Thr Thr Ala Ala Ala Ile Met Pro Arg Ala Val Pro Gln
                325                 330                 335

Ala Arg Lys Ala Ser Leu Ala Arg Phe Leu Glu Lys Arg Lys Glu Arg
            340                 345                 350

Val Thr Thr Val Ala Pro Tyr Pro Leu Ala Lys Ser Pro Leu Glu Ser
            355                 360                 365

Ser Asp Thr Met Gly Ser Ala Asn Asp Asn Lys Ser Ser Cys Thr Asp
            370                 375                 380

Ile Ala Leu Ser Ser Asn Arg Asp Glu Ser Leu Ser Leu Gly Gln Pro
385                 390                 395                 400

Arg Thr Ile Ser Phe Cys Glu Glu Ser Pro Ser Thr Lys Leu Gln Ile
                405                 410                 415

<210> SEQ ID NO 33
<211> LENGTH: 404
<212> TYPE: PRT
<213> ORGANISM: Zea mays

<400> SEQUENCE: 33
```

```
Met Ala Lys Ser Gly Ala Ser Phe Pro Glu Ser Ser Trp Met Glu Arg
 1               5                  10                  15

Asp Phe Leu Ala Ala Ile Gly Lys Glu Gln Gln His Pro His Lys Glu
             20                  25                  30

Glu Ala Gly Ala Glu Glu Ser Ala Tyr Phe Gly Gly Ala Gly Ala Ala
         35                  40                  45

Ala Ala Ala Pro Ala Met Asp Trp Ser Phe Ala Ser Lys Pro Gly Ala
 50                  55                  60

Ala Pro Ala Leu Met Ser Phe Arg Ser Ala Ser Phe Pro Gln Phe Ser
 65                  70                  75                  80

Ser Phe Asp Gly Ala Lys Asn Pro Ala Pro Arg Ile Leu Thr His Gln
             85                  90                  95

Arg Ser Phe Gly Pro Asp Ser Thr His Tyr Ala Ala His Arg Thr
        100                 105                 110

Gln His Ala Leu Asn Gly Ala Arg Val Thr Pro Val Ser Ser Pro Phe
        115                 120                 125

Asn Gln Asn Ser Pro Met Phe Arg Val Gln Ser Ser Pro Ser Leu Pro
        130                 135                 140

Asn Gly Thr Ala Phe Lys Gln Pro Pro Phe Ala Ile Asn Asn Asn Ala
145                 150                 155                 160

Ala Ala Ser Ser Thr Val Gly Phe Tyr Gly Thr Arg Asp Val Val Arg
                165                 170                 175

Pro Lys Thr Ala Gln Leu Thr Ile Phe Tyr Ala Gly Ser Val Asn Val
                180                 185                 190

Phe Asp Asn Val Ser Ala Glu Lys Ala Gln Glu Leu Met Leu Leu Ala
        195                 200                 205

Ser Arg Gly Ser Leu Pro Ser Ser Ala Pro Val Ala Arg Lys Pro Glu
        210                 215                 220

Ala Pro Ile Leu Ala Pro Ala Lys Val Thr Ala Pro Glu Val Leu His
225                 230                 235                 240

Ala Thr Gln Met Leu Phe Gln Lys Pro Gln His Val Ser Pro Pro Ser
                245                 250                 255

Ser Ala Ile Ser Lys Pro Ile Pro Gly Ile Leu Gln Ala Ala Ser Leu
                260                 265                 270

Pro Arg Ser Ala Ser Ser Ser Asn Leu Asp Ser Pro Phe Pro Lys Ser
        275                 280                 285

Ser Val Pro Phe Pro Val Ser Pro Val Ser Gln Ala Pro Arg Ala Gln
        290                 295                 300

Pro Ala Thr Ile Ala Ala Thr Thr Ala Ala Ile Met Pro Arg Ala
305                 310                 315                 320

Val Pro Gln Ala Arg Lys Ala Ser Leu Ala Arg Phe Leu Glu Lys Arg
                325                 330                 335

Lys Glu Arg Val Thr Thr Ala Ala Pro Tyr Pro Ser Ala Lys Ser Pro
                340                 345                 350

Met Glu Ser Ser Asp Thr Phe Gly Ser Gly Ser Ala Asn Asp Lys Ser
        355                 360                 365

Ser Cys Thr Asp Ile Ala Leu Ser Ser Asn His Glu Glu Ser Leu Cys
        370                 375                 380

Leu Gly Gln Pro Arg Asn Ile Ser Phe Ile Gln Glu Ser Pro Ser Thr
385                 390                 395                 400

Lys Leu Gln Ile

<210> SEQ ID NO 34
```

```
<211> LENGTH: 340
<212> TYPE: PRT
<213> ORGANISM: Glycine max

<400> SEQUENCE: 34
```

Met Glu Arg Asp Phe Met Gly Leu Asn Leu Lys Glu Pro Leu Ala Val
1               5                   10                  15

Val Lys Glu Glu Met Asn Asn Asp Gly Cys Lys Asn Ser Gly Phe Lys
            20                  25                  30

Lys Gly Arg Ile Ala Gln Trp Pro Phe Ser Asn Lys Val Ser Ala Leu
        35                  40                  45

Pro His Leu Met Ser Phe Lys Ala Ser Gln Asp Asp Lys Thr Lys Asn
50                  55                  60

Thr Val Ser Asp Thr Leu Ser Ser Ser Gly Phe Met Ser Ile Leu Ser
65                  70                  75                  80

Gln Glu Ala Phe Asp Thr Ser Gln Lys Arg Ser Ala Gly Glu Pro Gln
                85                  90                  95

Met Phe Ser Val Pro Asn Gln Ala Ile Ser Val Ser Leu Gly Asn Pro
            100                 105                 110

Phe Leu Lys Asn His Phe Ala Ala Ala Gly Gln Lys Pro Leu Leu Gly
        115                 120                 125

Gly Ile Pro Val Thr Thr Ser His Ser Val Leu Pro Ser Ala Val Ala
130                 135                 140

Val Ala Gly Met Thr Glu Ser Cys Asn Ser Val Lys Pro Ser Ala Gln
145                 150                 155                 160

Leu Thr Ile Phe Tyr Ala Gly Thr Val Asn Ile Phe Asp Asp Ile Ser
                165                 170                 175

Ala Glu Lys Ala Gln Ala Ile Met Leu Leu Ala Gly Asn Ser Leu Ser
            180                 185                 190

Ala Ala Ser Asn Met Ala Gln Pro Asn Val Gln Val Pro Ile Ser Lys
        195                 200                 205

Leu Gly Ala Gly Ala Gly Val Pro Val Ser Gln Pro Ala Asn Thr Ser
210                 215                 220

Pro Gly Ser Gly Leu Ser Ser Pro Leu Ser Val Ser Ser His Thr Gly
225                 230                 235                 240

Val Gln Ser Gly Ser Gly Leu Thr Ser Thr Asp Glu Phe Leu Ala Ala
                245                 250                 255

Lys Thr Thr Gly Val Pro Asn Thr Pro Ile Cys Asn Val Glu Pro Pro
            260                 265                 270

Lys Val Val Ser Ala Thr Thr Met Leu Thr Ser Ala Val Pro Gln Ala
        275                 280                 285

Arg Lys Ala Ser Leu Ala Arg Phe Leu Glu Lys Arg Lys Glu Arg Val
290                 295                 300

Met Ser Ala Ala Pro Tyr Asn Leu Asn Lys Lys Ser Glu Glu Cys Ala
305                 310                 315                 320

Thr Ala Glu Tyr Ala Gly Val Asn Phe Ser Ala Thr Asn Thr Val Leu
                325                 330                 335

Ala Lys Gln Gly
            340

```
<210> SEQ ID NO 35
<211> LENGTH: 427
<212> TYPE: PRT
<213> ORGANISM: Oryza sativa

<400> SEQUENCE: 35
```

-continued

```
Met Glu Arg Asp Phe Leu Gly Ala Ile Trp Arg Lys Glu Glu Ala Ala
1               5                   10                  15
Gly Lys Pro Glu Glu His Ser Asp Tyr Arg Gly Gly Gly Gly Ala
            20                  25                  30
Ser Ala Ala Met Gln Trp Gln Phe Pro Ala Thr Lys Val Gly Ala Ala
            35                  40                  45
Ser Ser Ala Phe Met Ser Phe Arg Ser Ser Ala Ala Ala Arg Glu
50                  55                  60
Glu Asp Pro Lys Glu Ala Val Phe Asp Arg Phe Ser Leu Ser Gly
65                  70                  75                  80
Phe Arg Pro Pro Arg Pro Ser Pro Gly Asp Ala Phe Asp Gly Ala
                85                  90                  95
Ala Ala Met Lys Gln Arg Gln Phe Gly Phe Asn Gly Arg Gln Gln Tyr
            100                 105                 110
Ala Ala Ala Ala Gln His Gly His Arg Glu Gln Gly Val Asp Ser Tyr
            115                 120                 125
Gly Val Ala Ala Pro His His Phe Pro Ser Pro Ser Pro Ser Pro Arg
130                 135                 140
His Pro Val Pro Phe Gly His Ala Asn Pro Met Leu Arg Val His Ser
145                 150                 155                 160
Leu Pro Asn Val Ala Gly Gly Ser Pro Tyr Arg Asn Gln Ser Phe Ser
                165                 170                 175
Val Gly Asn Ser Val Ala Gly Ser Thr Val Gly Val Tyr Gly Gly Pro
            180                 185                 190
Arg Asp Leu Gln Asn Pro Lys Val Thr Gln Met Thr Ile Phe Tyr Asp
            195                 200                 205
Gly Leu Val Asn Val Phe Asp Asn Ile Pro Val Glu Lys Ala Gln Glu
210                 215                 220
Leu Met Leu Leu Ala Ser Arg Ala Ser Ile Pro Ser Pro Ser Ala
225                 230                 235                 240
Ala Arg Lys Ser Asp Ser Pro Ile Ser Ala Ala Lys Leu Thr Val
                245                 250                 255
Pro Glu Ala Leu Pro Ala Arg Gln Ile Val Val Gln Lys Pro Glu Ala
            260                 265                 270
Ser Val Pro Leu Val Ser Gly Val Ser Asn Pro Ile Thr Ile Val Ser
275                 280                 285
Gln Ala Val Thr Leu Pro Lys Ser Phe Ser Ser Asn Asp Ser Ala
            290                 295                 300
Gly Pro Lys Ser Gly Gly Leu Pro Leu Ala Val Thr Pro Leu Ser Gln
305                 310                 315                 320
Ala Ser Pro Ser Gln Pro Ile Pro Val Ala Thr Thr Asn Ala Ser Ala
                325                 330                 335
Ile Met Pro Arg Ala Val Pro Gln Ala Arg Lys Ala Ser Leu Ala Arg
            340                 345                 350
Phe Leu Glu Lys Arg Lys Glu Arg Val Ser Ser Val Ala Pro Tyr Pro
            355                 360                 365
Ser Ser Lys Ser Pro Leu Glu Ser Ser Asp Thr Ile Gly Ser Pro Ser
370                 375                 380
Thr Pro Ser Lys Ser Ser Cys Thr Asp Ile Thr Pro Ser Thr Asn Asn
385                 390                 395                 400
Cys Glu Asp Ser Leu Cys Leu Gly Gln Pro Arg Asn Ile Ser Phe Ser
                405                 410                 415
```

```
Ser Gln Glu Pro Pro Ser Thr Lys Leu Gln Ile
        420                 425
```

<210> SEQ ID NO 36
<211> LENGTH: 157
<212> TYPE: PRT
<213> ORGANISM: Triticum aestivum
<220> FEATURE:
<221> NAME/KEY: VARIANT
<222> LOCATION: (1)...(157)
<223> OTHER INFORMATION: Xaa = Any Amino Acid

<400> SEQUENCE: 36

```
Leu Ala Asn Gly Arg Ser Gly Met Leu Pro Met Ser Ser Pro Pro Ala
 1               5                  10                  15

Asn Pro Gly Gln Leu Thr Ile Phe Tyr Gly Gly Ser Val Cys Val Tyr
             20                  25                  30

Asp Ser Val Pro Pro Glu Lys Ala Gln Ala Ile Met Leu Ile Ala Ala
         35                  40                  45

Ala Ala Ala Ala Ala Ser Lys Ser Asn Gly Thr Ala Ala Val Lys Pro
     50                  55                  60

Pro Ala Met Ser Ala Thr Asn Ala Ile Gln Ala Met Leu Thr Arg Ser
 65                  70                  75                  80

Leu Ser Leu Gln Ser Thr Ser Val Ala Xaa Gly Gln Pro Gln Ala Val
                 85                  90                  95

Ala Asp Pro Gly Ser Ile Cys Lys Leu Gln Ala Asp Leu Pro Ile Ala
            100                 105                 110

Arg Arg His Ser Leu Gln Arg Phe Leu Glu Lys Arg Arg Asp Arg Val
        115                 120                 125

Val Ser Lys Ala Pro Tyr Gly Ala Arg Lys Pro Phe Glu Gly Met Gly
    130                 135                 140

Ala Ser Ser Gly Met Glu Ser Val Ala Glu Gly Arg Pro
145                 150                 155
```

<210> SEQ ID NO 37
<211> LENGTH: 216
<212> TYPE: PRT
<213> ORGANISM: Zea mays

<400> SEQUENCE: 37

```
Met Ala Gly His Ala Pro Ala Arg Asp Lys Thr Thr Ser Gly Phe Ala
 1               5                  10                  15

Ala Thr Cys Ser Leu Leu Ser Gln Phe Leu Lys Glu Lys Lys Gly Gly
             20                  25                  30

Leu Gln Gly Leu Gly Gly Leu Ala Met Ala Pro Ala Pro Ala Ala Gly
         35                  40                  45

Ala Gly Ala Phe Arg Pro Pro Thr Thr Met Asn Leu Ser Ala Leu
     50                  55                  60

Asp Ala Ala Lys Ala Thr Val Gly Glu Pro Glu Gly His Gly Gln Arg
 65                  70                  75                  80

Thr Gly Gly Asn Pro Arg Glu Ala Ala Gly Glu Glu Ala Gln Gln Leu
                 85                  90                  95

Thr Ile Phe Tyr Gly Gly Lys Val Val Val Phe Asp Arg Phe Pro Ser
            100                 105                 110

Ala Lys Val Lys Asp Leu Leu Gln Ile Val Ser Pro Pro Gly Ala Asp
        115                 120                 125

Ala Val Val Asp Gly Ala Gly Ala Ala Val Pro Thr Gln Asn Leu Pro
    130                 135                 140
```

Arg Pro Pro His Asp Ser Leu Ser Ala Asp Leu Pro Ile Ala Arg Arg
145                 150                 155                 160

Asn Ser Leu His Arg Phe Leu Glu Lys Arg Lys Asp Arg Ile Thr Ala
                165                 170                 175

Lys Ala Pro Tyr Gln Val Asn Ser Ser Val Gly Ala Glu Ala Ser Lys
            180                 185                 190

Ala Glu Lys Pro Trp Leu Gly Leu Gly Gln Glu Gly Ser Asp Gly Arg
        195                 200                 205

Gln Ala Gly Asp Val Ile Asp Glu
    210                 215

<210> SEQ ID NO 38
<211> LENGTH: 258
<212> TYPE: PRT
<213> ORGANISM: Glycine max

<400> SEQUENCE: 38

Met Ser Ser Ser Ser Glu Tyr Ser Glu Phe Ser Gly Gln Lys Pro Ala
1               5                   10                  15

Arg Ser Pro Glu Lys Ser Ser Phe Ser Gln Thr Cys Ser Leu Leu Ser
            20                  25                  30

Gln Tyr Ile Lys Glu Lys Gly Ser Phe Gly Asp Leu Thr Leu Gly Met
        35                  40                  45

Thr Ser Cys Gly Ser Pro Glu Thr Ser Cys Gln Ser Ala Thr Thr Met
50                  55                  60

Asn Leu Phe Pro Pro Lys Glu Asn Asn Val Ala Pro Lys Asn Leu Thr
65                  70                  75                  80

Ala Met Asp Leu Leu Ser Pro Gln Ala Ser Ser Tyr Gly Pro Ser Glu
                85                  90                  95

Glu Ile Pro Thr Leu Val Asn Ser Ser Ala Ile Lys Ser Val Ser Lys
            100                 105                 110

Gly Ala Lys Thr Ala Gln Met Thr Ile Phe Tyr Gly Gly Gln Val Val
        115                 120                 125

Val Phe Asp Asp Phe Pro Ala Asp Lys Ala Ser Glu Ile Met Ser Tyr
130                 135                 140

Ala Thr Lys Gly Gly Ile Pro Gln Ser Gln Asn Asn Ser Val Tyr Thr
145                 150                 155                 160

Tyr Thr Gln Ser Gln Pro Ser Phe Pro Pro Thr Leu Ile Arg Thr Ser
                165                 170                 175

Ala Asp Ser Ser Ala Pro Ile Ile Pro Ser Val Asn Ile Thr Asn Ser
            180                 185                 190

Ile Arg Glu His Pro Gln Ala Ser Ser Arg Pro Val Val Tyr Leu Pro
        195                 200                 205

Ile Ala Arg Lys Ala Ser Leu His Arg Phe Leu Glu Lys Arg Lys Asp
210                 215                 220

Arg Ile Ala Ser Lys Ala Pro Tyr Gln Val Ala Asn Gly Pro Ser Asn
225                 230                 235                 240

Lys Ala Ala Glu Ser Met Pro Trp Leu Gly Leu Ser Ala Ser Ser Pro
                245                 250                 255

Gln Ile

<210> SEQ ID NO 39
<211> LENGTH: 204
<212> TYPE: PRT
<213> ORGANISM: Triticum aestivum

<400> SEQUENCE: 39

Met Asp Leu Leu Glu Arg Ser Ala Ala Thr Ile Lys Ala Glu Ala Gly
1               5                   10                  15

Glu Ala Gln Arg Lys Glu Ala Glu Arg Lys Glu Gln Glu Leu Glu Lys
            20                  25                  30

Glu Gln Glu Thr Gln Gln Pro Gly Leu Thr Gly Arg Pro Pro Leu Ala
        35                  40                  45

Asn Gly Arg Ser Gly Met Leu Pro Met Ser Ser Pro Ala Asn Pro
    50                  55                  60

Gly Gln Leu Thr Ile Phe Tyr Gly Gly Ser Val Cys Val Tyr Asp Ser
65                  70                  75                  80

Val Pro Pro Glu Lys Ala Gln Ala Ile Met Leu Ile Ala Ala Ala
                85                  90                  95

Ala Ala Ala Ser Lys Ser Asn Gly Thr Ala Ala Val Lys Pro Pro Ala
                100                 105                 110

Met Ser Ala Thr Asn Ala Ile Gln Ala Met Leu Thr Arg Ser Leu Ser
            115                 120                 125

Leu Gln Ser Thr Ser Val Ala Asn Gly Gln Pro Gln Ala Val Ala Asp
130                 135                 140

Pro Gly Ser Ile Cys Lys Leu Gln Ala Asp Leu Pro Ile Ala Arg Arg
145                 150                 155                 160

His Ser Leu Gln Arg Phe Leu Glu Lys Arg Arg Asp Arg Val Val Ser
                165                 170                 175

Lys Ala Pro Tyr Gly Ala Gly Lys Pro Ser Glu Gly Met Gly Ala Ser
                180                 185                 190

Ser Gly Met Glu Ala Val Ala Glu Gly Lys Ala Gln
            195                 200

<210> SEQ ID NO 40
<211> LENGTH: 235
<212> TYPE: PRT
<213> ORGANISM: Zea mays

<400> SEQUENCE: 40

Met Ala Ala Ser Ala Arg Pro Gly Glu Arg Ala Thr Ser Phe Ala Val
1               5                   10                  15

Ala Cys Ser Leu Leu Ser Arg Phe Val Arg Gln Asn Gly Val Ala Ala
            20                  25                  30

Ala Glu Leu Gly Leu Arg Ile Lys Gly Glu Val Glu Gln Gln Arg Thr
        35                  40                  45

Pro Ala Thr Thr Ser Leu Leu Pro Gly Ala Glu Gly Glu Val Glu
    50                  55                  60

Arg Arg Lys Glu Thr Met Glu Leu Phe Pro Gln Ser Val Gly Phe Ser
65                  70                  75                  80

Ile Lys Asp Ala Ala Ala Pro Arg Glu Glu Gln Gly Asp Lys Glu
                85                  90                  95

Lys Pro Lys Gln Leu Thr Ile Phe Tyr Gly Gly Lys Val Leu Val Phe
                100                 105                 110

Asp Asp Phe Pro Ala Asp Lys Ala Lys Asp Leu Met Gln Leu Ala Ser
            115                 120                 125

Lys Gly Ser Pro Val Val Gln Asn Val Leu Pro Gln Pro Ser Ala
    130                 135                 140

Ala Ala Ala Val Thr Thr Asp Lys Ala Val Leu Asp Pro Val Ile Ser
145                 150                 155                 160

```
Leu Ala Ala Ala Ala Lys Lys Pro Ala Arg Thr Asn Ala Ser Asp Met
                165                 170                 175

Pro Ile Met Arg Lys Ala Ser Leu His Arg Phe Leu Glu Lys Arg Lys
            180                 185                 190

Asp Arg Leu Asn Ala Lys Thr Pro Tyr Gln Thr Ala Pro Ser Asp Ala
        195                 200                 205

Ala Pro Val Lys Lys Glu Pro Glu Ser Gln Pro Trp Leu Gly Leu Gly
    210                 215                 220

Pro Asn Ala Val Asp Ser Ser Leu Asn Leu Ser
225                 230                 235

<210> SEQ ID NO 41
<211> LENGTH: 257
<212> TYPE: PRT
<213> ORGANISM: Glycine max

<400> SEQUENCE: 41

Met Ser Ser Ser Ser Glu Tyr Ser Gln Phe Ser Gly Gln Lys Pro Ala
1               5                   10                  15

Arg Ser Pro Glu Lys Ser Ser Phe Ser Gln Thr Cys Ser Leu Leu Ser
            20                  25                  30

Gln Tyr Ile Lys Glu Lys Gly Ser Phe Gly Asp Leu Thr Leu Gly Met
        35                  40                  45

Thr Ser Cys Gly Ser Pro Glu Thr Ser Cys Gln Ser Ala Thr Thr Met
    50                  55                  60

Asn Leu Phe Pro Thr Lys Glu Asn Asn Val Thr Pro Lys Asp Leu Thr
65                  70                  75                  80

Ala Met Asp Leu Phe Ser Pro Gln Ala Ser Ser Tyr Arg Pro Ser Glu
                85                  90                  95

Glu Ile Pro Thr Leu Ile Asn Ser Ser Ala Ile Lys Ser Val Ser Lys
            100                 105                 110

Ser Ala Lys Thr Ala Gln Met Thr Ile Phe Tyr Gly Gly Gln Val Val
        115                 120                 125

Val Phe Asp Asp Phe Pro Ala Asp Lys Ala Ser Glu Ile Met Ser Tyr
    130                 135                 140

Ala Thr Lys Gly Ile Pro Gln Ser Gln Asn Asn Ser Val Phe Thr Tyr
145                 150                 155                 160

Thr Pro Ser Gln Pro Ser Phe Pro Ala Asn Leu Val Arg Thr Ser Ala
                165                 170                 175

Asp Ser Ser Ala Pro Ile Ile Pro Ser Val Asn Ile Thr Asn Ser Ile
            180                 185                 190

His Glu His Pro Gln Ala Ser Ser Arg Pro Val Val Tyr Leu Pro Ile
        195                 200                 205

Ala Arg Lys Ala Ser Leu His Arg Phe Leu Glu Lys Arg Lys Asp Arg
    210                 215                 220

Ile Ala Ser Lys Ala Pro Tyr Gln Leu Ala Asn Gly Ser Ser Asn Gln
225                 230                 235                 240

Pro Ala Glu Ser Met Pro Trp Leu Gly Leu Ser Ala Ser Ser Pro Arg
                245                 250                 255

Ile

<210> SEQ ID NO 42
<211> LENGTH: 244
<212> TYPE: PRT
<213> ORGANISM: Oryza sativa
```

```
<400> SEQUENCE: 42

Met Ala Ala Ser Ala Arg Pro Val Gly Val Gly Gly Glu Arg Ala Thr
1               5                   10                  15

Ser Phe Ala Met Ala Cys Ser Leu Leu Ser Arg Tyr Val Arg Gln Asn
            20                  25                  30

Gly Ala Ala Ala Ala Glu Leu Gly Leu Gly Ile Arg Gly Glu Gly Glu
        35                  40                  45

Ala Pro Arg Ala Ala Pro Gly Thr Met Ser Leu Leu Pro Gly Glu Ala
    50                  55                  60

Glu Arg Lys Lys Glu Thr Met Glu Leu Phe Pro Gln Ser Ala Gly Phe
65                  70                  75                  80

Gly Gln Gln Asp Ala Ile Thr Ala Asp Ser Ala Ala Asp Ala Arg Glu
                85                  90                  95

Gln Glu Pro Glu Lys Arg Gln Leu Thr Ile Phe Tyr Gly Gly Lys Val
            100                 105                 110

Leu Val Phe Asn Asp Phe Pro Ala Asp Lys Ala Lys Gly Leu Met Gln
        115                 120                 125

Leu Ala Ser Lys Gly Ser Thr Val Ala Pro Gln Asn Ala Val Ala Pro
    130                 135                 140

Ala Pro Ala Ala Val Thr Asp Asn Thr Lys Ala Pro Met Ala Val Pro
145                 150                 155                 160

Ala Pro Val Ser Ser Leu Pro Thr Ala Gln Ala Asp Ala Gln Lys Pro
                165                 170                 175

Ala Arg Ala Asn Ala Ser Asp Met Pro Ile Ala Arg Lys Ala Ser Leu
            180                 185                 190

His Arg Phe Leu Glu Lys Arg Lys Asp Arg Leu Asn Ala Lys Thr Pro
        195                 200                 205

Tyr Gln Ala Ser Pro Ser Asp Ala Thr Pro Val Lys Lys Glu Pro Glu
    210                 215                 220

Ser Gln Pro Trp Leu Gly Leu Gly Pro Asn Ala Val Val Lys Pro Ile
225                 230                 235                 240

Glu Arg Gly Gln

<210> SEQ ID NO 43
<211> LENGTH: 213
<212> TYPE: PRT
<213> ORGANISM: Zea mays

<400> SEQUENCE: 43

Met Asp Gly Gly Arg Asp Val Asp Glu Gly Gly Val Thr Gly Ala Val
1               5                   10                  15

Ala Ala Ala Ala Ala Gln Glu Arg Arg Trp Arg Gly Gly Gly Gly Asp
            20                  25                  30

Asp Glu Glu Ser Ser Gly Leu Ser Asn Gly Gly Gly Val Glu Leu
        35                  40                  45

Ser Leu Arg Leu Arg Thr Gly Ala Asp Asp Gly Ala Thr Ala Ala
    50                  55                  60

Ala Leu Ser Pro Leu Pro Leu Pro Pro Ala Glu Ala Arg Arg Asn
65                  70                  75                  80

Met Thr Ile Phe Tyr Asn Gly Arg Val Cys Ala Ala Asp Val Thr Glu
                85                  90                  95

Ile Gln Ala Arg Ala Ile Ile Ser Met Ala Ser Glu Glu Thr Leu Ala
            100                 105                 110
```

```
Asp His Arg Gly Arg Arg Arg Gln Gln Gln Gln Leu Thr Arg
            115                 120                 125

Gly Asp Gly Gly Asp Gly Arg Gln Gln Asp Gly Asp Ser Ser Ser Ser
130                 135                 140

Thr Thr Thr Ser Ala Val Ala Leu Ala Arg Arg Cys Ala Arg Gly Arg
145                 150                 155                 160

Gly Leu Val Gly Pro Ala Val Glu Ile Asp Gln Ala Ala Asp Ala Gly
                165                 170                 175

Leu Ser Met Lys Arg Ser Leu Gln Leu Phe Leu Gln Lys Arg Lys Ala
            180                 185                 190

Arg Thr Ala Ala Ala Ala Pro Pro Tyr Ala Gly Gly Arg Gln Ala
            195                 200                 205

Gln Ala Val Arg Arg
    210
```

<210> SEQ ID NO 44
<211> LENGTH: 133
<212> TYPE: PRT
<213> ORGANISM: Glycine max

<400> SEQUENCE: 44

```
Met Arg Arg Asn Cys Asn Leu Glu Leu Ala Leu Phe Pro Pro Ser Asp
1               5                   10                  15

Ser Gly Pro Pro Met Val Asp Asn Val Glu Glu Glu Ala Ser Glu Ile
                20                  25                  30

Ser Pro Met Gln Asn Leu Phe His Arg Gln Glu Gln Gln Gln Pro Leu
            35                  40                  45

Thr Ile Phe Tyr Asp Gly Lys Ile Cys Val Ala Asp Val Thr Glu Leu
50                  55                  60

Gln Ala Lys Ser Ile Leu Met Leu Ala Asn Arg Lys Leu Glu Glu Arg
65                  70                  75                  80

Val Arg Thr Pro Thr Gly Ser Glu Pro Ser Pro Thr Val Met Gln
                85                  90                  95

Ser Asn Asn Gln Leu Tyr Ser Pro Gly Thr Gly Pro Ser Met Arg Lys
            100                 105                 110

Ser Leu Gln Arg Phe Leu Gln Lys Arg Arg Asn Arg Val Gln Glu Ala
        115                 120                 125

Ser Pro Tyr Arg His
    130
```

<210> SEQ ID NO 45
<211> LENGTH: 166
<212> TYPE: PRT
<213> ORGANISM: Triticum aestivum

<400> SEQUENCE: 45

```
Met Ala Ala Ala Ser Arg Ser Ala Pro Glu Trp Trp Arg Asp Gly Gly
1               5                   10                  15

Ser Val Asp Asp Gly Gly Ala Glu Val Glu Leu Ser Leu Arg Leu Arg
                20                  25                  30

Thr Gly Ser Ser Ser Thr Ala Arg Arg Ser Met Thr Ile Phe Tyr Asn
            35                  40                  45

Gly Arg Val Val Ala Val Asp Val Thr Glu Leu Gln Ala Arg Glu Ile
        50                  55                  60

Ile Thr Met Ala Ser Gln Gln Ile Leu Thr Glu Gln Gln Asp Ser Gly
65                  70                  75                  80
```

```
Gly Gly Gly Gly Gly Thr Ala Val Ala Gln Tyr Gly Ala His Glu Asn
                85                  90                  95
Pro Ser Gln Pro Ala Pro Gln Arg Trp Ala Pro Leu Leu Ala Ser Arg
            100                 105                 110
Ser Leu Arg Gln Gly Ala Gly Ala Ala Ala Pro Val Thr Ser Gln Ala
        115                 120                 125
Ala Ala Ala Gly Leu Ser Met Lys Arg Ser Leu Gln Arg Phe Leu Gln
    130                 135                 140
Lys Arg Lys Thr Arg Val Ala Ala Met Gly Ser Pro Tyr Ala Gly Gly
145                 150                 155                 160
Arg Arg Ala Met Pro Ser
                165

<210> SEQ ID NO 46
<211> LENGTH: 353
<212> TYPE: PRT
<213> ORGANISM: Zea mays

<400> SEQUENCE: 46

Met Asp Trp Ser Phe Ala Ser Lys Pro Cys Ala Ala Pro Ala Leu Met
1               5                   10                  15
Ser Phe Arg Ser Ala Ala Arg Glu Glu Pro Ser Phe Pro Gln Phe Ser
            20                  25                  30
Ala Leu Asp Gly Thr Lys Asn Thr Ala Pro Arg Met Leu Thr His Gln
        35                  40                  45
Arg Ser Phe Gly Pro Asp Ser Thr Gln Tyr Ala Ala Leu His Arg Ala
    50                  55                  60
Gln Asn Gly Ala Arg Val Val Pro Val Ser Ser Pro Phe Ser Gln Ser
65                  70                  75                  80
Asn Pro Met Phe Arg Val Gln Ser Ser Pro Ser Leu Pro Asn Ser Thr
                85                  90                  95
Ala Phe Lys Gln Pro Pro Phe Ala Ile Ser Asn Ala Val Ala Ser Ser
            100                 105                 110
Thr Val Gly Ser Tyr Gly Gly Thr Arg Asp Ala Val Arg Pro Arg Thr
        115                 120                 125
Ala Gln Leu Thr Ile Phe Tyr Ala Gly Ser Val Asn Val Phe Asn Asn
    130                 135                 140
Val Ser Ala Glu Lys Ala Gln Glu Leu Met Phe Leu Ala Ser Arg Gly
145                 150                 155                 160
Ser Ser Ala Pro Val Ala Cys Lys Pro Glu Ala Pro Thr Leu Ala
                165                 170                 175
Pro Ala Lys Val Thr Ala Pro Glu Val Leu Leu Pro Ala Lys Gln Met
            180                 185                 190
Leu Phe Gln Lys Pro Gln His Leu Ser Pro Pro Ser Ser Val Pro
        195                 200                 205
Gly Ile Leu Gln Ser Ala Ala Leu Pro Arg Ser Ala Ser Ser Ser
    210                 215                 220
Asn Leu Asp Ser Pro Ala Pro Lys Ser Ser Val Pro Leu Ala Val Pro
225                 230                 235                 240
Pro Val Ser Gln Ala Pro Pro Ala Thr Leu Ile Ala Thr Thr Thr Ala
                245                 250                 255
Ala Ala Ile Met Pro Arg Ala Val Pro Gln Ala Arg Lys Ala Ser Leu
            260                 265                 270
Ala Arg Phe Leu Glu Lys Arg Lys Glu Arg Val Thr Thr Ala Ala Pro
        275                 280                 285
```

```
Tyr Pro Ser Ala Lys Ser Pro Leu Glu Ser Ser Asp Thr Phe Gly Ser
    290                 295                 300

Gly Ser Ala Ser Ala Asn Ala Asn Asp Lys Ser Ser Cys Thr Asp Ile
305                 310                 315                 320

Ala Leu Ser Ser Asn His Glu Glu Ser Leu Cys Leu Gly Gly Gln Pro
                325                 330                 335

Arg Ser Ile Ile Ser Phe Ser Glu Glu Ser Pro Ser Thr Lys Leu Gln
            340                 345                 350

Ile

<210> SEQ ID NO 47
<211> LENGTH: 320
<212> TYPE: PRT
<213> ORGANISM: Glycine max

<400> SEQUENCE: 47

Met Glu Arg Asp Phe Met Gly Leu Asn Leu Lys Glu Pro Leu Ala Val
1               5                   10                  15

Val Lys Glu Glu Met Asn Asn Asp Gly Cys Lys Asn Ser Gly Phe Lys
                20                  25                  30

Lys Gly Arg Ile Ala Gln Trp Pro Phe Ser Asn Lys Val Ser Ala Leu
            35                  40                  45

Pro His Leu Met Ser Phe Lys Ala Ser Gln Asp Asp Lys Thr Lys Asn
        50                  55                  60

Thr Val Ser Asp Thr Leu Ser Ser Ser Gly Phe Met Ser Ile Leu Ser
65                  70                  75                  80

Gln Glu Ala Phe Asp Thr Ser Gln Lys Arg Ser Ala Gly Glu Pro Gln
                85                  90                  95

Met Phe Ser Val Pro Asn Gln Ala Ile Ser Val Ser Leu Gly Asn Pro
            100                 105                 110

Phe Leu Lys Asn His Phe Ala Ala Ala Gly Gln Lys Pro Leu Leu Gly
        115                 120                 125

Gly Ile Pro Val Thr Thr Ser His Ser Val Leu Pro Ser Ala Val Ala
    130                 135                 140

Val Ala Gly Met Thr Glu Ser Cys Val Lys Pro Ser Ala Gln Leu Thr
145                 150                 155                 160

Ile Phe Tyr Ala Gly Thr Val Asn Ile Phe Asp Asp Ile Ser Ala Glu
                165                 170                 175

Lys Ala Gln Ala Ile Met Leu Leu Ala Gly Asn Ser Leu Ser Ala Ala
            180                 185                 190

Ser Asn Met Ala Gln Pro Asn Val Gln Val Pro Ile Ser Lys Leu Gly
        195                 200                 205

Ala Gly Ala Gly Val Pro Val Ser Gln Pro Ala Asn Thr Ser Pro Gly
    210                 215                 220

Ser Gly Leu Ser Ser Pro Leu Val Ser Ser His Thr Gly Val Gln
225                 230                 235                 240

Ser Gly Ser Gly Leu Thr Ser Thr Asp Glu Phe Leu Ala Ala Lys Thr
                245                 250                 255

Thr Gly Val Pro Asn Thr Pro Ile Cys Asn Val Glu Pro Pro Lys Val
            260                 265                 270

Val Ser Ala Thr Thr Met Leu Thr Ser Ala Val Pro Gln Ala Arg Lys
        275                 280                 285

Ala Ser Leu Ala Arg Phe Leu Glu Lys Arg Lys Glu Arg Val Met Ser
    290                 295                 300
```

-continued

Ala Ala Pro Tyr Asn Leu Asn Lys Lys Ser Glu Glu Cys Ala Thr Ala
305                 310                 315                 320

<210> SEQ ID NO 48
<211> LENGTH: 308
<212> TYPE: PRT
<213> ORGANISM: Oryza sativa

<400> SEQUENCE: 48

Met Gln Gln Ala Ser His Val Leu Ala Arg Gln Pro Pro His Val Leu
1               5                   10                  15

Asn Gly Ala Arg Val Ile Pro Ala Ser Ser Pro Phe Asn Pro Asn Asn
            20                  25                  30

Pro Met Phe Arg Val Gln Ser Ser Pro Asn Leu Pro Asn Ala Val Gly
        35                  40                  45

Ala Gly Gly Gly Ala Phe Lys Gln Pro Pro Phe Ala Met Gly Asn Ala
    50                  55                  60

Val Ala Gly Ser Thr Val Gly Val Tyr Gly Thr Arg Asp Met Pro Lys
65                  70                  75                  80

Ala Lys Ala Ala Gln Leu Thr Ile Phe Tyr Ala Gly Ser Val Asn Val
                85                  90                  95

Phe Asn Asn Val Ser Pro Glu Lys Ala Gln Glu Leu Met Phe Leu Ala
            100                 105                 110

Ser Arg Gly Ser Leu Pro Ser Ala Pro Thr Thr Val Ala Arg Met Pro
        115                 120                 125

Glu Ala His Val Phe Pro Pro Ala Lys Val Thr Val Pro Glu Val Ser
    130                 135                 140

Pro Thr Lys Pro Met Met Leu Gln Lys Pro Gln Leu Val Ser Ser Pro
145                 150                 155                 160

Val Pro Ala Ile Ser Lys Pro Ile Ser Val Ser Gln Ala Thr Ser
                165                 170                 175

Leu Pro Arg Ser Ala Ser Ser Ser Asn Val Asp Ser Asn Val Thr Lys
            180                 185                 190

Ser Ser Gly Pro Leu Val Val Pro Pro Thr Ser Leu Pro Pro Pro Ala
        195                 200                 205

Gln Pro Glu Thr Leu Ala Thr Thr Ala Ala Ala Ile Met Pro Arg
    210                 215                 220

Ala Val Pro Gln Ala Arg Lys Ala Ser Leu Ala Arg Phe Leu Glu Lys
225                 230                 235                 240

Arg Lys Glu Arg Val Thr Thr Val Ala Pro Tyr Pro Leu Ala Lys Ser
                245                 250                 255

Pro Leu Glu Ser Ser Asp Thr Met Gly Ser Ala Asn Asp Asn Lys Ser
            260                 265                 270

Ser Cys Thr Asp Ile Ala Leu Ser Ser Asn Arg Asp Glu Ser Leu Ser
        275                 280                 285

Leu Gly Gln Pro Arg Thr Ile Ser Phe Cys Glu Glu Ser Pro Ser Thr
    290                 295                 300

Lys Leu Gln Ile
305

<210> SEQ ID NO 49
<211> LENGTH: 218
<212> TYPE: PRT
<213> ORGANISM: Zea mays

<400> SEQUENCE: 49

```
Met Ala Gly His Ala Pro Ala Arg Asp Lys Thr Thr Thr Gly Phe Ala
1               5                   10                  15

Ala Thr Cys Ser Leu Leu Ser Gln Phe Leu Lys Glu Lys Lys Gly Gly
                20                  25                  30

Leu Gln Gly Leu Gly Gly Leu Ala Met Ala Pro Ala Pro Ala Ala Gly
            35                  40                  45

Ala Gly Ala Phe Arg Pro Pro Thr Thr Met Asn Leu Leu Ser Ala Leu
        50                  55                  60

Asp Ala Ala Lys Ala Thr Val Gly Glu Pro Glu Gly His Gly Gln Arg
65                  70                  75                  80

Thr Gly Gly Asn Pro Arg Glu Ala Ala Gly Glu Glu Ala Gln Gln Leu
                85                  90                  95

Thr Ile Phe Tyr Gly Gly Lys Val Val Phe Asp Arg Phe Pro Ser
                100                 105                 110

Ala Lys Val Lys Asp Leu Leu Gln Ile Val Ser Pro Pro Gly Ala Asp
            115                 120                 125

Ala Val Val Asp Gly Ala Gly Ala Ala Val Pro Thr Gln Asn
130                 135                 140

Leu Pro Arg Pro Ser His Asp Ser Leu Ser Ala Asp Leu Pro Ile Ala
145                 150                 155                 160

Arg Arg Asn Ser Leu His Arg Phe Leu Glu Lys Arg Lys Asp Arg Ile
                165                 170                 175

Thr Ala Lys Ala Pro Tyr Gln Val Asn Ser Ser Val Gly Ala Glu Ala
            180                 185                 190

Ser Lys Ala Glu Lys Pro Trp Leu Gly Leu Gly Gln Gln Glu Gly
                195                 200                 205

Ser Asp Gly Arg Gln Ala Gly Glu Glu Met
210                 215

<210> SEQ ID NO 50
<211> LENGTH: 201
<212> TYPE: PRT
<213> ORGANISM: Glycine max

<400> SEQUENCE: 50

Met Ala Ala Gly Val Thr Val Lys Ser Glu Val Leu Glu Ser Ser Pro
1               5                   10                  15

Pro Glu Gly Val Cys Ser Asn Thr Val Glu Asn His Leu Val Gln Thr
                20                  25                  30

Asn Leu Ser Asp Gly Ser Pro Asn Lys Ser Val Pro Ala Ser Gly Leu
            35                  40                  45

Asp Ala Val Ile Pro Ser Ala Asn Gln Leu Thr Ile Phe Tyr Asn Gly
        50                  55                  60

Ser Val Cys Val Tyr Asp Gly Ile Pro Ala Glu Lys Val His Glu Ile
65                  70                  75                  80

Met Leu Ile Ala Ala Ala Ala Lys Ser Thr Glu Met Lys Lys Ile
                85                  90                  95

Gly Thr Gln Thr Thr Leu Ile Ser Pro Ala Pro Ser Arg Pro Ser Ser
                100                 105                 110

Pro His Gly Ile Thr Asn Asn Ile Gly Ser Ser Gln Lys Ser Ser Ile
            115                 120                 125

Cys Arg Leu Gln Ala Glu Phe Pro Ile Ala Arg Arg His Ser Leu Gln
130                 135                 140

Arg Phe Leu Glu Lys Arg Arg Asp Arg Leu Gly Ser Lys Thr Pro Tyr
```

```
            145                 150                 155                 160
        Pro Ser Ser Pro Thr Thr Lys Val Ala Asp Asn Ile Glu Asn Asn Phe
                        165                 170                 175

Cys Ala Asp Asn Ala Pro Glu Leu Ile Ser Leu Asn Arg Ser Glu Glu
                        180                 185                 190

Glu Phe Gln Pro Thr Val Ser Ala Ser
                        195                 200

<210> SEQ ID NO 51
<211> LENGTH: 188
<212> TYPE: PRT
<213> ORGANISM: Oryza sativa

<400> SEQUENCE: 51

Met Ser Thr Arg Ala Pro Val Glu Leu Asp Phe Leu Gly Leu Arg Ala
1               5                   10                  15

Ala Ala Ala Asp Ala Asp Arg His Ala Lys Ser Gly Gly Ser Ser
                20                  25                  30

Ala Ser Ser Ser Ser Ile Arg Gly Met Glu Thr Ser Ala Ile Ala
        35                  40                  45

Arg Ile Gly Pro His Leu Leu Arg Arg Val Ile Ala Ala Gly Pro
    50                  55                  60

Pro Pro Pro Pro Ser Thr Ala Pro Val Pro Glu Glu Met Pro Gly Ala
65                  70                  75                  80

Ala Ala Ala Ala Ala Pro Met Thr Leu Phe Tyr Asn Gly Ser Val Ala
                85                  90                  95

Val Phe Asp Val Ser His Asp Lys Ala Glu Ala Ile Met Arg Met Ala
                100                 105                 110

Thr Glu Ala Thr Lys Ala Lys Gly Leu Ala Arg Gly Asn Ala Ile Val
            115                 120                 125

Gly Asn Phe Ala Lys Glu Pro Leu Thr Arg Thr Lys Ser Leu Gln Arg
    130                 135                 140

Phe Leu Ser Lys Arg Lys Glu Arg Leu Thr Ser Leu Gly Pro Tyr Gln
145                 150                 155                 160

Val Gly Gly Pro Ala Ala Val Gly Ala Thr Thr Ser Thr Thr Thr Lys
                165                 170                 175

Ser Phe Leu Ala Lys Glu Glu Glu His Thr Ala Ser
                180                 185

<210> SEQ ID NO 52
<211> LENGTH: 468
<212> TYPE: PRT
<213> ORGANISM: Zea mays

<400> SEQUENCE: 52

Met Ser Gln Gln Glu Ala Val Asp Pro Pro Ser Ala Thr Asp Glu Arg
1               5                   10                  15

Leu Gly Gly Leu Pro Arg Ser Gly Ser Thr Ser Arg Leu Asn Ala Gln
                20                  25                  30

Ala Pro Glu Phe Val Pro Arg Ala Ala Ala Val Pro Pro Pro Pro
            35                  40                  45

Gln Gln Lys Val Val Arg Leu Phe Ala Pro Pro His Ala Ala Phe
    50                  55                  60

Phe Val Ala Ala Pro Arg Pro Pro Pro Phe Glu Tyr Tyr Ala
65                  70                  75                  80

Ala Val Ala Thr Gly Gly Gly Gly Arg Phe Gly Pro Pro Ala Ala Ala
```

```
                    85                  90                  95
Ala Glu Gln Glu Ala Glu Ala Glu Gln Pro Pro Arg Asp Gly Ser Phe
                100                 105                 110

Asp Asp Pro Val Pro Lys Ile Arg Lys Gln Val Glu Tyr Tyr Phe Ser
                115                 120                 125

Asp Ile Asn Leu Ala Thr Thr Glu His Leu Met Arg Phe Ile Ser Lys
            130                 135                 140

Asp Pro Glu Gly Tyr Val Pro Ile Ser Val Val Ala Gly Phe Lys Lys
145                 150                 155                 160

Ile Lys Ala Leu Val Gln Ser Asn Ser Met Leu Ala Ser Ala Leu Arg
                165                 170                 175

Thr Ser Ser Lys Leu Val Val Ser Asp Asp Gly Ala Arg Val Lys Arg
            180                 185                 190

Glu Gln Pro Phe Thr Glu Ser Asp Leu Glu Glu Leu Gln Ala Arg Ile
                195                 200                 205

Val Val Ala Glu Asn Leu Pro Asp Asp His Cys Tyr Gln Asn Leu Met
    210                 215                 220

Arg Leu Phe Ser Val Val Gly Ser Val Arg Thr Ile Arg Thr Cys Tyr
225                 230                 235                 240

Pro Gln Thr Pro Asn Gly Thr Gly Pro Ala Thr Asn Arg Ser Ala Lys
                245                 250                 255

Leu Asp Met Leu Phe Ala Asn Lys Leu His Ala Phe Val Glu Tyr Asp
            260                 265                 270

Thr Ile Glu Asp Ala Ala Arg Ala Ile Val Glu Leu Asn Asp Glu Arg
            275                 280                 285

Asn Trp Arg Ser Gly Leu Arg Val Arg Leu Leu Ser Thr Cys Met Gly
            290                 295                 300

Gly Lys Gly Lys Gly Gly His Glu Ser Asp Gly Tyr Gly Asp Glu
305                 310                 315                 320

Glu Asn Val Ser Thr Ser Asp Gln Pro Tyr Asp Lys Tyr Leu Glu Glu
                325                 330                 335

Thr Pro Gln Met Ser Asp Val Pro Gly Glu His Met Thr Glu Asp Ser
            340                 345                 350

Ala Gly Asp Met Gly Arg Gly Arg Val Arg Gly Arg Gly Arg Gly Gly
            355                 360                 365

Arg Gly Arg Gly Arg Gly Tyr His Gln Gln Asn Asn Asn Gln His His
            370                 375                 380

Gln His Tyr Gln Asn Ser Ser His His Ser Asn Ser Ser Ser Thr Arg
385                 390                 395                 400

Pro Val Gly Thr Pro Pro Ser Gly His Pro Val Met Ile Glu Gln
                405                 410                 415

Gln Gln Gln Gln Ala Ala Gln Pro Gln Pro Leu Thr Ala Ala Asn
            420                 425                 430

Lys Gln Pro Pro Gly Pro Arg Met Pro Asp Gly Ser Arg Gly Phe Ser
            435                 440                 445

Met Gly Arg Gly Lys Pro Gln Thr Leu Thr Pro Lys Val Ser Glu Ser
450                 455                 460

Glu Pro Glu Gln
465

<210> SEQ ID NO 53
<211> LENGTH: 470
<212> TYPE: PRT
<213> ORGANISM: Arabidopsis thaliana
```

<400> SEQUENCE: 53

```
Met Gly Asp Gly Ser Ser Arg Ser Asn Ser Ser Asn Ser Thr Ser
1               5                   10                  15

Glu Lys Pro Glu Trp Leu Gln Gln Tyr Asn Leu Val Gly Lys Ile Gly
            20                  25                  30

Glu Gly Thr Tyr Gly Leu Val Phe Leu Ala Arg Thr Lys Thr Pro Pro
        35                  40                  45

Lys Arg Pro Ile Ala Ile Lys Lys Phe Lys Gln Ser Lys Asp Gly Asp
    50                  55                  60

Gly Val Ser Pro Thr Ala Ile Arg Glu Ile Met Leu Leu Arg Glu Ile
65                  70                  75                  80

Ser His Glu Asn Val Val Lys Leu Val Asn Val His Ile Asn Phe Ala
                85                  90                  95

Asp Met Ser Leu Tyr Leu Ala Phe Asp Tyr Ala Glu Tyr Asp Leu Tyr
            100                 105                 110

Glu Ile Ile Arg His His Arg Asp Lys Val Gly His Ser Leu Asn Thr
        115                 120                 125

Tyr Thr Val Lys Ser Leu Leu Trp Gln Leu Leu Asn Gly Leu Asn Tyr
    130                 135                 140

Leu His Ser Asn Trp Ile Ile His Arg Asp Leu Lys Pro Ser Asn Ile
145                 150                 155                 160

Leu Val Met Gly Asp Ala Glu Glu His Gly Ile Val Lys Ile Ala Asp
                165                 170                 175

Phe Gly Leu Ala Arg Ile Tyr Gln Ala Pro Leu Lys Pro Leu Ser Asp
            180                 185                 190

Asn Gly Val Val Val Thr Ile Trp Tyr Arg Ala Pro Glu Leu Leu Leu
        195                 200                 205

Gly Ser Lys His Tyr Thr Ser Ala Val Asp Met Trp Ala Val Gly Cys
    210                 215                 220

Ile Phe Ala Glu Leu Leu Thr Leu Lys Pro Leu Phe Gln Gly Ala Glu
225                 230                 235                 240

Ala Lys Ser Ser Gln Asn Pro Phe Gln Leu Asp Gln Leu Asp Lys Ile
                245                 250                 255

Phe Lys Ile Leu Gly His Pro Thr Met Asp Lys Trp Pro Thr Leu Val
            260                 265                 270

Asn Leu Pro His Trp Gln Asn Asp Val Gln His Ile Gln Ala His Lys
        275                 280                 285

Tyr Asp Ser Val Gly Leu His Asn Val Val His Leu Asn Gln Lys Ser
    290                 295                 300

Pro Ala Tyr Asp Leu Leu Ser Lys Met Leu Glu Tyr Asp Pro Leu Lys
305                 310                 315                 320

Arg Ile Thr Ala Ser Gln Ala Leu Glu His Glu Tyr Phe Arg Met Asp
                325                 330                 335

Pro Leu Pro Gly Arg Asn Ala Phe Val Ala Ser Gln Pro Met Glu Lys
            340                 345                 350

Asn Val Asn Tyr Pro Thr Arg Pro Val Asp Thr Asn Thr Asp Phe Glu
        355                 360                 365

Gly Thr Thr Ser Ile Asn Pro Pro Gln Ala Val Ala Ala Gly Asn Val
    370                 375                 380

Ala Gly Asn Met Ala Gly Ala His Gly Met Gly Ser Arg Ser Met Pro
385                 390                 395                 400

Arg Pro Met Val Ala His Asn Met Gln Arg Met Gln Gln Ser Gln Gly
```

```
                  405                 410                 415
Met Met Ala Tyr Asn Phe Pro Ala Gln Ala Gly Leu Asn Pro Ser Val
                420                 425                 430

Pro Leu Gln Gln Gln Arg Gly Met Ala Gln Pro His Gln Gln Gln Gln
            435                 440                 445

Leu Arg Arg Lys Asp Pro Gly Met Gly Met Ser Gly Tyr Ala Pro Pro
        450                 455                 460

Asn Lys Ser Arg Arg Leu
465             470

<210> SEQ ID NO 54
<211> LENGTH: 2561
<212> TYPE: DNA
<213> ORGANISM: Arabidopsis thaliana

<400> SEQUENCE: 54
```

| | | | | | |
|---|---|---|---|---|---|
| gcaagtggct | aaaaaaatta | caaatctagt | ttccattctc | agcgtcggct | gcttggaacg | 60 |
| tcaccgtttt | ctggaaaacg | caatcttctc | ccttccgtga | cgtctcaccg | gaattttctc | 120 |
| gcttttgtct | actctcctcc | atctccgagg | ttctccaagc | tcagctcctc | ttcccatcat | 180 |
| tcatccgacc | gccttatccg | gtcagatcct | ttacgtattt | ctattttcct | gatcgtcgat | 240 |
| ttttgagaaa | tgtaaaaaca | gatcgtataa | ggcctcgaag | ttttaattt | gaaagtggta | 300 |
| tcgaaatttt | ttggtctttg | attaggttag | ggcaccgtag | ctctgggtat | tgaatttgta | 360 |
| gggttttcct | ctggttattg | gtctttggag | cttggtaatt | tctgctgaat | tgattgatcc | 420 |
| cttttccatc | ttttgaagta | aagtctcgag | ctttcgtgtc | tcgatgtaga | tgaattctat | 480 |
| tttgaatatg | agatttgata | agacgtcaat | tgctgataat | ttggagtctt | tgtgtctgaa | 540 |
| tttgttcata | tgaagttttc | tgagggatgt | gaatttatt | gtctgctaat | tttgaaacgt | 600 |
| tccttttgga | atttggtttg | tgaggagtcc | tagatctttt | tctgtgaagt | ttcttgcttg | 660 |
| taagttttct | ggatcacttg | attgagtcta | gaatctagat | agattacatg | tacgtttga | 720 |
| ttcctttggc | tgattttcca | agtttttgtt | caaatttcag | gagaactaca | agaggaaac | 780 |
| caagattgtt | ttgttttgtt | agactctacc | ccttttccga | ttcacatggt | aaggacattg | 840 |
| aggtagagaa | taatactaaa | aagcaatggg | agatgggagt | tccagtagat | ccaacagctc | 900 |
| aaacagcact | agtgagaaac | cagagtggct | gcaacagtac | aatctcgttg | gtaagattgg | 960 |
| tgaaggcact | tatggtcttg | ttttcttggc | tagaaccaag | actccgccta | aaagaccat | 1020 |
| tgctatcaag | aagtttaagc | agtccaaaga | tggagatgga | gtttccccga | ctgctatccg | 1080 |
| cgagatcatg | ttgcttagag | agatttccca | tgagaacgtc | gtgaagcttg | tgaatgtcca | 1140 |
| catcaatttt | gcagacatgt | ctctgtatct | tgcctttgat | tatgccgagt | acgatctcta | 1200 |
| tgaaatcatc | aggcaccaca | gagacaaagt | cggccattcg | ttaaacacat | acacagttaa | 1260 |
| gtctttgctc | tggcagcttc | tcaacggatt | gaactatctt | cacagtaatt | ggattataca | 1320 |
| cagagatttg | aaaccgtcga | atatcttggt | tatgggtgat | gcagaagagc | acggaatagt | 1380 |
| gaaaatagct | gatttcgggc | tcgcaaggat | atatcaagct | ccgttgaaac | cactatcgga | 1440 |
| taacggagtt | gtggtcacaa | tctggtaccg | agcaccagag | ctgcttcttg | gttcgaagca | 1500 |
| ctacacgagc | gctgttgata | tgtgggcagt | tgggtgtata | ttcgcggagt | tactaactct | 1560 |
| taaaccgttg | tttcaaggag | cagaagcgaa | atcgtctcaa | aacccttcc | agttagatca | 1620 |
| acttgacaag | atattcaaga | tcttaggcca | cccgacgatg | gataaatggc | caacactagt | 1680 |
| taaccttcca | cactggcaaa | atgatgttca | acacattcaa | gctcacaaat | acgacagtgt | 1740 |

```
gggtctccac aacgtggttc acctgaatca gaaaagtcct gcgtatgatc tgttatccaa    1800
aatgctggaa tatgatcctc taaagcggat cacggcttca caagcactag aacacgagta    1860
tttccgaatg gatcctctcc caggacggaa cgcatttgta gccagccaac cgatggagaa    1920
gaatgtgaat tacccaactc gtccagtaga tacaaacacc gatttcgaag gcacgacaag    1980
catcaatccg cctcaagcag tagcagcagg aaacgtagca gggaacatgg caggagctca    2040
tggaatgggc agtagatcga tgccaagacc aatggttgca cataacatgc agaggatgca    2100
gcaatctcaa ggcatgatgg cttataattt cccggcacag gcagggctta acccgagtgt    2160
tccgctgcag cagcagcgcg ggatggctca accgcaccag cagcaacagc taagaaggaa    2220
agatcccgga atgggtatgt caggttacgc acctcctaac aaatccagac gcctctaaag    2280
gtaaaatcga gatcatcagt ctcgggttag aatctgtgtg tttgccgcag aagaaagcgt    2340
tgcgatttgc tttatagagt agagttagat tgtaatgcag catgtggaat gttgctattc    2400
atatggatgg attggattct ctgtagtttt tgtataaaca tcctctcaag tatttgttaa    2460
ttatattaga tcatcatttc tcttaacatc atttctcaaa acgtagtaaa taggagattt    2520
gccaagtgaa aaatatatat aatgagacag ttattatgaa c                       2561

<210> SEQ ID NO 55
<211> LENGTH: 2561
<212> TYPE: DNA
<213> ORGANISM: Artificial Sequence
<220> FEATURE:
<223> OTHER INFORMATION: A synthetic oligonucleotide

<400> SEQUENCE: 55
gcaagtggct aaaaaaatta caaatctagt ttccattctc agcgtcggct gcttggaacg      60
tcaccgtttt ctggaaaacg caatcttctc ccttccgtga cgtctcaccg gaattttctc     120
gcttttgtct actctcctcc atctccgagg ttctccaagc tcagctcctc ttcccatcat     180
tcatccgacc gccttatccg gtcagatcct ttacgtattt ctattttcct gatcgtcgat     240
ttttgagaaa tgtaaaaaca gatcgtataa ggcctcgaag ttttttaattt gaaagtggta     300 tcgaaatttt ttggtctttg attaggttag ggcaccgtag ctctgggtat tgaatttgta     360
gggttttcct ctggttattg gtcttttggag cttggtaatt tctgctgaat tgattgatcc     420
cttttccatc ttttgaagta aagtctcgag cttccgtgtc tcgatgtaga tgaattctat     480
tttgaatatg agatttgata agacgtcaat tgctgataat ttggagtctt tgtgtctgaa     540
tttgttcata tgaagttttc tgagggatgt gaattttatt gtctgctaat tttgaaacgt     600
tccttttgga atttggtttg tgaggagtcc tagatctttt tctgtgaagt ttcttgcttg     660
taagttttct ggatcacttg attgagtcta gaatctagat agattacatg tacggtttga     720
ttcctttggc tgattttcca aagttttgtt caaatttcag gagaactaca aagaggaaac     780
caagattgtt ttgttttgtt agactctacc ccttttccga ttcacatggt aaggacattg     840
aggtagagaa taatactaaa aagcaatggg agatgggagt tccagtagat ccaacagctc     900
aaacagcact agtgagaaac cagagtggct gcaacagtac aatctcgttg gtaagattgg     960
tgaaggcact tatggtcttg ttttcttggc tagaaccaag actccgccta aaagacctat    1020
tgctatcaag aagtttaagc agtccaaaga tggagatgga gtttccccga ctgctatccg    1080
cgagatcatg ttgcttagag agatttccca tgagaacgtc gtgaagcttg tgaatgtcca    1140
catcaatttt gcagacatgt ctctgtatct tgcctttgat tatgccgagt acgatctcta    1200
```

```
tgaaatcatc aggcaccaca gagacaaagt cggccattcg ttaaacacat acacagttaa    1260
gtctttgctc tggcagcttc tcaacggatt gaactatctt cacagtaatt ggattataca    1320
cagagatttg aaaccgtcga atatcttggt tatgggtgat gcagaagagc acggaatagt    1380
gaaaatagct gatttcgggc tcgcaaggat atatcaagct ccgttgaaac cactatcgga    1440
taacggagtt gtggtcacaa tctggtaccg agcaccagag ctgcttcttg gttcgaagca    1500
ctacacgagc gctgttgata tgtgggcagt tgggtgtata ttcgcggagt tactaactct    1560
taaaccgttg tttcaaggag cagaagcgaa atcgtctcaa aacccttccc agttagatca    1620
acttgacaag atattcaaga tcttaggcca cccgacgatg gataaatggc caacactagt    1680
taaccttcca cactggcaaa atgatgttca acacattcaa gctcacaaat acgacagtgt    1740
gggtctccac aacgtggttc acctgaatca gaaaagtcct gcgtatgatc tgttatccaa    1800
aatgctggaa tatgatcctc taaagcggat cacggcttca caagcactag aacacgagta    1860
tttccgaatg gatcctctcc caggacggaa cgcatttgta gccagccaac cgatggagaa    1920
gaatgtgaat tacccaactc gtccagtaga tacaaacacc gatttcgaag gcacgacaag    1980
catcaatccg cctcaagcag tagcagcagg aaacgtagca gggaacatgg caggagctca    2040
tggaatgggc agtagatcga tgccaagacc aatggttgca cataacatgc agaggatgca    2100
gcaatctcaa ggcatgatgg cttataattt cccggcacag gcagggctta acccgagtgt    2160
tccgctgcag cagcagcgcg ggatggctca accgcaccag cagcaacagc taagaaggaa    2220
agatcccgga atgggtatgt caggttacgc acctcctaac aaatccagac gcctctaaag    2280
gtaaaatcga gatcatcagt ctcgggttag aatctgtgtg tttgccgcag aagaaagcgt    2340
tgcgatttgc tttatagagt agagttagat tgtaatgcag catgtggaat gttgctattc    2400
atatggatgg attggattct ctgtagtttt tgtataaaca tcctctcaag tatttgttaa    2460
ttatattaga tcatcatttc tcttaacatc atttctcaaa acgtagtaaa taggagattt    2520
gccaagtgaa aaatatatat aatgagacag ttattatgaa c                       2561
```

<210> SEQ ID NO 56
<211> LENGTH: 471
<212> TYPE: PRT
<213> ORGANISM: Zea mays

<400> SEQUENCE: 56

```
Met Gly Asp Gly Arg Thr Gly Gly Ala Asn Arg Pro Ala Trp Leu Gln
1               5                   10                  15

Gln Tyr Glu Leu Ile Gly Lys Ile Gly Glu Gly Thr Tyr Gly Leu Val
            20                  25                  30

Phe Leu Ala Arg Leu Lys Pro Pro His Pro Ala Pro Gly Arg Arg Gly
        35                  40                  45

Pro Pro Ile Ala Ile Lys Lys Phe Lys Gln Ser Lys Glu Gly Asp Gly
    50                  55                  60

Val Ser Pro Thr Ala Ile Arg Glu Ile Met Leu Leu Arg Glu Ile Asn
65                  70                  75                  80

His Glu Asn Val Val Lys Leu Val Asn Val His Ile Asn His Ala Asp
                85                  90                  95

Met Ser Leu Tyr Leu Ala Phe Asp Tyr Ala Glu His Asp Leu Tyr Glu
            100                 105                 110

Ile Ile Arg His His Arg Glu Lys Leu Ser Ser Ser Ile Asn Pro Tyr
        115                 120                 125

Thr Val Lys Ser Leu Leu Trp Gln Leu Leu Asn Gly Leu Asn Tyr Leu
```

His Ser Asn Trp Ile Ile His Arg Asp Leu Lys Pro Ser Asn Ile Leu
145                 150                 155                 160

Val Met Gly Glu Gly Asp His Gly Ile Ile Lys Ile Ala Asp Phe
            165                 170                 175

Gly Leu Ala Arg Ile Tyr Gln Ala Pro Leu Lys Pro Leu Cys Asp Asn
            180                 185                 190

Gly Val Val Thr Ile Trp Tyr Arg Ala Pro Glu Leu Leu Leu Gly
        195                 200                 205

Gly Lys His Tyr Thr Ser Ala Val Asp Met Trp Ala Val Gly Cys Ile
        210                 215                 220

Phe Ala Glu Leu Leu Thr Leu Lys Pro Leu Phe Gln Gly Val Glu Ala
225                 230                 235                 240

Lys Asn Pro Pro Asn Pro Phe Gln Leu Asp Gln Leu Asp Lys Ile Phe
                245                 250                 255

Lys Val Leu Gly His Pro Thr Val Glu Lys Trp Pro Thr Leu Ala Asn
                260                 265                 270

Leu Pro Trp Trp Gln Asn Asp His Gln His Ile Gln Gly His Lys Tyr
            275                 280                 285

Glu Asn Pro Gly Phe His Asn Ile Val His Leu Pro Pro Lys Ser Pro
290                 295                 300

Ala Phe Asp Leu Leu Ser Lys Met Leu Glu Tyr Asp Pro Arg Lys Arg
305                 310                 315                 320

Ile Thr Ala Ala Gln Ala Leu Glu His Glu Tyr Phe Arg Met Asp Pro
            325                 330                 335

Leu Pro Gly Arg Asn Ala Leu Leu Pro Ser Gln Pro Gly Glu Lys Ile
            340                 345                 350

Val Gln Tyr Pro Ile Arg Pro Val Asp Thr Thr Thr Asp Phe Glu Gly
        355                 360                 365

Thr Thr Ser Leu Gln Pro Thr Gln Pro Pro Ser Gly Asn Ala Pro Pro
        370                 375                 380

Gly Gly Gln Ser Val Ala Arg Pro Met Pro Arg Gln Met Pro Gln Gln
385                 390                 395                 400

Pro Met Val Gly Gly Ile Pro Arg Val Ala Gly Val Thr Met Ala
            405                 410                 415

Ala Phe Asn Ala Ala Ser Gln Ala Gly Met Ala Gly Leu Asn Pro Gly
            420                 425                 430

Asn Met Pro Met Gln Arg Gly Ala Gly Gly Gln Ser His Pro His Gln
            435                 440                 445

Leu Arg Arg Lys Ala Asp Gln Gly Met Gly Met Gln Asn Pro Gly Tyr
    450                 455                 460

Pro Gln Gln Lys Arg Arg Phe
465                 470

<210> SEQ ID NO 57
<211> LENGTH: 1948
<212> TYPE: DNA
<213> ORGANISM: Zea mays

<400> SEQUENCE: 57
gatatgttag cacttagcag cattctttgg tccaacaagt cgagagaagc gggccgtacg    60
ccaccacggc aacggagaag aggactttca gctgcggcgg ctggccggcg cggcgacggg   120
gatgggggat gggcgcacag gcggcgccaa ccgtccggcg tggctgcagc agtacgaact   180

```
gattggcaag attggggagg ggacctatgg cctcgtcttc ctcgcgcgcc ttaagccgcc      240
ccacccggca cctggccgac gcggccccccc tatcgccata aagaagttta agcagtcaaa     300 ggaggggac ggagtatcac ccaccgcaat tagagagatc atgctcctgc gcgagatcaa       360
ccacgagaat gtcgtcaagc tcgtcaatgt gcacatcaac cacgctgaca tgtccctata      420
cctcgcattc gattacgcag agcacgacct ctatgagatt atcaggcatc acagggagaa      480
gctgagttcc tccattaacc catacactgt caaatccttg ctgtggcaac tgctcaacgg      540
cctcaactat cttcacagta actggattat acatcgagat ctaaagcctt ccaacatact      600
ggtcatggga gaaggagatg aacatggaat tataaagata gccgattttg gacttgctag      660
gatatatcaa gctccactga accattatg tgataatggg gttgttgtaa ctatctggta       720
tcgtgctcct gagctgttac ttgggggaa acactacacc agtgctgtcg atatgtgggc       780
agttggttgc atttttgctg aactgcttac actgaaacct ctattccaag gtgtggaagc      840
aaaaaatcct ccgaacccat tccagcttga tcaactcgac aagattttta aggtcttagg      900
ccaccctaca gttgaaaagt ggcctaccct tgccaatctt ccatggtggc aaaacgacca      960
ccaacacatt caaggacata agtatgaaaa cccaggtttc cataacattg ttcatttacc     1020
accaaagagt cctgcatttg atcttctctc aaaaatgctt gagtatgatc cccgaaagcg     1080
tataacagct gcacaagctt tggagcatga gaccttagta accaggttcc cggatcgatg     1140
ggatcgagga acgggaacgt ggtacgcgat actttcggat ggacccacta cctggacgaa     1200
acgcgctttt accatcccag ccaggggaga aaattgtaca gtatcctatt cgtccagtag     1260
atactacaac agattttgaa ggaacaacaa gccttcaacc aactcaaccg ccatcaggga     1320
acgctcctcc tggaggtcaa tctgtagcaa gacccatgcc acgacaaatg ccgcagcaac     1380
ctatggttgg ggggattcca agagtggcag gtggagtaac catggctgcc ttcaacgctg     1440
cctcacaggc tggcatggct gggctaaatc ctggtaacat gcctatgcag agaggcgcag     1500
gtggtcagtc tcatccgcac cagttgagaa ggaaggcgga tcaagggatg gggatgcaga     1560
accctgggta tcctcagcag aagagacgat tctgacgcta tcaagatgga gccatctgct     1620
gtatatcagg tgtttgaaac acgttgcctg tgtaagctgc tgtagttttg ttatcagcat     1680
ccgaatgcca atgctggcac ctgtaaaaca cattaatcag tcgagagtcc agataccagt     1740
tgtccttatg ggttatgatc taagctgctc gaatttggct gatttggttt gcaacagaaa     1800
ggtcttgctt ttgctcatgg cccagtggaa ttatccacat gcgtaggaaa tttagcatct     1860
atttggcttg agaaaagatt ttcattaaat tctagtggca gtaaatattt ttatggccac     1920
aaactacaca gaattgagca gttgagct                                        1948
```

<210> SEQ ID NO 58
<211> LENGTH: 501
<212> TYPE: PRT
<213> ORGANISM: Zea mays

<400> SEQUENCE: 58

```
Met Gly Asp Gly Arg Thr Gly Gly Ala Asn Arg Pro Ala Trp Leu Gln
 1               5                  10                  15

Gln Tyr Glu Leu Ile Gly Lys Ile Gly Glu Gly Thr Tyr Gly Leu Val
            20                  25                  30

Phe Leu Ala Arg Leu Lys Pro Pro His Pro Ala Pro Gly Arg Arg Gly
        35                  40                  45

Pro Pro Ile Ala Ile Lys Lys Phe Lys Gln Ser Lys Glu Gly Asp Gly
    50                  55                  60
```

```
Val Ser Pro Thr Ala Ile Arg Glu Ile Met Leu Leu Arg Glu Ile Asn
 65                  70                  75                  80

His Glu Asn Val Val Lys Leu Val Asn Val His Ile Asn His Ala Asp
                 85                  90                  95

Met Ser Leu Tyr Leu Ala Phe Asp Tyr Ala Glu His Asp Leu Tyr Glu
                100                 105                 110

Ile Ile Arg His His Arg Glu Lys Leu Ser Ser Ile Asn Pro Tyr
                115                 120                 125

Thr Val Lys Ser Leu Leu Trp Gln Leu Leu Asn Gly Leu Asn Tyr Leu
            130                 135                 140

His Ser Asn Trp Ile Ile His Arg Asp Leu Lys Pro Ser Asn Ile Leu
145                 150                 155                 160

Val Trp Cys His Gln Leu Tyr Arg Asn Ile Ile Ala Gln Phe Leu Gln
                165                 170                 175

Thr Cys Pro Leu Ala Asp Thr Tyr Phe Ile Cys Ala Thr Lys Val Met
            180                 185                 190

Gly Glu Gly Asp Glu His Gly Ile Ile Lys Ile Ala Asp Phe Gly Leu
            195                 200                 205

Ala Arg Ile Tyr Gln Ala Pro Leu Lys Pro Leu Cys Asp Asn Gly Val
            210                 215                 220

Val Val Thr Ile Trp Tyr Arg Ala Pro Glu Leu Leu Gly Gly Lys
225                 230                 235                 240

His Tyr Thr Ser Ala Val Asp Met Trp Ala Val Gly Cys Ile Phe Ala
                245                 250                 255

Glu Leu Leu Thr Leu Lys Pro Leu Phe Gln Gly Val Glu Ala Lys Asn
                260                 265                 270

Pro Pro Asn Pro Phe Gln Leu Asp Gln Leu Asp Lys Ile Phe Lys Val
            275                 280                 285

Leu Gly His Pro Thr Val Glu Lys Trp Pro Thr Leu Ala Asn Leu Pro
            290                 295                 300

Trp Trp Gln Asn Asp His Gln His Ile Gln Gly His Lys Tyr Glu Asn
305                 310                 315                 320

Pro Gly Phe His Asn Ile Val His Leu Pro Lys Ser Pro Ala Phe
                325                 330                 335

Asp Leu Leu Ser Lys Met Leu Glu Tyr Asp Pro Arg Lys Arg Ile Thr
            340                 345                 350

Ala Ala Gln Ala Leu Glu His Glu Tyr Phe Arg Met Asp Pro Leu Pro
            355                 360                 365

Gly Arg Asn Ala Leu Leu Pro Ser Gln Pro Gly Glu Lys Ile Val Gln
            370                 375                 380

Tyr Pro Ile Arg Pro Val Asp Thr Thr Asp Phe Glu Gly Thr Thr
385                 390                 395                 400

Ser Leu Gln Pro Thr Gln Pro Ser Gly Asn Ala Pro Pro Gly Gly
                405                 410                 415

Gln Ser Val Ala Arg Pro Met Pro Arg Gln Met Pro Gln Pro Met
                420                 425                 430

Val Gly Gly Ile Pro Arg Val Ala Gly Gly Val Thr Met Ala Ala Phe
            435                 440                 445

Asn Ala Ala Ser Gln Ala Gly Met Ala Gly Leu Asn Pro Gly Asn Met
            450                 455                 460

Pro Met Gln Arg Gly Ala Gly Gly Gln Ser His Pro His Gln Leu Arg
465                 470                 475                 480
```

Arg Lys Ala Asp Gln Gly Met Gly Met Gln Asn Pro Gly Tyr Pro Gln
                485                 490                 495

Gln Lys Arg Arg Phe
            500

<210> SEQ ID NO 59
<211> LENGTH: 461
<212> TYPE: PRT
<213> ORGANISM: Glycine max

<400> SEQUENCE: 59

Met Gly Asp Gly Ser Gly Asn Arg Trp Ser Arg Ala Glu Trp Val Gln
1               5                   10                  15

Gln Tyr Asp Leu Leu Gly Lys Ile Gly Glu Gly Thr Tyr Gly Leu Val
            20                  25                  30

Phe Leu Ala Arg Thr Lys Gly Thr Pro Ser Lys Ser Ile Ala Ile Lys
        35                  40                  45

Lys Phe Lys Gln Ser Lys Asp Gly Asp Gly Val Ser Pro Thr Ala Ile
    50                  55                  60

Arg Glu Ile Met Leu Leu Arg Glu Ile Thr His Glu Asn Val Val Lys
65                  70                  75                  80

Leu Val Asn Val His Ile Asn His Ala Asp Met Ser Leu Tyr Leu Ala
                85                  90                  95

Phe Asp Tyr Ala Glu His Asp Leu Tyr Glu Ile Ile Arg His His Arg
            100                 105                 110

Asp Lys Leu Asn His Ser Ile Asn Gln Tyr Thr Val Lys Ser Leu Leu
        115                 120                 125

Trp Gln Leu Leu Asn Gly Leu Ser Tyr Leu His Ser Asn Trp Met Ile
    130                 135                 140

His Arg Asp Leu Lys Pro Ser Asn Ile Leu Val Met Gly Glu Gly Glu
145                 150                 155                 160

Glu His Gly Val Val Lys Ile Ala Asp Phe Gly Leu Ala Arg Ile Tyr
                165                 170                 175

Gln Ala Pro Leu Lys Pro Leu Ser Asp Asn Gly Val Val Val Thr Ile
            180                 185                 190

Trp Tyr Arg Ala Pro Glu Leu Leu Leu Gly Ala Lys His Tyr Thr Ser
        195                 200                 205

Ala Val Asp Met Trp Ala Val Gly Cys Ile Phe Ala Glu Leu Leu Thr
    210                 215                 220

Leu Lys Pro Leu Phe Gln Gly Ala Glu Val Lys Ala Thr Ser Asn Pro
225                 230                 235                 240

Phe Gln Leu Asp Gln Leu Asp Lys Ile Phe Lys Val Leu Gly His Pro
                245                 250                 255

Thr Leu Glu Lys Trp Pro Ser Leu Ala Ser Leu Pro His Trp Gln Gln
            260                 265                 270

Asp Val Gln His Ile Gln Gly His Lys Tyr Asp Asn Ala Gly Leu Tyr
        275                 280                 285

Asn Val Val His Leu Ser Pro Lys Ser Pro Ala Tyr Asp Leu Leu Ser
    290                 295                 300

Lys Met Leu Glu Tyr Asp Pro Arg Lys Arg Leu Thr Ala Ala Gln Ala
305                 310                 315                 320

Leu Glu His Glu Tyr Phe Lys Ile Glu Pro Leu Pro Gly Arg Asn Ala
                325                 330                 335

Leu Val Pro Cys Gln Leu Gly Glu Lys Ile Val Asn Tyr Pro Thr Arg
            340                 345                 350

```
Pro Val Asp Thr Thr Asp Leu Glu Gly Thr Thr Asn Leu Pro Pro
            355                 360                 365

Ser Gln Thr Val Asn Ala Val Ser Gly Ser Met Pro Gly Pro His Gly
    370                 375                 380

Ser Asn Arg Ser Val Pro Arg Pro Val Asn Val Val Gly Met Gln Arg
385                 390                 395                 400

Met Pro Pro Gln Ala Met Ala Ala Tyr Asn Leu Ser Ser Gln Ala Ala
                405                 410                 415

Met Gly Asp Gly Met Asn Pro Gly Gly Ile Ser Lys Gln Arg Gly Val
            420                 425                 430

Pro Gln Ala His Gln Pro Gln Gln Leu Arg Arg Lys Glu Gln Met Gly
        435                 440                 445

Met Pro Gly Tyr Pro Ala Gln Gln Lys Ser Arg Arg Ile
    450                 455                 460

<210> SEQ ID NO 60
<211> LENGTH: 1874
<212> TYPE: DNA
<213> ORGANISM: Glycine max

<400> SEQUENCE: 60
```

| | | | | | |
|---|---|---|---|---|---|
| catttcaatt | ttaggacacg | gctgcctatc | cccttgcgat | cgaagagaga | tgggggacgg | 60 |
| aagtgggaac | cggtggagca | gggcggagtg | ggtgcagcag | tacgatctct | taggcaaaat | 120 |
| cggagaaggc | acttacggcc | tcgtcttcct | ggcccgaacc | aaaggcactc | cctccaaatc | 180 |
| catcgccatc | aaaaagttca | agcaatccaa | ggacggcgac | ggcgtctccc | ccaccgccat | 240 |
| ccgcgaaatc | atgctgctca | gggagattac | gcacgagaac | gtcgtcaagc | tcgtcaatgt | 300 |
| ccacatcaac | cacgccgaca | tgtcgctcta | cctcgccttt | gattacgccg | agcacgatct | 360 |
| ctatgaaatt | attaggcatc | acagggataa | actcaaccat | tccattaacc | aatacactgt | 420 |
| taagtctttg | ctctggcagt | tgctcaatgg | actaagctat | ctgcacagta | attggatgat | 480 |
| acatcgagat | ttgaagccat | cgaatatatt | ggttatggga | gaaggagagg | aacatggagt | 540 |
| tgttaagatt | gctgactttg | gacttgcgag | gatatatcaa | gctcctctga | agccgttatc | 600 |
| tgataatggg | gttgttgtaa | ccatttggta | tcgtgcaccc | gagttgcttc | ttggagcaaa | 660 |
| acattatact | agtgctgttg | atatgtgggc | tgtgggatgc | attttttgctg | agttgttgac | 720 |
| cttgaagccg | ctatttcaag | gggcagaagt | caaagctaca | tcaaatccct | tcagctcga | 780 |
| ccaacttgac | aagatattta | aggttttagg | ccatcccaca | ttagaaaagt | ggccttcctt | 840 |
| agcaagtctt | ccacattggc | aacaagatgt | gcaacatata | caaggacaca | aatatgataa | 900 |
| tgctggtctc | tataatgttg | tacacctgtc | tccaaaaagc | cccgcatatg | acctcttgtc | 960 |
| aaagatgctt | gaatatgatc | ctcgtaagcg | tttaacagca | gcacaagctt | tggagcatga | 1020 |
| gtatttcaaa | attgaaccat | tacctggacg | gaatgcactt | gtaccctgcc | aacttggaga | 1080 |
| gaaaattgta | aattatccca | ctcgtccagt | ggacaccact | actgatcttg | aaggaacaac | 1140 |
| caatctgcca | ccttcacaaa | cggtaaatgc | agtttctggc | agcatgcctg | gtcctcatgg | 1200 |
| gtcaaataga | tctgttcctc | ggccagtgaa | tgttgttgga | atgcaaagaa | tgccccctca | 1260 |
| agcaatggca | gcttataatc | tctcatctca | ggcagccatg | ggagacggaa | tgaatcctgg | 1320 |
| gggtatctca | aagcaacgag | gtgttccaca | ggcccatcag | ccgcaacagt | tgagaaggaa | 1380 |
| ggagcaaatg | gggatgccgg | gataccctgc | acaacagaag | tcaagacgaa | tataaggttt | 1440 |
| ctgctggaag | agagactacg | tgaagataaa | tttggggtca | atacttcagt | gcctgaactc | 1500 |

```
atgcaggaca tttctggaca gggtttgtct caatacttgc aaacctctca ctttattgca    1560
atcaaagatt gggtgcattc ttctctggaa ttttgatgct aaaatgccaa atgtatgctg    1620
gaacaccaat gaagccataa aagggtataa acgtatgaaa gggttaagct actgtaagca    1680
catgtatatc atgattataa caatgcaatt ctattgtatt tctcagcttt tgggcaagat    1740
caatgtcagt gaaaccaaat gttaatcatc cattgggttt tcataatgaa acttttcacg    1800
attaaattta taatatgcta ctttgtattc gtcgaatatt ttgcctcaca tgattgaaga    1860
tagttcaaat atca                                                     1874
```

<210> SEQ ID NO 61
<211> LENGTH: 464
<212> TYPE: PRT
<213> ORGANISM: Glycine max

<400> SEQUENCE: 61

```
Met Gly Asp Gly Ser Gly Ser Arg Trp Ser Arg Ala Glu Trp Val Gln
1               5                   10                  15

Gln Tyr Asp Leu Leu Gly Lys Ile Gly Glu Gly Thr Tyr Gly Leu Val
            20                  25                  30

Phe Leu Ala Arg Thr Lys Ser Pro Val Gly Thr Pro Ser Lys Ser Ile
        35                  40                  45

Ala Ile Lys Lys Phe Lys Gln Ser Lys Asp Gly Asp Gly Val Ser Pro
    50                  55                  60

Thr Ala Ile Arg Glu Ile Met Leu Leu Arg Glu Ile Thr His Glu Asn
65                  70                  75                  80

Val Val Lys Leu Val Asn Val His Ile Asn His Ala Asp Met Ser Leu
                85                  90                  95

Tyr Leu Ala Phe Asp Tyr Ala Glu His Asp Leu Tyr Glu Ile Ile Arg
            100                 105                 110

His His Arg Asp Lys Leu Asn His Ser Ile Asn Gln Tyr Thr Val Lys
        115                 120                 125

Ser Leu Leu Trp Gln Leu Leu Asn Gly Leu Ser Tyr Leu His Ser Asn
    130                 135                 140

Trp Met Ile His Arg Asp Leu Lys Pro Ser Asn Ile Leu Val Met Gly
145                 150                 155                 160

Glu Gly Glu Glu His Gly Val Val Lys Ile Ala Asp Phe Gly Leu Ala
                165                 170                 175

Arg Ile Tyr Gln Ala Pro Leu Lys Pro Leu Ser Asp Asn Gly Val Val
            180                 185                 190

Val Thr Ile Trp Tyr Arg Ala Pro Glu Leu Leu Gly Ala Lys His
        195                 200                 205

Tyr Thr Ser Ala Val Asp Met Trp Ala Met Gly Cys Ile Phe Ala Glu
    210                 215                 220

Leu Leu Thr Leu Lys Pro Leu Phe Gln Gly Ala Glu Val Lys Ala Thr
225                 230                 235                 240

Ser Asn Pro Phe Gln Leu Asp Gln Leu Asp Lys Ile Phe Lys Val Leu
                245                 250                 255

Gly His Pro Thr Leu Glu Lys Trp Pro Ser Leu Ala Ser Leu Pro His
            260                 265                 270

Trp Gln Gln Asp Val Gln His Ile Gln Gly His Lys Tyr Asp Asn Ala
        275                 280                 285

Gly Leu Tyr Asn Val Val His Leu Ser Pro Lys Ser Pro Ala Tyr Asp
    290                 295                 300
```

| | | | | | | | | | | | |
|---|---|---|---|---|---|---|---|---|---|---|---|
|Leu|Leu|Ser|Lys|Met|Leu|Glu|Tyr|Asp|Pro|Arg|Lys|Arg|Leu|Thr|Ala|
|305| | | |310| | | |315| | | |320|

Ala Gln Ala Leu Glu His Glu Tyr Phe Lys Ile Glu Pro Leu Pro Gly
                325                 330                 335

Arg Asn Ala Leu Val Pro Cys Gln Leu Gly Glu Lys Ile Val Asn Tyr
            340                 345                 350

Pro Thr Arg Pro Val Asp Thr Thr Thr Asp Leu Glu Gly Thr Thr Asn
        355                 360                 365

Leu Pro Pro Ser Gln Thr Val Asn Ala Val Ser Gly Ser Met Pro Gly
    370                 375                 380

Pro His Gly Ser Asn Arg Ser Val Pro Arg Pro Met Asn Val Val Gly
385                 390                 395                 400

Met Gln Arg Leu Pro Pro Gln Ala Met Ala Ala Tyr Asn Leu Ser Ser
                405                 410                 415

Gln Ala Ala Met Gly Asp Gly Met Asn Pro Gly Asp Ile Ser Lys His
            420                 425                 430

Arg Gly Val Pro Gln Ala His Gln Pro Gln Gln Leu Arg Arg Lys Glu
        435                 440                 445

Gln Met Gly Met Pro Gly Tyr Pro Ala Gln Gln Lys Ser Arg Arg Leu
    450                 455                 460

```
<210> SEQ ID NO 62
<211> LENGTH: 2045
<212> TYPE: DNA
<213> ORGANISM: Glycine max

<400> SEQUENCE: 62
```

| | | |
|---|---|---|
|tttcaatttt cagacgctgc tgcctatccc cttgcgatcg aacagaacag aagagagatg|60|
|ggggacggaa gtgggagccg gtggagcagg gcggagtggg tgcagcagta cgatctctta|120|
|ggaaaaatcg gcgaaggcac ttacggcctc gtcttcctcg cccgaaccaa atccccgtt|180|
|ggcactccct ccaaatccat tgccataaaa aagttcaagc aatccaagga cggcgacggc|240|
|gtctccccca ccgccatccg gaaaatcatg ttgctgaggg agattacgca cgagaacgtc|300|
|gtcaagctcg tcaacgtaca catcaaccac gccgacatgt ctctctacct cgccttcgat|360|
|tacgccgagc acgatctcta tgaaattatt aggcatcaca gggacaaact caaccattcc|420|
|attaatcagt acactgttaa gtctttgctc tggcagttgc tcaatggact aagctatctg|480|
|cacagtaatt ggatgataca tcgtgatttg aagccatcga atatattggt tatgggtgaa|540|
|ggagaggaac atggagttgt taagattgct gactttggac ttgcgaggat atatcaagct|600|
|cctctgaagc cgttatctga caatgggggtt gttgtaacca tttggtatcg tgcacctgag|660|
|ttgcttcttg gagcaaaaca ttataccagt gctgttgata tgtgggctat gggatgcatt|720|
|tttgctgagt tgttgacctt gaagccacta tttcaagggg cagaagtcaa agctacatca|780|
|aatccctttc agcttgacca acttgacaag atatttaagg ttttaggcca tcccacatta|840|
|gaaaagtggc cttccttagc aagtcttcca cattggcaac aagatgtgca acatatacaa|900|
|ggacacaaat atgacaatgc cggtctctat aatgttgtac acctgtctcc aaaaagccct|960|
|gcatatgacc tcttgtcaaa gatgcttgaa tatgatcctc gtaagcgttt aacagcagca|1020|
|caagctttgg agcatgagta tttcaaaatt gaaccattac ctggacgaaa tgcacttgta|1080|
|ccctgccaac ttggagagaa aattgtaaat tatcccactc gtccagtgga cactacaact|1140|
|gatcttgaag ggacaaccaa tctgccacct tcacaaacgg taaatgcagt ttctggtagc|1200|

-continued

```
atgcctggtc tcatgggtc aaatagatct gtgcctcggc caatgaatgt tgttggaatg    1260
caaagactgc cccctcaagc aatggcagct tataatctct catctcaggc agccatggga    1320
gatggaatga atcctgggga tatctcaaag catcgaggtg ttccacaggc ccatcagcca    1380
caacagttga aaggaagga gcaaatgggg atgccgggat accctgcaca acagaagtca    1440
agacgattat aaggtttctg ctggaagaga gactaagtga agatagattt ggggtcaata    1500
cttcagtacc tgaactcatg caggacattt ctggacagtg tttgccttca atacttgcaa    1560
gcctcacttt attgcaatca aagattgggt gcattcttct ctggaatttt gatgctaaaa    1620
tgccaaatgt atgctggaac accaatgaag ccataaaagg gaataaacgt atgaaagggt    1680
taagctactg taagcacatg tatatcatga ttataacaat gcaattctat tgtatttctt    1740
agcttttggg caagatcaat gtcagtaaac caaatgttga tcatccatta ggttttcata    1800
atggaacttt tcttgattaa atctataaca tgctacttttg tatttgtaga atattttgcc    1860
tcacatgatt gaagatagtt caaatatcac ttgcctttgg tatttccgtt ttgaattttt    1920
ctgtgatcac tggaatcaca gacttttcac tcccaaggag attattgaag ctttctgtga    1980
gtatgatgta aactttgttc ggagacgtag tagtatgaag atatgaaaag cagcaattgg    2040
gagaa                                                               2045
```

<210> SEQ ID NO 63
<211> LENGTH: 294
<212> TYPE: PRT
<213> ORGANISM: Triticum aestivum

<400> SEQUENCE: 63

```
Met Glu Gln Tyr Glu Lys Val Glu Lys Ile Gly Glu Gly Thr Tyr Gly
1               5                   10                  15

Val Val Tyr Lys Ala Arg Asp Arg Thr Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Gly Asn Ile Val
    50                  55                  60

Lys Leu His Asp Val Val His Ser Glu Lys Arg Ile Trp Leu Val Phe
65                  70                  75                  80

Glu Tyr Leu Asp Leu Asp Leu Lys Lys Phe Met Asp Ser Cys Pro Glu
                85                  90                  95

Phe Ala Lys Ser Pro Ala Leu Ile Lys Ser Tyr Leu Tyr Gln Ile Leu
            100                 105                 110

Arg Gly Val Ala Tyr Cys His Ser His Arg Val Leu His Arg Asp Leu
        115                 120                 125

Lys Pro Gln Asn Leu Leu Ile Asp Arg Arg Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ala Arg Gln Tyr Ser Thr Pro Val Asp Val Trp Ser Val Gly Cys
            180                 185                 190

Ile Phe Ala Glu Met Val Asn Gln Lys Pro Leu Phe Pro Gly Asp Ser
        195                 200                 205

Glu Ile Asp Glu Leu Phe Lys Ile Phe Arg Val Leu Gly Thr Pro Asn
    210                 215                 220
```

Glu Gln Thr Trp Pro Gly Val Ser Ser Leu Pro Asp Tyr Lys Ser Ala
225                 230                 235                 240

Phe Pro Arg Trp Gln Ala Glu Asp Leu Ala Thr Val Val Pro Asn Leu
            245                 250                 255

Glu Pro Val Gly Leu Asp Leu Leu Ser Lys Met Leu Arg Phe Glu Pro
        260                 265                 270

Asn Lys Arg Ile Thr Ala Arg Gln Ala Leu Glu His Glu Tyr Phe Lys
    275                 280                 285

Asp Met Glu Met Val Gln
    290

<210> SEQ ID NO 64
<211> LENGTH: 1170
<212> TYPE: DNA
<213> ORGANISM: Triticum aestivum

<400> SEQUENCE: 64

| | | | | | |
|---|---|---|---|---|---|
| gccccctct | ccccctcccc | cccacccccc | caatggcggc | agcagcagca | gcagcagcag | 60 |
| cagcttcgcc | cgccgcagcc | gctctccccc | gcccctcctc | cccgtgatcc | ccttcccctt | 120 |
| cccctccccc | gcttcctcct | ctccccccct | ccgcctcctc | acccatttcc | cacgcccgcg | 180 |
| ccgccgccgc | cgccgtagca | ttggacgccg | acccgatgga | gcagtacgag | aaggtggaga | 240 |
| agatcgggga | gggcacgtac | ggggtggtgt | acaaggcccg | ggacaggacc | accaacgaga | 300 |
| ccatcgcgct | caagaagatc | cgcctggagc | aggaggacga | gggcgtcccc | tccaccgcca | 360 |
| tccgcgagat | ctcgctcctc | aaggagatgc | agcacggcaa | catcgtcaag | ctgcacgatg | 420 |
| ttgtccacag | cgagaagcgc | atatggctcg | tctttgagta | cctggatctg | gacctgaaga | 480 |
| agttcatgga | ctcctgtcca | gagttttgcca | agagccccgc | cttgatcaag | tcatatctct | 540 |
| atcagatact | ccgcggcgtt | gcttactgtc | attctcatag | agttcttcat | cgagatttga | 600 |
| aacctcagaa | tttattgata | gaccggcgta | ctaatgcact | gaagcttgca | gactttggtt | 660 |
| tagcaagggc | atttggaatt | cctgtccgta | catttactca | tgaggtagta | acattatggt | 720 |
| acagagctcc | tgaaatcctt | cttggagcaa | ggcagtattc | cacaccagtt | gacgtgtggt | 780 |
| cagtgggctg | tatctttgca | gaaatggtga | accagaaacc | actgttccct | ggcgattctg | 840 |
| agattgatga | gctatttaag | atattcaggg | tactcggcac | tccaaatgaa | caaacttggc | 900 |
| caggcgtgag | ttccttgcct | gactacaagt | ccgccttccc | caggtggcag | gcagaggacc | 960 |
| ttgcaaccgt | tgtccccaat | cttgaacctg | ttggcctgga | ccttctctcg | aaaatgcttc | 1020 |
| ggttcgagcc | aaacaagagg | atcacggcta | ggcaggctct | tgagcatgag | tacttcaagg | 1080 |
| acatggagat | ggtacagtga | gctggctatg | tggtagtgac | tggcatatgt | atgagctgag | 1140 |
| ctgctcgttt | cattcctttt | gtgaacgctc | | | | 1170 |

<210> SEQ ID NO 65
<211> LENGTH: 475
<212> TYPE: PRT
<213> ORGANISM: Oryza sativa

<400> SEQUENCE: 65

Met Gly Asp Gly Arg Val Gly Gly Gly Thr Asn Arg Pro Ala Trp Leu
1               5                   10                  15

Gln Gln Tyr Glu Leu Val Gly Lys Ile Gly Glu Gly Thr Tyr Gly Leu
                20                  25                  30

Val Phe Leu Ala Arg Leu Lys Gln Ser His Pro His Ala Ala Ala Gly

```
                35                  40                  45
Val Gly Arg Arg Gly Ser Pro Ile Ala Ile Lys Lys Phe Lys Gln Ser
 50                  55                  60
Lys Glu Gly Asp Gly Val Ser Pro Thr Ala Ile Arg Glu Ile Met Leu
65                  70                  75                  80
Leu Arg Glu Ile Asn His Glu Asn Val Val Lys Leu Val Asn Val His
                85                  90                  95
Ile Asn His Ala Asp Met Ser Leu Tyr Leu Ala Phe Asp Tyr Ala Glu
            100                 105                 110
His Asp Leu Tyr Glu Ile Ile Arg His His Arg Glu Lys Leu Asn Leu
        115                 120                 125
Pro Ile Asn Pro Tyr Thr Val Lys Ser Leu Leu Trp Gln Leu Leu Asn
    130                 135                 140
Gly Leu Asn Tyr Leu His Ser Asn Trp Ile Ile His Arg Asp Leu Lys
145                 150                 155                 160
Pro Ser Asn Ile Leu Val Met Gly Glu Gly Glu His Gly Ile Ile
                165                 170                 175
Lys Ile Ala Asp Phe Gly Leu Ala Arg Ile Tyr Gln Ala Pro Leu Lys
            180                 185                 190
Pro Leu Ser Asp Asn Gly Val Val Thr Ile Trp Tyr Arg Ala Pro
        195                 200                 205
Glu Leu Leu Leu Gly Ala Lys His Tyr Thr Ser Ala Val Asp Met Trp
    210                 215                 220
Ala Val Gly Cys Ile Phe Ala Glu Leu Leu Thr Leu Lys Pro Leu Phe
225                 230                 235                 240
Gln Gly Val Glu Ala Lys Ala Thr Pro Asn Pro Phe Gln Leu Asp Gln
                245                 250                 255
Leu Asp Lys Ile Phe Lys Val Leu Gly His Pro Thr Val Glu Lys Trp
            260                 265                 270
Pro Thr Leu Ala Asn Leu Pro Cys Trp Gln Asn Asp Gln Gln His Ile
        275                 280                 285
Gln Gly His Lys Tyr Glu Asn Thr Gly Leu His Asn Ile Val His Leu
    290                 295                 300
Pro Gln Lys Ser Pro Ala Phe Asp Leu Leu Ser Lys Met Leu Glu Tyr
305                 310                 315                 320
Asp Pro Arg Lys Arg Ile Thr Ala Ala Gln Ala Leu Glu His Glu Tyr
                325                 330                 335
Phe Arg Met Asp Pro Leu Pro Gly Arg Asn Ala Leu Leu Pro Ser Gln
            340                 345                 350
Ala Gly Glu Lys Ile Val Gln Tyr Pro Val Arg Pro Val Asp Thr Thr
        355                 360                 365
Thr Asp Phe Glu Gly Thr Thr Ser Leu Gln Pro Thr Gln Ala Pro Ser
    370                 375                 380
Gly Asn Ala Ala Pro Gly Asn Gln Ser Val Val Pro Arg Pro Ile Pro
385                 390                 395                 400
Arg Gln Met Gln Gln Pro Met Val Gly Met Ser Arg Met Gly Gly Thr
                405                 410                 415
Asn Met Ala Ala Phe Gly Ala Pro Gln Gly Gly Ile Ala Gly Met
            420                 425                 430
Asn Pro Gly Asn Ile Pro Met Gln Arg Gly Ala Gly Ala Gln Ser His
        435                 440                 445
Pro His Gln Leu Arg Arg Lys Ala Asp Gln Gly Met Gly Met Gln Asn
    450                 455                 460
```

Pro Gly Tyr Pro Thr Gln Gln Lys Arg Arg Phe
465                 470                 475

<210> SEQ ID NO 66
<211> LENGTH: 1832
<212> TYPE: DNA
<213> ORGANISM: Oryza sativa

<400> SEQUENCE: 66

| | |
|---|---|
| gagcgtattt tggctttacg ccttcgtgtg gagtaaacgc cctttctgtt gggcgggttc | 60 |
| ggctggatct tttgttcccc cttttccttt cttctccggc agcggcggcg gcgatggggg | 120 |
| acggccgcgt cggaggtgga acgaatcggc cggcatggct gcagcaatac gaactagtgg | 180 |
| gcaagattgg cgaggggacc tacgcctcg tcttcctcgc tcgcctcaaa caatcgcatc | 240 |
| cccacgctgc cgctggcgtt ggccgccgtg gctctcccat cgccatcaag aagttcaagc | 300 |
| agtccaagga gggcgacggt gtctcgccca ccgccatcag agagatcatg cttctgcgtg | 360 |
| agatcaacca cgagaatgtt gtcaagctcg tcaatgttca catcaaccac gccgacatgt | 420 |
| ccctctacct cgccttcgat tacgccgagc acgatctcta tgagattatc aggcatcaca | 480 |
| gagagaagct taacctcccc ataaatccct acacagtcaa atctttgctc tggcaactgc | 540 |
| tcaatggtct caactatctc catagtaact ggattatcca tcgagatctc aagccttcta | 600 |
| atatactggt catgggagaa ggagaagaac atggaattat aaagattgct gattttggac | 660 |
| tcgctaggat atatcaagct ccattaaagc cattaagtga taacggggtt gttgttacca | 720 |
| tctggtatcg ggctccagag ttgttacttg ggcaaagca ctacacaagt gctgttgata | 780 |
| tgtgggcagt tggttgcatt tttgctgaat gcttacact caaaccactg ttccaaggtg | 840 |
| ttgaagccaa agctactcca aacccgtttc aacttgatca actagacaag atttttaagg | 900 |
| tcttaggtca tcctaccgtt gagaaatggc ctaccctcgc taatcttcca tgctggcaaa | 960 |
| acgatcaaca acacattcaa gggcataagt atgagaacac aggacttcat aatattgttc | 1020 |
| acttgcctca gaagagtcct gcgtttgatc ttctctcaaa aatgctcgag tatgatcctc | 1080 |
| gaaagcgtat aacagctgcg caagctttgg aacatgagta ctttcgaatg gatcctctgc | 1140 |
| ctggacggaa tgcacttta ccatcgcagg ctggagaaa aattgtgcaa tatcctgtgc | 1200 |
| gtccagttga taccaaact gattttgaag gaacaacaag ccttcaacca actcaagcgc | 1260 |
| catcagggaa cgcagctcct ggcaaccagt ctgtggtacc gagacccatt ccgaggcaaa | 1320 |
| tgcaacaacc catggtcggt atgtcgagaa tgggtggtac aaacatggcg gcctttggtg | 1380 |
| cagctccgca aggaggcata gctgggatga atcctggtaa tattccaatg cagaggggcg | 1440 |
| ctggagccca atctcatccg catcagttga aaggaaagc tgatcaaggg atggggatgc | 1500 |
| agaaccccgg ttatcctact caacagaaga ggcggttctg accgactgaa tttgtaattg | 1560 |
| tatatctatt tggtgtgtta cttgtgagca cgcttagctt ttgcggtggt tgctcctagt | 1620 |
| cgtacagtga gaattgtatc tgttctgttg taattgaacg ccatcacaac caacacctct | 1680 |
| actagttagt tactagagtg actacgcaga cagggccagg ttgccgatga tgccatcacc | 1740 |
| aatggagaca ggcatacccca gccagagttt cgccaatact ctgcccctg aacccaacca | 1800 |
| atgaatgaat tggcatcgta cgatctattt ca | 1832 |

<210> SEQ ID NO 67
<211> LENGTH: 20
<212> TYPE: DNA
<213> ORGANISM: Artificial Sequence

```
<220> FEATURE:
<223> OTHER INFORMATION: A synthetic oligonucleotide

<400> SEQUENCE: 67
accgagacac attcccgatt                                              20

<210> SEQ ID NO 68
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 68
catcaggctt gcatgccatt                                              20

<210> SEQ ID NO 69
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 69
acgaataaga gcgtccattt tagag                                        25

<210> SEQ ID NO 70
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 70
tcttcctcgt gacaaaacgc a                                            21

<210> SEQ ID NO 71
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 71
ccaaacacag aaccatctcc aca                                          23

<210> SEQ ID NO 72
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 72
ccggatcgta tcggttttcg                                              20

<210> SEQ ID NO 73
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 73
acggttcctc tatgcctcaa gtc                                          23
```

```
<210> SEQ ID NO 74
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 74
gtggagtggt ctaaagcaac cttc                                            24

<210> SEQ ID NO 75
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 75
ataacgctgc ggacatctac att                                             23

<210> SEQ ID NO 76
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 76
tcaggaagac agagtgttcc c                                               21

<210> SEQ ID NO 77
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 77
tgcgtttctc taagaaccga g                                               21

<210> SEQ ID NO 78
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 78
ttgggtgatg gttcacgtag                                                 20

<210> SEQ ID NO 79
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 79
gcttataccg aaaccccgat tccag                                           25

<210> SEQ ID NO 80
<211> LENGTH: 25
<212> TYPE: DNA
<213> ORGANISM: Artificial Sequence
<220> FEATURE:
<223> OTHER INFORMATION: A synthetic oligonucleotide
```

<400> SEQUENCE: 80
ggctcattga gatcaggaag aacca                         25

<210> SEQ ID NO 81
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 81
ttgggtgatg gttcacgtag                               20

<210> SEQ ID NO 82
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 82
gacacacatc actgtcactt c                             21

<210> SEQ ID NO 83
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 83
agtttctgag gtctctacct tc                            22

<210> SEQ ID NO 84
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 84
ccgttttgta tatcccgttt ccgt                          24

<210> SEQ ID NO 85
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 85
atgcgacttg gaacttcgcc                               20

<210> SEQ ID NO 86
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 86
ggaggatccg aaccgtctg                                19

<210> SEQ ID NO 87

```
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 87
acgtccgcaa tgtgttatta                                                    20

<210> SEQ ID NO 88
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 88
tgtcctaaga gtccgccgtt gt                                                 22

<210> SEQ ID NO 89
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 89
tttggaggat ccgacccgtt tg                                                 22

<210> SEQ ID NO 90
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 90
taccgcataa tcatggtcgt c                                                  21

<210> SEQ ID NO 91
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 91
tcatgctcat tgcattagtc g                                                  21

<210> SEQ ID NO 92
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 92
ctttgaagac gtggttggaa cg                                                 22

<210> SEQ ID NO 93
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 93
```
atttctcgat cgccgtcgta gt                                    22

<210> SEQ ID NO 94
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 94
gccaaagagc tttggtctta gagtg                                 25

<210> SEQ ID NO 95
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 95
gtctaagcgt caatttgttt acacc                                 25

<210> SEQ ID NO 96
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 96
gcacgtgacc aaatttgcag a                                     21

<210> SEQ ID NO 97
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 97
tgaagagagg aggatgatga gga                                   23

<210> SEQ ID NO 98
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 98
aaacctcctc ggattccatt gc                                    22

<210> SEQ ID NO 99
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 99
atgtcgagtt ctatggaatg                                       20

<210> SEQ ID NO 100
<211> LENGTH: 20
<212> TYPE: DNA

<213> ORGANISM: Artificial Sequence
<220> FEATURE:
<223> OTHER INFORMATION: A synthetic oligonucleotide

<400> SEQUENCE: 100
tcatatttca gctgctaaac                                              20

<210> SEQ ID NO 101
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 101
atgtcgagtt tttctgccga                                              20

<210> SEQ ID NO 102
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 102
ttaccgtgaa ctgagccaag                                              20

<210> SEQ ID NO 103
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 103
atggagagag attttctcgg g                                            21

<210> SEQ ID NO 104
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 104
ttaggttgca gagctgagag aag                                          23

<210> SEQ ID NO 105
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 105
atggagagag attttctcgg gctgg                                        25

<210> SEQ ID NO 106
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 106
ttagtgcaga tgatgagctg gagga                                        25

<210> SEQ ID NO 107
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 107
atgtcgtcga gcaatgaaaa						20

<210> SEQ ID NO 108
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 108
ctatagcctt agatcgagat						20

<210> SEQ ID NO 109
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 109
atgtcaacgg gacaagcgc						19

<210> SEQ ID NO 110
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 110
ctaaagcttg agttcaaggt						20

<210> SEQ ID NO 111
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 111
atgatcatca tcatcaaaaa ctg					23

<210> SEQ ID NO 112
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 112
ctatcggtaa cggtggtaag						20

<210> SEQ ID NO 113
<211> LENGTH: 20
<212> TYPE: DNA
<213> ORGANISM: Artificial Sequence
<220> FEATURE:

<223> OTHER INFORMATION: A synthetic oligonucleotide

<400> SEQUENCE: 113
atggaaagag attttctggg                                          20

<210> SEQ ID NO 114
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 114
ttatgtagga gaagtagaag                                          20

<210> SEQ ID NO 115
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 115
atgtcgaaag ctaccataga ac                                       22

<210> SEQ ID NO 116
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 116
gatagtaagg agatgttgat actaatctct                               30

<210> SEQ ID NO 117
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 117
atgaagggtt gcagcttaga                                          20

<210> SEQ ID NO 118
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 118
ttagaaatta tgaagagagg agg                                      23

<210> SEQ ID NO 119
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 119
atggctgatg gtgaagacat tcaa                                     24

```
<210> SEQ ID NO 120
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 120
tcagaagcac ttcctgtgaa caat                                            24

<210> SEQ ID NO 121
<211> LENGTH: 64
<212> TYPE: DNA
<213> ORGANISM: Artificial Sequence
<220> FEATURE:
<223> OTHER INFORMATION: A synthetic oligonucleotide

<400> SEQUENCE: 121
ccttccacac tggcaaaatg atgttcaaca cattcaagct cacaaatacg acagtgtggg     60
tctc                                                                  64
```

ELEVATED RESISTANCE TO INSECTS AND PLANT PATHOGENS WITHOUT COMPROMISING SEED PRODUCTION

This application claims benefit of priority to the filing date of U.S. Provisional Application Ser. No. 62/916,609, filed Oct. 17, 2019, the contents of which are specifically incorporated herein by reference in their entirety.

GOVERNMENT FUNDING

This invention was made with government support under DE-FG02-91ER20021 awarded by the U.S. Department of Energy. The government has certain rights in the invention.

BACKGROUND OF THE INVENTION

Currently, a main control strategy for insect pests is the application of insecticides, aimed at killing adults, juveniles and eggs. Besides the substantial costs of insecticide application this practice has a severe environmental impact. Emerging resistance to insecticides makes control of insect pests difficult.

Sustainable food production for an increasing world population likely depends on the next generation of "designer" crops that exhibit both superior yield and resilience to harsh environmental conditions, including environmental and biotic stresses. Such environmental and biotic stresses include drought, insects, and salt stresses. High yield/growth potential, however, is typically associated with reduced plant immunity, and vice versa; this phenomenon is often referred to as the plant "dilemma" to grow or defend.

There is a need for new ways of controlling crop damage and losses due to plant insect pests, both in field-grown and greenhouse-grown crops without adversely affecting plant immunity.

SUMMARY

Described herein are plants and methods providing improved defenses to increased resistance to pests and environmental stresses. The plants and method involve jaz mutations to reduce JAZ repressors of defense (that can reduce plant growth) combined with CYCLIN-DEPENDENT KINASE 8 (CDK8) mutations that restore growth of the jaz mutant plants without compromising the elevated pest defense.

Plants with reduced JAZ expression and/or reduced JAZ functioning have reduced growth, and a smaller stature. However, as shown herein, combining loss of JAZ with loss of CDK8 functioning can lead to plants that exhibit good vegetative growth stature while simultaneously maintaining strong biotic stress resistance to insects and pathogens. One example of a plant line with reduced JAZ functioning is the jazD plant line. Mutation of CDK8 in the jazD genetic background improved the reproductive output of jazD, achieving seed yields that were comparable to or even greater than wild type plants. Therefore, described herein is a useful strategy to promote strong pest and biotic stress resistance while improving seed production and growth.

The plants can have one or more loss of function mutations in at least one JAZ gene. For example, plants, and seeds described herein have endogenous jazD mutations that include mutations in the genes encoding JAZ1, JAZ2, JAZ3, JAZ4, JAZ5, JAZ6, JAZ7, JAZ9, JAZ10, and/or JAZ13 proteins. Such mutations have reduced JAZ1, JAZ2, JAZ3, JAZ4, JAZ5, JAZ6, JAZ7, JAZ9, JAZ10, and/or JAZ13 activity. For example, in some cases the expression of JAZ1, JAZ2, JAZ3, JAZ4, JAZ5, JAZ6, JAZ7, JAZ9, JAZ10, and/or JAZ13 proteins is undetectable. Similarly, in mutant cdk8 plant cells, mutant cdk8 plants, and/or mutant cdk8 seeds the endogenous CDK8 proteins have reduced activity or their expression is undetectable. However, in some cases endogenous JAZ8, JAZ11 and JAZ12 genes are not modified or mutated in the jaz cdk8 plant cells, plants and plant seeds. Hence, endogenous JAZ8, JAZ11, and JAZ12 proteins can still be active in some cells and can be expressed in the mutant Jaz cdk8 plant cells, plants and/or plant seeds.

In some cases, the plants or a plant grown from the seeds described herein have at least 5% less leaf damage from insect feeding than a wild type plant of the same species grown under the same conditions. In some cases, the plants or a plant grown from the seeds described herein have the same or at least about 10% more seed yield than a wild type plant of the same species grown under the same conditions.

Methods of generating such plants, seed, and plant cells as well as methods of cultivating such plant seeds and plants are also described herein.

DESCRIPTION OF THE FIGURES

FIGS. 1A-1D illustrate the pedigree and structure mutated JAZ genes in the *Arabidopsis* jazD plant line. FIGS. 1A-1 to 1A-4 illustrate the jazD pedigree. The jazD plants have loss-of-function mutations in ten JAZ genes: Jaz1, Jaz2, Jaz3, Jaz4, Jaz5, Jaz6, Jaz7, Jaz9, Jaz10, and Jaz13. The 'x' and the term 'self' indicate cross-pollination and self-pollination, respectively. The Jaz single mutants in boxes were previously characterized. FIG. 1A-1 illustrates crosses for generating jaz3-4/jaz3-3 jaz4-1 jaz9-4/+gl1-2/+ genotypes. FIG. 1A-2 illustrates crosses for generating jaz5-1/+jaz10-1/+gl1-2/+genotypes and the jaz-2 gl1-2 genotypes. FIG. 1A-3 illustrates crosses for generating jaz1-2 jaz4-1/+jaz9-4/+jaz3-4/+jaz10-1 gl1-2/+ genotypes, and jaz-5-1 jaz1-2 jaz4-1 jaz9-4 jaz3-4 jaz10-1 jaz7-1/+gla-2+ genotypes, and jaz3-4+jaz13-1/+ genotypes. FIG. 1A-4 illustrates crosses for generating the jazD genotype (jaz5-jaz1-2 jaz4-1 jaz9-4 jaz6-4 jaz2-3 jaz7-1 jaz3-4 jaz13-1 jaz10-1). The jaz2-1, jaz3-3, jaz9-1 alleles were characterized by Thines et al. *Nature* 448:661-665 (2007); and Chini et al. *Nature* 448:666-671 (2007). The jaz6-Wisc was characterized by the inventors, but jaz2-3, jaz3-4, jaz6-4 and jaz9-4 were later selected as alternative alleles for construction of jazD. gl1-2 was included to study trichome development. Male sterility of coil-1 mutants was exploited to assist in selection of rare recombination events between closely linked loci (Barth & Jander *Plant J* 46:549-562 (2006)). FIG. 1B illustrates a phylogenetic tree of thirteen JAZ proteins in *Arabidopsis*. Black and open (white) asterisks denote JAZ genes that contain insertion mutations in jazQ and jazD, respectively. FIG. 1C shows schematic diagrams of insertion mutations used for construction of jazQ and jazD. The jazQ plant lines have loss-of-function mutations in the Jaz1, Jaz3, Jaz4, Jaz9, and Jaz10. White boxes represent untranslated regions (UTRs), while shaded boxes represent exons. The identity and position of each insertion mutation is shown. Arrows beneath the exons show the position of primers used to assess expression of JAZ genes by RT-PCR. FIG. 1D illustrates expression of JAZ genes in wild-type Col-0 (WT), jazQ, and jazD in *Arabidopsis* plant leaves as evaluated by RT-PCR analysis. RNA was extracted from rosette leaves of 23-day-old plants grown under long-day conditions. The ACTIN1 gene (At2g37620) was used as a positive control. Arrows denote PCR products that have the predicted size of full-length JAZ transcripts. Note that some bands in the Jaz4 gel are artefacts and do not indicate that a Jaz4 transcript was expressed.

FIG. 2A graphically illustrates root length of 8-day-old wild type Col-0 (WT), jazQ, and jazD seedlings grown in the presence of 0, 5, or 25 µM methyljasmonate (MeJA). The data show the mean±SD of 30 plants per genotype at each concentration. Capital letters denote significant differences according to Tukey's honest significant difference (HSD) test (P<0.05). FIG. 2B shows that jazD leaves are hypersensitive to coronatine (COR). The eighth leaf of 40-day-old plants from different plant types grown under 12-hour light/12-hour dark photoperiods was treated with 5 µL water (mock) or 50 µM coronatine (COR). Leaves were excised and photographed after 2 or 4 days of treatment. Arrows denote location of visible anthocyanin accumulation at the site of coronatine application. The images to the right are enlargements of photograph of the COR-treated jazD leaves. (Scale bars: 1 cm.) FIG. 2C graphically illustrates the relative growth rate (RGR) of soil-grown wild type (WT), jazQ, and jazD plants. FIG. 2D graphically illustrates the total fatty acid content in wild type (WT), jazQ, and jazD seeds. Data show the mean±SD of seeds obtained from five plants per genotype. FIG. 2E graphically illustrates the time course of seed germination. Bars indicate the percentage of germinated seeds at various times after sowing on water agar: lowest stippled portion, day 1; open portion, day 2; striped portion, day 3; and all later times: top hatched portion, nongerminated seeds.

FIGS. 3A-3F illustrates that jazD plants are highly resistant to insect herbivores and necrotrophic pathogens. FIG. 3A shows images of representative short-day grown wild type Col-0 (WT), jazQ, and jazD plants before and after challenge with four T. ni larvae for 12 days (scale bar: 3 cm). FIG. 3B graphically illustrates weight gain of T. ni larvae reared on plants shown in FIG. 3A. Data shown are the mean±SD of at least 30 larvae per genotype. Capital letters denote significant differences according to Tukey's HSD test (P<0.05). FIG. 3C is a heat map displaying the expression level of various jasmonate/ethylene-responsive genes in leaves of jazQ and jazD normalized to wild type. ACT, agmatine coumaroyl transferase (accession no. At5g61160). FIG. 3D shows images of representative leaves illustrating symptoms following 5 days of treatment with B. cinerea spores or mock solution (scale bars: 2 cm). FIG. 3E graphically illustrates disease lesion size on leaves of the indicated genotypes following 5 days of treatment with B. cinerea spores for the indicated plant lines. Data show the mean±SD of at least 19 leaves per genotype. Capital letters denote significant differences (Tukey's HSD test, P<0.05). FIG. 3F graphically illustrates apical hook angles of seedlings grown in the presence of various concentrations of the ethylene precursor 1-aminocyclopropane-1-carboxylic acid (ACC). Data shown are the mean±SD of at least 21 seedlings per genotype. Asterisks denote significant difference compared with WT (Tukey's HSD test, *P<0.05).

FIG. 4A schematically illustrates that mapping of differentially regulated genes in jazD to various metabolic pathways results in elevated production of defense metabolites derived from amino acids. Mapped pathways include photosynthesis (1), pentose phosphate pathway (2), shikimate pathway (3), amino acids from pentose phosphate intermediates (4), glycolysis (5), amino acids from glycolysis intermediates (6). TCA cycle (7), amino acids from TCA intermediates (8), sulfur metabolism (9), and defense metabolites from amino acids (0.10). Shading on the arrows denotes the average fold-change of differentially expressed transcripts mapping to a particular pathway (P<0.05). FIG. 4B shows a schematic of the tryptophan biosynthetic pathway from erythrose 4-phosphate (E4P), phosphoenolpyruvate (PEP), and 3-phosphoglycerate (3PG) showing up-regulation of genes and proteins in jazD. Each arrow represents an enzymatic reaction in the pathway. Boxes represent individual genes with at least 2-fold-change for jazD relative to wild type according to RNA-seq data, whereas genes without boxes denote genes with no significant change in expression. Gene names within boxes denote significantly increased protein levels according to proteomics data. Gene abbreviations: AnPRT, anthranilate phosphoribosyltransferase; AS, anthranilate synthase; CS, chorismate synthase; DHQS, 3-dehydroquinate synthase; DHS, 3-deoxy-7-phosphoheptulonate synthase; DQD/SDH, 3-dehydroquinate dehydratase/shikimate dehydrogenase; EPSP, 5-enolpyruvylshikimate-3-phosphate synthase; IGPS, indole-3-glycerol-phosphate synthase; IGs, indole glucosinolates; OAS, 0-acetylserine lyase; PAI, phosphoribosylanthranilate isomerase; PGDH, phosphoglycerate dehydrogenase; PSAT, phosphoserine aminotransferase; PSP, phosphoserine phosphatase; SAT, serine acetyltransferase; SK, shikimate kinase; TSA, tryptophan synthase alpha subunit; TSB, tryptophan synthase β-subunit. FIG. 4C graphically illustrates indole glucosinolate levels in jazD leaves relative to indole glucosinolate levels in wild type leaves. Asterisks denote significant differences in comparison with WT (Student's t test. *P<0.05). Abbreviations: I3M, indol-3-ylmethyl (glucobrassicin); OH-I3M, 4-hydroxyindol-3-ylmethyl (hydroxyglucobrassicin); 4MOI3M, 4-methoxyindol-3-ylmethyl (methoxyglucobrassicin); 1MOI3M, 1-methoxyindol-3-ylmethyl (neoglucobrassicin). FIG. 4D graphically illustrates net gas exchange rates in wild type and jazD rosette leaves measured at 400 µmol $CO_2$ and 20° C. after acclimation in 500 µmol $m^{-2}$ $s^{-1}$ in light. FIG. 4E graphically illustrates net gas exchange rate in wild type and jazD rosette leaves measured at 400 µmol $CO_2$ and 20° C. after acclimation in 500 µmol $m^{-2}$ $s^{-1}$ in the dark. FIG. 4F graphically illustrates daytime respiration on a leaf area basis. Daytime respiration was determined from the intersection of $CO_2$ response curves measured at sub-saturating light intensities. FIG. 4G graphically illustrates nighttime dark respiration. Data shown for FIGS. 4F-4G are the mean±SD of four replicates per genotype.

FIG. 5A shows a time course of starch levels in wild type Col-0 (WT) and jazD plants during a long day photoperiod. FIG. 5B shows a time course of sucrose levels in wild type Col-0 (WT) and jazD plants during a long day photoperiod. Asterisks in FIGS. 5A-5B show that significant differences exist in comparison with WT (Student's t test, *P<0.05). FIG. 5C shows a heat map illustrating the expression level of sugar starvation marker (SSM) genes in jazQ and jazD leaves. Gene-expression levels determined by RNA-seq are represented as fold-change (log 2) over WT. FIG. 5D shows a photograph of 16-day-old wild type, jazQ, and jazD seedlings grown horizontally on MS medium containing the indicated concentration of sucrose (scale bar: FIG. 5D, 0.5 cm). FIG. 5E graphically illustrates dry weight (DW) of 16-day-old wild type, jazQ, and jazD seedlings grown horizontally on MS medium containing one of the concentrations of sucrose indicated in the key above graph. FIG. 5F graphically illustrates the root length of 11-day-old wild type, jazQ, and jazD seedlings grown vertically on MS medium lacking sucrose (open bar) or containing 23 mM sucrose (filled bar). Two-way ANOVA was used to test the effect of sucrose on growth (FIGS. 5E and 5F) and showed that, whereas genotype (P<0.001 for both WT vs. jazQ and WT vs. jazD) and sucrose (P<0.001 for both WT vs. jazQ and WT vs. jazD) significantly affect shoot and root growth, the genotype×sucrose interaction was significant only for jazD comparisons.

FIG. 6A illustrates root length of 10-day-old wild type Col-0 (WT), jazD, and jazU seedlings grown in the presence of 0, 0.2, or 1 µM MeJA. Data show the mean SD of 14-20 seedlings per genotype at each concentration. Capital letters denote significant differences according to Tukey's HSD test (P<0.05). FIG. 6B shows a photograph of WT, jazQ, jazD, and jazU rosettes of 28-d-old plants. FIG. 6C shows a photograph of WT, jazD, and jazU inflorescence of 8-week-old plants.

FIG. 7A graphically illustrates total rosette biomass of short day-grown plants of the indicated genotypes. FIG. 7B graphically illustrates total seed yield of plants of the indicated genotypes. FIG. 7C graphically illustrates resistance to insect feeding by *Trichoplusia ni* insect larvae on plants of the indicated genotypes. Data points show the mean±SD of at least five plants per genotype. As shown, jazD plants strongly defend against larval infestation and the cdk8 loss of function mutation helps jazD plants maintain good growth improved seed production.

FIGS. 8A-8D illustrate increased growth and improved defenses against insects by the cdk8 loss-of-function mutant line (sjd56), which has the cdk8 loss-of-function mutation in the jazD genetic background. The results for the sjd56 plants are compared to those for the jazD and wild type plants. FIG. 8A graphically illustrates rosette fresh weight of 58-day-old wild type Col-0 (WT), jazD and sjd56 plants grown under short-day (8-h-light/16-h-dark) conditions. FIG. 8B graphically illustrates projected leaf area of 58-day-old wild type Col-0 (WT), jazD and sjd56 plants grown under short-day (8-h-light/16-h-dark) conditions. Data shown for FIGS. 8A-8B are the mean±SD of five plants per genotype. Letters denote significant difference according to Tukey's HSD test (P<0.05). Scar bar, 2 cm. FIG. 8C graphically illustrates anthocyanin levels in leaves of 23-day-old WT, jazD and sjd56 plants grown under long-day (16-h-light/8-h-dark) conditions. Data show the mean±SD of five plants per genotype. FIG. 8D graphically illustrates *Trichoplusia ni (T. ni)* weight after feeding on WT, jazD and sjd56 plants for ten days. Plants were grown under the photoperiods of 16-h-light/8-h-dark for 67 days. Data show the mean±SD of at least ten larvae per genotype.

FIG. 9A illustrates the growth and rosette fresh weights (numbers under the images) of representative Col-0 (WT), cdk8-1, cdk8-2, jazD, jazD cdk8-1 and jazD cdk8-2 plants. Plants were grown under short-day conditions (8-h-light/16-h-dark) for 58 days. Data show the mean±SD of five plants per genotype. Letters denote significant difference according to Tukey's HSD test (P<0.05). Scale bar, 2 cm. FIG. 9B graphically illustrates the number of days until the first flower opens for WT, cdk8-1, cdk8-2, jazD, jazD cdk8-1 and jazD cdk8-2 plants. FIG. 9C graphically illustrates the number of rosette leaves at bolting for WT, cdk8-1, cdk8-2, jazD, jazD cdk8-1 and jazD cdk8-2 plants. For FIGS. 9B-9C, plants were grown under long-day (16-h-light/8-h-dark) conditions in soil. Data show the mean±SD of ten plants per genotype. Letters denote significant difference according to Tukey's HSD test (P<0.05). FIG. 9D graphically illustrates the seed yield from WT, cdk8-1, cdk8-2, jazD, jazD cdk8-1 and jazD cdk8-2 plants FIG. 9E graphically illustrates the average seed mass of seeds from WT, cdk8-1, cdk8-2, jazD, jazD cdk8-1 and jazD cdk8-2 plants. Seed yield was determined by collecting all seeds from individual plants. Average seed mass was determined by weighing batches of 100 seeds. Data show the mean±SD of at least five plants per genotype. Letters denote significant difference compared with WT plants according to Tukey's HSD test (P<0.05). FIG. 9F graphically illustrates projected leaf area of different plant types, showing that loss of cdk8 positively impacts the growth of jazD. The leaf area of Col-0 (WT), cdk8-1, cdk8-2, jazD, jazD cdk8-1 and jazD cdk8-2 plants was measured after growth under short-day (8-h-light/16-h-dark) conditions for 58-days. Data show the mean±SD of five plants per genotype. Letters denote significant difference according to Tukey's HSD test (P<0.05). FIG. 9G graphically illustrates the rosette diameter of Col-0 (WT), cdk8-1, cdk8-2, jazD, jazD cdk8-1 and jazD cdk8-2 plants measured after growth under short-day (8-h-light/16-h-dark) conditions for 58-days. Data show the mean±SD of five plants per genotype. Letters denote significant difference according to Tukey's HSD test (P<0.05). FIG. 9H graphically illustrates silique number per plant for WT, cdk8-1, cdk8-2, jazD, jazD cdk8-1 and jazD cdk8-2 plants grown under long-day (16-h-light/8-h-dark) conditions in soil. Fully elongated 7th, 9th, and 11th siliques were collected for measurements of silique traits (silique length and number of seeds per silique). These traits were used with total seed yield to calculate the number of siliques per plant. Letters denote significant difference according to Tukey's HSD test (P<0.05).

FIG. 10A shows representative images of *Trichoplusia ni (T. ni)* larvae after feeding on short-day-grown (8-h-light/16-h-dark) WT Col-0 (WT), cdk8-1, cdk8-2, jazD, jazD cdk8-1 and jazD cdk8-2 plants for nine days. Scale bar, 1 cm. FIG. 10B graphically illustrates the larval weight of *T. ni* shown in FIG. 10A. Data shown are the mean±SD of at least 18 larvae per genotype. Letters denote significant difference according to Tukey's HSD test (P<0.05).

FIG. 1A graphically illustrates anthocyanin levels in leaves of 25-day-old WT Col-0 (WT), cdk8, jazD and jazD cdk8 plants. Plants were grown under long-day conditions (16-h-light/8-h-dark) in soil. Data show the mean±SD of three plants per genotype. Letters denote significant differences according to Tukey's HSD test (P<0.05). FIG. 1B graphically illustrates comparison of indole glucosinolates levels in WT, cdk8, jazD and jazD cdk8 leaves. FIG. 11C graphically illustrates Nδ-acetylornithine levels in WT, cdk8, jazD and jazD cdk8 leaves. FIG. 1D graphically illustrates hydroxycinnamic acid amides (HCAAs) levels in WT, cdk8, jazD and jazD cdk8-1 leaves. Defense compounds were extracted from leaves of 23-day-old plants grown under long-day conditions (16-h-light/8-h-dark). Peak area for the indicated compound in the WT sample was set to "1" and the peak area of the same compound in other genotypes was normalized to the WT sample. Abbreviations: I3M: indol-3-ylmethyl, glucobrassicin; OH-I3M: 4-hydroxyindol-3-ylmethyl, hydroxyglucobrassicin; 4MOI3M: 4-methoxyindol-3-ylmethyl, methoxyglucobrassicin; 1MOI3M: 1-methoxyindol-3-ylmethyl, neoglucobrassicin. Data show the mean±SD of three biological replicates per genotype. Letters denote significant differences according to Tukey's HSD test (P<0.05). FIG. 11E graphically illustrates relative expression levels of VEGETATIVE STORAGE PROTEIN 2 (VSP2, accession no. AT5G24770) while FIG. 11F graphically illustrates relative expression levels of PLANT DEFENSIN 1.2 (PDF1.2, accession no. AT5G44420) in leaves of 25-day-old WT, cdk8, jazD and jazD cdk8 plants grown under long-day conditions (16-h-light/8-h-dark). PP2A (AT1g13320) was used for qPCR normalization. Data show the mean±SD of three biological replicates per genotype. Letters denote significant differences according to Tukey's HSD test (P<0.05).

FIG. 13A is a schematic of tryptophan biosynthesis from chorismate. Tryptophan feedback inhibits the activity of anthranilate synthase (AS). Although 5-methyl-tryptophan (5-MT) inhibits anthranilate synthase activity, it cannot be used for the production of proteins. The abbreviations used in FIG. 13A are: TRP, anthranilate phosphoribosyltransferase: PAI, phosphoribosylanthranilate isomerase; IGPS, indole-3-glycerol-phosphate synthase; TSA, tryptophan synthase alpha subunit: TSB, tryptophan synthase beta subunit. FIG. 13B graphically illustrates root length of WT, cdk8-1, jazD, and jazD cdk8-1 10-day-old seedlings grown on medium supplemented with 0 or 15 µM of 5-methyl-tryptophan (5-MT). Data shown are the mean±SD of at least 24 seedlings per genotype at each 5-MT concentration. Letters denote significant differences according to Tukey's HSD test (P<0.05).

DETAILED DESCRIPTION

Figures 1, 1A:
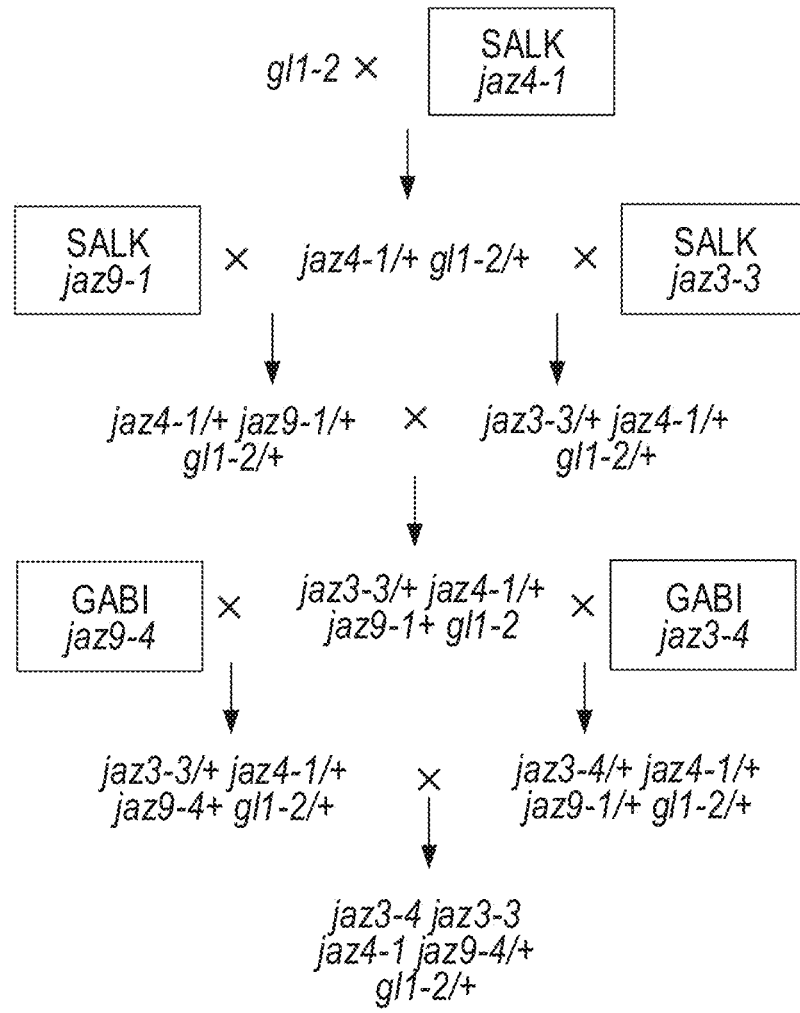
Figures 1, 1A, 2:
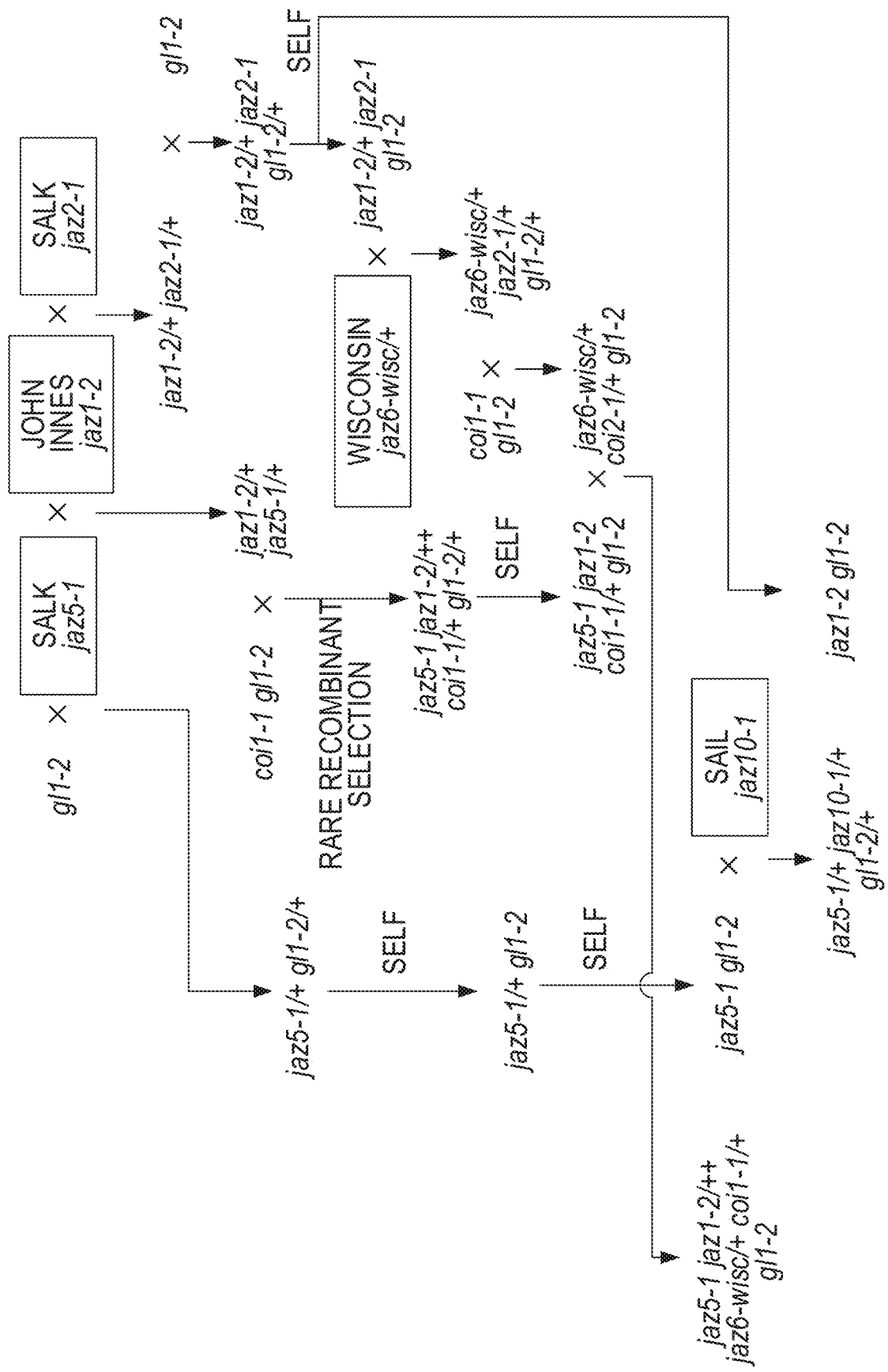

Described herein are plants that have loss-of-function jaz decuple (jazD) mutations and loss-of-function CYCLIN-DEPENDENT KINASE 8 (CDK8) mutations. The jazD plants, by comparison to wild-type (WT) and jazQ plants, are highly resistant to both insect herbivores and necrotrophic pathogens but also exhibit reduced vegetative growth and reduced seed yield. However, when the jazD loss-of-function mutations are coupled with CDK8 loss-of-function mutations, plant growth is restored while the plants maintain strong biotic stress resistance to insects and pathogens. Moreover, mutation of CDK8 in the jazD genetic background seemed to improve the reproductive output of jazD, achieving seed yields that were comparable to or even greater than wild type plants.

Hence, described herein are jazD, cdk8 loss-of-function plants and seeds with resistance to insects and pathogens that grow as well as wild type plants and that have seed yields that were comparable to or even greater than wild type plants.

Methods of making such plants and seeds as well as methods of cultivating such plants and seeds are also described herein.

Mutation Methods

Plants and methods of making such plants are described herein that grow well and are resistant to environmental stresses such as drought and insects. The plants have mutations that reduce or eliminate the expression or function of proteins that modulate jasmonic acid responses (e.g., JAZ genes/proteins). Plants with such mutations are referred to herein as jaz mutants or jaz plants. Such reduction/elimination of jasmonic acid regulatory protein expression and/or function improves the resistance (compared to wild type plants) of jaz mutant plants to insects and biotic stress. An additional mutation that reduces or eliminates the function of the cdk8 gene improves the growth of jazD mutant plants.

Plants with jazD mutations exhibit significantly improved resistance to insects and biotic stress, and when combined with loss-of-function cdk8 mutations, the plants grow reproduce well.

The jazD plants have loss-of-function mutations in ten JAZ genes: JAZ1, JAZ2, JAZ3, JAZ4, JAZ5, JAZ6, JAZ7, JAZ9, JAZ10, and JAZ13. Such jazD plants therefore have three remaining intact JAZ genes: JAZ8, JAZ11, and JAZ12. For example, plants with jazD mutations have transcription and/or translation of JAZ1, JAZ2, JAZ3, JAZ4, JAZ5, JAZ6, JAZ7, JAZ9, JAZ10, and JAZ13 reduced by at least 20%, or at least 30%, or at least 40%, or at least 50%, or at least 60%, or at least 70%, or at least 80%, or at least 90%, or at least 95%, or at least 97%, or at least 99% compared to wild type plant cells, plants, and seeds of the same species (that do not have the jazD). In some cases, plants with jazD mutations have transcription and/or translation of JAZ1, JAZ2. JAZ3, JAZ4, JAZ5, JAZ6, JAZ7, JAZ9, JAZ10, and JAZ13 reduced by at least 100%.

The jazD mutations are combined with loss-of-function cdk8 mutations. For example, plants with loss-of-function cdk8 mutations have transcription and/or translation of CDK8 reduced by at least 20%, or at least 30%, or at least 40%, or at least 50%, or at least 60%, or at least 70%, or at least 80%, or at least 90%, or at least 95%, or at least 97%, or at least 99% compared to wild type plant cells, plants, and seeds of the same species (that do not have the cdk8 loss-of-function mutation). In some cases, plants with cdk8 mutations have transcription and/or translation of CDK8 proteins reduced by at least 100%.

Non-limiting examples of methods of introducing a modification into the genome of a plant cell can include microinjection, viral delivery, recombinase technologies, homologous recombination, TALENS, CRISPR, and/or ZFN, see, e.g. Clark and Whitelaw Nature Reviews Genetics 4:825-833 (2003); which is incorporated by reference herein in its entirety.

For example, nucleases such as zinc finger nucleases (ZFNs), transcription activator like effector nucleases (TALENs), and/or meganucleases can be employed with guide nucleic acid that allows the nuclease to target the genomic JAZ and CDK8 site(s). In some cases of the various aspects described herein, a targeting vector can be used to introduce a deletion or modification of the genomic JAZ and CDK8 chromosomal sites.

A "targeting vector" is a vector generally has a 5' flanking region and a 3' flanking region homologous to segments of the gene of interest. The 5' flanking region and a 3' flanking region can surround a DNA sequence comprising a modification and/or a foreign DNA sequence to be inserted into the gene. For example, the genomic JAZ and CDK8 site(s) can be disrupted by insertion of T-DNA. In another example, the foreign DNA to be inserted may encode a selectable marker, such as an antibiotics resistance gene. Examples for suitable selectable markers include chloramphenicol resistance, gentamycin resistance, kanamycin resistance, spectinomycin resistance (SpecR), neomycin resistance gene (NEO) and hygromycin β-phosphotransferase markers (genes). The 5' flanking region and the 3' flanking region can be homologous to regions within the gene, or such flanking regions can flank the coding region of gene to be deleted, mutated, or replaced with the unrelated DNA sequence. In some cases, the targeting vector does not comprise a selectable marker. DNA comprising the targeting vector and the native gene of interest are contacted under conditions that favor homologous recombination (e.g., by transforming plant cell(s) with the targeting vector).

A typical targeting vector contains nucleic acid fragments of not less than about 0.1 kb nor more than about 10.0 kb from both the 5' and the 3' ends of the genomic locus which encodes the gene to be modified (e.g. the genomic JAZ and/or CDK8 site(s)). These two fragments can be separated by an intervening fragment of nucleic acid that includes the modification to be introduced. When the resulting construct recombines homologously with the chromosome at this locus, it results in the introduction of the modification, e.g. an insertion, substitution, or a deletion of a portion of the genomic JAZ and/or CDK8 site(s).

In some cases, a Cas9/CRISPR system can be used to create a modification in genomic JAZ and/or CDK8 site(s). Clustered regularly interspaced short palindromic repeats (CRISPR)/CRISPR-associated (Cas) systems are useful for, e.g. RNA-programmable genome editing (see e.g., Marraffini & Sontheimer. Nature Reviews Genetics 11: 181-190 (2010); Sorek et al. Nature Reviews Microbiology 2008 6: 181-6; Karginov and Hannon. Mol Cell 2010 1:7-19; Hale et al. Mol Cell 2010:45:292-302: Jinek et al. Science 2012 337:815-820; Bikard and Marraffini Curr Opin Immunol 2012 24:15-20: Bikard et al. Cell Host & Microbe 2012 12: 177-186; all of which are incorporated by reference herein in their entireties). A CRISPR guide RNA can be used that can target a Cas enzyme to the desired location in the genome, where it generates a double strand break. This technique is available in the art and described. e.g. at Mali et al. Science 2013 339:823-6; which is incorporated by reference herein in its entirety and kits for the design and use of CRISPR-mediated genome editing are commercially available, e.g. the PRECISION X CAS9 SMART NUCLEASE™ System (Cat No. CAS900A-1) from System Biosciences, Mountain View, CA.

In other cases, a cre-lox recombination system of bacteriophage P1, described by Abremski et al. 1983. *Cell* 32:1301 (1983), Sternberg et al., *Cold Spring Harbor Symposia on Quantitative Biology*. Vol. XLV 297 (1981) and others, can be used to promote recombination and alteration of the genomic JAZ and/or CDK8 site(s). The cre-lox system utilizes the cre recombinase isolated from bacteriophage P1 in conjunction with the DNA sequences (termed lox sites) it recognizes. This recombination system has been effective for achieving recombination in plant cells (U.S. Pat. No. 5,658,772), animal cells (U.S. Pat. Nos. 4,959,317 and 5,801,030), and in viral vectors (Hardy et al., *J. Virology* 71:1842 (1997).

The plant cells, plants, and plant seeds can have genomic mutations that alter one or more amino acids in the encoded JAZ and/or CDK8 proteins. For example, plant cells, plants, and seeds can be modified so that at least one amino acid of a JAZ and/or CDK8 polypeptide is deleted or mutated to reduce the function of JAZ and/or CDK8 proteins. In some cases, a conserved amino acid or a conserved domain of the JAZ and/or CDK8 polypeptide is modified. For example, a conserved amino acid or several amino acids in a conserved domain of the JAZ and/or CDK8 polypeptide can be modified to change the physical and/or chemical properties of the conserved amino acid(s). For example, to change the physical and/or chemical properties of the conserved amino acid(s), the amino acid(s) can be deleted or replaced by amino acid(s) of another class, where the classes are identified in the following Table 1.

TABLE 1

| Classification | Genetically Encoded | Genetically Non-Encoded |
|---|---|---|
| Hydrophobic | | |
| Aromatic | F, Y, W | Phg, Nal, Thi, Tic, Phe(4-Cl), Phe(2-F), Phe(3-F), Phe(4-F), Pyridyl Ala, Benzothienyl Ala |
| Apolar | M, G, P | |
| Aliphatic | A, V, L, I | t-BuA, t-BuG, MeIle, Nle, MeVal, Cha, bAla, MeGly, Aib |
| Hydrophilic | | |
| Acidic | D, E | |
| Basic | H, K, R | Dpr, Orn, hArg, Phe(p-$NH_2$), DBU, $A_2BU$ |
| Polar | Q, N, S, T, Y | Cit, AcLys, MSO, hSer |
| Cysteine-Like | C | Pen, hCys, β-methyl Cys |

Different types of amino acids can be in the modified JAZ and/or CDK8 polypeptide(s) such as any of those listed in Table 2.

TABLE 2

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |

TABLE 2-continued

| Amino Acid | One-Letter Symbol | Common Abbreviation |
|---|---|---|
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| β-Alanine | | bAla |
| N-Methylglycine (sarcosine) | | MeGly |
| Ornithine | | Orn |
| Citrulline | | Cit |
| N-methylisoleucine | | MeIle |
| Phenylglycine | | Phg |
| Norleucine | | Nle |
| Penicillamine | | Pen |
| Homoarginine | | hArg |
| N-acetyl lysine | | AcLys |

TABLE 2-continued

| Amino Acid | One-Letter Symbol | Common Abbreviation |
|---|---|---|
| ρ-Aminophenylalanine | | Phe(pNH$_2$) |
| N-methylvaline | | MeVal |
| Homocysteine | | hCys |
| Homoserine | | hSer |

For example, modified JAZ and/or CDK8 proteins can have any naturally occurring amino acid within the protein replaced with any of the amino acids listed in Tables 1 or 2.

In some cases, jaz and/or cdk8 mutations are introduced by insertion of foreign DNA into the gene of interest. For example, this can involve the use of either transposable elements (see, e.g., Parinov et al., Plant Cell 11, 2263-2270 (1999)) or T-DNA. The foreign DNA not only disrupts the expression of the gene into which it is inserted but also acts as a marker for subsequent identification of the mutation. Because some plant introns are small, and because there can be very little intergenic material in plant chromosomes, the insertion of a piece of T-DNA on the order of 5 to 25 kb in length generally produces a dramatic disruption of gene function. If a large enough population of T-DNA-transformed lines is available, one has a very good chance of finding a plant carrying a T-DNA insert within any gene of interest.

Mutations that are homozygous lethal can be maintained in the population in the form of heterozygous plants.

Table 3 illustrates jaz mutations that can be combined to generate jazD mutant strains.

TABLE 3

Mutants used for construction of jazD and jazU.

| Mutant | Original name | Source | Accession | Mutagen | Resistance[1] |
|---|---|---|---|---|---|
| jaz1-2 | SM_3.22668 | JIC SM | Col-0 | dSpm transposon | Basta (confirmed) |
| jaz2-3 | RIKEN_13-5433-1 | RIKEN | No-0 | Ds transposon | Hygromycin (confirmed) |
| jaz3-4 | GK-097F09 | GABI Kat | Col-0 | T-DNA (pAC161) | Sulfadiazine (confirmed) |
| jaz4-1 | SALK_141628 | SALK | Col-0 | T-DNA (pROK2) | Kanamycin (silenced) |
| jaz5-1 | SALK_053775 | SALK | Col-0 | T-DNA (pROK2) | Kanamycin (confirmed) |
| jaz6-4 | CSHL_ET30 | CSHL | Ler | Ds transposon (Enhancer trap GUS) | Kanamycin (confirmed) |
| jaz7-1 | WiscDsLox7H11 | Wisconsin | Col-0 | T-DNA (pWiscDsLox) | Basta (not tested) |
| jaz8-V[2] | N/A | ABRC | Vash-1 | SNP | N/A |
| jaz9-4 | GK_265H05 | GABI kat | Col-0 | T-DNA (pAC161) | Sulfadiazine (confirmed) |
| jaz10-1 | SAIL_92_D08 | SAIL | Col-0 | T-DNA (pCSA110) | Basta (confirmed) GUS |
| jaz13-1 | GK_193G07 | GABI kat | Col-0 | T-DNA (pAC161) | Sulfadiazine (not tested) |

[1]Resistance of the mutant line to the indicated selectable marker was tested and confirmed.
[2]The C-to-A nonsense mutation present in JAZ8 from accession Vash-1 was backcrossed four times to Col-0 to generate a line (#28-6-30) that was used for subsequent genetic crosses (Thireault et al., Plant J 82: 669-679 (2015)).

N/A, not applicable.

JazD Mutations

A series of JAZ transcriptional repressor genes can be modified to improve insect and biotic resistance in plants. The JAZ transcriptional repressor genes can encode JAZ1, JAZ2, JAZ3, JAZ4, JAZ5, JAZ6, JAZ7, JAZ9, JAZ10, JAZ13, and/or related proteins. Reduction or deletion of genes that encode JAZ1, JAZ2, JAZ3, JAZ4, JAZ5, JAZ6, JAZ7, JAZ9, JAZ10, JAZ13, and/or related proteins can provide insect and biotic resistance to plants.

JAZ1 proteins are repressors of the jasmonic acid signaling pathway. One example, of an *Arabidopsis thaliana* jasmonate-zim-domain protein 1 (JAZ1) protein sequence is shown below (SEQ ID NO: 1).

```
  1  MSLFPCEASN MDSMVQDVKP TNLFPRQPSF SSSSSSLPKE
 41  DVLKMTQTTR SVKPESQTAP LTIFYAGQVI VFNDFSAEKA
 81  KEVINLASKG TANSLAKNQT DIRSNIATIA NQVPHPRKTT
121  TQEPIQSSPT PLTELPIARR ASLHRFLEKR KDRVTSKAPY
161  QLCDPAKASS NPQTTGNMSW LGLAAEI
```

A chromosomal DNA sequence for the *Arabidopsis thaliana* jasmonate-zim-domain protein 1 (JAZ1) protein with SEQ ID NO:1 is shown below as SEQ ID NO:2.

```
   1  ATATTGGAGG TAGGAAGAAG AACTCTGCAA CCAAACCAAC
  41  CAACCCCAAA GCCAAACAAA GTTTTATAGA GACCTTCCAT
 121  TTCTCCCTCT CGTGACAAAC GCAATTTGCA GAGAAGCAAC
 201  AGCAACAACA AGAAGAAGAA GAAAAAGATT TGAGATTACT
 241  TTGTATCGAT TTAGCTATTC GAGAAACTCT TGCCGTTTGA
 281  AAGTTTTAAT TGTTAAAGAT GTCGAGTTCT ATGGAATGTT
 321  CTGAGTTCGT CGGTAGCCGG AGATTTACTG GGAAGAAGCC
 361  TAGCTTCTCA CAGACGTGTA GTCGATTGAG TCAGTATCTA
 401  AAAGAGAACG GTAGCTTTGG AGATCTGAGC TTAGGAATGG
 441  CATGCAAGCC TGATGTCAAT GGTAAGAAAC CTTCTCTTTC
 481  TCCTAGATCC ACTTCTTTTT TCGTTTTCTC TGTTTTTTAT
 521  TTCTTGAATC TTGATCTTGA AAACTTTTCA AGAAAATTTT
 561  GAATCGATTT CAAAGAAATT AGGGAGAGTT AGTTTGCTAA
 601  ATTTTGACAT AGAAAATGAT TGGAGAGAGT TCTAACTTTT
 641  GGATCATATA TATTTGCAGG AACTTTAGGC AACTCACGTC
 681  AGCCGACAAC AACCATGAGT TTATTCCCTT GTGAAGCTTC
 721  TAACATGGAT TCCATGGTTC AAGATGTTAA ACCGACGAAT
 761  CTGTTTCCTA GGCAACCAAG CTTTTCTTCC TCATCTTCCT
 801  CTCTTCCAAA GGAAGATGTT TTGAAAATGA CACAGACTAC
 841  CAGATCTGTG AAACCAGAGT CTCAAACTGC ACCATTGACT
 881  ATATTCTACG CCGGGCAAGT GATTGTATTC AATGACTTTT
 921  CTGCTGAGAA AGCCAAAGAA GTGATCAACT TGGCGAGCAA
 961  AGGCACCGCT AATAGCTTAG CCAAGAATCA AACCGATATC
1001  AGAAGCAACA TCGCTACTAT CGCAAACCAA GTTCCTCATC
1041  CAAGAAAAAC CACAACACAA GAGCCAATCC AATCCTCCCC
1081  AACACCATTG ACAGAACTTC CTATTGCTAG AAGAGCTTCA
1121  CTTCACCGGT TCTTGGAGAA GAGAAAGGAC AGAGTTACGT
1161  CAAAGGCACC ATACCAATTA TGCGATCCAG CCAAAGCGTC
1201  TTCAAACCCT CAAACCACAG GCAACATGTC GTGGCTCGGT
1241  TTAGCAGCTG AAATATGAAT GCTAACCACC CTCAAGCCGT
1281  ACCAAGAAAT TCTTTTGACG ACGTTGCTTC AAGACAAGAT
1321  ATAAAAGCTC CTATCTTCAT GCTTTTTGAT TTAAGATACA
1361  AACTACTCAA TGATTAGGAA ACTTCATATA TTTGTATGTA
1401  TTGATTAGTG ATCAATTATT GTTAGTATTC GTTATAGTCT
1441  GTTTTTCTAC TAGTTATTGT CGCCTGTCTA AATCCCCTTG
1481  CTATGGGTTA TCTCAAAATT AGTTTCGTAT GTAACTAATT
1521  TTGTAAGAAC AATAATTTTT GTTGACGAAC CATACTATCA
1561  AATACTCTAA ATTATATCTT GATAAATCTA CCTATCAGGT
1601  AAGTAGG
```

JAZ2 is a coronatine (COR) and jasmonate isoleucine (JA-Ile) co-receptor, and is constitutively expressed in guard cells and modulates stomatal dynamics during bacterial invasion. It is expressed in cotyledons, hypocotyls, roots, sepals, petal vascular tissue and stigmas of developing flowers. JAZ2 is also expressed in stamen filaments after jasmonic acid treatment. One example, of an *Arabidopsis thaliana* jasmonate-zim-domain protein 2 (JAZ2) protein sequence is shown below (SEQ ID NO:3).

```
  1  MSSFSAECWD FSGRKPSFSQ TCTRLSRYLK EKGSFGDLSL
 41  GMTCKPDVNG GSRQPTMMNL FPCEASGMDS SAGQEDIKPK
 81  TMFPRQSSFS SSSSSGTKED VQMIKETTKS VKPESQSAPL
121  TIFYGGRVMV FDDFSAEKAK EVIDLANKGS AKSFTCFTAE
161  VNNNHSAYSQ KEIASSPNPV CSPAKTAAQE PIQPNPASLA
201  CELPIARRAS LHRFLEKRKD RITSKAPYQI DGSAEASSKP
241  TNPAWLSSR
```

The *Arabidopsis thaliana* jasmonate-zim-domain 2 (JAZ2) gene resides on chromosome 1. A cDNA encoding the protein with SEQ ID NO:3 is shown below as SEQ ID NO:4.

```
  1  GCAACCAGCG AAAAAAAAGT AATAAAGAGG TCCTCCATTT
 41  CTTCCTCGTG ACAAAACGCA CTTGGCAGAG AAAGATAAAC
 81  AAGAACCCTA AGTTTTTTTA TAAGATTCGA GAAAATTCAA
121  CAACTCAGGA AGGAAGATCC TTTTGCTCCA ATTTCTCAAT
161  CGAAACGATT TCAATTTCGG TTTCAACGAT GTCGAGTTTT
201  TCTGCCGAGT GTTGGGACTT CTCTGGTCGT AAACCGAGCT
241  TTTCACAAAC ATGTACTCGA TTGAGTCGTT ACCTGAAGGA
281  GAAGGGTAGT TTTGGAGATC TGAGCTTAGG GATGACATGC
321  AAGCCCGACG TTAATGGAGG TTCACGTCAG CCTACAATGA
361  TGAATCTGTT CCCTTGTGAA GCTTCAGGAA TGGATTCTTC
401  TGCTGGTCAA GAAGACATTA AACCGAAGAC TATGTTTCCG
441  AGACAATCAA GCTTTTCTTC TTCCTCTTCC TCTGGGACCA
481  AAGAAGATGT ACAGATGATC AAAGAGACTA CTAAATCTGT
521  GAAGCCAGAG TCTCAATCTG CTCCGTTGAC TATATTCTAC
561  GGTGGTCGAG TTATGGTGTT TGATGATTTT TCTGCTGAGA
601  AAGCTAAAGA AGTCATTGAT TTGGCTAACA AAGGAAGTGC
641  CAAAAGCTTC ACATGTTTCA CAGCTGAAGT AAACAATAAC
```

-continued

```
 681 CATAGTGCTT ATTCTCAAAA AGAGATTGCT TCTAGCCCAA

721 ATCCTGTTTG TAGTCCTGCA AAAACCGCAG CACAAGAGCC

761 AATTCAGCCT AACCCGGCCT CTTTAGCCTG CGAACTCCCG

801 ATTGCAAGAA GAGCTTCACT TCATCGGTTC CTTGAGAAGA

841 GGAAGGATAG GATCACATCA AAGGCACCAT ACCAAATAGA

881 CGGTTCAGCT GAAGCGTCTT CCAAGCCTAC TAACCCAGCT

921 TGGCTCAGTT CACGGTAAAC TTCGAGCCTG TCCGACCCAG

961 AAGGCACAAC TTGAGAGACC TTCTTGTAAG ATTCTTCTGA

1001 TGCTCCATCG TTACAAATAT CAAGCTGCTC CTCTGTTCAT

1041 TTTTTCTATA GATTAATTTC ACCCCTAGTA GTTTTGTTTG

1081 TTTAACTCCC CCGAAAACTC ATTATATTTG TATGAAATCA

1121 ATATCAATAG TGTTCAATGT TTGCTTCTGG GGTTTAAGTT

1161 TTAGCCAGTG TGTATAACCC TTTCCTCTGC CGATCTCAAC

1201 ATTAGCTTGC AACTTTTGTA AGAAACATCA CTTGTGTTTT

1241 TGTGTTGATG GCCATTAATA TAATCCAAGT TTATTTAATC

1281 CG
```

JAZ3 is also a repressor of jasmonate responses, and it is targeted by the SCF(COI1) complex for proteasome degradation in response to jasmonate. One example, of an *Arabidopsis thaliana* jasmonate-zim-domain protein 3 (JAZ3) protein sequence is shown below (SEQ ID NO:5).

```
  1 MERDFLGLGS KNSPITVKEE TSESSRDSAP NRGMNWSFSN

41 KVSASSSQFL SFRPTQEDRH RKSGNYHLPH SGSFMPSSVA

81 DVYDSTRKAP YSSVQGVRMF PNSNQHEETN AVSMSMPGFQ

121 SHHYAPGGRS FMNNNNNSQP LVGVPIMAPP ISILPPPGSI

161 VGTTDIRSSS KPIGSPAQLT IFYAGSVCVY DDISPEKAKA

201 IMLLAGNGSS MPQVFSPPQT HQQVVHHTRA SVDSSAMPPS

241 FMPTISYLSP EAGSSTNGLG ATKATRGLTS TYHNNQANGS

281 NINCPVPVSC STNVMAPTVA LPLARKASLA RFLEKRKERV

321 TSVSPYCLDK KSSTDCRRSM SECISSSLSS AT
```

A chromosomal DNA sequence for the *Arabidopsis thaliana* jasmonate-zim-domain protein 3 (JAZ3) protein with SEQ ID NO:5 is shown below as SEQ ID NO:6.

```
  1 GCGATTTGTT AATAAAACTA GAAATTGCGG TGAATTAACT

41 TCATTCCACG TTTTTTCATT TTCTCCCTCA AAAGTCTCTG

81 TTTTTTTTCC TTTTTCCGGC GAAGCTCTAT TTAGCTTGAT

121 TCCGGCGTTT AACACGCGTT TTAATCGAAA CAGACATTTG

161 AGATCGAATT AATTTTGTAG CGGGCTGTGT CTTTATTATA

201 GATGGAGAGA GATTTTCTCG GGTTGGGTTC GAAAAATTCT

241 CCGATCACTG TCAAGGAGGA AACCAGCGAA AGCTCTAGAG

281 ATTCAGGTTA TTTATTACTC TTCTCAATTT TTCTGATTCT

321 GATTGTTTTT AAATCGTAGA TTTGTTTGAT TGATTAGGAG

361 TTATTAGGAC TACTTGTAGT ATGGAATTTG TTTTTGGATA

401 GCTGATTTTA TGGCTTGCTC GGGAACTGGA ATTGTCAGTT

441 TGTTGCTTGG AGCAGAACAT TGTCCTTTGC TTTTCTCGGG

481 AGATGTAGAA TTTGGATTTG GAAAAACTAG TGTTCTTTTC

521 CAAAGCCTTG TCTTAAACAT GCTTTCGGTC GGAGAAATTA

561 ACGAGAACTA ATCTCAAGCT TCTAACATAA TTAAACTCGG

601 TAAACTTTTT TTTACTAGAG TAAATTTTTT TGTTTTGTTT

641 GAAGAGTCTT ATAATTGAGA AATACTTTAT TAGTTTATAC

681 TAAAAAAAAA ACGAATACGT AAAATGTTGG AAAAGAGGGG

721 ATGTATAGAG ACTGATACAA AAATGATAAA ATAGAGACGG

761 TTGGTAGTAG GTAGAAAGAT TAAATATACT CAAAAGAGTG

801 AGTTGGATTA GTTTATAAGA TGATTAACTT CTTGATTGTG

841 TGAGTTGGAT TAGTTTATGA GATTATTAAA ATATTGATTG

881 TGTATTTGTG TTGTGTGTTG ATTAAGCGGA ACTTGCGTTA

921 GAATATTGTT CAAGGTACAA TCTGGAAATA ATAGTTTTCT

961 CACCACGAGG AATATAATTA TTTCAACTTT GTTTTCTTAT

1001 CAGCCAAAAC GTGCCACACC ATAAAAGTAG TGCATCAACA

1041 TGTGGTGTGG TGTGGTGGGG TTAAAGTTTG AATCTCTCTT

1081 TAATTTAAAC TATTAAAACA AACTTAAATT ATTGGAGTTT

1121 CGTACAATGA CTTTCAATCA AATGTTTTAG AATTAGACAC

1161 GGTTTTCGAA AGTGGTTTTC CCTCGTTGAA TTTGTCAACA

1201 GTATGAGATT CTACATTGTT GGTTACTAAT CTTTTCCTTG

1241 AAGTAGGTGT TGAATTAATC CTCTGTTGTT TATGTAAGGA

1281 GATCTCGAGA CATTTATGGT TAACAGTTAA CACTACATGT

1321 TTGACTTTAA ACTGATTATC TTTTATTCTT TTTCTTTTGT

1361 AGCTCCCAAC AGAGGAATGA ACTGGTCTTT CTCAAACAAA

1401 GTATCAGCTT CTTCTTCTCA GTTTCTATCC TTCAGGCCAA

1441 CTCAAGAAGA TAGACATAGA AAGTCTGGAA ATTATCATCT

1481 TCCTCACTCT GGTTCCTTCA TGCCATCATC AGTAGCTGAT

1521 GTTTATGATT CAACCCGCAA AGCTCCTTAC AGTTCTGTAC

1561 AGGTATTTGT CATCAAAACC TATGTTAACC AAGACCCTTG

1601 TGTTTTTTTT ATCCTTCGCA AGATAGCTTT AAAAGTGAGC

1641 CCTGTTTTAT GAGCATATAG TAATTGGTTT TGAGTCTAGT

1681 TTAGCACAAG TTCATGGCAA TTAGTTTGTG GATCTAATCT

1721 TGGTTTAATA CTGATTCATT TTAAGTGTAA GCTAAGCTTC

1761 TCATTTTTGA TAAGTTAGTT CATACAATGC CTCACACCTA

1801 CTTTATGGCT TGTTACTCTC AGGGAGTGAG GATGTTCCCT

1841 AATTCCAATC AACACGAAGA AACTAACGCA GTTCCATGT

1881 CGATGCCGGG TTTCCAGTCT CATCATTATG CACCAGGAGG

1921 AAGAAGCTTC ATGAACAATA ACAATAACTC ACAACCTTTG
```

-continued

```
1961  GTAGGAGTTC CTATCATGGC ACCTCCAATT TCAATCCTTC
2001  CTCCTCCAGG TTCCATTGTA GGGACTACTG ATATTAGGTA
2041  CCCACTAGTC ATCATATCAT ACAGAAACTC TTTCTACATT
2081  TTCATAGTTG ACTAAAGACT TATTTTTGTC AGATCTTCTT
2121  CCAAGCCAAT AGGTTCACCT GCGCAGTTGA CGATCTTTTA
2161  TGCCGGTTCA GTTTGTGTTT ACGATGACAT ATCTCCTGAA
2201  AAGGTATCTC AATCATTTTC TTCCATATAT GCATCTCTTT
2241  TACTCGTAAG GTATGGTACT CATTTGCTTT CTTTCATTTC
2281  TCAGGCAAAG GCGATAATGT TGCTAGCTGG AACGGTTCC
2321  TCTATGCCTC AAGTCTTTTC GCCGCCTCAA ACTCATCAAC
2361  AAGTGGTCCA TCATACTCGT GCCTCTGTCG ATTCTTCAGC
2401  TATGCCTCCT AGCTTCATGC CTACAATATC TTATCTTAGC
2441  CCTGAAGCTG GAAGTAGCAC AAACGGACTC GGAGCCACAA
2481  AAGCGACAAG AGGCTTGACG TCAACATATC ACAACAACCA
2521  AGCTAATGGA TCCAATATTA ACTGCCCAGT ACCAGTTTCT
2561  TGTTCTACCA ATGTAATGGC TCCAACAGGT AAAAAACAAA
2601  GTCAGAGACC TGATACTACA TTCGCCATCT AACTTACTAG
2641  TATTTTCATG GATGTAACTT CATTCTCGTT CTGTTTCTTA
2681  TGCAGTGGCA TTACCTCTGG CTCGCAAAGC ATCCCTGGCT
2721  AGGTTTTTAG AGAAACGCAA AGAAAGGTAC GCAACACTTC
2761  TTTAGAATAC ACCATTCAAT AGTTTCTTGG GCTAACTCTC
2801  TTTCTCGCTG TGGGTTTCTC AGGGTCACGA GCGTATCCCC
2841  ATATTGCTTA GACAAGAAGT CATCGACAGA TTGTCGCAGA
2881  TCAATGTCTG AATGCATTAG TTCTTCTCTC AGCTCTGCAA
2921  CCTAATTTCA TCTACAGTAA GAAGGTTGCT TTAGACCACT
2961  CCACATCCAT ATTTGCATTT CAATGGCGGT CTTTTCAATG
3001  TCTCAGTTAA TTTTTCCTCA CTCGCCACAC TGAGTTTCTC
3041  CTTAGCTTTA TATATACGAT AGTGTATACT TTGTTTACAT
3081  GTTTTTTGGT GGAATGGAAC TTATGAGAGC ATATCAGATA
3121  TGTACTTGGG AAAAATTAGTA GAAACTGTTT GTTTCTTTTT
3161  TTTTAACTCT GTTCTTTTGT ATATATCACT GAAGCTCGCA
3201  TATGTATAAT TCATGTAATG GAATTGCATC GCTTCTGTTT
3241  CCCTAAGTTA TTT
```

JAZ4 is also a repressor of jasmonate responses. One example of an *Arabidopsis thaliana* jasmonate-zim-domain protein 4 (JAZ4) protein sequence is shown below (SEQ ID NO:7).

```
  1  MERDFLGLGS KLSPITVKEE TNEDSAPSRG MMDWSFSSKV
 41  GSGPQFLSFG TSQQETRVNT VNDHLLSSAA MDQNQRTYFS
 81  SLQEDRVFPG SSQQDQTTIT VSMSEPNYIN SFINHQHLGG
121  SPIMAPPVSV FPAPTTIRSS SKPLPPQLTI FYAGSVLVYQ
161  DIAPEKAQAI MLLAGNGPHA KPVSQPKPQK LVHHSLPTTD
201  PPTMPPSFLP SISYIVSETR SSGSNGVTGL GPTKTKASLA
241  STRNNQTAAF SMAPTVGLPQ TRKASLARFL EKRKERVINV
281  SPYYVDNKSS IDCRTLMSEC VSCPPAHHLH
```

A chromosomal DNA sequence for the *Arabidopsis thaliana* jasmonate-zim-domain protein 4 (JAZ4) protein with SEQ ID NO:7 is shown below as SEQ ID NO:8.

```
   1  ATTAGAGGAA TCATAAATCG GCGGTGTGTG TAACTTCAAC
  41  TCACGTTTTT CATTTCTCTC CAAAGTCCTT CAATTGTTAC
  81  TAATTCTCTC TGATCTCTCA TTTCTTCTCT TCTCCGGTGA
 121  CATTTTTTTT CTCCCCCGCG AAAGCTAAAC CGTTTTTGTA
 161  TTCTCAACGA TTGATAAGCC TGATGGAGAG AGATTTTCTC
 201  GGGCTGGGAT CAAAGTTATC TCCGATAACT GTGAAGGAGG
 241  AAACTAACGA AGATTCAGGT AATTCATCTT CAACATCTTC
 281  CATTATGATC TGATGATTGT GTTTTTCATC TCACTTTTTT
 321  TTGTTTCTAT TTTTGTAATC TCTTTTTTTG TTTATTGTTC
 361  AAGTACATAT ATATTGTTTT TCTAGCTTGA TTGGGAGTCC
 401  TACTGTCTGG TTTTTTCTTG AACAAGAAAT TTTTTCTTCG
 441  TTTTCTCGGG AAGAGAAAAA ATAAATTAGG GTTTCTTTTT
 481  TCTTGATATA TATTTAAGAA ATTAGGTTTT AGTACTATAG
 521  ACAGAAATTT AGCTACTCGA ATTTGTTTGA CGTAGCCGAT
 561  GAAAAAACAC GTTTTGGGAC TCGATAGTTA GAAAATTCAT
 601  ACGTTCACGA TCTACTTTTG AAGTTTTTTT CATTAAATAT
 641  TTTTTGCAAA CTACAAATGT ACAAGTATAC AACTATACAA
 681  GCAAACACCA AACTTGTTGA CGTTAGTAAT TTAACAAGTG
 721  TTAGTATTAT CTTTGAAAAA TAATATTCAG AGAACAAACT
 761  TGATTTTCTA GGTGACTAGG TGATGCATGT TTCTAAAGCT
 801  GTTGGTAATG TTGAGTGTTT TCAAAATAAT TTCGTTTTTT
 841  TCTTCAAACA GCCGACACCG ACAGAACAAA AATGCTATAT
 881  TTTTITTGTT GCTTACAAAA TTGATCAATT GGTTTCAATA
 921  CAATAGTATC TTCTTTAGAA AAGATTGTTT TTTTCAAAGC
1001  CGGATTGAAT ATTGAGAATT AGAACATTGG CTGGTTATTC
1041  TTTTTGAAAA GTTTATGCCA TTTTTTAAGG TTTATTAAGC
1081  AACTTGAATT CTATCAGTAT TATTTAAAAA CGAAGACGTG
1121  AAATGTTGGG AAAAGAATGC GTTATATAGC GACCGGCTGA
1161  CGATTAGAGA TTTAACAACA AATGCAAGTT GAATTATATA
1201  AAAGCAAGAT TGATTGTGAC TTGATTAAGT TTTATTTCTA
1241  TCCAAGTAGA CTCATTGATT AAGTTAGGAT CATGTTGGGT
1281  ATTAAATTTA GATCAAGTTA CAATTTGGAT GAATAATTTA
1321  CTTACCCACG AGGAATTTAA TAGTTAGTTC TTGTCTTTTT
```

```
1361 ATATTCCGAA ACGTGCCATT TCTTGAAAGT ATTTGTATGA
1401 TCACTATTTT CCCCAGTGTG TTTGGCTTTA TGCAGATTTG
1441 TTCATTGTTG ATGAATCTAA TGTTAAGAGT CGTCCACTTT
1481 AGCATAGCTA GATCTGAGTG TTTCCTAGTT TGATAAAATC
1521 TAAAGACATT TGCTCATGTT TCAGCCCCAA GTAGAGGTAT
1561 GATGGATTGG TCATTCTCAA GCAAAGTCGG TTCTGGTCCT
1601 CAGTTTCTTT CTTTTGGGAC ATCCCAACAA GAAACGCGTG
1641 TAAACACAGT CAATGATCAT TTGCTTTCTT CTGCTGCAAT
1681 GGATCAAAAC CAGAGAACTT ACTTCAGCTC ACTACAGGTT
1721 AGGCTATTTC TTGAAAAGAA AAAAGTAGT GATAAAGTGT
1761 GATTTAGTGA CCTTGTAAGA AAGCTTGGCA ATTGGTTTAG
1801 TTTCTTCTGG TCTCAAAATT GATACAAAAT GATCTCAGGA
1841 AGACAGAGTG TTCCCAGGTT CCAGTCAGCA AGACCAAACA
1881 ACCATCACAG TCTCCATGTC CGAACCAAAC TACATCAACA
1921 GTTTCATAAA CCACCAACAT TTAGGAGGAT CTCCTATCAT
1961 GGCACCTCCA GTTTCAGTAT TTCCTGCTCC AACCACTATT
2001 AGGCATGCAC TGCATTCTAT CTTCTTCTGT TTAACATCAG
2041 ATACAGAACC TCTTTACTTC TATAGTTGAC TCGAGCTCCT
2081 TTATGTTCAT CTCCAGATCT TCTTCAAAAC CACTTCCCCC
2121 TCAGTTGACA ATCTTTTATG CCGGTTCAGT ATTAGTTTAC
2161 CAAGACATAG CTCCTGAAAA GGTAACCAAA TTTCCTTCAA
2221 TATGTGTTAC ATTAGAGTCC AAGCTATCCA CTGACTAAGT
2241 ATTCAATCAA AGAAATAAGT TTCACGTATA GACATGCTGA
2281 AGTTATAGAA AGTTACTAAC CTGGTTTCAA CATACAGTAT
2321 GTTAATGATT CATAGATATG ATAAATCTTT GTCCTTACTT
2361 CTTCATTTAT TTTGTATTCA TAGGCCCAAG CTATCATGTT
2401 GCTAGCCGGA ATGGACCTC ATGCTAAACC GGTTTCACAA
2441 CCTAAACCTC AAAAACTGGT TCATCACTCT CTTCCAACCA
2481 CTGATCCTCC AACTATGCCT CCTAGTTTCC TGCCTTCCAT
2521 CTCTTACATT GTCTCTGAAA CCAGAAGTAG TGGATCCAAC
2561 GGGGTTACTG GACTTGGACC AACAAAAACA AAGGCGAGTT
2601 TAGCATCCAC GCGCAACAAC CAAACTGCTG CCTTCTCTAT
2641 GGCTCCAACA GGTTATAAAT GAAGTCTTAA CTCCTATTAA
2681 TGTTTTGTCA TCAAACTTCT ATCTTAGGTT TAGTTTGTTA
2721 TAACCAAAAA ATCTTGCTAT GATTTAATAC AGTGGGTTTA
2761 CCACAAACAC GCAAAGCATC CTTGGCTCGG TTCTTAGAGA
2801 AACGCAAAGA AAGGTACTGA GCTACAAGAT TATTCACTTA
2841 TTCACAATAT CAAAACACAG GTTTGCTGTA TATTGGCTTC
2881 GTTTTCTTGC AGGGTCATTA ACGTATCACC TTATTACGTA
2921 GACAACAAGT CATCAATAGA CTGTAGAACA CTGATGTCTG
2961 AATGTGTAAG CTGTCCTCCA GCTCATCATC TGCACTAAAA
3041 CCAATTTAGA CCCCTCATTG TTCTAAAGGC TTTTTCTTTT
3081 TTCTCTGGCT CTGTATCCTA TAGACTATAG TATAGTTGTT
3121 ATAGCTTTTG TTTATTCAGA TTTTAGTACA CTGGGCTTGT
3161 AAAAGCAAGT TATTTATATA TATCCTATAA ATTTAATTTG
3201 GATACTGTAT GTTTTGTCTT TACTCTTGCA TGTGTATAAA
3241 AAACATAAAA GTAAGACTAT TCAAGCT
```

JAZ5 is also a repressor of jasmonate responses. One example of an *Arabidopsis thaliana* jasmonate-zim-domain protein 5 (JAZ5) protein sequence is shown below (SEQ ID NO:9).

```
  1  MSSSNENAKA QAPEKSDFTR RCSLLSRYLK EKGSFGNIDL
 41  GLYRKPDSSL ALPGKFDPPG KQNAMHKAGH SKGEPSTSSG
 81  GKVKDVADLS ESQPGSSQLT IFFGGKVLVY NEFPVDKAKE
121  IMEVAKQAKP VTEINIQTPI NDENNNNKSS MVLPDLNEPT
161  DNNHLTKEQQ QQQEQNQIVE RIARRASLHR FFAKRKDRAV
201  ARAPYQVNQN AGHHRYPPKP EIVTGQPLEA GQSSQRPPDN
241  AIGQTMAHIK SDGDKDDIMK IEEGQSSKDL DLRL
```

A cDNA sequence for the *Arabidopsis thaliana* jasmonate-zim-domain protein 5 (JAZ5) protein with SEQ ID NO:9 is shown below as SEQ ID NO:10.

```
  1  TAATCATGGA TGAAAATTCC TTTCTTCACA CTAGATATAG
 41  TTCTTTAACT AGTTAAAAAT GCATGCGATG GAATATTACT
 81  AAATATGATA TAATCTCATG GCTTTATGTA AGATTTGTTT
121  TTTGGTTTTT TTGGTTGTTG TTAATAAATT TATTATTGAG
161  AAGTTTAATT CTATTTTGGT CACAATATAT TGAAATATTT
201  TTAAGAAACT AAAAAGTTCC TATTTATTTT TGTTTTCATT
241  AATTTATGAG AGGCTATTAA AGTCACAGAA ACTTATTGGG
281  TGAATGAGTT TATAAACACA TGAGCTATTG AGCTAGTAGC
321  CTCTTGTACT CTTCCATTTT ACGCGCAATC CACGCACCAA
361  CAAAAGAAA AGAAAGAAG AGATAAAGAA TATCTTTAAA
401  AAGTAAGTGT GGAGAATTCT TTCTTCTCAA TAAACAACAA
441  CATGTCGTCG AGCAATGAAA ATGCTAAGGC ACAAGCGCCG
481  GAGAAATCTG ACTTTACCCG GAGATGTAGT TTGCTCAGCC
521  GTTACTTGAA GGAGAAGGGT AGTTTCGGAA ACATTGATCT
561  TGGCTTATAC CGAAAACCCG ATTCCAGTCT CGCGTTGCCC
601  GGAAAATTCG ATCCACCAGG GAAACAAAAT GCGATGCATA
641  AGGCAGGGCA TTCCAAAGGC GAACCCTCTA CCTCATCAGG
681  AGGCAAAGTC AAAGATGTTG CTGACCTCAG TGAATCACAG
721  CCAGGAAGTT CGCAGCTGAC CATATTCTTC GGAGGGAAAG
761  TTTTAGTATA TAATGAGTTC CCCGTAGACA AAGCTAAAGA
801  GATTATGGAA GTAGCAAAAC AAGCCAAGCC TGTGACTGAG
```

```
 841  ATTAACATTC AGACACCAAT CAATGACGAA AACAACAACA
 881  ACAAGAGCAG CATGGTTCTT CCTGATCTCA ATGAGCCTAC
 921  TGATAATAAT CACCTAACAA AGGAACAACA ACAGCAACAA
 961  GAACAAAATC AGATCGTGGA ACGTATAGCA CGTAGAGCTT
1001  CCCTCCATCG ATTCTTTGCT AAACGGAAAG ACAGAGCTGT
1041  GGCTAGGGCT CCGTACCAAG TTAACCAAAA CGCAGGTCAT
1081  CATCGTTATC CTCCCAAGCC AGAGATTGTA ACCGGTCAAC
1121  CACTAGAGGC AGGACAGTCG TCACAAAGAC CGCCGGATAA
1161  CGCCATTGGT CAAACCATGG CCCATATCAA ATCAGACGGT
1201  GATAAAGATG ATATTATGAA GATTGAAGAA GGCCAAAGTT
1241  CGAAAGATCT CGATCTAAGG CTATAGTAAT ATTTGCTAAA
1281  TTTCTTGTAG GAACTGAGTT TTTAGATTAA CGTTTCGATT
1321  TTTCTGACTT ATCTAAGTGA TTTTATTTTG CTTTGTACTA
1361  CAGTATGTAA TCTTATTCTA ACTTGAATAT TCATTCATAA
1401  ACACAATAGA CGATAGTAAA GTTATATTAT AATTAGTTAA
1441  CTACGTACAA CACTTGGGAG TTAAATTACA TAACGTTAAG
1481  CGAGAAATAG CAAATTAGAC AAGAGGAAGA ATATTTAGGA
1521  GTTGTGAATT GATCTGACTG CAATAACATG AAGAGGAATC
1561  TGACTGCAAT CGTAATGCGG GTAAAGATGG TTGAAAGTGA
1601  TCAGAGCTCC TTTCTAATTT ATTTAGGGTG TAATTTATGA
1641  AAATGATTAT TATTGGAGTG TATATCAAGT TTTCACTAAA
1681  CTCAGGGGTG TTTATTGTAA TTAGTTGTCA GGTTCAAGTT
1721  CATTGAAGGC GTGTCTGATT TGGACAGTGA TTGGGCCTGA
1761  GCCAT
```

JAZ6 is also a repressor of jasmonate responses. One example of an *Arabidopsis thaliana* jasmonate-zim-domain protein 6 (JAZ6) protein sequence is shown below (SEQ ID NO:11).

```
  1  MSTGQAPEKS NFSQRCSLLS RYLKEKGSFG NINMGLARKS
 41  DLELAGKFDL KGQQNVIKKV ETSETRPFKL IQKFSIGEAS
 81  TSTEDKAIYI DLSEPAKVAP ESGNSQLTIF FGGKVMVFNE
121  FPEDKAKEIM EVAKEANHVA VDSKNSQSHM NLDKSNVVIP
161  DLNEPTSSGN NEDQETGQQH QVVERIARRA SLHRFFAKRK
201  DRAVARAPYQ VNQHGSHLPP KPEMVAPSIK SGQSSQHIAT
241  PPKPKAHNHM PMEVDKKEGQ SSKNLELKL
```

A cDNA sequence for the *Arabidopsis thaliana* jasmonate-zim-domain protein 6 (JAZ6) protein with SEQ ID NO:11 is shown below as SEQ ID NO: 12.

```
   1  AAATTAATAG CCTATAATAT GTTTGACCAT AAAAAGAATT
  41  TCTTCTTCTT GAACCATCAT AAGAAAAATG TGTGTTTAGT
  81  CTATTGATCA GTTTTGTGTT GAAAAAAAAA AAAAAAATGT
 121  CTATCCATCA GTTAGGTGTA AAAAAAAAG TTACAAAACT
 161  CCTGACAAAA ACATTCTATA TTGGACACAC ATCACTGTCA
 201  CTTCAGACTA AATAAAAAAA AAGAACACGT TATTTCGTTT
 241  TCTTTATTTA TTCGGGAGAG GTTAAAAGCC ACAGAAACTT
 281  ATTGGCTAGA ATTGGTTATT TATAACAACA ACACATGAGC
 321  AAAAAGCTCA AACATCTAC ATACTCTTTG GAATCCTCGA
 361  TTTTTTGTAC GTGTAAAGAA GTCACACAAG AAAATCTTGG
 401  GTTGTTGTAA TCTTCATCAC ACTAGTATGT CAACGGGACA
 441  AGCGCCGGAG AAGTCCAATT TTTCTCAGAG ATGTAGTCTG
 481  CTCAGCCGGT ACTTGAAGGA GAAGGGAAGT TTTGGGAATA
 521  TTAATATGGG GTTGGCTCGA AAATCCGATC TTGAACTCGC
 561  CGGAAAATTC GATCTCAAAG GACAACAAAA TGTGATTAAG
 601  AAGGTAGAGA CCCTCAGAAAC TAGACCGTTC AAGTTGATTC
 641  AGAAGTTTTC TATTGGTGAG GCCTCTACTT CTACCGAAGA
 681  CAAAGCCATA TATATTGATC TCAGTGAACC GGCAAAAGTA
 721  GCACCGGAGT CTGGAAATTC ACAGTTGACC ATATTCTTTG
 761  GAGGAAAAGT TATGGTTTTC AACGAGTTTC CTGAAGACAA
 801  AGCTAAGGAG ATAATGGAAG TAGCTAAAGA AGCGAATCAT
 841  GTTGCTGTTG ATTCTAAGAA CAGTCAGAGT CACATGAATC
 881  TTGACAAAAG CAACGTGGTG ATTCCCGATC TTAACGAGCC
 921  AACGAGTTCC GGGAACAATG AAGATCAAGA AACTGGGCAG
 961  CAACATCAGG TTGTGGAACG CATTGCAAGA AGAGCTTCTC
1001  TTCATCGATT CTTTGCTAAA CGAAAAGACA GGGCTGTGGC
1041  TAGAGCTCCA TATCAAGTGA ACCAACACGG TAGTCATCTT
1081  CCTCCCAAGC CAGAGATGGT TGCTCCATCG ATAAAGTCAG
1121  GCCAATCGTC GCAACACATT GCAACTCCTC CAAAACCAAA
1161  GGCCCATAAC CATATGCCGA TGGAGGTGGA CAAGAAAGAA
1201  GGACAATCTT CCAAAAACCT TGAACTCAAG CTTTAGGGCG
1241  TATAAAATGC ACGATCGAGT TCACGTTTCT AGTTTTCACT
1281  TATTTAGGAT TTGAACCCAA ATACCCTTTT ATATTTTCTT
1321  CCATTACTTT TGACCAATTT AAGTTATTTA TAGTACTGTA
1361  TTACGTAGCT AGTATTTATA TTTCAAAACA TAGATATTTT
1401  GATACTTGTT TTTTAGATTC TTTAATTAAA ATTGTCATCT
1441  GGATTACCCT TTATCGAAAT TTTTTAATCA CCTGATATAA
1481  TCTCACCAGT GATGGATTTG CGTTGTTAGT AATTTTTCTA
1521  AGTGGCAAAA GTATATTAAC CTATAATAGG TTTCAAAGAT
1561  ATACATATAA TGTTTCTATC AAAGATATTA GTATAATATT
1601  TTAC
```

JAZ7 is also a repressor of jasmonate responses. One example of an *Arabidopsis thaliana* jasmonate-zim-domain protein 7 (JAZ7) protein sequence is shown below (SEQ ID NO: 13).

```
  1  MIIIKNCDK PLLNFKEMEM QTKCDLELRL LTSSYDSDFH

41  SSLDESSSSE ISQPKQESQI LTIFYNGHMC VSSDLTHLEA

81  NAILSLASRD VEEKSLSLRS SDGSDPPTIP NNSTRFHYQK

121  ASMKRSLHSF LQKRSLRIQA TSPYHRYR
```

A cDNA sequence for the *Arabidopsis thaliana* jasmonate-zim-domain protein 7 (JAZ7) protein with SEQ ID NO: 13 is shown below as SEQ ID NO: 14.

```
  1  GTTGTGTTCT GTCCAAACTC TGTTCTAATG CCAGCTTTTG

41  TCTCGTCTTT TCTCTATCCT TATCTTCCCT CTATCTTCGA

81  TCCCAACACA TACACAACAC GCACACACAC ATATATAAAT

121  CAACTGACTG ACACATACAA TCATGATCAT CATCATCAAA

161  AACTGCGACA AGCCTTTACT CAATTTCAAA GAGATGGAGA

201  TGCAAACAAA ATGCGACTTG GAACTTCGCC TTCTTACTTC

241  TTCTTATGAT TCTGATTTCC ATAGCTCGTT GGACGAATCA

281  AGCAGCTCTG AAATTTCACA ACCAAAGCAA GAATCTCAGA

321  TATTAACCAT TTTCTACAAC GGGCACATGT GTGTTTCTTC

361  AGATCTTACC CATCTTGAGG CTAACGCTAT ACTATCGCTA

401  GCGAGTAGAG ATGTGGAAGA GAAATCTTTA TCCTTGAGAA

441  GTTCAGACGG TTCGGATCCT CCAACAATCC CAAACAATTC

481  GACTCGATTT CATTATCAAA AGGCCTCTAT GAAGAGATCT

521  CTTCACAGTT TTCTTCAGAA ACGAAGTCTT CGGATTCAAG

561  CAACTTCCCC TTACCACCGT TACCGATAGC ACTATCTATT

601  TGATTTCATT TTTGTGATTC TCTTCAATTT TTTTTTTACT

641  GTAACATAAT AATCCAATTG TCTTGAATTC TTTTTCTGTG

681  TGTTTGGATG GATTAGAGAC CTTAATTAGG TAGAGTATTA

721  AAGTTTCATA ATTTCCAGTA ACTTGTGTTT AGAGTTCAAG

761  AGGTTGACAA AATTTATCAA CGGTCTCCTA AAATGGGTAA

801  ACCGAGAAAC TTTTATACGA AAA
```

JAZ9 is also a repressor of jasmonate responses. One example of an *Arabidopsis thaliana* jasmonate-zim-domain protein 9 (JAZ9) protein sequence is shown below (SEQ ID NO: 15).

```
  1  MERDFLGLSD KQYLSNNVKH EVNDDAVEER GLSTKAAREW

41  GKSKVFATSS FMPSSDFQEA KAFPGAYQWG SVSAANVFRR

81  CQFGGAFQNA TPLLLGGSVP LPTHPSLVPR VASSGSSPQL

121  TIFYGGTISV FNDISPDKAQ AIMLCAGNGL KGETGDSKPV

161  REAERMYGKQ IHNTAATSSS SATHTDNFSR CRDTPVAATN

201  AMSMIESFNA APRNMIPSVP QARKASLARF LEKRKERLMS

241  AMPYKKMLLD LSTGESSGMN YSSTSPT
```

A chromosomal DNA sequence for the *Arabidopsis thaliana* jasmonate-zim-domain protein 9 (JAZ9) protein with SEQ ID NO: 15 is shown below as SEQ ID NO: 16.

```
   1  GCAAAGAGTT AAATAAGCCT CTCCAAAAGT GTGTCTGTAA

41  CATTACCAAA ACGAAACCTT CCTTGTGGAT TCCCACTTCT

81  TTCTTCTGTT TTCTTCTTCC TCTTCTTTAA ATTGGATGTT

121  TTGGGCAAGA AACAGAGAGA AACACGTTAA TTTGAGAGTT

161  TGTCATTGAA TATTTGGTTT GCAATGGAAA GAGATTTTCT

201  GGGTTTGAGC GACAAGCAGT ATCTAAGTAA TAACGTTAAG

241  CATGAGGTTA ACGATGATGC TGTCGAAGAA CGAGGTTTGT

281  GTTCTTGTCT CGAGAATCTT TTATTTTAAT GTTTCAAGAA

321  GAGATCAGTT TTCACTTTTA ACATAGCCGT ATAAAGTTGT

361  TTATTTAAAT ATAATTTTTC AGATTCCAAA ACTTGAAAAA

401  AAAAAGATTC CATTAAATCT TTTATAAAAA TGAGATTGGA

441  TAGATTAGTC AAATTGACGA CCATAAAAAA TGATACTTAT

481  AGGGTTAAGT ACGAAGGCAG CTAGAGAATG GGGGAAGTCA

521  AAGGTTTTTG CTACTTCAAG TTTCATGCCT TCTTCAGATT

561  TCCAGGTTGG TTCATCTTAA AATTTAACTT ACTCTGTATC

601  AGTTTCAGAT GTTATGGCTA ATCTAATGGT TCTATAAGCT

641  ACCGCATAAT CATGGTCGTC TTTTAGCATG TGCAAGAGGA

681  GTACTCAATT ATGGTCTTGA TTAAAAAGAA GAATTTACTT

721  TCAAATTATG TTAAACACAT CAATCACATA TTTATGAGAA

761  AAGTTGTTTT CGTAAGAGAT AGCCACCGGA AAATGGTCGG

801  ATAAATGGCC GAACTTTATC ATTTTTGTGT ATGTGGCCAA

841  TCATTAACCA GGGAAAAAAA ATTGTTGGAT AAGTGCTAGT

881  TAAGAGCTGG TAGGGTCGGT CGTCTGCCAG CCGCAAAGTT

921  AGGGAAAAAA TAATTTAATA TTTTGTGGCG TTTGGTGTTT

961  GGCGTTTGGA TCACGTTTAT TTCTTGGCAT TTTTCTAAAT

1001  TTAGAATGTA CAAAAAATTT AAAGACGTTG ACGATTAAAA

1041  TTTGAATTTA ACAAATTAGG AGGCTAAGGC GTTTCCGGGT

1081  GCATACCAGT GGGGATCAGT TTCTGGGCC AATGTTTTCC

1121  GCAGATGCCA ATTTGGTGGT GCGTTTCAAA ACGCGACGCC

1161  GCTTTTACTA GGCGGTTCAG TTCCTTTACC AACTCATCCT

1201  TCTCTTGTTC CACGGTAATT TCCATATTAT GATGCAAAAA

1241  CATTCAACAA TTTTTTTGCT CTTTTCATAT TTGATTTGG

1281  TTATGTGGGT TTGTGGAAAC AGAGTGGCTT CCTCCGGATC

1321  ATCTCCTCAG CTCACAATCT TTTATGGCGG AACTATAAGC

1361  GTCTTTAATG ACATATCTCC CGATAAGGTA TATATAATCA
```

```
1401  AGATTCATAC AAATAACATT TACATAACAT TTACATGTTC
1441  TAAAACGGAC TATTCATGAT ATGTGAGTAG GCTCAAGCCA
1481  TCATGTTATG CGCCGGGAAC GGTTTGAAAG GTGAAACTGG
1521  AGATAGCAAA CCGGTTCGAG AAGCTGAAAG AATGTATGGA
1561  AAACAAATCC ATAACACTGC TGCTACCTCA TCAAGCTCTG
1601  CCACTCACAC TGATAATTTC TCAAGGTGTA GGGACACACC
1641  CGTTGCTGCG ACTAATGCAA TGAGCATGAT CGAATCATTC
1681  TATGCAGCTC CTCGTAACAT GATTCCTTCA GGTATGTGTG
1721  TCTAATATCA ACATCAAAAC AAAATATAAT CAAGATTTTT
1761  GCTTCCTCAA ATCATATGTC TAAACTCGAA AATTGCTTTT
1801  TTCCAGTCCC TCAAGCTCGG AAAGCATCCT TGGCTCGGTT
1841  CTTGCAGAAG CCCAAAGAGA GGTTTGATTT TGTATTTTTT
1881  TTCTTTATAG AAAATTTTGA GGTTTTTCAA TTGAATCTAA
1921  AAGAATTGAT GTTGTTGGTG CAGGCTTATG AGTGCAATGC
1961  CATACAAGAA GATGCTTCTT GATTTGTCGA CCGGAGAATC
2001  CAGTGGAATG AATTACTCTT CTACTTCTCC TACATAAAAC
2041  CTACACTTTT TTTTTTTTTT TTTACAATGG TAATTTGTAA
2081  TTGTAATCAT TAGATTATGA TTATATAGTT ACCATTTATA
2121  TTCTTACGAG CAGGAGAAGA CGTTAGGGCG TCTCTGTATT
2161  TGATCATTGT TTGTAATGCT TTGGTCTGTT TATTGTAGGA
2201  TTACATTATA ACTTTAAGAA CTAACAGATA TATGTTTGTC
2241  ATGGACTCAT GTCTGTCAAG AATTTAATAT CAAATAAAAT
2281  TCACTATAAT TTTTTTT
```

JAZ10 is also a repressor of jasmonate responses. One example of an *Arabidopsis thaliana* jasmonate-zim-domain protein 10 (JAZ10) protein sequence is shown below (SEQ ID NO:17).

```
  1  MSKATIELDF LGLEKKQTNN APKPKFQKFL DRRRSFRDIQ
 41  GAISKIDPEI IKSLLASTGN NSDSSAKSRS VPSTPREDQP
 81  QIPISPVHAS LARSSTELVS GTVPMTIFYN GSVSVFQVSR
121  NKAGEIMKVA NEAASKKDES SMETDLSVIL PTTLRPKLFG
161  QNLEGDLPIA RRKSLQRFLE KRKERLVSTS PYYPTSA
```

A chromosomal DNA sequence for the *Arabidopsis thaliana* jasmonate-zim-domain protein 10 (JAZ10) protein with SEQ ID NO:17 is shown below as SEQ ID NO:18.

```
   1  AAAAACTCTC ACATGAGAAA TCAGAATCCG TTATTATTCC
  41  TCCATTTATT CATCTCAAAA CCCATATCTC TCTGTCTTGA
  81  TCTCTCTCTC ACTTTCTAAT AAGATCAAAG AAGATGTCGA
 121  AAGCTACCAT AGAACTCGAT TTCCTCGGAC TTGAGAAGAA
 161  ACAACCAAC AACGCTCCTA AGCCTAAGTT CCAGAAATTT
 201  CTCGATCGCC GTCGTAGTTT CCGAGGTTCG TTTGGTTTTT
 241  AGTCGCTCTC TCTTTTTTTT TTCTTGCGAT AAATCGAATT
 281  TATTCATATG GAACTCCTGC AGATATTCAA GGTGCGATTT
 321  CGAAAATCGA TCCGGAGATT ATCAAATCGC TGTTAGCTTC
 361  CACTGGAAAC AATTCCGATT CATCGGCTAA ATCTCGTTCG
 401  GTTCCGTCTA CTCCGAGGGA AGATCAGCCT CAGATCCCGA
 441  TTTCTCCGGT CCACGCGTCT CTCGCCAGGT ATTTTTGTCT
 481  TTCCGGTAAA GTTTTTTTTT TCTTTCTAAC TTTTTTGGCG
 521  CTACCGAAAA AGACGAAAAA ATTTGAAATT CAAATTTTCA
 561  AAACATTCAT TTTCCTCAGG TCTAGTACCG AACTCGTTTC
 601  GGGAACTGTT CCTATGACGA TTTTCTACAA TGGAAGTGTT
 641  TCAGTTTTCC AAGTGTCTCG TAACAAAGCT GGTGAAATTA
 681  TGAAGGTCGC TAATGAAGCA GCATCTAAGA AAGACGAGTC
 721  GTCGATGGAG ACAGATCTTT CGGTAATTCT TCCGACCACT
 761  CTAAGACCAA AGCTCTTTGG CCAGAATCTA GAAGGAGGTT
 801  AGTATAATAA TAATAAATAT CACTTAGTGC TGGATTCTTC
 841  TAGAATTTTA GTTACATATT ATTGCATGTA GAGATCTAAG
 881  AAGAGTTTGT TGTTAGAGAG GAATTGGTTG CTAATTAGTT
 921  TGCAATTAGA TATCAAAGAG TTAAAGACTA TAGTTTATGT
 961  CTATACGTAT TAATATACGT TATTAATAAA AGTATAAACA
1001  TGTTGTTTAA TTTCTGATAA GAAACTGGTT TATGCGTGTG
1041  TATGCAGATC TTCCCATCGC AAGGAGAAAG TCACTGCAAC
1081  GTTTTCTCGA GAAGCGCAAG GAGAGGTAAT GATTCTTCAA
1121  CAATCCAAGG ATTTTTACCC CCAAATAATT AAAGAAAGGT
1161  TTTTATTTTT CTCTCTCTCG ACCTTTTTTT TACTATAAGT
1201  TATTTAAGAT AGTAATTATG GGTCCTGCCT CTTTTACTCT
1241  CACATACAAC TTAAGATTCA ACTAGTTTTG TTCAACAACG
1281  CACATGCTTA TACGTAGATA GATAATGGAG ATCAGTAGTA
1321  ATATCGGTAT ACGTAGGTTA CTATTGTAAT GGAACTTTTA
1361  AAAAGCGCGT TGACTTTGAG TCTTTGACTC TAGTTCTGTT
1401  TGCTACACCG ACAAGTTATA TTTTTCAAAA TGATGAGAAA
1441  ACGAGGAGAA ACACCGGAAA AAAATTTGAA CTTTTACTTT
1481  TATCAGACCA TACGGCCAAA GAAAGATCTG TATATTATAT
1521  AAGTTATCAC AAAACGCGGT TTCACATTTT CTTTTTCGTC
1561  TTGTTGTGTT TGCAGATTAG TATCAACATC TCCTTACTAT
1601  CCGACATCGG CCTAAACGAT CTCTTTTTAG ATTGGGACAT
1641  GGACCAAATT TGTCTTTTTC AATCGGAAGA CATCCATGTT
1681  CGTTTTTGCA TTTGGCTTAT TTCCAATCTT CTTTTGAAGC
1721  CTTCTTCGTC GTTGCTAAAT CGTATACTAT TCACGACAAA
1761  CGTTTTTAGG AGATTACGTT ACCTACTAAG ATTATATATA
1801  TTGGTTTGTT TTTAAAAATG TCTATTATCT TTATTGTCAT
1841  TGATAGCTTG ATTTAAGAAG CTCTCTCTTA TCCCGTGACC
```

```
1881  TTCTACTTTT GTTTTATTTT TTAGTATATG GTAAAGAAAA

1921  TTATAAC
```

JAZ13 is also a repressor of jasmonate responses. One example of an *Arabidopsis thaliana* jasmonate-zim-domain protein 13 (JAZ13) protein sequence is shown below (SEQ ID NO:19).

```
  1   MKGCSLDLHL SPMASTLQSC HQDSTVNDRS STIRSKEINA

41   FYSGRLSEYD LVEIQMRAII EMASKDREVT ALELVPVRLE

81   SPLGCSVKRS VKRFLEKRKK RSKSFTLTPN YISSTSSSSS

121   SLHNF
```

The *Arabidopsis thaliana* Jaz13 gene encoding the JAZ13 protein with SEQ ID NO:19 is located on chromosome 3, and a cDNA encoding the SEQ ID NO:19 is shown below as SEQ ID NO:20.

```
  1   TTGATTACTT TGATACGAAA ATCGACCAAA GTAAGAATAT

41   TTACCTAGAG AGGATCATGA AGGGTTGCAG CTTAGATCTT

81   CACCTATCTC CAATGGCCTC TACGCTTCAA TCTTGTCATC

121   AAGATTCTAC AGTTAATGAT CGTTCTTCAA CCATAAGATC

161   TAAGGAAATC AATGCATTTT ATAGTGGGAG ATTAAGTGAG

201   TACGATCTTG TAGAGATCCA GATGAGAGCA ATAATAGAGA

241   TGGCGAGCAA GGATCGTGAA GTAACAGCGT TAGAGTTAGT

281   GCCGGTGAGA CTGGAATCAC CGTTAGGATG TTCGGTGAAG

321   AGATCTGTGA AAAGGTTCTT GGAGAAGAGG AAGAAGAGAA

361   GCAAATCTTT TACACTTACA CCTAATTACA CCTCAAGTAC

401   TTCCTCATCA TCCTCCTCTC TTCATAATTT CTAATCATAA

441   TTTTATTATG TTTTCCTTCT AGTTATCAAT CAAAACAAAA

481   AAATCTTTGT TTCTTTCTTT TTTCTTTTTT CCATTATGGG

521   TTTCTATAGC TCTCATTTAT CTCTTGTAAT TTTTCCCGAT

561   ACTCGACGAT GAATTTCGAG TTTTTTTTTT TGATCTGTTT

601   TAAATCAAGA CATTCTAGTA CCATTGGAGT CTGTATAAAA
```

```
641   TTCAGATCAT TTGGATCGTT ATTTTTTTCC TAATTCATGT

681   ATGAAGTGTC ACACTTCTCC TACAATGAAT TATGAGGTTG

721   TCCGTTTATT CCAAGTTAGC TCTATGTACT TTGACGTAAG

761   CTAATGCAAC TTGTAAAATG TTGGGAACTC TTCTATTACT

801   TTTTTTCCTT TACAAAATAA GAAAATGCAC GCAT
```

Chromosomal sequences that encode repressors of jasmonic acid responses from many plant types and species can be modified to reduce or eliminate the expression and/or function of the encoded protein. For example, chromosomal sequences encoding jasmonic acid repressor genes from agriculturally important plants such as alfalfa (e.g., forage legume alfalfa), algae, avocado, barley, broccoli, Brussels sprouts, cabbage, canola, cassava, cauliflower, cole vegetables, collards, corn, crucifers, grain legumes, grasses (e.g., forage grasses), jatropa, kale, kohlrabi, maize, miscanthus, mustards, nut sedge, oats, oil firewood trees, oilseeds, potato, radish, rape, rapeseed, rice, rutabaga, sorghum, soybean, sugar beets, sugarcane, sunflower, switchgrass, tobacco, tomato, turnips, and/or wheat can be modified reduce or eliminate the expression and/or function of one or more encoded jasmonic acid regulatory proteins.

In some cases, more than one genetic or chromosomal segment encoding a jasmonic acid regulatory protein can be modified to reduce or eliminate the expression and/or function of the encoded protein(s). In some cases, more than two genes or chromosomal segments encoding jasmonic acid regulatory proteins can be modified to reduce or eliminate the expression and/or function of the encoded proteins. In some cases, more than three genes or chromosomal segments encoding jasmonic acid regulatory proteins can be modified to reduce or eliminate the expression and/or function of the encoded proteins. In some cases, more than four genes or chromosomal segments encoding jasmonic acid regulatory proteins can be modified to reduce or eliminate the expression and/or function of the encoded proteins.

The following are examples of "JAZ-related" proteins and nucleic acids that can be modified to reduce or eliminate the expression and/or function thereof, and thereby generate plants with improved resistance to insects.

One example of a *Brassica rapa* protein called TIFY 10A-like (NCBI accession no. XP_009117562.1; GI:685367109; SEQ ID NO:21) has significant sequence identity to the *Arabidopsis thaliana* JAZ1 protein with SEQ ID NO:1, as illustrated by the sequence comparison shown below. Domains of sequence homology are identified by asterisks below the sequence comparison.

```
73.0% identity in 211 residues overlap; Score: 634.0; Gap frequency:
11.4%
Seq:1      1 MSLFPCEASNMDSMVQDVKPTNFFPRQPSFSSSSSSLPKEDVEKMTQ---TTRSVKPESQ
Seq21     63 MSLFPCEASNMEPIGQDVKPKNLFPRQPSFSSSSSSLPKEDILKMTQATSSTRSVKPEPQ
             ***********  ***** ***************** ***** *      ******* *

Seq:1     58 TAPLTIFYAGQVIVFNDFSAEKAKEVINLASKGTANS------------------LAKN
Seq21    123 TAPLTIFYGGQVIVFNDFSAEKAKEVMDLASKGTANTFTGFTSNVNNNIQSVYTTNLANN
             ******** *****************  ********                    ** *

Seq:1     99 QTDIRSNIATIANQVPHPRKTTTQEPIQSSPTPLT-ELPIARRASLHRFLEKRKDRVTSK
Seq21    183 QTEMRSNIAPIPNQLPHLMKTTTQNPVQSSTAMACELPIARRASLHRFLAKRKDKVTSK
             ** ***** ** **  ***** * *****  *             ************** *********

Seq:1    158 APYQLCDPANASSNPQTTGNM-SWLGLAAEI
Seq21    243 APYQLNDPAKASSKPQTGDNTTSWLGLAAEM
             ***** ***** *** *   *  *******
```

This JAZ-related *Brassica rapa* protein, called TIFY 10A-like (NCBI accession no. XP_009117562.1; GI:685367109), has the following sequence (SEQ ID NO:21).

```
  1  MSSPMESSDF AATRRFSRKP SFSQTCSRLS QYLKENGSFG
 41  DLSLGMACKP EVNGISRQPT TTMSLFPCEA SNMEPIGQDV
 81  KPKNLFPRQP SFSSSSSSLP KEDILKMTQA TSSTRSVKPE
121  PQTAPLTIFY GGQVIVFNDF SAEKAKEVMD LASKGTANTF
161  TGFTSNVNNN IQSVYTTNLA NNQTEMRSNI APIPNQLPHL
201  MKTTTQNPVQ SSSTAMACEL PIARRASLHR FLAKRKDRVT
241  SKAPYQLNDP AKASSKPQTG DNTTSWLGLA AEM
```

A cDNA encoding the SEQ ID NO:21 protein is available as NCBI accession number XM_009119314.1 (GI: 685367108), and a chromosomal segment encoding the SEQ ID NO:21 protein is available as NCBI accession number AENI01008623.1 (GI:339949964).

One example of *Brassica oleracea* protein, also referred to as protein TIFY 10A-like (NCBI accession no. XP_013583936.1; GI:922487335; SEQ ID NO:22), has significant sequence identity to the *Arabidopsis thaliana* JAZ1 protein with SEQ ID NO: 1, as illustrated by the sequence comparison shown below. Domains of sequence homology are identified by asterisks below the sequence comparison.

```
72.9% identity in 192 residues overlap; Score: 633.0; Gap frequency:
Seq:1     1 MSLFPCEASNMDSMV--QDVKPTNLFPRQPSFSSSSSSLPKEDVLKMTQTT-RSVKPESQ
Seq22    61 MSLFPCEASNVGSMAALQDVKPKNLFPRQPSFSSSSSSIPKEDVPKMTQTTTRSLKPEPQ
            **********  **   ***** ****************  ***** ****** ** *** *

Seq:1    58 TAPLTIFYAGQVIVFNDFSAEKAKEVINLASKGTANSLAKNQTDIRSNIATIANQVPHPR
Seq22   121 TAPLTIFYGGQVIVFNDFSAEKAKEVMNLANKGTANTFTGFTSTLNNNIAPTPNQVPHLM
            ********  *****************  *** *****     ***    *****

Seq:1   118 KTTTQEPIQSSPTPLT-ELPIARRASLHRFLEKRKDRVTSKAPYQLCDPAKASSNPQTTG
Seq22   181 KAATQDPKQTSSAAMACELPIARRASLHRFLAKRKDRVTSKAPYQLNDPAKAYSKPQTGN
            *  ** * *          *************** **************** *  ***

Seq:1   111 NM-SWLGLAAEI
Seq22   241 TTTSWLGLAADM
                *******
```

This JAZ-related *Brassica oleracea* protein referred to as protein TIFY 10A-like (NCBI accession no. XP_013583936.1; GI:922487335) has the following sequence (SEQ ID NO:22.

```
  1  MSSSMECSTT RRSSSGKPSF SLTCSRLSQY LKENGSFGDL
 41  SLGMSCKPDT NGMSPKPTTT MSLFPCEASN VGSMAAAQDV
 81  KPKNLFPRQP SFSSSSSSIP KEDVPKMTQT TIRSLKPEPQ
121  TAPLTIFYGG QVIVFNDFSA EKAKEVMNLA NKGTANTFTG
161  FTSTLNNNTA PTPNQVPHLM KAATQDPKQT SSAAMACELP
201  IARRASLHRF LAKRKDRVTS KAPYQLNDPA KAYSKPQTGN
241  ITTSWLGLAA DM
```

A cDNA encoding the SEQ ID NO:22 protein is available as NCBI accession number XM_013728482.1 (GI: 922487334), and a chromosomal segment encoding the SEQ ID NO:22 protein is available as NCBI accession number NC_027752.1 (GI:919506312).

An uncharacterized *Zea mays* protein referred to as LOC100276383 (NCBI accession no. NP_001308779.1 (GI: 1013071036) has significant sequence identity to the *Arabidopsis thaliana* JAZ1 protein with SEQ ID NO:1, as illustrated by the sequence comparison shown below. Domains of sequence homology are identified by asterisks below the sequence comparison.

```
39.0% identity in 123 residues overlap; Score: 201.0; Gap frequency:
0.8%
Seq:1     61 LTIFYAGQVIVFNDFSAEKAYEVINLASKGTANSLAKNQTDIRSNIATIANQVPHPRKTT
Seq23    100 LTIFYGGKVLVFDDFPADKAKDLMQLASKGSPVVQNVALPQPSAAAAVTTDKAVLDPVIS
             ***** * * ** ** * ***      *****                 *

Seq:1    121 TQEPIQSSPTPLTELPIARRASLHRFLEKRKDRVTSKAPYQLCDPAKASSNPQTTGNMSW
Seq23    160 LAAAKKPARTNASDMPIMRKASLHRFLEKRKDRLNAKTPYQTA-PSDAAPVKKEPESQPW
                    *   ** * ************* * ***    * *                *

Seq:1    181 LGL
Seq23    219 LGL
             ***
```

This JAZ-related uncharacterized *Zea mays* protein referred to as LOC100276383 (NCBI accession no. NP_001308779.1 (GI:1013071036) has the following sequence (SEQ ID NO:23).

```
  1  MAASARPGER ATSFAVACSL LSRFVRQNGV AAADLGLRIK
 41  GEVEQQRTPA TTNSLPGAEG EEVERRKETM ELFPQSVGFS
 81  IKDAAAPREE QGDKEKPKQL TIFYGGKVLV FDDFPADKAK
121  DLMQLASKGS PVVQNVALPQ PSAAAAVTTD KAVLDPVISL
161  AAAKKPARTN ASDMPIMRKA SLHRFLEKRK DRLNAKTPYQ
201  TAPSDAAPVK KEPESQPWLG LGPNAVDSSL NLS
```

A cDNA encoding the SEQ ID NO:23 protein is available as NCBI accession number NM_001321850.1 (GI: 1013071035), and a chromosomal segment encoding the SEQ ID NO:23 protein is on *Zea mays* chromosome 7 at NC_024465.1 (165496371 ... 165497455), sequence available as NCBI accession number NC_024465.1 (GI: 662248746).

A *Glycine max* protein referred to as protein TIFY 10A-like (NCBI accession no. NP_001276307.1 (GI: 574584782)) has significant sequence identity to the *Arabidopsis thaliana* JAZ1 protein with SEQ ID NO:1, as illustrated by the sequence comparison shown below. Domains of sequence homology are identified by asterisks below the sequence comparison.

```
45.5% identity in 145 residues overlap; Score: 271.0; Gap frequency:
4.8%
Seq:1     42 VLKMTQTTRSVKPESQTAPLTIFYAGQVIVFNDFSAEKAKEVINLASKGTANSLAKNQTD
Seq24    101 IMVKSSAFKSMEKEPKAAQLTIFYAGQVVVFDDFPAEKLEEITSLAGKGISQS-----QN
                *    *   *        ********* ** ** ***  *   ** **      *

Seq:1    102 IRSNIATIANQVPHPRKTTTQEPIQSSPTPLTELPIARRASLHRFLEKRKDRVTSKAPYQ
Seq24    156 TSAYAHTHNQQVNHPSFVPNISPQAPSRPLVCDLPIARKASLHRFLSKRYDRIAAKAPYQ
               * ** **    * *   *   *      *****  ******* *****   *****

Seq:1    162 LCDPAKASSNPQTTGNMSWLGLAAE
Seq24    216 INNPNSASSKPAE--SMSWLGLGAQ
                *  ***  *    ****** *
```

This JAZ-related *Glycine max* protein referred to as protein TIFY 10A-like (NCBI accession no. NP_001276307.1 (GI: 574584782) has the following sequence (SEQ ID NO:24).

```
  1  MSSSSEYLVF SSHHPANSPA EKSTFSQTCS LLSQYIKEKG
 41  TFGDLTLGMT CTAETNGSPE TSCHSATTME LFPTIITQRN
 61  PTTVDFLSPQ TAYPHHSEVP IMVKSSAFKS MEKEPKAAQL
121  TIFYAGQVVV FDDFPAEKLE EITSLAGKGI SQSQNTSAYA
```

-continued
```
161  HTHNQQVNHP SFVPNISPQA PSRPLVCDLP IARKASLHRF
201  LSKRKDRIAA KAPYQINNPN SASSKPAESM SWLGLGAQST
```

A cDNA encoding the SEQ ID NO:24 protein is available as NCBI accession number NM_001289378.1 (GI: 574584781), and a chromosomal segment encoding the SEQ ID NO:24 protein is on *Glycine max* chromosome 13 at NC_016100.2 (22541885 ... 22544240), sequence available as NCBI accession number NC_016100.2 (GI:952545303).

An *Oryza sativa* protein referred to as protein TIFY 10b (*Japonica* Group; NCBI accession no. XP_015647536.1 (GI:1002286463) has significant sequence identity to the *Arabidopsis thaliana* JAZ1 protein with SEQ ID NO:1, as illustrated by the sequence comparison shown below. Domains of sequence homology are identified by asterisks below the sequence comparison.

```
38.5% identity in 156 residues overlap; Score: 213.0; Gap frequency:
4.5%

Seq:1     34 SSSLPKEDVLKMTQTTRSVKPESQTAPLTIFYAGQVIVFNDFSAEKAKEVINLASKGTA-
Seq25     77 SAGFGQQDAITADSAADAREQEPEKRQLTIFYGGKVLVFNDFPADKAKGLMQLASKGSPV
                 *        *           *     ***** * * ***** * ***      *****

Seq:1     93 ---NSLAKNQTDIRSNI-ATIANQVPHPRKTTTQEPIQS-SPTPLTELPIARRASLHRFL
Seq25    137 APQNAAAPAPAAVTDNTKAPMAVPAPVSSLPTAQADAQKPARANASDMPIARKASLHRFL
                * *       * * *     *      * *    *            **** *******

Seq:1    148 EKRKDRVTSKAPYQLCDPAKASSNPQTTGNMSWLGL
Seq25    197 EKRKDRLNAKTPYQ-ASPSDATPVKKEPESQPWLGL
             ******    * ***   * *              ****
```

This JAZ-related *Oryza sativa* protein referred to as protein TIFY 10b (*Japonica* Group; NCBI accession no. XP_015647536.1 (GI:1002286463) that has significant sequence identity to the *Arabidopsis thaliana* JAZ1 protein, has the following sequence (SEQ ID NO:25).

```
  1  MAASARPVGV GGERATSFAM ACSLLSRYVR QNGAAAAELG
 41  LGIRGEGEAP RAAPATMSLL PGEAERKKET MELFPQSAGF
 81  GQQDAITADS AADAREQEPE KRQLTIFYGG KVLVFNDFPA
121  DKAKGLMQLA SKGSPVAPQN AAAPAPAAVT DNTKAPMAVP
161  APVSSLPTAQ ADAQKPARAN ASDMPIARKA SLHRFLEKRK
201  DRLNAKTPYQ ASPSDATPVK KEPESQPWLG LGPNAVVKPI
241  ERGQ
```

A cDNA encoding the SEQ ID NO:25 protein is available as NCBI accession number XM_015792050.1 (GI: 1002286462), and a chromosomal segment encoding the SEQ ID NO:25 protein is on *Oryza sativa* chromosome 7 at NC_029262.1 (25347990 . . . 25350243), sequence available as NCBI accession number NC_029262.1 (GI:996703426).

An uncharacterized *Zea mays* protein with NCBI accession no. ACF88234.1 (SEQ ID NO:26) has significant sequence identity to the *Arabidopsis thaliana* JAZ2 protein with SEQ ID NO:3, as illustrated by the sequence comparison shown below. Domains of sequence homology are identified by asterisks below the sequence comparison.

```
35.1% identity in 235 residues overlap; Score: 221.0; Gap frequency:
9.8%

Seq:3     14 RKPSFSQTCTRLSRYLKEKGSFGDLSLGMTCKPDVNGGSRQPTMMNLFPCEASGMDSSAG
Seq26     10 RATSFAVACSLLSRFVRQNGA-APAQLGLGIKGEVEQ-QRTPATINLLP----GADGEET
                * **   *  ***         *    **    *  * *  ** *    * *

Seq:3     74 QEDIKPKTMFPRQSSFSSSSSSGTKEDVQMIKETTKSVKPESQSAPLTIFYGGRVMVFDD
Seq26     64 ERRKETMELFPQSAGF------GVKDAAAAPREQENKEKPKQ----LTIFYGGKVLVFDD
                ** *   * *       * *     *    **       ******* * ****

Seq:3    134 FSAEKAKEVIDLANKGSAKSFTCFTAEVNNNHSAYSQKEIASSPNPVCSPAKTAAQEPIQ
Seq26    114 FPADKAKDLMQLASKGGPVVQNVVLPQPSAPAAAVTDKAV---PVPVIS--LPAAQADAK
             * * ***   ** **                         *   *  *** *   ***

Seq:3    194 PNPASLACELPIARRASLHRFLEKRKDRITSKAPYQIDGS--AEASSKPTNPAWL
Seq26    169 KPTRTNASDMPIMRKASLHRFLEKRKDRLNANAPYQTSPSDAAPVKKEPESQAWL
                 ** * *************    ****  *    *     * ***
```

This JAZ-related *Zea mays* protein with NCBI accession no. ACF88234.1 that has significant sequence identity to the *Arabidopsis thaliana* JAZ2 protein, has the following sequence (SEQ ID NO:26).

```
  1  MAASAPPGER ATSFAVACSL LSRFVRQNGA APAQLGLGIK
 41  GEVEQQRTPA TINLLPGADG EETERRKETM ELFPQSAGFG
 81  VKDAAAAPRE QENKEKPKQL TIFYGGKVLV FDDFPADKAK
121  DLMQLASKGG PVVQNVVLPQ PSAPAAAVTD KAVPVPVISL
161  PAAQADAKKP TRTNASDMPI MRKASLHRFL EKRKDRLNAN
201  APYQTSPSDA APVKKEPESQ AWLGLGPNAV KSNLNLS
```

This JAZ-related *Zea mays* protein with NCBI accession no. ACF88234.1 is encoded by a gene on chromosome 2 at NC_024460.2 (218018545 . . . 218021029) of the *Zea mays* genome.

An uncharacterized *Triticum aestivum* (wheat) protein with NCBI accession no. SPT16989.1 (SEQ ID NO:27) has significant sequence identity to the *Arabidopsis thaliana* JAZ2 protein with SEQ ID NO:3, as illustrated by the sequence comparison shown below. Domains of sequence homology are identified by asterisks below the sequence comparison.

```
44.8% identity in 116 residues overlap; Score: 201.0; Gap frequency:
5.2%
Seq3   114 ESQSAPLTIFYGGRVMVFDDFSAEKAKEVIDLANKGSAKSFTCFTAEVNNNHSAYSQKEI
Seq21   91 EEDKSQLTIFYGGKVLVFNDFPADKAKGLMQLAGKGSPVVQNVSATTTAADTDKVQTAVL
               ******* * ** ** * ***    ** ***

Seq3   174 ASSPNPVCSPAKTAAQEPIQPNPASLACELPIARRASLHRFLEKRKDRITSKAPYQ
Seq27  151 APASSLPTGPVD--APKPARPN----ASDLPIARKASLHRFLEKRKDRLHAKAPYQ
            *       *   * **    *  ***** *************  *****
```

This JAZ-related *Triticum aestivum* (wheat) with NCBI accession no. SPT16989.1 that has significant sequence identity to the *Arabidopsis thaliana* JAZ2 protein, has the following sequence (SEQ ID NO:27).

```
  1  MAASARQGER ATSFAMACSL LSRYVRQNGA AAAELGLGIN
 41  KGEAEAQRAA DTKSPLPGAE GEEAGRKKET MELFPQSAGL
 81  QDAAAPDATR EEDKSQLTIF YGGKVLVFND FPADKAKGLM
121  QLAGKGSPVV QNVSATTTAA DTDKVQTAVL APASSLPTGP
161  VDAPKPARPN ASDLPIARKA SLHRFLEKRK DRLHAKAPYQ
201  APPSDATPVK KEFENQPWLG LGPNAALKRN Q
```

An uncharacterized *Glycine max* (soybean) protein with NCBI accession no. XP_003542368.1 (SEQ ID NO:28) has significant sequence identity to the *Arabidopsis thaliana* JAZ2 protein with SEQ ID NO:3, as illustrated by the sequence comparison shown below. Domains of sequence homology are identified by asterisks below the sequence comparison.

```
42.6% identity in 230 residues overlap; Score: 314.0; Gap frequency:
12.6%

Seq:3   15 KPSFSQTCTRLSRYLKEKGSFGDLSLGMTCKPDVNGGSR----QPTMMNLFPCEASGMDS
Seq28   22 KSTFSQTCSLLSQYIKEKGTFGDLTLGMTCTAETNGSPETSCHSATTMELFPTIITQRNP
             * ***** ** * **** **** *****       **       * * ***

Seq:3   71 SAGQEDIKPKTMFPRQSSFSSSSSSGTKEDVQMIKETTKSVKPESQSAPLTIFYGGRVMV
Seq28   82 TT-VDFLSPQTAYPHHS---------EVPIMVKSSAFKSMEKEPKAAQLTIFYAGQVVV
            *  *  *                      **   *    * ***** * *

Seq:3  131 FDDFSAEKAKEVIDLANKGSAKSFTCFTAEVNNNHSAYSQKEIASSPNPVCSPAKTAAQE
Seq28  131 FDDFPAEKLEEITSLAGKGISQS---------QNTSAYAHTHNQQVNHPSFVP-NISPQA
           **** ***  *  ** ** *          * ***       *    *    *

Seq:3  191 PIQPNPASLACELPIARRASLHRFLEKRKDRITSKAPYQIDGSAEASSKP
Seq28  181 PSRP----LVCDLPIARKASLHRFLSKRKDRIAAKAPYQINNPNSASSKP
            * *     * ***** ******* ****** *******     *****
```

This JAZ-related *Glycine max* protein with NCBI accession no. XP_003542368.1 that has significant sequence identity to the *Arabidopsis thaliana* JAZ2 protein, has the following sequence (SEQ ID NO:28).

```
  1   MSSSSEYLVF SGHHPANSPA EKSTFSQTCS LLSQYIKEKG
 41   TFGDLTLGMT CTAETNGSPE TSCHSATTME LFPTIITQRN
 81   PTTVDFLSPQ TAYPHHSEVP IMVKSSAFKS MEKEPKAAQL
121   TIFYAGQVVV FDDFPAEKLE EITSLAGKGI SQSQNTSAYA
181   HTHNQQVNHP SFVPNISPQA PSRPLVCDLP IARKASLHRF
201   LSKRKDRIAA KAPYQINNPN SASSKPAESM SWLGLGAQST
241   QV
```

This JAZ-related *Glycine max* protein with NCBI accession no. XP_003542368.1 is encoded by agene at NC_038249.1 (22541885 ... 22544240) on chromosome 13 of the *Glycine max* genome.

An uncharacterized *Zea mays* protein referred to as LOC103647411 (NCBI accession no. NP_001288506.1; SEQ ID NO:29) has significant sequence identity to the *Arabidopsis thaliana* JAZ3 protein with SEQ ID NO:5, as illustrated by the sequence comparison shown below. Domains of sequence homology are identified by asterisks below the sequence comparison.

```
36.6% identity in 161 residues overlap; Score: 165.0; Gap frequency:
6.8%

Seq5:  177 AQLTIFYAGSVCVYDDISPEKAKAIMLLAGNGSSMPQVFSPPQTHQQVVHHTRASVDSSA
Seq29: 167 AQLTIFYAGSVNVFNNVSAEKAQELMFLASRGSSAPVACKPEAPPTLAPAKVTAPEVLLP
           *********** *   * ***  * **  *** *     *                *

Seq5:  237 MPPSFMPTISYLSPEAGSSTNGLGATKATRGLTSTYH-NNQANGSNINCPVP--------
Seq29: 227 AKQMLFQKPQHLSPPPSSVPGILQSAALPRSASSSSNLDSPAPKSSVPLAVPPVSQAPPA
               ***  *   *     *  *      *    *  *   **

Seq5:  288 --VSCSTNVMAPTVALPLARKASLARFLEKRKERVTSVSPY
Seq29: 287 TLIATTTAAAIMPRAVPQARKASLARFLEKRKERVTTAAPY
               *   * * ****************** **
```

This JAZ-related *Zea mays* protein referred to as LOC13647411 (NCBI accession no. NP_001288506.1) has the following sequence (SEQ ID NO:29).

```
  1   MERDFLAAIG KEQQHPRKEK AGGGAEESAY FGAAAVPAMD
 41   WSFASKPCAA PALMSFRSAA REEPSFPQFS ALDGTKNTAP
 81   RMLTHQRSFG PDSTQYAALH RAQNGARVVP VSSPFSQSNP
121   MFRVQSSPSL PNSTAFKQPP FAISNAVASS TVGSYGGTRD
161   AVRPRTAQLT IFYAGSVNVF NNVSAEKAQE LMFLASRGSS
201   APVACKPEAP PTLAPAKVTA PEVLLPAKQM LFQKPQHLSP
241   PPSSVPGILQ SAALPRSASS SSNLDSPAPK SSVPLAVPPV
281   SQAPPATLIA TTTAAAIMPR AVPQARKASL ARFLEKRKER
```

-continued
```
321   VTTAAPYPSA KSPLESSDTF GSGSASANAN DKSSCTDIAL
361   SSNHEESLCL GGQPRSIISF SEESPSTKLQ I
```

A cDNA encoding the SEQ ID NO:29 protein is available as NCBI accession number NM_001301577.1 and a chromosomal segment encoding the SEQ ID NO:29 protein is on chromosome 2 at NC_024460.2 (184842608 ... 184845336 complement) of the *Zea mays* genome, sequence available as NCBI accession number NC_024460.1 (GI:662249846).

A *Triticum aestivum* jasmonate ZIM-domain transcriptional repressor protein with (NCBI accession no. QBQ83004.1; SEQ ID NO:30) has significant sequence identity to the *Arabidopsis thaliana* JAZ3 protein with SEQ ID NO:5, as illustrated by the sequence comparison shown below, where the two sequences have about 30% sequence identity. Domains of sequence homology are identified by asterisks below the sequence comparison.

```
Seq5     1 MERDFLG-LGSKNSPITVKEETSESS--------RDSAPNRG-----MNWSFSNKVSASS
Seq30    1 MERDFLGTIGHEQLQQQQQQQQRQRAAAEDAAARKESAYFGGGGVPPMDWSFAGRAGAAP
           *******  *                          **   *      * ***      *

Seq5    47 SQFLSFR--PTQEDRH-----RKSGNYHLPHSGSFMPSSVADV-YDSTRKAPYSSVQGVR
Seq30   61 A-VMSFRSAPREEQRGELAYPKQQASRVLTPQRSFGAESHGSVQYAAAARAAYGGQP---
              ***  *   * * *          *    *    *  **       *  *

Seq5    99 MFPNSNQHEETNAVSMSMPGFQSHHYAPGGRSFMNNNNNSQP---LVGVPIMAPPISIL-
Seq30  117 --PQQHQHAPNGARVIPM----SSPFNPNNPMFRVQSSPNLPNGVAAGSPFKQPPFVMNN
             *  **   *     *      *    *     *   *        *  **    *

Seq5   155 PPPGSIVGTTDIRSSSKPIGSPAQLTIFYAGSVCVYDDISPEKAKAIMLLAGNGSS----
Seq30  171 AVAASTVGVYKSRDMPKP--KTAQLTIFYAGSVNVFNNVSAEKAQELMFLASRGSLPTAP
             * **     *   **    *********** *    ***    *  ** **

Seq5   211 -----------MPQVFSPPQTH--QQVVHHTRASVD----SSAMPPSFMPTISYLSPEA
Seq30  229 TTVTRSPDATFFTPAKLAAPEASPAKQMLAHIPQRVSPPLPAISKPMSIMSQAACL-PKS
                         *    *          *     *

Seq5   253 GSSTNGLGATKATRGLTSTYHNNQANGSNINCPVPVSCSTNVMAPTVALPLARKASLARF
Seq30  288 TSSSNTDSAVPKSSGQLVVPPTSQTSSST--HPVTLSSTTAASIMPRAVPQARKASLARF
            ** *  *     *       *    *        *  *           * *********

Seq5   313 LEKRKERVTSVSPY  326
Seq30  346 LEKRKERVTTTAPY  359
           *********   **
```

This *Triticum aestivum* jasmonate ZIM-domain transcriptional repressor protein with significant sequence identity to the *Arabidopsis thaliana* JAZ3 protein with SEQ ID NO:5 and NCBI accession no. QBQ83004.1 has the following sequence (SEQ ID NO:30).

```
  1 MERDFLGTIG HEQLQQQQQQ QQRQRAAAED AAARKESAYF
 41 GGGGVPPMDW SFAGRAGAAP AVMSFRSAPR EEQRGELAYP
 81 KQQASRVLTP QRSFGAESHG SVQYAAAARA AYGGQPPQQH
121 QHAPNGARVI PMSSPFNPNN PMFRVQSSPN LPNGVAAGSP
161 FKQPPFVMNN AVAASTVGVY KSRDMPKPKT AQLTIFYAGS
201 VNVFNNVSAE KAQELMFLAS RGSLPTAPTT VTRSPDATFF
241 TPAKLAAPEA SPAKQMLAHI PQRVSPPLPA ISKPMSIMSQ
281 AACLPKSTSS SNTDSAVPKS SGQLVVPPTS QTSSSTHPVT
321 LSSTTAASIM PRAVPQARKA SLARFLEKRK ERVTTTAPYP
361 SAKSPMESSD TVGSANDNNS KSSSCTEIAF SSNHEESLRL
401 GRPRNISFSG ESPSTKLHI
```

A cDNA encoding the SEQ ID NO:30 *Triticum aestivum* jasmonate protein has the sequence provided as NCBI accession number MH063273.1.

A *Glycine max* protein referred to as protein TIFY 6B-like isoform X1 (NCBI accession no. XP_003534135.1 (GI: 356531138; SEQ ID NO:31) has significant sequence identity to the *Arabidopsis thaliana* JAZ3 protein with SEQ ID NO:5, as illustrated by the sequence comparison shown below. Domains of sequence homology are identified by asterisks below the sequence comparison.

```
38.9% identity in 378 residues overlap; Score: 417.0; Gap frequency: 8.5%

Seq5:    1 MERDFLGLGSKNSP-ITVKEETSESSRDSAPNRGMNWSFSNKVSASSSQFLSFRPTQEDR
Seq31:   1 MEREFFGLSSKNGAWTTMKDDAVNKSRDQVRSSGMQWSFPNKVSALP-QFLSFKTNQEDK
           *** * ** ***    *         ***    **  ** ***** *  *****   ***

Seq5:   60 HRKSGNYHLPHSGSFMPSSVADVYDSTRKA--------------PYSSVQGVRMFPNS--
Seq31:  60 PRKTILEPLASSG-YMAMSTQYAFDSNQKSFLGLTNRNLSISKHAAGNKQGMTVYPLQCC
            **      *  *  *  *  *  ** *                  **    *     *

Seq5:  104 -NQHEETNAVSMSMPGFQ-----SHHYAPGGRSFMNNNNNSQPLVGVPIMAPPISILPPP
Seq31: 119 DAQSEEARIFSVSNQSNQVSPVLQSNLASTGLNMVNSVIKPQPF-GSKSSGTPLSILPSI
             * **    * **   *      *           **  *  *      ** ****

Seq5:  158 GSIVGTTDIRSSSKPIGSPAQLTIFYAGSVCVDDDISPEKAKAIMLLAGNGSSMPQVFSP
Seq31: 178 GSIVGSTDLRNNSKSSTMPTQLTIFYAGSVCVYDDISPEKAKAIMLMAGNGYTPTEKMEL
           ***** ** *  **    * *********** *************** ****    ****

Seq5:  218 PQTHQQVVHHTRASVD----SSAMPPSFMPTISYLSPEAGSSTNGLGATKATRGLTSTYH
Seq31: 238 PTVKLQPAISIPSKDDGFMISQSYPPSTFPTPLPLTSHVNSQPGGGSSSNKEISIIRQVG
            *     *        *    *** *      ***  *     *         *
```

```
Seq5:   274 NNQANGSNINCPV--PVSCSTNVMAPTVALPLARKASLARFLEKRKERVTSVSPYCLDKK
Seq31   298 PSTAPTNHLESPIIGSIGSASKEKAQPVCLPQARKASLARFLEKRKGRMMRTSPYLYMSK
                *       *       *  * ** ************** *    ***     *

Seq5:   332 SSIDCRRSMSECISSSLS
Seq31   358 KSPECSSSGSDSVSFSLN
              *   *  *    *  **
```

This JAZ-related *Glycine max* protein referred to as protein TIFY 6B-like isoform X1 (NCBI accession no. XP_003534135.1 (GI:356531138) has the following sequence (SEQ ID NO:31).

```
  1   MEREFFGLSS KNGAWTTMKD DAVNKSRDQV RSSGMQWSFP
 41   NKVSALPQFL SFKTNQEDKP RKTILEPLAS SGYMAMSTQY
 81   AFDSNQKSFL GLTNRNLSIS KHAAGNKQGM TVYPLQCCDA
121   QSEEARIFSV SNQSNQVSPV LQSNLASTGL NMVNSVIKPQ
161   PFGSKSSGTP LSILPSIGSI VGSTDLRNNS KSSTMPTQLT
201   IFYAGSVCVY DDISPEKAKA IMLMAGNGYT PTEKMELPTV
241   KLQPAISIPS KDDGFMISQS YPPSTFPTPL PLTSHVNSQP
281   GGGSSSNKEI SIIRQVGPST APTNHLESPI IGSIGSASKE
321   KAQPVCLPQA RKASLARFLE KRKGRMMRTS PYLYMSKKSP
361   ECSSSGSDSV SFSLNFSGSC SLPATN
```

A cDNA encoding the SEQ ID NO:3 protein is available as NCBI accession number XM_003534087.3 (GI: 955341633), and a chromosomal segment encoding the SEQ ID NO:31 protein is on *Glycine max* chromosome 9 at NC_016096.2 (0.39883473.39889992) sequence available as NCBI accession number NC_016096.2 (GI:952545307).

An *Oryza sativa* protein referred to as protein TIFY 6b (NCBI accession no. XP_015612402.1 (GI:1002297967), SEQ ID NO:32) has significant sequence identity to the *Arabidopsis thaliana* JAZ3 protein with SEQ ID NO:5, as illustrated by the sequence comparison shown below. Domains of sequence homology are identified by asterisks below the sequence comparison.

```
37.3% identity in 177 residues overlap; Score: 142.0; Gap frequency:
10.2%

Seq5:   172 PIGSPAQLTIFYAGSVCVYDDISPEKAKAIMLLAGNGS---------SMFQ--VFSPPQT
Seq32   187 PKAKAAQLTIFYAGSVNVFNNVSPEKAQELMFLASRGSLPSAPTTVARMPEAHVFPPAKV
                 *  ********** *    *****  * ** **        **   ** **  *

Seq5:   221 HQQVVHHTRASV-DSSAMPPSFMPTISY---LSPEAGSSTNGLGATKATRGLTSTYHNNQ
Seq32   247 TVPEVSPTKPMMLQKPQLVSSPVPAISKPISVVSQATSLPRSASSSNVDSNVTKSSGPLV
              * *          *   * **     * **       *   *         *

Seq5:   277 ANGSNINCPV-PVSCSTNVMAPTV--ALPLARKASLARFLEKRKERVTSVSPYCLDK
Seq32   307 VPPTSLPPPAQPETLATTTAAAIMPRAVPQARKASLARFLEKRKERVTTVAPYPLAK
                *     *   *      *    * *  ******************* ** *  *
```

This JAZ-related *Oryza sativa* protein, referred to as protein TIFY 6b (NCBI accession no. XP_015612402.1 (GI: 1002297967), has the following sequence (SEQ ID NO: 32).

```
  1   MERDFLGAIG KDEEQRRHAE ERKESDYFGA GGGAAAAAMD
 41   WSFASRAALM SFRSSSSAAA AAAREETREL AFPHFSALDG
 81   AKMQQASHVL ARQKSFGAES HGIPQYAAAA AVHGAHRGQP
121   PHVLNGARVI PASSPFNPNN PMFRVQSSPN LPNAVGAGGG
161   AFKQPPFAMG NAVAGSTVGV YGTRDMPKAK AAQLTIFYAG
201   SVNVFNNVSP FKAQELMFLA SRGSLPSAPT TVARMPEAHV
241   FPPAKVTVPE VSPTKPMMLQ KPQLVSSPVP AISKPISVVS
281   QATSLPRSAS SSNVDSNVTK SSGPLVVPPT SLPPPAQPET
321   LATTTAAAIM PRAVPQARKA SLARFLEKRK ERVTTVAPYP
361   LAKSPLESSD TMGSANDNKS SCTDIALSSN RDESLSLGQP
401   RTISFCEESP STKLQI
```

A cDNA encoding the SEQ ID NO:32 protein is available as NCBI accession number XM_015756916.1 (GI: 1002297966), and a chromosomal segment encoding the SEQ ID NO:32 protein is on *Oryza sativa* chromosome 9 at NC_029264.1 (14056084 . . . 14060320, complement), sequence available as NCBI accession number NC_029264.1 (GI:996703424).

An uncharacterized *Zea mays* protein referred to as LOC100273108 (NCBI accession no. NP_001141029.1 (GI: 226500626), SEQ ID NO:33) has significant sequence identity to the *Arabidopsis thaliana* JAZ4 protein with SEQ ID NO:7. For example, the *Zea mays* SEQ ID NO:33 protein has domains of 40 residues having 55% sequence identity from positions 138-178, and 26 residues having 77% sequence identity from positions 258-284 homology with the *Arabidopsis thaliana* JAZ4 protein. This JAZ-related uncharacterized *Zea mays* protein, referred to as LOC100273108 (NCBI accession no. NP_001141029.1 (GI: 226500626), has the following sequence (SEQ ID NO:33).

```
  1   MAKSGASFPE SSWMERDFLA AIGKEQQHPH KEEAGAEESA
 41   YFGGAGAAAA APAMDWSFAS KPGAAPALMS FRSASFPQFS
 81   SFDGAKNPAP RILTHQRSFG PDSTHYAAAH RTQHALNGAR
121   VTPVSSPFNQ NSPMFRVQSS PSLPNGTAFK QPPFAINNNA
161   AASSTVGFYG TRDVVRPKTA QLTIFYAGSV NVFDNVSAEK
```

```
201 AQELMLLASR GSLPSSAPVA RKPEAPILAP AKVTAPEVLH

241 ATQMLFQKPQ HVSPPSSAIS KPIPGILQAA SLPRSASSSN

281 LDSPFPKSSV PFPVSPVSQA PRAQPATIAA TTAAAIMPRA

321 VPQARKASLA RFLEKRKERV TTAAPYPSAK SPMESSDTFG

361 SGSANDKSSC TDIALSSNHE ESLCLGQPRN ISFIQESPST

401 KLQI
```

A cDNA encoding the SEQ ID NO:33 protein is available as NCBI accession number NM_001147557.1 (GI: 226500625), and a chromosomal segment encoding the SEQ ID NO:33 protein is on *Zea mays* chromosome 7 at NC_024465.1 (108871356 . . . 108874213, complement), sequence available as NCBI accession number NC_024465.1 (GI:662248746).

A *Glycine max* protein, referred to as protein TIFY 6B isoform X5 (NCBI accession number XP_006580448.1 (GI: 571456655; SEQ ID NO:34), has significant sequence identity to the *Arabidopsis thaliana* JAZ4 protein with SEQ ID NO:7, as illustrated by the sequence comparison shown below. Domains of sequence homology are identified with asterisks below the sequence comparison.

```
37.0% identity in 322 residues overlap; Score: 273.0; Gap frequency:
8.7%

Seq7:    1 MERDFLGLGSKLSPITVKEETNEDSAPSRG-----MMDWSFSSKVGSGPQFLSFGTSQQE
Seq34:   1 MERDFMGLNLKEPLAVVKFFMNNDGCKNSGFKKGRIAQWPFSNKVSALPHLMSFKASQDD
           ***** ** *    **** * *      *       * ** **   *   ** **

Seq7:   56 TRVNTVNDHLLSSAAMD-QNQRTYFSSLQEDRVFPGSSQQDQTTITVSMSEPNYINSFI-
Seq34:  61 KTKNTVSDTLSSSGFMSILSQEAFDTSQKRSAGEPQMFSVPNQAISVSLGNPFLKNHFAA
           *** * * **     *    *    *      *      * **   *   *   *

Seq7:  114 --NHQHLGGSPIMAP----PVSVFPAPTTIRSSSKPLPPQLTIFYAGSVLVYQDIAPEKA
Seq34: 121 AGQKPLLGGIPVTTSHSVLPSAVAVAGMTESCNSVKPSAQLTIFYAGTVNIFDDISAEKA
             *** *        *   * *  *      ******** *    ** ***

Seq7:  168 QAIMLLAGNG-PHAKPVSQPKPQKLVHHSLPTTDPPTMPPSFLPSISYIVSETRSSGSNG
Seq34: 181 QAIMLLAGNSLSAASNMAQPNVQVPISKLGAGAGVPVSQPANTSPGSGLSSPLSVSSHTG
           *********  *   * **   *       *    *       *      *   *

Seq7:  227 V-TGLGPTKTKASLASTRNN--QTAAFSMAP----------TVGLPQTRKASLARFLEKR
Seq34: 241 VQSGSGLTSTDEFLAAKTTGVPNTPICNVEPPKVVSATTMLTSAVPQARKASLARFLEKR
           *  *   *     **    *      *      *  ** ************

Seq7:  274 KERVINVSPYYVDNKSSIDCRT
Seq34: 301 KERVMSAAPYNL-NEESEECAT
           ****    **  **  *  *
```

This JAZ-related *Glycine max* protein, referred to as protein TIFY 6B isoform X5 (NCBI accession number XP_006580448.1 (GI:571456655), has the following sequence (SEQ ID NO:34).

```
  1 MERDFMGLNL KEPLAVVKEE MNNDGCKNSG FKKGRIAQWP

41 FSNKVSALPH LMSFKASQDD KTKNTVSDTL SSSGFMSILS

61 QEAFDTSQKR SAGEPQMFSV PNQAISVSLG NPFLKNHFAA

121 AGQKPLLGGI PVTTSHSVLP SAVAVAGMTE SCNSVKPSAQ

161 LTIFYAGTVN IFDDISAEKA QAIMLLAGNS LSAASNMAQP

201 NVQVPISKLG AGAGVPVSQP ANTSPGSGLS SPLSVSSHTG

241 VQSGSGLTST DEFLAAKTTG VPNTPICNVE PPKVVSATTM

281 LTSAVPQARK ASLARFLEKR KERVMSAAPY NLNKKSEECA

321 TAEYAGVNFS ATNTVLAKQG
```

A cDNA encoding the SEQ ID NO:34 protein is available as NCBI accession number XM_006580385.2 (GI: 955322108), and a chromosomal segment encoding the SEQ ID NO:34 protein is on *Glycine max* chromosome 5 at NC_016092.2 (41222014 . . . 41225906), sequence available as NCBI accession number NC_016092.2 (GI:952545311).

An *Oryza sativa* protein, referred to as protein TIFY 6a isoform X2 (NCBI accession number XP_015651050.1 (GI: 1002293416; SEQ ID NO:35), has significant sequence identity to the *Arabidopsis thaliana* JAZ4 protein with SEQ ID NO:7. For example, the *Oryza sativa* SEQ ID NO:35 protein has domains of 26 residues having 81% sequence identity from positions 258-284 of the *Arabidopsis thaliana* JAZ4 protein with SEQ ID NO:7, and 47 residues having 45% sequence identity from positions 138-185 of the *Arabidopsis thaliana* JAZ4 protein with SEQ ID NO:7. This JAZ-related *Oryza sativa* protein, referred to as protein TIFY 6a isoform X2 (NCBI accession number XP_015651050.1 (GI:1002293416), has the following sequence (SEQ ID NO:35).

```
  1 MERDFLGAIW RKEEAAGKPE EHSDYRGGGG GASAAMQWQF

41 PATKVGAASS AFMSFRSSAA AAREEDPKEA AVFDRFSLSG

81 FRPPPRPSPG DAFDGAAAMK QRQFGFNGRQ QYAAAAQHGH

121 REQGVDSYGV AAPHHFPSPS PSPRHPVPFG HANPMLRVHS

161 LPNVAGGSPY RNQSFSVGNS VAGSTVGVYG GPRDLQNPKV

201 TQMTIFYDGL VNVFDNIPVE KAQELMLLAS RASIPSPPSA

241 ARKSDSPISA AAKLTVPEAL PARQIVVQKP EASVPLVSGV

281 SNPITIVSQA VTLPKSFSSS NDSAGPKSGG LPLAVTPLSQ

321 ASPSQPIPVA TTNASAIMPR AVPQARKASL ARFLEKPKER
```

```
361 VSSVAPYPSS KSPLESSDTI GSPSTPSKSS CTDITPSTNN

401 CEDSLCLGQP RNISFSSQEP PSTKLQI
```

A cDNA encoding the SEQ ID NO:35 protein is available as NCBI accession number XM_015795564.1 (GI: 1002293415), and a chromosomal segment encoding the SEQ ID NO:35 protein is on *Oryza sativa* chromosome 8 at NC_029263.1 (20624989 . . . 20627964, complement), sequence available as NCBI accession number NC_029263.1 (GI:996703425).

A *Triticum aestivum* jasmonate ZIM-domain transcriptional repressor protein with NCBI accession no. ABK63978.1 (SEQ ID NO:36) has significant sequence identity to the *Arabidopsis thaliana* JAZ4 protein with SEQ ID NO:7. For example, the *Triticum aestivum* SEQ ID NO:36 protein has domains of 36 residues having 67% sequence identity from positions 139-175 of the *Arabidopsis thaliana* JAZ4 protein with SEQ ID NO:7 and 26 residues having 58% sequence identity from positions 258-284 of the *Arabidopsis thaliana* JAZ4 protein with SEQ ID NO:7. This *Triticum aestivum* jasmonate ZIM-domain transcriptional repressor protein with NCBI accession no. ABK63978.1, has the following sequence (SEQ ID NO:36).

```
  1 LANGRSGMLP MSSPPANPGQ LTIFYGGSVC VYDSVPPEKA

41 QAIMLIAAAA AAASKSNGTA AVKPPAMSAT NAIQAMLTRS

81 LSLQSTSVAX GQPQAVADPG SICKLQADLP IAPRHSLQRF

121 LEKRRDRVVS KAPYGARKPF EGMGASSGME SVAEGRP
```

A *Zea mays* protein referred to a hypothetical protein Zm00014a_023069 protein with NCBI accession no. PWZ14661.1 (SEQ ID NO:37) has significant sequence identity to the *Arabidopsis thaliana* JAZ5 protein with SEQ ID NO:9, as illustrated by the sequence comparison shown below. Domains of sequence homology are identified by asterisks below each sequence comparison.

```
31.4% identity in 207 residues overlap; Score: 131.0; Gap frequency:
11.6%
Seq9      7 NAKAQAPEKSDFTRRCSLLSRYLKEKGSFGNIDLGLYRKPDSSLALPGKFDPPGKQNAMH
Seq37     4 HAPARDKTTSGFAATCSLLSQFLKEKKG-GLQGLGGLAMAPAPAAGAGAFRPPTTMNLLS
            *  *      * *   *****  ****   *   **       *   *  * ** **  *

Seq9     67 KAGHSKGEPSTSSGGKVKDVADLSESQ-PGSSQLTIFFGGKVLVYNEFPVDKAKEIMEVA
Seq37    63 ALDAAKATVGEPEGHGQRTGGNPREAAGEEAQQLTIFYGGKVVVFDRFPSAKVKDLLQIV
              *    *  *         *          ***** ****  **  * *

Seq9    126 KQAKPVTEINIQTPINDENNNNKSSMVLPDLNEPTDNNHLTKEQQQQQEQNQIVERIARR
Seq37   123 ------------SPPGADAVVDGAGAAVPTQNLPRPPHDSLSADLP----------IARR
                         *             * * *                         ****

Seq9    186 ASLHRFFAKRKDRAVARAPYQVNQNAG
Seq37   761 NSLHRFLEKRKDRITAKAPYQVNSSVG
            ***** ***** * ******  *
```

This *Zea mays* protein referred to as hypothetical protein Zm00014a_023069 with NCBI accession no. PWZ14661.1, has the following sequence (SEQ ID NO:37).

```
  1 MAGHAPARDK TTSGFAATCS LLSQFLKEKK GGLQGLGGLA

41 MAPAPAAGAG AFRPPTTMNL LSALDAAKAT VGEPEGHGQR

81 TGGNPREAAG EEAQQLTIFY GGKVVVFDRF PSAKVKDLLQ

121 IVSPPGADAV VDGAGAAVPT QNLPRPPHDS LSADLPIARR

161 NSLHRFLEKR KDRITAKAPY QVNSSVGAEA SKAEKPWLGL

201 GQEGSDGRQA GDVIDE
```

A *Glycine max* protein referred to as a TIFY 10A protein with NCBI accession no. XP_003546514.1 (SEQ ID NO:38) has significant sequence identity to the *Arabidopsis thaliana* JAZ5 protein with SEQ ID NO:9, as illustrated by the sequence comparison shown below. Domains of sequence homology are identified by asterisks below each sequence comparison.

```
35.6% identity in 219 residues overlap; Score: 206.0; Gap frequency:
9.6%
Seq9:    10 AQAPEKSDFTRRCSLLSRYLKEKGSFGNIDLGLYR--KPDSSL--ALPGKFDPPGKQNAM
Seq38    16 ARSPEKSSFSQTCSLLSQYIKEKGSFGDLTLGMTSCGSPETSCQSATTMNLFPPKENNVA
              * **** *   *****  * ******       **    *      *  ** *
```

```
Seq9:    66  HK--AGHSKGEPSTSSGGKVKDVADLSESQPQSS--------QLTIFFGGKVLVYNEFPV
Seq38    76  PKNLTAMDLLSPQASSYGPSEEIPTLVNSSAIKSVSKGAKTAQMTIFYGGQVVVFDDFPA
                *     *  ** *          *   *      *   * *** ** **   **

Seq9:   116  DKAKEIMEVA-KQAKPVTEINIQTPINDENNNNKSSMVLPDLNE-----PTDN-NHLTKE
Seq38   136  DKASEIMSYATKGGIPQSQNNSVYTYTQSQPSFPPTLIRTSADSSAPIIPSVNITNSIRE
             *** ***  *  *    *                     *          *  *    *

Seq9:   169  QQQQQEQNQIVERIARRASLHRFFAKRKDRAVARAPYQV
Seq38   196  HPQASSRPVVYLPIARKASLHRFLEKRKDRIASKAPYQV
                  *      *** ****** *****    *****
```

This *Glycine max* protein referred to as a TIFY 10A protein with NCBI accession no. XP_003546514.1, has the following sequence (SEQ ID NO:38).

```
  1  MSSSSEYSEF SGQKPARSPE KSSFSQTCSL LSQYIKEKGS

41  FGDLTLGMTS CGSPETSCQS ATTMNLFPPK ENNVAPKNLT

81  AMDLLSPQAS SYGPSEEIPT LVNSSAIKSV SKGAKTAQMT

121  IFYGGQVVVF DDFPADKASE IMSYATKGGI PQSQNNSVYT

161  YTQSQPSFPP TLIRTSADSS APIIPSVNIT NSIREHPQAS

201  SRPVVYLPIA RKASLHRFLE KRKDRIASKA PYQVANGPSN

241  KAAESMPWLG LSASSPQI
```

A cDNA encoding the SEQ ID NO:38 protein is available as NCBI accession no. XM_003546466.4 and a chromosomal segment encoding the SEQ ID NO:38 protein is on *Glycine max* chromosome 15 at NC_038251.1 (17292772 . . . 17295396).

An unnamed *Triticum aestivum* protein with NCBI accession no. SPT20417.1 (SEQ ID NO:39) has significant sequence identity to the *Arabidopsis thaliana* JAZ5 protein with SEQ ID NO:9, as illustrated by the sequence comparison shown below. Domains of sequence homology are identified by asterisks below each sequence comparison.

```
31.5% identity in 124 residues overlap; Score: 109.0; Gap frequency:
5.6%
Seq9:    89  LSESQPGSSQLTIFFGGKVLVYNEFPVDKAKEIMEVAKQAKPVTEINIQTPINDE--NNN
Seq39    57  MSSPPANPGQLTIFYGGSVCVYDSVPPEKAQAIMLIAAAAAAASKSNGTAAVKPPAMSAT
                      ***** ** ** **  * **  ** **               *

Seq9:   147  NKSSMVLPDLNEPTDNNHLTKEQQQQQEQNQIVER-----IARRASLHRFFAKRKDRAVA
Seq39   117  NAIQAMLTRSLSQSTSVANGQPQAVADPGSICKLQADLPIARRHSLQRFLEKRRDRVVS
                *    *               *      *       **** ** ** ** **  *

Seq9:   202  RAPY
Seq39   177  KAPY
                ***
```

This unnamed *Triticum aestivum* protein with NCBI accession no. SPT20417.1, has the following sequence (SEQ ID NO:39).

```
  1  MDLLERSAAT IKAEAGEAQR KEAERKEQEL EKEQETQQPG

41  LTGRPPLANG RSGMLPMSSP PANPGQLTIF YGGSVCVYDS

81  VPPEKAQAIM LIAAAAAAAS KSNGTAAVKP PAMSATNAIQ

121  AMLTRSLSLQ STSVANGQPQ AVADPGSICK LQADLPIARR

161  HSLQRFLEKR RDRVVSKAPY GAGKPSEGMG ASSGMEAVAE

201  GKAQ
```

A *Zea mays* protein referred to as TIFY 10b with NCBI accession no. PWZ12604.1 (SEQ ID NO:40) has significant sequence identity to the *Arabidopsis thaliana* JAZ6 protein with SEQ ID NO: 11, as illustrated by the sequence comparison shown below. Domains of sequence homology are identified by asterisks below each sequence comparison.

```
38.1% identity in 105 residues overlap; Score: 156.0; Gap frequency:
1.9%
Seq11   106  QLTIFFGGKVMVFNEFPEDKAKEIMEVAKEANHVAVDSKNSQSHMNLDKSNVVIPDLNEP
Seq40   100  QLTIFYGGKVLVFDDFPADKAYDLMQLASKGSPVVQNVVLPQP--SAAAAVTTDKAVLDP
             ***** **** ** **** *  *   *     *              *    *      *
```

```
Seq11   166  TSSGNNEDQETGQQHQVVERIARRASLHRFFAKRKDRAVARAPYQ
Seq40   158  VISLAAAAKKPARTNASDMPIMRKASLHRFLEKRKDRLNAKTPYQ
               *  *  * ******  *****  *  ***
```

This TIFY 10b *Zea mays* protein with NCBI accession no. PWZ12604.1 has the following sequence (SEQ ID NO:40).

```
  1  MAASARPGER ATSFAVACSL LSRFVRQNGV AAALLGLRIK
 41  GEVEQQRTPA TTSLLPGAEG EEVERRKETM ELFPQSVGFS
 81  IKDAAAPPRE EQGDKEKPKQ LTIFYGGKVL VFDDFPADKA
121  KDLMQLASKG SPVVQNVVLP QPSAAAAVTT DKAVLDPVIS
161  LAAAAKKPAR TNASDMPIMR KASLHRFLEK RKDRLNAKTP
201  YQTAPSDAAP VKKEPESQPW LGLGPNAVDS SLNLS
```

A *Glycine max* protein referred to as TIFY 10a-like isoform X1 with NCBI accession no. XP_006587054.1 (SEQ ID NO:41) has significant sequence identity to the *Arabidopsis thaliana* JAZ6 protein with SEQ ID NO: 11, as illustrated by the sequence comparison shown below. Domains of sequence homology are identified by asterisks below each sequence comparison.

```
33.0% identity in. 227 residues overlap; Score: 233,0; Gap frequency:
6.2%
Seq11    5  QAPEKSNFSQRCSLLSRYLKEKGSFGNINMGLARKSDLELAGKFDLKGQQNVIKKVETSE
Seq41   17  RSPEKSSFSQTCSLLSQYIKEKGSFGDLTLGMTSCGSPETSCQSATTMNLFPTKENNVTP
            ****  ***  ***** *  *******        *         *           *

Seq11   65  TRPFKLIQKFSIGEASTSTEDKAIYIDLSEPAKVAPESGNSQLTIFFGGKVMVFNEFPED
Seq41   77  KDLTAMDLFSPQASSYRPSEEIPTLINSSAIKSVSKSAKTAQMTIFYGGQVVVFDDFPAD
                *    *   *         *         *    *  *** ** * **  ** *

Seq11  125  KAKEIMEVAKEA------NHVAVDSKNSQS------HMNLDKSNVVIPDLNEPTSSGNNE
Seq41  137  KASEIMSYATKGIPQSQNNSVFTYTPSQPSFPANLVRTSADSSAPIIPSVN--ITNSIHE
            ** ***  *          *  *       *           *   **  *       *

Seq11  173  DQETGQQHQVVERIARRASLHRFFAKRKDRAVAPAPYQVNQHGSHLP
Seq41  195  HPQASSRPVVYLPIARKASLHRFLEKRKDRIASKAPYQLANGSSNQP
               *   ***   ****** *****   ****       * *
```

This *Glycine max* protein (TIFY 10a-like isoform X1) with NCBI accession no. XP_006587054.1 has the following sequence (SEQ ID NO:41).

```
  1  MSSSSEYSQF SGQKPARSPE KSSFSQTCSL LSQYIKEKGS
 41  FGDLTLGMTS CGSPETSCQS ATTMNLFPTK ENNVTPKDLT
 81  AMDLFSPQAS SYRPSEEIPT LINSSAIKSV SKSAKTAQMT
121  IFYGGQVVVF DDEPADKASE IMSYATKGIP QSQNNSVFTY
161  TPSQPSFPAN LVRTSADSSA PIIPSVNITN SIHEHPQASS
201  RPVVYLPIAR KASLHRFLEK RKDRIASKAP YQLANGSSNQ
241  PAESMPWLGL SASSPRI
```

A chromosomal segment encoding the SEQ ID NO:41 protein is on *Glycine max* chromosome 9 at NC_038245.1 (7366501 . . . 7369207).

An *Oryza sativa* protein referred to as TIFY 10b with NCBI accession no. A2YNP2.1 (SEQ ID NO:42) has significant sequence identity to the *Arabidopsis thaliana* JAZ6 protein with SEQ ID NO: 11, as illustrated by the sequence comparison shown below. Domains of sequence homology are identified by asterisks below each sequence comparison.

```
31.6% identity in 206 residues overlap; Score: 182.0; Gap frequency:
5.8%
Seq11   10  SNFSQRCSLLSRYLKEKGSFGNINMGLARKSDLELAGKFDLKGQQNVIKKVETSETRPFK
Seq42   16  TSFAMACSLLSRYVRQNGAAA-AELGLGIRGEGE-APRAAPGTMSLLPGEAERKKETMEL
              *  *******  *         *  *      *                   *

Seq11   70  LIQKFSIGEASTSTEDKAIYIDLSEPAKVAPESGNSQLTIFFGGKVMVFNEFPEDKAKEI
Seq42   74  FPQSAGFGQQDAITADSAADAREQEPEK------RQLTIFYGGKVLVFNDFPADKAKGL
             *    *    *   **   *   ****  *** *** *** ** ****
```

-continued

```
Seq11  130 MEVAKEANHVAVDSKNSQSHMNLD---KSNVVIPDLNEPTSSGNNEDQETGQQHQVVERI
Seq42  127 MQLASKGSTVAPQNAVAPAPAAVTDNTKAPMAVPAPVSSLPTAQADAQKPARANASDMPI
            *  *   **                *     *            *           *

Seq11  187 ARRASLHRFFAKRKDRAVARAPYQVN
Seq42  187 ARKASLHRFLEKRKDRLNAKTPYQAS
           ** ****** *****  *  ***
```

This *Oryza sativa* protein (TIFY 10b) with NCBI accession no. A2YNP2.1 has the following sequence (SEQ ID NO:42).

```
  1  MAASARPVGV GGERATSFAM ACSLLSRYVR QNGAAAAELG
 41  LGIRGEGEAP RAAPGTMSLL PGEAERKKET MELFPQSAGF
 81  GQQDAITADS AADAREQEPE KRQLTIFYGG KVLVFNDFPA
121  DKAKGLMQLA SKGSTVAPQN AVAPAPAAVT DNTKAPMAVP
161  APVSSLPTAQ ADAQKPARAN ASDMPIARKA SLHRFLEKRK
201  DRLNAKTPYQ ASPSDATPVK KEPESQPWLG LGPNAVVKPI
241  ERGQ
```

A *Zea mays* protein referred to as protein TIFY5 with NCBI accession no. PWZ15752.1 (SEQ ID NO:43) has significant sequence identity to the *Arabidopsis thaliana* JAZ7 protein with SEQ ID NO: 13. For example, the *Zea mays* SEQ ID NO:43 protein has domains of 65 residues having 32% sequence identity from positions 26-91 of the *Arabidopsis thaliana* JAZ7 protein with SEQ ID NO: 13 and 21 residues having 62% sequence identity from positions 122-143 of the *Arabidopsis thaliana* JAZ7 protein with SEQ ID NO:13. This *Zea mas* protein referred to as protein TIFY 5 with NCBI accession no. PWZ15752.1 has the following sequence (SEQ ID NO:43).

```
  1  MDGGRDVDEG GVTGAVAAAA AQERRWRGGG GDDEESSGLS
 41  NGGGGVELSL RLRTGADDGA ATAAALSPLP LPPPAEARRN
 81  MTIFYNGRVC AADVTEIQAR AIISMASEET LADHRGRRRR
121  QQQQQLTRGD GGDGRQODGD SSSSTTTSAV ALARRCARGR
161  GLVGPAVEID QAADAGLSMK RSLQLFLQKR KARTAAAAAP
201  PYAGGRQAQA VRR
```

A *Glycine max* protein referred to as protein TIFY5A with NCBI accession no. XP_003546080.1 (SEQ ID NO:44) has significant sequence identity to the *Arabidopsis thaliana* JAZ7 protein with SEQ ID NO:13, as illustrated by the sequence comparison shown below. Domains of sequence homology are identified by asterisks below each sequence comparison.

This *Glycine max* protein referred to as protein TIFY5A with NCBI accession no. XP_003546080.1 has the following sequence (SEQ ID NO:44).

```
  1  MRRNCNLELA LFPPSDSGPP MVDNVEEEAS EISPMQNLFH
 41  RQEQQQPLTI FYDGKICVAD VTELQAKSIL MLANRKLEER
 81  VRTPTGSEPS SPTVMQSNNQ LYSPGTGPSM RKSLQRFLQK
121  RRNPVQEASP YRH
```

An unnamed *Triticum aestivum* protein with NCBI accession no. SPT17867.1 (SEQ ID NO:45) has significant sequence identity to the *Arabidopsis thaliana* JAZ7 protein with SEQ ID NO:13. For example, the *Triticum aestivum* SEQ ID NO:45 protein has domains of 31 residues having 45% sequence identity from positions 61-92 of the *Arabidopsis thaliana* JAZ7 protein with SEQ ID NO:13 and 24 residues having 67% sequence identity from positions 122-146 of the *Arabidopsis thaliana* JAZ7 protein with SEQ ID NO:13. This unnamed *Triticum aestivum* protein with NCBI accession no. SPT17867.1 has the following sequence (SEQ ID NO:45).

```
  1  MAAASRSAPE WWRDGGSVDD GGAFVELSLR LRTGSSSTAR
 41  RSMTIFYNGR VVAVDVIELQ AREIITMASQ QILTEQQDSG
 81  GGGGGTAVAQ YGAHENPSQP APQRWAPLLA SRSLRQGAGA
121  AAPVTSQAAA AGLSMKRSLQ RFLQKRKTRV AAMGSPYAGG
161  RRAMPS
```

A *Zea mays* protein referred to as putative tify domain/CCT motif transcription factor family protein (NCBI accession no. DAA40037.1 (GI:414589466); SEQ ID NO:46) has significant sequence identity to the *Arabidopsis thaliana* JAZ9 protein with SEQ ID NO:15. For example, the *Zea mays* SEQ ID NO:46 protein has domains of 48 residues having 52% sequence identity from positions 218-266 of the *Arabidopsis thaliana* JAZ9 protein with SEQ ID NO:15, and 31 residues having 55% sequence identity from positions 119-150 of the *Arabidopsis thaliana* JAZ9 protein with SEQ ID NO:15. This JAZ-related uncharacterized *Zea mays* protein, referred to as putative tify domain/CCT motif

```
41.8% identity in 91 residues overlap; Score: 157.0; Gap frequency: 2.2%

Seq13   55 KQESQILTIFYNGHMCVSSDLTHLEANAILSLASRDVEEKSLSLRSSDGSDPPTIPNNST
Seq44   42 QEQQQPLTIFYDGKICVA-DVTELQAKSILMLANRKLEERVRTPTGSEPSSPTVMQSNNQ
            * ***** *  **  *  *  *  *   **  **  *          *  *   *

Seq13  115 RFHYQKA-SMKRSLHSFLQKRSLRIQATSPY
Seq44  101 LYSPGTGPSMRKSLQRFLQKRRNVQEASPY
                  ** ***   *****   *   ***
``` transcription factor family protein (NCBI accession no. DAA40037.1 (GI:414589466)), has the following sequence (SEQ ID NO:46).

```
  1  MDWSFASKPC AAPALMSFRS AAREEPSFPQ FSALDGTKNT
 41  APRMLTHQRS FGPDSTQYAA LHRAQNGARV VPVSSPFSQS
 81  NPMERVQSSP SLPNSTAFKQ PPFAISNAVA SSTVGSYGGT
121  RDAVRPRTAQ LTIFYAGSVN VFNNVSAEKA QELMFLASRG
161  SSAPVACKPE APPTLAPAKV TAPEVLLPAK QMLFQKPQHL
201  SPPPSSVPGI LQSAALPRSA SSSSNLDSPA PKSSVPLAVP
241  PVSQAPPATL IATTTAAAIM PRAVPQARKA SLARFLEKRK
281  ERVTTAAPYP SAKSPLESSD TFCSGSASAN ANDKSSCTDI
321  ALSSNHEESL CLGGQPRSII SFSEESPSTK LQI
```

A chromosomal segment encoding the SEQ ID NO:46 protein is on *Zea mays* chromosome 2 at NC_024460.1 (180086924 ... 180089758, complement), sequence available as NCBI accession number NC_024460.1 (GI: 662249846).

A *Glycine max* protein referred to as protein TIFY 6A isoform X6 (NCBI accession no XP_006580449.1 (GI: 571456657; SEQ ID NO:47) has significant sequence identity to the *Arabidopsis thaliana* JAZ9 protein with SEQ ID NO:15, as illustrated by the sequence comparison shown below. Domains of sequence homology are identified by asterisks below each sequence comparison.

```
39.8% identity in 176 residues overlap
Seq15   117  SPQLTIFYGGTISVFNDISPDKAQAIMLCAGNGIKGETGDSKP----------------
Seq41   156  SAQLTIFYAGTVNIFDDISAEKAQAIMLLAGNSLSAASNMAQPNVQVPISKLGAGAGVPV
             * ****** **  * ***  ****** *** *              *

Seq15   160  VRFAERMYGKQIHN-------TAATSSSSATHTDNFSRCRDTPVAATNAMSMIESFNAAP
Seq47   216  SQPANTSPGSGLSSPLSVSSHTGVQSGSGLTSTDEFLAAKTTGVPNPTICNVEPPKVVSA
              *   *        *  * ****      *   *   *

Seq15   213  RNMIPS-VPQARKASLARFLEKRKERLMSAMPYK--KMLLDLSTGESSGMNYSSTS
Seq47   276  TTMLTSAVPQARKASLARFLFKRKERVMSAAPYNLNKKSFECATAEYAGVNFSATN
                * ******************* *** **   *    *  *  *
```

This JAZ-related *Glycine max* protein, referred to as protein TIFY 6A isoform X6 (NCBI accession no. XP_006580449.1 (GI:571456657)) has the following sequence (SEQ ID NO:47).

```
  1  MERDFMGLNL KEPLAVVKEE MNNDGCKNSG FKKGRIAQWP
 41  FSNKVSALPH LMSFKASQDD KTKNTVSDTL SSSGFMSILS
 81  QEAFDTSQKR SAGEPQMFSV PNQAISVSLG NPFLKNHFAA
121  AGQKPLLGGI PVTTSHSVLP SAVAVAGMTE SCVKPSAQLT
161  IFYAGTVNIF DDISAEKAQA IMLLAGNSLS AASNMAQPNV
201  QVPISKLGAG AGVPVSQPAN TSPGSGLSSP LSVSSHTGVQ
241  SGSGLTSTDE FLAAKTTGVP NTPICNVEPP KVVSATTMLT
281  SAVPQARKAS LARFLEKRKE RVMSAAPYNL NKKSEECATA
321  EYAGVNFSAT NTVLAKQG
```

A cDNA encoding the SEQ ID NO:47 protein is available as NCBI accession number XM_006580386.2 (GI: 955322109), and a chromosomal segment encoding the SEQ ID NO:47 protein is on *Glycine max* chromosome 5 at NC_016092.2 (41222014 ... 41225906), sequence available as NCBI accession number NC_016092.2 (GI:952545311).

An unknown *Oryza saliva* protein with NCBI accession no. BAD28520.1 (GI:50251455; SEQ ID NO:48) has significant sequence identity to the *Arabidopsis thaliana* JAZ9 protein with SEQ ID NO:15. For example, the *Oryza saliva* SEQ ID NO:48 protein has domains of 66 residues having 41% sequence identity from positions 84-150 of the *Arabidopsis thaliana* JAZ9 protein with SEQ ID NO:15, and 41 residues having 56% sequence identity from positions 218-259 of the *Arabidopsis thaliana* JAZ9 protein with SEQ ID NO:15. This JAZ-related *Oryza sativa* protein with NCBI accession no. BAD28520.1 (GI:50251455) has the following sequence (SEQ ID NO:48).

```
  1  MQQASEVLAR QPPHVLNGAR VIPASSPFNP NNPMFRVQSS
 41  PNLPNAVGAG GGAFKQPPFA MGNAVAGSTV GVYGTRDMPK
 81  AKAAQLTIFY AGSVNVFNNV SPEKAQELMF LASRGSLPSA
121  PTTVARMPEA HVFPPAKVTV PEVSPTKPMM LQKPQLVSSP
161  VPAISKPISV VSQATSLPRS ASSSNVDSNV TKSSGPLVVP
201  PTSLPPPATP ETLATTTAAA IMPRAVPQAR KASLARFLEK
241  RKERVTTVAP YPLAKSPLES SDTMGSANDN KSSCTDIALS
281  SNRDESLSLG QPRTISFCEE SPSTKLQI
```

A chromosomal segment encoding the SEQ ID NO:48 protein is on *Oryza sativa* chromosome 9 at NC_029264.1 (14056084 ... 14060320, complement), sequence available as NCBI accession number NC_029264.1 (GI:996703424).

An uncharacterized *Zea mays* protein referred to as LOC100384222 (NCBI accession no. NP_001182812.1 (GI: 308044557); SEQ ID NO:49) has significant sequence identity to the *Arabidopsis thaliana* JAZ10 protein with SEQ ID NO:17, as illustrated by the sequence comparison shown below. Domains of sequence homology are identified by asterisks below each sequence comparison.

```
36.2% identity in 94 residues overlap; Score: 126.0; Gap frequency:
3.2%
Seq17    105 MTIFYNGSVSVF-QVSRNKAGEIMKVANEAASKKDESSMETDLSVILPTTLRPKLFGQNL
Seq49     96 LTIFYGGKVVVFDRFPSAKVKDLLQIVSPPGA--DAVVDGAGAGAAVPTQNLPRPSHDSL
              **** * * **        *                   **   *        *

Seq17    164 EGDLPIARRKSLQRFLEKRKERLVSTSPYYPTSA
Seq49    154 SADLPIARRNSLHRFLEKRKDRITAKAPYQVNSS
                ******* ** ******* *    **   *
```

This JAZ-related uncharacterized *Zea mays* protein referred to as LOC100384222 (NCBI accession no. NP_001182812.1 (GI:308044557)) has the following sequence (SEQ ID NO:49).

```
  1 MAGHAPARDK TTTGFAATCS LLSQFLKEKK GGLQGLGGLA

41 MAPAPAAGAG AFRPPTTMNL LSALDAAKAT VGEPEGHGQR

81 TGGNPREAAG FEAQQLTITY GGKVVVFDRF PSAKVKDLLQ

121 IVSPPGADAV VDGAGAGAAV PTQNLPRPSH DSLSADLPIA

161 RRNSLHRFLE KRKDRITAKA PYQVNSSVGA EASKAEKPWL

201 GLGQEQEGSD GRQAGEEM
```

A cDNA encoding the SEQ ID NO:49 protein is available as NCBI accession number NM_001195883.1 (GI:308044556), and a chromosomal segment encoding the SEQ ID NO:49 protein is on *Zea mays* chromosome 7 at NC_024465.1 (121257106 . . . 121259180, complement), sequence available as NCBI accession number NC_024465.1 (GI:662248746).

An uncharacterized *Glycine max* protein referred to as LOC100306524 (NCBI accession number NP_001236269.1 (GI:351723837; SEQ ID NO:50) has significant sequence identity to the *Arabidopsis thaliana* JAZ10 protein with SEQ ID NO:17, as illustrated by the sequence comparison shown below. Domains of sequence homology are identified by asterisks below each sequence comparison.

```
36.6% identity in 123 residues overlap; Score: 114.0; Gap frequency:
12.2%
Seq17     85 SPVHASLARSSTELVSGTVPMTIFYNGSVSVFQ-VSRNKAGEIMKVANEAASKKDESSME
Seq50     38 SPNKSVPASGLDAVIPSANQLTIFYNGSVCVYDGIPAEKVHEIMLIAAAAAKSTEMKKIG
              **    *                ******** *        *  ***  *   **

Seq17    144 TDLSVILPTTLRP---------------KLFGWLEGDLPIARRKSLQRFLEKRNERLVST
Seq50     98 TQTTLISPAPSRPSSPHGITNNIGSSQKSSICRLQAEFPIARRHSLQRFLEKRRDRLGSK
              *   *   **              *    *   *****  ********* **  *

Seq17    190 SPY
Seq50    158 TPY
              **
```

This JAZ-related uncharacterized *Glycine max* protein referred to as LOC100306524 (NCBI accession number NP_001236269.1 (GI:351723837) has the following sequence (SEQ ID NO:50).

```
  1 MAAGVTVKSE VLESSPPEGV CSNTVENHLV QTNLSDGSPN

41 KSVPASGLDA VIPSANQLTI FYNGSVCVYD GIPAEKVHEI

81 MLIAAAAAKS TEMKKIGTQT TLISPAPSRP SSPHGITNNI

121 GSSQKSSICR LQAEFPIARR HSLQRFLEKR RDRLGSKTPY

161 PSSPTTKVAD NIENNFCADN APELISLNRS EEEFQPTVSA

201 S
```

A cDNA encoding the SEQ ID NO:50 protein is available as NCBI accession number NM_001249340.2 (GI: 402766138), and a chromosomal segment encoding the SEQ ID NO:50 protein is on *Glycine max* chromosome 15 at NC_016102.2 (18552881 . . . 18556339), sequence available as NCBI accession number NC_016102.2 (GI:952545301).

An *Oryza sativa* protein referred to as protein TIFY 9 with NCBI accession no. XP_015634258.1 (GI:1002259863) has significant sequence identity to the *Arabidopsis thaliana* JAZ10 protein with SEQ ID NO:17, as illustrated by the sequence comparison shown below. Domains of sequence homology are identified by asterisks below each sequence comparison.

```
40.0% identity in 110 residues overlap; Score: 119.0; Gap frequency:
13.6%
Seq17     83  PISPVHASLARSSTELVSGTVPMTIFYNGSVSVFQVSRNKAGEIMKVANEAASKKDESSM
Seq51     65  PPPPSTAPVPEEMPGAAAAAAPMTLFYNGSVAVFDVSHDKAEAIMRMATEATKAKGLA--
               *  *         ***  ****** **       **  **  * **    *

Seq17    143  ETDLSVILPTTLRPKLFGQNLEGDLPIARRKSLQRFLEKRKERLVSTSPY
Seq51    123  ------------RGNAIVGNFAKE-PLTRTKSLQRFLSKRKERLTSLGPY
                           *      *   * ******* ****** * **

66.7% identity in 12 residues overlap; Score: 44.0; Gap frequency:
0.0%
Seq17      2  SKATIELDFLGL
Seq51      3  TRAPVELDFLGL
                * *******
```

This JAZ-related *Oryza sativa* protein referred to as protein TIFY 9 with NCBI accession no. XP_015634258.1 (GI: 1002259863) has the following sequence (SEQ ID NO:51).

```
  1   MSTRAPVELD FLGLRAAAAD ADDRHAKSGG SSASSSSSIR
 41   GMETSAIARI GPHLLRRVIA AAGPPPPPST APVPEEMPGA
 81   AAAAAPMTLF YNGSVAVFDV SHDKAEAIMR MATEATKAKG
121   LARGNAIVGN FAKEPLTRTK SLQPELSKRK ERLTSLGPYQ
161   VGGPAAVGAT TSTTTKSFLA KEEEHTAS
```

A cDNA encoding the SEQ ID NO:5 protein is available as NCBI accession number XM_015778772.1 (GI: 1002259862), and a chromosomal segment encoding the SEQ ID NO:51 protein is on *Oryza sativa* chromosome 4 at NC_029259.1 (19492605 ... 19497181), sequence available as NCBI accession number NC_029259.1 (GI:996703429).

An uncharacterized *Zea mays* protein referred to as LOC100217316 isoform X2 with NCBI accession no. XP_008667401.1 (SEQ ID NO:52) has significant sequence identity to the *Arabidopsis thaliana* JAZ13 protein with SEQ ID NO: 19, as illustrated by the sequence comparison shown below. Domains of sequence homology are identified by asterisks below each sequence comparison.

```
28.0% identity in 50 residues overlap; Score: 54.0; Gap
frequency: 6.0%
Seq19     16  TLQSCHDQSTVNDRSSTIRSKEINAFYSGRLS---EYDLVEIQMRAIIEM
Seq52    235  TIRTCYPQTPNGTGFATNRSAYIDMLFANKLHAFVEYDTIEDAARAIVEL
               *   *         * **          *   ***  *  *** *

42.9% identity in 14 residues overlap; Score: 33.0; Gap
frequency: 0.0%
Seq19     47  SEYDLVEIQMRAII
Seq52    197  TESDLEELQARIVV
                 ** *  * **

50.0% identity in 14 residues overlap; Score: 31.0; Gap
frequency: 0.0%
Seq19    101  RSKSFTLTPNYTSS
Seq52    451  RGKPQTLTPKVSES
              * *  ****    *
```

This uncharacterized *Zea mays* protein referred to as LOC100217316 isoform X2 with NCBI accession no. XP008667401.1 has the following sequence (SEQ ID NO:52).

```
  1   MSQQEAVDPP SATDERLGGL PRSGSTSRLN AQAPEFVPRA
 41   AAVPPPPPQQ KVVRLFAPPP HAAFFVAAPR PPPPPFEYYA
 81   AVATGGGGRF GPPAAAAEQE AEAEQPPRDG SFDDPVPKIR
121   KQVEYYFSDI NLATTEHLMR FISKDPEGYV PISVVAGFKK
161   IKALVQSNSM LASALRTSSK LVVSDDGARV KREQPFTESD
201   LEELQARIVV AENLPDDHCY QNLMRLFSVV GSVRTIRTCY
241   PQTPNGTGPA TNRSAKLDML FANKLHAFVE YDTIEDAARA
281   IVELNDERNW RSGLRVRLLS TCMGGKGKKG GHESDGYGDE
321   ENVSTSDQPY DKYLEETPQM SDVPGEHMTE DSAGDMGRGR
361   VRGRGRGGRG RGRGYHQQNN NQHHQHYQNS SHHSNSSSTR
401   PVGTPPPSGH PVMIEQQQQQ QAAQPQPLTA ANKQPPGPRM
441   PDGSRGFSMG RGKPQTLIPK VSESEPEQ
```

A cDNA encoding the SEQ ID NO:52 protein is available as NCBI accession number XM_008669179.2, and a chromosomal segment encoding the SEQ ID NO:52 protein is on *Zea mays* chromosome 2 at NC_024460.2 (226688215 ... 226698574).

Chromosomal sites encoding any of the conserved amino acids and conserved domains illustrated by the sequence comparisons shown above can be deleted or mutated to reduce the activity of the proteins described herein.

For example, a wild type plant can express JAZ polypeptides or JAZ-related polypeptides with at least 70%, or at least 75%, or at least 80%, or at least 85%, or at least 90%, or at least 95%, or at least 97%, or at least 98% or at least 99% sequence identity to any of SEQ ID NOs:1, 3, 5, 7, 9, 11, 13, 17, 19, 21-51 or 52.

However, the mutant jazD plant cells, plants, and/or seeds with improved insect and biotic stress resistance can express some JAZ and/or JAZ-related polypeptides such as the JAZ8, JAZ11, and JAZ12 proteins. In other words, endogenous JAZ8, JAZ11, and JAZ12 genes are not modified or mutated in the jazD plant cells, plants, and seeds described herein.

However, such jazD plant cells, plants, and/or seeds having reduced activity of JAZ1, JAZ2, JAZ3, JAZ4, JAZ5, JAZ6, JAZ7, JAZ9, JAZ10, and JAZ13 can have less than 99%, or less than 98%, or less than 95%, or less than 90%, or less than 85%, or less than 75%, or less than 60%, or less than 50%, or less than 40%, or less than 30%, or less than 20% sequence identity to any of SEQ ID NOs: 1, 3, 5, 7, 9, 11, 13, 17, 19, 21-51 or 52.

The mutant JAZ and/or JAZ-related polypeptides can, for example, have mutations in at least one conserved amino acid position, or at least two conserved amino acid positions, or at least three conserved amino acid positions, or at least five conserved amino acid positions, or at least seven conserved amino acid positions, or at least eight conserved amino acid positions, or at least ten conserved amino acid positions, or at least fifteen amino acid positions, or at least twenty conserved amino acid positions, or at least twenty-five amino acid positions. In some cases, an entire conserved JAZ and/or JAZ-related domain or the entire endogenous JAZ and/or JAZ-related gene or chromosomal segment is deleted or mutated.

The conserved amino acids and/or domains are in some cases mutated by deletion or replacement with amino acids that have dissimilar physical and/or chemical properties. Examples of amino acids with different physical and/or chemical properties that can be employed are shown in Tables 1 and 2.

Cdk8 Mutations

As described herein, loss-of-function mutations of cdk8 can improve the pest resistance, poor growth, and poor reproduction of jazD mutant plants. The Cdk8 gene is also named the CdkE1 or Hen3 gene in some species.

One example of a wild type *Arabidopsis thaliana* CDK8 protein sequence is provided by accession no. AT5G63610.1, shown below as SEQ ID NO:53.

```
  1 MGDGSSSRSN SSNSTSEKPE WLQQYNLVGK IGEGTYGLVF
 41 LARTKIPPKR PIAIKKEKQS KDGDGVSPTA IREIMLLREI
 81 SHENVVKLVN VHINFADMSL YLAFDYAEYD LYEIIRHHRD
121 KVGHSLNIYI VKSLLWQLLN GLNYLHSNWI IHRDLKPSNI
161 LVMGDAEEHG IVKIADEGLA RIYQAPLKPL SDNGVVVTIW
201 YRAPELLLGS KHYTSAVDMW AVGCIFAELT TLKPLFQGAE
241 AKSSQNPFQL DQLDKIFKIL GHPIMDKWPT LVNLPHWQND
281 VQHIQAHKYD SVGLHNVVHL NQKSPAYDLL SKMLEYDPLK
321 RITASQALEH EYFRMDPLPG RNAFVASQPM EKNVNYPTRP
361 VDTNTDFEGT TSINPPQAVA AGNVAGNMAG AHGMGSRSMP
401 RPMVAHNMQR MQQSQGMMAY NFPAQAGLNP SVPLQQQRGM
441 AQPHQQQQLR RKDPGMGMSG YAPPNKSRRL
```

The wild type *Arabidopsis thaliana* CDK8 protein with SEQ ID NO:53 is encoded by a cDNA (At5G63610) with the following sequence (SEQ ID NO:54).

```
   1 GCAAGTGGCT AAAAAAATTA CAAATCTAGT TTCCATTCTC
  41 AGCGTCGGCT GCTTGGAACG TCACCGTTTT CTGGAAAACG
  81 CAATCTTCTC CCTTCCGTGA CGTCTCACCG GAATTTTCTC
 121 GCTTTTGTCT ACTCTCCTCC ATCTCCGAGG TTCTCCAAGC
 161 TCAGCTCCTC TTCCCATCAT TCATCCGACC GCCTTATCCG
 201 GTCAGATCCT TTACGTATTT CTATTTTCCT GATCGTCGAT
 241 TTTTGAGAAA TGTAAAAACA GATCGTATAA GGCCTCGAAG
 281 TTTTTAATTT GAAAGTGGTA TCGAAATTTT TTGGTCTTTG
 321 ATTAGGTTAG GGCACCGTAG CTCTGGGTAT TGAATTTGTA
 361 GGGTTTTCCT CTGGTTATTG GTCTTGGAG CTTGGTAATT
 401 TCTGCTGAAT TGATTGATCC CTTTTCCATC TTTTGAAGTA
 441 AAGTCTCGAG CTTTCGTGTC TCGATGTAGA TGAATTCTAT
 481 TTTGAATATG AGATTTGATA AGACGTCAAT TGCTGATAAT
 521 TTGGAGTCTT TGTGTCTGAA TTTGTTCATA TGAAGTTTTC
 561 TGAGGGATGT GAATTTTATT GTCTGCTAAT TTTGAAACGT
 601 TCCTTTTGGA ATTTGGTTTG TGAGGAGTCC TAGATCTTTT
 641 TCTGTGAAGT TTCTTGCTTG TAAGTTTTCT GGATCACTTG
 681 ATTGAGTCTA GAATCTAGAT AGATTACATG TACGGTTTGA
 721 TTCCTTTGGC TGATTTTCCA AAGTTTTGTT CAAATTTCAG
 761 GAGAACTACA AAGAGGAAAC CAAGATTGTT TTGTTTTGTT
 801 AGACTCTACC CCTTTTCCGA TTCACATGGT AAGGACATTG
 841 AGGTAGAGAA TAATACTAAA AAGCAATGGG AGATGGGAGT
 881 TCCAGTAGAT CCAACAGCTC AAACAGCACT AGTGAGAAAC
 921 CAGAGTGGCT GCAACAGTAC AATCTCGTTG GTAAGATTGG
 961 TGAAGGCACT TATGGTCTTG TTTTCTTGGC TAGAACCAAG
1001 ACTCCGCCTA AAAGACCTAT TGCTATCAAG AAGTTTAAGC
1041 AGTCCAAAGA TGGAGATGGA GTTTCCCCGA CTGCTATCCG
1081 CGAGATCATG TTGCTTAGAG AGATTTCCCA TGAGAACGTC
1121 GTGAAGCTTG TGAATGTCCA CATCAATTTT GCAGACATGT
1161 CTCTGTATCT TGCCTTTGAT TATGCCGAGT ACGATCTCTA
1201 TGAAATCATC AGGCACCACA GAGACAAAGT CGGCCATTCG
1241 TTAAACACAT ACACAGTTAA GTCTTTGCTC TGGCAGCTTC
1281 TCAACGGATT GAACTATCTT CACAGTAATT GGATTATACA
1321 CAGAGATTTG AAACCGTCGA ATATCTTGGT TATGGGTGAT
1361 GCAGAAGAGC ACGGAATAGT GAAAATAGCT GATTTCGGGC
1401 TCGCAAGGAT ATATCAAGCT CCGTTGAAAC CACTATCGGA
1441 TAACGGAGTT GTGGTCACAA TCTGGTACCG AGCACCAGAG
1481 CTGCTTCTTG GTTCGAAGCA CTACACGAGC GCTGTTGATA
```

-continued

```
1521 TGTGGGCAGT TGGGTGTATA TTCGCGGAGT TACTAACTCT
1561 TAAACCGTTG TTTCAAGGAG CAGAAGCGAA ATCGTCTCAA
1601 AACCCTTTCC AGTTAGATCA ACTTGACAAG ATATTCAAGA
1641 TCTTAGGCCA CCCGACGATG GATAAATGGC CAACACTAGT
1681 TAACCTTCCA CACTGGCAAA ATGATGTTCA ACACATTCAA
1721 GCTCACAAAT ACGACAGTGT GGGTCTCCAC AACGTGGTTC
1761 ACCTGAATCA GAAAAGTCCT GCGTATGATC TGTTATCCAA
1801 AATGCTGGAA TATGATCCTC TAAAGCGGAT CACGGCTTCA
1841 CAAGCACTAG AACACGAGTA TTTCCGAATG GATCCTCTCC
1881 CAGGACGGAA CGCATTTGTA GCCAGCCAAC CGATGGAGAA
1921 GAATGTCAAT TACCCAACTC GTCCAGTAGA TACAAACACC
1961 GATTTCGAAG GCACGACAAG CATCAATCCG CCTCAAGCAG
2001 TAGCAGCAGG AAACGTAGCA GGGAACATGG CAGGAGCTCA
2041 TGGAATGGGC AGTAGATCGA TGCCAAGACC AATGGTTGCA
2081 CATAACATGC AGAGGATGCA GCAATCTCAA GGCATGATGG
2121 CTTATAATTT CCCGGCACAG GCAGGGCTTA ACCCGAGTGT
2161 TCCGCTGCAG CAGCAGCGCG GGATGGCTCA ACCGCACCAG
2201 CAGCAACAGC TAAGAAGGAA AGATCCCGGA ATGGGTATGT
2241 CAGGTTACGC ACCTCCTAAC AAATCCAGAC GCCTCTAAAG
2281 GTAAAATCGA GATCATCAGT CTCGGGTTAG AATCTGTGTG
2321 TTTGCCGCAG AAGAAAGCGT TGCGATTTGC TTTATAGAGT
2361 AGAGTTAGAT TGTAATGCAG CATGTGGAAT GTTGCTATTC
2401 ATATGGATGG ATTGGATTCT CTGTAGTTTT TGTATAAACA
2441 TCCTCTCAAG TATTTGTTAA TTATATTGA TCATCATTTC
2481 TCTTAACATC ATTTCTCAAA ACGTAGTAAA TAGGAGATTT
2521 GCCAAGTGAA AAATATATAT AATGAGACAG TTATTATGAA
2561 C
```

In *Arabidopsis thaliana*, the CDK8 gene resides on chromosome 5 at 25463362-25465922 bp.

Chromosomal sequences that encode CDK8 proteins from many plant types and species can be modified to reduce or eliminate the expression and/or function of the encoded protein. For example, the *Arabidopsis thaliana* CDK8 gene can be mutated to generate a null allele such as the sjd56 mutant CDK8 allele, which has a C1684T mutation altering a glutamine reside to a stop codon in the encoded protein. For example, the .sjd56 mutation is shown in the CDK8 SEQ ID NO:54 nucleic acid sequence below, now referred to as SEQ ID NO:55 and illustrating that the position of this mutation can vary by 20-30 nucleotides.

```
   1 GCAAGTGGCT AAAAAAATTA CAAATCTAGT TTCCATTCTC
  41 AGCGTCGGCT GCTTGGAACG TCACCGTTTT CTGGAAAACG
  81 CAATCTTCTC CCTTCCGTGA CGTCTCACCG GAATTTTCTC
 121 GCTTTTGTCT ACTCTCCTCC ATCTCCGAGG TTCTCCAAGC
 161 TCAGCTCCTC TTCCCATCAT TCATCCGACC GCCTTATCCG
 201 GTCAGATCCT TTACGTATTT CTATTTTCCT GATCGTCGAT
 241 TTTTGAGAAA TGTAAAAACA GATCGTATAA GGCCTCGAAG
 281 TTTTTAATTT GAAAGTGGTA TCGAAATTTT TTGGTCTTIG
 321 ATTAGGTTAG GGCACCGTAG CTCTGGGTAT TGAATTTGTA
 361 GGGTTTTCCT CTGGTTATTG GTCTTTGGAG CTTGGTAATT
 401 TCTGCTGAAT TGATTGATCC CTTTTCCATC TTTTGAAGTA
 441 AAGTCTCGAG CTTTCGTGTC TCGATGTAGA TGAATTCTAT
 481 TTTGAATATG AGATTTGATA AGACGTCAAT TGCTGATAAT
 521 TTGGAGTCTT TGTGTCTCAA TTTGTTCATA TGAAGTTTTC
 561 TGAGGGATGT GAATTTTATT GTCTGCTAAT TTTGAAACGT
 601 TCCTTTTGGA ATTTGGTTTG TGAGGAGTCC TAGATCTTTT
 641 TCTGTGAAGT TTCTTGCTTG TAAGTTTTCT GGATCACTTG
 681 ATTGAGTCTA GAATCTAGAT AGATTACATG TACGGTTTGA
 721 TTCCTTTGGC TGATTTTCCA AAGTTTTGTT CAAATTTCAG
 761 GAGAACTACA AGAGCAAAC CAAGATTGTT TTGTTTTGTT
 801 AGACTCTACC CCTTTTCCGA TTCACATGGT AAGCACATTG
 841 AGGTAGAGAA TAATACTAAA AAGCAATGGG AGATGGGAGT
 881 TCCAGTAGAT CCAACAGCTC AAACAGCACT AGTGAGAAAC
 921 CAGAGTGGCT GCAACAGTAC AATCTCGTTG GTAAGATTGG
 961 TGAAGGCACT TATGGTCTTG TTTTCTTGGC TAGAACCAAG
1001 ACTCCGCCTA AAAGACCTAT TGCTATCAAG AAGTTTAAGC
1041 AGTCCAAAGA TGGAGATCGA GTTTCCCCGA CTGCTATCCG
1081 CGAGATCATG TTGCTTAGAG AGATTTCCCA TGAGAACGTC
1121 GTGAAGCTTG TGAATGTCCA CATCAATTTT GCAGACATGT
1161 CTCTGTATCT TGCCTTTGAT TATGCCGAGT ACGATCTCTA
1201 TGAAATCATC AGGCACCACA GAGACAAAGT CGGCCATTCG
1241 TTAAACACAT ACACAGTTAA GTCTTTGCTC TGGCAGCTTC
1281 TCAACGGATT GAACTATCTT CACAGTAATT GGATTATACA
1321 CAGAGATTTG AAACCGTCGA ATATCTTGGT TATGGGTGAT
1361 GCAGAAGAGC ACGGAATAGT GAAAATAGCT GATTTCGGGC
1401 TCGCAAGGAT ATATCAAGCT CCGTTGAAAC CACTATCGGA
1441 TAACGGAGTT GTGGTCACAA TCTGGTACCG AGCACCAGAG
1481 CTGCTTCTTG GTTCGAAGCA CTACACGAGC GCTGTTGATA
1521 TGTGGGCAGT TGGGTGTATA TTCGCGGAGT TACTAACTCT
1561 TAAACCGTTG TTTCAAGGAG CAGAAGCGAA ATCGTCTCAA
1601 AACCCTTTCC AGTTAGATCA ACTTGACAAG ATATTCAAGA
1641 TCTTAGGCCA CCCGACGATG GATAAATGGC CAACACTAGT
1681 TAACCTTCCA CACTGGCAAA ATGATGTTCA ACACATTCAA
1721 GCTCACAAAT ACGACAGTGT GGGTCTCCAC AACGTGGTTC
1761 ACCTGAATCA GAAAAGTCCT GCGTATGATC TGTTATCCAA
```

```
1801  AATGCTGGAA TATGATCCTC TAAAGCGGAT CACGGCTTCA
1841  CAAGCACTAG AACACGAGTA TTTCCGAATG GATCCTCTCC
1881  CAGGACGGAA CGCATTTGTA GCCAGCCAAC CGATGGAGAA
1921  GAATGTGAAT TACCCAACTC GTCCAGTAGA TACAAACACC
1961  GATTTCGAAG GCACGACAAG CATCAATCCG CCTCAAGCAG
2001  TAGCAGCAGG AAACGTAGCA GGGAACATGG CAGGAGCTCA
2041  TGGAATGGGC AGTAGATCGA TGCCAAGACC AATGGTTGCA
2081  CATAACATGC AGAGGATGCA GCAATCTCAA GGCATGATGG
2121  CTTATAATTT CCCGGCACAG GCAGGGCTTA ACCCGAGTGT
2161  TCCGCTGCAG CAGCAGCGCG GGATGGCTCA ACCGCACCAG
2201  CAGCAACAGC TAAGAAGGAA AGATCCCGGA ATGGGTATGT
2241  CAGGTTACGC ACCTCCTAAC AAATCCAGAC GCCTCTAAAG
2281  GTAAAATCGA GATCATCAGT CTCGGGTTAG AATCTGTGTG
2321  TTTGCCGCAG AAGAAAGCGT TGCGATTTGC TTTATAGAGT
2361  AGAGTTAGAT TGTAATGCAG CATGTGGAAT GTTGCTATTC
2401  ATATGGATGG ATTGGATTCT CTGTAGTTTT TGTATAAACA
2441  TCCTCTCAAG TATTTGTTAA TTATATTAGA TCATCATTTC
2481  TCTTAACATC ATTTCTCAAA ACGTAGTAAA TAGGAGATTT
2521  GCCAAGTGAA AAATATATAT AATGAGACAG TTATTATGAA
2561  C
```

As shown in the Examples, such sjd56 mutations of the CDK8 gene can improve plant pest resistance, growth, and seed production.

CDK8 genes from a variety of species can be modified (mutated) to improve their pest resistance, growth, and seed production. For example, chromosomal sequences encoding CDK8 genes from agriculturally important plants such as alfalfa (e.g., forage legume alfalfa), algae, avocado, barley, broccoli, Brussels sprouts, cabbage, canola, cassava, cauliflower, cole vegetables, collards, corn, crucifers, grain legumes, grasses (e.g., forage grasses), jatropa, kale, kohlrabi, maize, miscanthus, mustards, nut sedge, oats, oil firewood trees, oilseeds, potato, radish, rape, rapeseed, rice, rutabaga, sorghum, soybean, sugar beets, sugarcane, sunflower, switchgrass, tobacco, tomato, turnips, and/or wheat can be modified reduce or eliminate the expression and/or function of CDK8 proteins.

For example, a wild type Zea mays CDK8 protein has NCBI accession number AQK66278.1, and the sequence shown below as SEQ ID NO:56.

```
  1  MGDGRTGGAN RPAWLQQYEL IGKIGEGTYG LVFLARLKPP
 41  HPAPGRKGPP IAIKKFKQSK EGDGVSPTAI REIMLLREIN
 81  HENVVKLVNV HINHADMSLY LAFDYAEHDL YEIIRHHREK
121  LSSSINPYTV KSLLWQLLNG LNYLHSNWII HRDLKPSNIL
161  VMGEGDEHGI IKIADFGLAR IYQAPLKPLC DNGVVVTIWY
201  RAPELLLGGK HYTSAVDMWA VGCIFAELLT LKPLFQGVEA
241  KNPPNPFQLD QLDKIFKVLG HPTVEKWPTL ANLPWWQNDH
281  QHIQGHKYEN PGFHNIVHLP PKSPAFDLLS KMLEYDPRKR
321  ITAAQALEHE YFRMDPLPGR NALLPSQPGE KIVQYPIRPV
361  DTTTDFEGTT SLQPTOPPSG NAPPGGQSVA RPMPRQMPQQ
401  PMVGGIPRVA GGVTMAAFNA ASQAGMAGLN PGNMPMQRGA
441  GGQSHPHQLR RKADQGMGMQ NPGYPQQKRR F
```

The Zea mays CDK8 protein with SEQ ID NO:56 is encoded by the LOC100284562 gene on chromosome 5 at NC_024463.2 (46913511 . . . 46918664, complement). A cDNA that encodes the SEQ ID NO:55 CDK8 protein is shown below as SEQ ID NO:57.

```
   1  GATATGTTAG CACTTAGCAG CATTCTTTGG TCCAACAAGT
  41  CGAGAGAAGC GGGCCGTACG CCACCACGGC AACGGAGAAG
  81  AGGACTTTCA GCTGCGGCGG CTGGCCGGCG CGGCGACGGG
 121  GATGGGGGAT GGGCGCACAG GCGGCGCCAA CCGTCCGGCG
 161  TGGCTGCAGC AGTACGAACT GATTGGCAAG ATTGGGGAGG
 201  GGACCTATGG CCTCGTCTTC CTCGCGCGCC TTAAGCCGCC
 241  CCACCCGGCA CCTGGCCGAC GCGGCCCCCC TATCGCCATA
 281  AAGAAGTTTA AGCAGTCAAA GGAGGGGGAC GGAGTATCAC
 321  CCACCGCAAT TAGAGAGATC ATGCTCCTGC GCGAGATCAA
 361  CCACGAGAAT GTCGTCAAGC TCGTCAATGT GCACATCAAC
 401  CACGCTGACA TGTCCCTATA CCTCGCATTC GATTACGCAG
 441  AGCACGACCT CTATGAGATT ATCAGGCATC ACAGGGAGAA
 481  GCTGAGTTCC TCCATTAACC CATACACTGT CAAATCCTTG
 521  CTGTGGCAAC TGCTCAACGG CCTCAACTAT CTTCACAGTA
 561  ACTGGATTAT ACATCGAGAT CTAAAGCCTT CCAACATACT
 601  GGTCATGGGA GAAGGAGATG AACATGGAAT TATAAAGATA
 641  GCCGATTTTG GACTTGCTAG GATATATCAA GCTCCACTGA
 681  AACCATTATG TGATAATGGG GTTGTTGTAA CTATCTGGTA
 721  TCGTGCTCCT GAGCTGTTAC TTGGGGGGAA ACACTACACC
 761  AGTGCTGTCG ATATGTGGGC AGTTGGTTGC ATTTTTGCTG
 801  AACTGCTTAC ACTGAAACCT CTATTCCAAG GTGTGGAAGC
 841  AAAAAATCCT CCGAACCCAT TCCAGCTTGA TCAACTCGAC
 881  AAGATTTTTA AGGTCTTAGG CCACCCTACA GTTGAAAAGT
 921  GGCCTACCCT TGCCAATCTT CCATGGTGGC AAAACGACCA
 961  CCAACACATT CAAGGACATA AGTATGAAA CCCAGGTTTC
1001  CATAACATTG TTCATTTACC ACCAAAGAGT CCTGCATTTG
1041  ATCTTCTCTC AAAAATGCTT GAGTATGATC CCCGAAAGCG
1081  TATAACAGCT GCACAAGCTT TGGAGCATGA GACCTTAGTA
1121  ACCAGGTTCC CGGATCGATG GGATCGAGGA ACGGGAACGT
1161  GGTACGCGAT ACTTTCGGAT GGACCCACTA CCTGGACGAA
```

```
1201 ACGCGCTTTT ACCATCCCAG CCAGGGGAGA AAATTGTACA
1241 GTATCCTATT CGTCCAGTAG ATACTACAAC ACATTTTGAA
1281 GGAACAACAA GCCTTCAACC AACTCAACCG CCATCAGGGA
1321 ACGCTCCTCC TGGAGGTCAA TCTGTAGCAA GACCCATGCC
1361 ACGACAAATG CCGCAGCAAC CTATGGTTGG GGGGATTCCA
1401 AGAGTGGCAG GTGGAGTAAC CATGGCTGCC TTCAACGCTG
1441 CCTCACAGGC TGGCATGGCT GGGCTAAATC CTGGTAACAT
1481 GCCTATGCAG AGAGGCGCAG GTGGTCAGTC TCATCCGCAC
1521 CAGTTGAGAA GGAAGCCGGA TCAAGGCATG GGGATGCAGA
1561 ACCCTGGGTA TCCTCAGCAG AAGAGACGAT TCTGACGCTA
1601 TCAAGATGGA GCCATCTGCT GTATATCAGG TGTTTGAAAC
1641 ACGTTGCCTG TGTAAGCTGC TGTAGTTTTG TTATCAGCAT
1681 CCGAATGCCA ATGCTGGCAC CTGTAAAACA CATTAATCAG
1721 TCGAGAGTCC AGATACCAGT TGTCCTTATG GGTTATGATC
1761 TAAGCTGCTC GAATTTGGCT GATTTGGTTT GCAACAGAAA
1801 GGTCTTGCTT TTGCTCATGG CCCAGTGGAA TTATCCACAT
1841 GCGTAGGAAA TTTAGCATCT ATTTGGCTTG AGAAAAGATT
1881 TTCATTAAAT TCTAGTGGCA GTAAATATTT TTATGGCCAC
1921 AAACTACACA GAATTGAGCA GTTGAGCT
```

Another wild type *Zea mays* CDK8 protein has NCBI accession number PWZ24329.1, and the sequence shown below as SEQ ID NO:58.

```
  1 MGDGRTGGAN RPAWLQQYEL IGKIGEGTYG LVFLARLKPP
 41 HPAPGRRGPP IAIKKFKQSK EGDGVSPTAI REIMLLPEIN
 81 HENVVKLVNV HINHADMSLY LAFDYAEHDL YEIIRHHREK
121 LSSSINPYTV KSLLWQLLNG LNYLHSNWII HRDLKPSNIL
161 VWCHQLYRNI IAQFLQTCPL ADTYFICATK VMGEGDEHGI
201 IKIADFGLAR IYQAPLKPLC DNGVVVTIWY RAPELLLGGK
241 HYTSAVDMWA VGCIFAELLT LKPLFQGVEA KNPPNPFQLD
281 QLDKIFKVLG HPTVEKWPTL ANLPWWQNDH QHIQGHKYEN
321 PGFHNIVHLP PKSPAFDLLS KMLEYDPRKR ITAAQALEHE
361 YFRMDPLPGR NALLPSQPGE KIVQYPIRPV DTTTDFEGTT
401 SLQPTQPPSG NAPPGGQSVA RPMPRQMPQQ PMVGGIPRVA
441 GGVTMAAFNA ASQAGMAGLN PGNMPMQRGA GGQSHPHQLR
481 RKADQGMGMQ NPGYPQQKPR F
```

A wild type *Glycine max* CDK8 protein has NCBI accession number XP_003532085.1, and the sequence shown below as SEQ ID NO:59.

```
  1 MGDGSGNRWS RAEWVQQYDL LGKIGEGTYG LVFLARTKGT
 41 PSKSIAIKKF KQSKDGDGVS PTAIREIMLL PEITHENVVK
 81 LVNVHINHAD MSLYLAFDYA EHDLYEIIRH HRDKLNHSIN
121 QYTVKSLLWQ LLNGLSYLHS NWMIHRDLKP SNILVMGEGE
161 EHGVVKIADF GLARIYQAPL KPLSDNGVVV TIWYRAPELL
201 LGAKHYTSAV DMWAVGCIFA ELLTLKPLFQ GAEVKATSNP
241 FQLDQLDKIF KVLGHPTLEK WPSLASLPHW QQDVQHIQGH
281 KYDNAGLYNV VHLSPKSPAY DLLSKMLEYD PRKRLTAAQA
321 LEHEYFRIEP LPGRNALVPC QLCERIVNYP TRPVDTTTDL
361 EGTTNLPPSQ TVNAVSGSMP GPHGSNRSVP RPVNVVGMQR
401 MPPQAMAAYN LSSQAAMGDG MNPGGISKQR GVPQAEQPQQ
441 LBRKEQMGMP GYPAQQKSRR I
```

The *Glycine max* CDK8 protein with SEQ ID NO:59 is encoded by the LOC100807993 gene on chromosome 8 at NC_038244.1 (211278 . . . 221643, complement). A cDNA that encodes the SEQ ID NO:58 CDK8 protein is shown below as SEQ ID NO:60.

```
   1 CATTTCAATT TTAGGACACG GCTGCCTATC CCCTTGCGAT
  41 CGAAGAGAGA TGGGGACGG AAGTGGGAAC CGGTGGAGCA
  81 GGGCGGAGTG GGTGCAGCAG TACGATCTCT TAGGCAAAAT
 121 CGGAGAAGGC ACTTACGGCC TCGTCTTCCT GGCCCGAACC
 161 AAAGGCACTC CCTCCAAATC CATCGCCATC AAAAAGTTCA
 201 AGCAATCCAA GGACGGCGAC GGCGTCTCCC CCACCGCCAT
 241 CCGCGAAATC ATGCTGCTCA GGGAGATTAC GCACGAGAAC
 281 GTCGTCAAGC TCGTCAATGT CCACATCAAC CACGCCGACA
 321 TGTCGCTCTA CCTCGCCTTT GATTACGCCG AGCACGATCT
 361 CTATGAAATT ATTAGGCATC ACAGGGATAA ACTCAACCAT
 401 TCCATTAACC AATACACTGT TAAGTCTTTG CTCTGGCAGT
 441 TGCTCAATGG ACTAAGCTAT CTGCACAGTA ATTGGATGAT
 481 ACATCGAGAT TTGAAGCCAT CGAATATATT GGTTATGGGA
 521 GAAGGAGAGG AACATGGAGT TGTTAAGATT GCTGACTTTG
 561 GACTTGCGAG GATATATCAA GCTCCTCTGA AGCCGTTATC
 601 TGATAATGGG GTTGTTGTAA CCATTTGGTA TCGTGCACCC
 641 GAGTTGCTTC TTGGAGCAAA ACATTATACT AGTGCTGTTG
 681 ATATGTGGGC TGTGGGATGC ATTTTTGCTG AGTTGTTGAC
 721 CTTGAAGCCG CTATTTCAAG GGCAGAAGT CAAAGCTACA
 761 TCAAATCCCT TTCAGCTCGA CCAACTTGAC AAGATATTTA
 801 AGGTTTTAGG CCATCCCACA TTAGAAAAGT GGCCTTCCTT
 841 AGCAAGTCTT CCACATTGGC AACAAGATGT GCAACATATA
 881 CAAGGACACA AATATGATAA TGCTGGTCTC TATAATGTTG
 921 TACACCTGTC TCCAAAAAGC CCCGCATATG ACCTCTTGTC
 961 AAAGATGCTT GAATATGATC CTCGTAAGCG TTTAACAGCA
1001 GCACAAGCTT TGGAGCATGA GTATTTCAAA ATTGAACCAT
1041 TACCTGGACG GAATGCACTT GTACCCTGCC AACTTGGAGA
```

-continued

```
1081  GAAAATTGTA AATTATCCCA CTCGTCCAGT GGACACCACT
1121  ACTGATCTTG AAGGAACAAC CAATCTGCCA CCTTCACAAA
1161  CGGTAAATGC AGTTTCTGGC AGCATGCCTG GTCCTCATGG
1201  GTCAAATAGA TCTGTTCCTC GGCCAGTGAA TGTTGTTGGA
1241  ATGCAAAGAA TGCCCCCTCA AGCAATGGCA GCTTATAATC
1281  TCTCATCTCA GGCAGCCATG GGAGACGGAA TGAATCCTGG
1321  GGGTATCTCA AAGCAACGAG GTGTTCCACA GGCCCATCAG
1361  CCGCAACAGT TGAGAAGGAA GGAGCAAATG GGGATGCCGG
1401  GATACCCTGC ACAACAGAAG TCAAGACGAA TATAAGGTTT
1441  CTGCTGGAAG AGAGACTACG TGAAGATAAA TTTGGGGTCA
1481  ATACTTCAGT GCCTGAACTC ATGCAGGACA TTTCTGGACA
1521  GGGTTTGTCT CAATACTTGC AAACCTCTCA CTTTATTGCA
1561  ATCAAAGATT GGGTGCATTC TTCTCTGGAA TTTTGATGCT
1601  AAAATGCCAA ATGTATGCTG GAACACCAAT GAAGCCATAA
1641  AAGGGTATAA ACGTATGAAA GGGTTAAGCT ACTGTAAGCA
1681  CATGTATATC ATGATTATAA CAATGCAATT CTATTGTATT
1721  TCTCAGCTTT TGGGCAAGAT CAATGTCAGT GAAACCAAAT
1761  GTTAATCATC CATTGGGTTT TCATAATGAA ACTTTTCACG
1801  ATTAAATTTA TAATATGCTA CTTTGTATTC GTCGAATATT
1841  TTGCCTCACA TGATTGAAGA TAGTTCAAAT ATCA
```

Another wild type *Glycine max* CDK8 protein has NCBI accession number XP_003525137.1, and the sequence shown below as SEQ ID NO:61.

```
  1  MGDGSGSRWS RAEWVQQYDL LGKIGEGTYG LVFLARTKSP
 41  VGTPSKSIAI KKFKQSKDGD GVSPTAIREI MLLREITHEN
 81  VVKLVNVHIN HADMSLYLAF DYAEHDLYEI IRHHRDKLNH
121  SINQYTVKSL LWQLLNGLSY LHSNNMIHRD LKPSNILVMG
161  EGEEHGVVKI ADFGLARIYQ APLKPLSDNG VVVTIWYRAP
201  ELLLGAKHYT SAVDMWAMGC IFAELLTLKP LFQGAEVKAT
241  SNPFQLDQLD KIFKVLGHPT LEKWPSLASL PHWQQDVQHI
281  QGHKYDNAGL YNVVHLSPKS PAYDLLSKML EYDPRKRLTA
321  AQALEHEYFK IEPLPGRNAL VPCQLGEKIV NYPTRPVDTT
361  TDLEGTTNLP PSQTVNAVSG SMPGPHGSNR SVPRPMNVVG
401  MQRLPPQAMA AYNLSSQAAM GDGMNPGDIS KHRGVPQAHQ
441  PQQLRRKEQM GMPGYPAQQK SRRL
```

The wild type *Glycine max* CDK8 protein with SEQ ID NO:61 is encoded by the LOC100794990 gene on chromosome 5 at NC_038241.1 (37955973 ... 37967547, complement). A cDNA that encodes the SEQ ID NO:61 CDK8 protein is shown below as

```
   1  TTTCAATTTT CAGACGCTGC TGCCTATCCC CTTGCGATCG
  41  AACAGAACAG AAGAGAGATG GGGGACGGAA GTGGGAGCCG
  81  GTGGAGCAGG GCGGAGTGGG TGCAGCAGTA CGATCTCTTA
 121  GGAAAAATCG GCGAAGGCAC TTACGGCCTC GTCTTCCTCG
 161  CCCGAACCAA ATCCCCCGTT GGCACTCCCT CCAAATCCAT
 201  TGCCATAAAA AAGTTCAAGC AATCCAAGGA CGGCGACGGC
 241  GTCTCCCCCA CCGCCATCCG CGAAATCATG TTGCTGAGGG
 281  AGATTACGCA CGAGAACGTC GTCAAGCTCG TCAACGTACA
 321  CATCAACCAC GCCGACATGT CTCTCTACCT CGCCTTCGAT
 361  TACGCCGAGC ACGATCTCTA TGAAATTATT AGGCATCACA
 401  GGGACAAACT CAACCATTCC ATTAATCAGT ACACTGTTAA
 441  GTCTTTGCTC TGGCAGTTGC TCAATGGACT AAGCTATCTG
 481  CACAGTAATT GGATGATACA TCGTGATTTG AAGCCATCGA
 521  ATATATTGGT TATGGGTGAA GGAGAGGAAC ATGGAGTTGT
 561  TAAGATTGCT GACTTTGGAC TTGCGAGGAT ATATCAAGCT
 601  CCTCTGAAGC CGTTATCTGA CAATGGGGTT GTTGTAACCA
 641  TTTGGTATCG TGCACCTGAG TTGCTTCTTG GAGCAAAACA
 681  TTATACCAGT GCTGTTGATA TGTGGGCTAT GGGATGCATT
 721  TTTGCTGAGT TGTTGACCTT GAAGCCACTA TTTCAACCGG
 761  CAGAAGTCAA AGCTACATCA AATCCCTTTC AGCTTGACCA
 801  ACTTGACAAG ATATTTAAGG TTTTAGGCCA TCCCACATTA
 841  GAAAAGTGGC CTTCCTTAGC AAGTCTTCCA CATTGGCAAC
 881  AAGATGTGCA ACATATACAA GGACACAAAT ATGACAATGC
 921  CGGTCTCTAT AATGTTGTAC ACCTGTCTCC AAAAAGCCCT
 961  GCATATGACC TCTTGTCAAA GATGCTTCAA TATGATCCTC
1001  GTAAGCGTTT AACAGCAGCA CAAGCTTTGG AGCATGAGTA
1041  TTTCAAAATT GAACCATTAC CTGGACGAAA TGCACTTGTA
1081  CCCTGCCAAC TTGGAGAGAA AATTGTAAAT TATCCCACTC
1121  GTCCAGTGGA CACTACAACT GATCTTGAAG GACAACCAA
1161  TCTGCCACCT TCACAAACGG TAAATGCAGT TTCTGGTAGC
1201  ATGCCTGGTC CTCATGGGTC AAATAGATCT GTGCCTCGGC
1241  CAATGAATGT TGTTCCAATG CAAAGACTGC CCCCTCAAGC
1281  AATGGCAGCT TATAATCTCT CATCTCAGGC AGCCATGGGA
1321  GATGGAATGA ATCCTGGGGA TATCTCAAAG CATCGAGGTG
1361  TTCCACAGGC CCATCAGCCA CAACAGTTGA GAAGGAAGGA
1401  GCAAATGGGG ATGCCGGGAT ACCCTGCACA ACAGAAGTCA
1441  AGACGATTAT AAGGTTTCTG CTGGAAGAGA GACTAAGTGA
```

```
1481 AGATAGATTT GGGGTCAATA CTTCAGTACC TGAACTCATG

1521 CAGGACATTT CTGGACAGTG TTTGCCTTCA ATACTTGCAA

1561 GCCTCACTTT ATTGCAATCA AAGATTGGGT GCATTCTTCT

1601 CTGGAATTTT GATGCTAAAA TGCCAAATGT ATGCTGGAAC

1641 ACCAATGAAG CCATAAAAGG GAATAAACGT ATGAAAGGGT

1681 TAAGCTACTG TAAGCACATG TATATCATGA TTATAACAAT

1721 GCAATTCTAT TGTATTTCTT AGCTTTTGGG CAAGATCAAT

1761 GTCAGTAAAC CAAATGTTGA TCATCCATTA GGTTTTCATA

1801 ATGGAACTTT TCTTGATTAA ATCTATAACA TGCTACTTTG

1841 TATTTGTAGA ATATTTTGCC TCACATGATT GAAGATAGTT

1881 CAAATATCAC TTGCCTTTGG TATTTCCGTT TTGAATTTTT

1921 CTGTGATCAC TGGAATCACA GACTTTTCAC TCCCAAGGAG

1961 ATTATTGAAG CTTTCTGTGA GTATGATGTA AACTTTGTTC

2001 GGAGACGTAG TAGTATGAAG ATATCAAAAG CAGCAATTGG

2041 GAGAA
```

A wild type *Triticum aestivum* CDK8 protein has NCBI accession number AAD10483.1, and the sequence shown below as SEQ ID NO:63.

```
  1 MEQYEKVEKI GEGTYGVVYK ARDRTTNETI ALKKIRLEQE

41 DEGVPSTAIR EISLLKEMQH GNIVKLHDVV HSEKRIWLVF

81 EYLDLDLKKF MDSCPEFAKS PALIKSYLYQ ILPGVAYCHS

121 HRVLHRDLKP QNLLIDRRTN ALKLADFGLA RAFGIPVRTF

161 THEVVTLWYR APEILLGARQ YSTPVDVWSV GCIFAEMVNQ

201 KPLFPGDSEI DELFKIFRVL GTPNEQTWPG VSSLPDYKSA

241 FPRWQAEDLA TVVPNLEPVG LDLLSKMLRF EPNKRITARQ

281 ALEHFYFKDM EMVQ
```

The *Triticum aestivum* CDK8 protein with SEQ ID NO:63 is encoded by the cdc2TaA gene. A cDNA that encodes the SEQ ID NO:62 CDK8 protein is shown below as SEQ ID NO:64.

```
  1 GCCCCCCTCT CCCCCTCCCC CCCACCCCCC CAATGGCGGC

41 AGCAGCAGCA GCAGCAGCAG CAGCTTCGCC CGCCGCAGCC

81 GCTCTCCCCC GCCCCTCCTC CCCGTGATCC CCTTCCCCTT

121 CCCCTCCCCC GCTTCCTCCT CTCCCCCCTC CCGCCTCCTC

161 ACCCATTTCC CACGCCCGCG CCGCCGCCGC CGCCGTAGCA

201 TTGGACGCCG ACCCGATGGA GCAGTACGAG AAGGTGGAGA

241 AGATCGGGGA GGGCACGTAC GGGGTGGTGT ACAAGGCCCG

281 GGACAGGACC ACCAACGAGA CCATCGCGCT CAAGAAGATC

321 CGCCTGGAGC AGGAGGACGA GGGCGTCCCC TCCACCGCCA

361 TCCGCGAGAT CTCGCTCCTC AAGGAGATGC AGCACGGCAA

401 CATCGTCAAG CTGCACGATG TTGTCCACAG CGAGAAGCGC
```

```
441 ATATGGCTCG TCTTTGAGTA CCTGGATCTG GACCTGAAGA

481 AGTTCATGGA CTCCTGTCCA GAGTTTGCCA AGAGCCCCGC

521 CTTGATCAAG TCATATCTCT ATCAGATACT CCGCGGCGTT

561 GCTTACTGTC ATTCTCATAG AGTTCTTCAT CGAGATTTGA

601 AACCTCAGAA TTTATTGATA GACCGGCGTA CTAATGCACT

641 GAAGCTTGCA GACTTTGGTT TAGCAAGGGC ATTTGGAATT

681 CCTGTCCGTA CATTTACTCA TGAGGTAGTA ACATTATGGT

721 ACAGAGCTCC TGAAATCCTT CTTGGAGCAA GGCAGTATTC

761 CACACCAGTT GACGTGTGGT CAGTGGGCTG TATCTTTGCA

801 GAAATGGTGA ACCAGAAACC ACTGTTCCCT GGCGATTCTG

841 AGATTGATGA GCTATTTAAG ATATTCAGGG TACTCGGCAC

881 TCCAAATGAA CAAACTTGGC CAGGCGTGAG TTCCTTGCCT

921 GACTACAAGT CCGCCTTCCC CAGGTGGCAG GCAGAGGACC

961 TTGCAACCGT TGTCCCCAAT CTTGAACCTG TTGGCCTGGA

1001 CCTTCTCTCG AAAATGCTTC GGTTCGAGCC AAACAAGAGG

1041 ATCACGGCTA GGCAGGCTCT TGAGCATGAG TACTTCAAGG

1081 ACATGGAGAT GGTACAGTGA GCTGGCTATG TGGTAGTGAC

1121 TGGCATATGT ATGAGCTGAG CTGCTCGTTT CATTCCTTTT

1161 GTGAACGCTC
```

A wild type *Oryza sativa* Japonica Group CDK8 protein has NCBI accession number XP_015614383.1, and the sequence shown below as SEQ ID NO:65.

```
  1 MGDGRVGGGT NRPAWLQQYE LVGKIGEGTY GLVFLARLKQ

41 SHPHAAAGVG RRGSPIAIKK FKQSKEGDGV SPTAIREIML

81 LREINHENVV KLVNVHINHA DMSLYLAFDY AEHDLYEIIR

121 HHREKLNLPI NPYTVKSLLW QLLNGLNYLH SNWIIHRDLK

161 PSNILVMGEG EEHGIIKIAD FGLARIYQAP LKPLSDNGVV

201 VTIWYRAPEL LLGAKHYTSA VDMWAVGCIF AELLTLKPLF

241 QGVEAKATPN PFQLDQLDKI FKVLGHPTVE KWPTLANLPC

281 WQNDQQHIQG HKYENTGLHN IVHLPQKSPA FDLLSKMLEY

321 DPRKRITAAQ ALEHEYFRMD PLPGRNALLP SQAGEKIVQY

361 PVRPVDTTTD FEGTTSLQPT QAPSGNAAPG NQSVVPRPIP

401 RQMQQPMVGM SRMGGTNMAA FGAAPQGGIA GMNPGNIPMQ

441 RGAGAQSHPH QLRRKADQGM GMQNPGYPTQ QKRRF
```

The *Oryza sativa* CDK8 protein with SEQ ID NO:65 is encoded by the LOC4349519 gene on chromosome 10 at NC_029265.1 (23148732 . . . 23153285, complement). A cDNA that encodes the SEQ ID NO:65 CDK8 protein is shown below as SEQ ID NO:66.

```
  1 GAGCGTATTT TGGCTTTACG CCTTCGTGTG GAGTAAACGC

41 CCTTTCTGTT GGGCGGGTTC GGCTGGATCT TTTGTTCCCC

81 CTTTTCCTTT CTTCTCCGGC AGCGGCGGCG GCGATGGGGG
```

```
 121 ACGGCCGCGT CGGAGGTGGA ACGAATCGGC CGGCATGGCT

161 GCAGCAATAC GAACTAGTGG GCAAGATTGG CGAGGGGACC

201 TACGGCCTCG TCTTCCTCGC TCGCCTCAAA CAATCGCATC

241 CCCACGCTGC CGCTGGCGTT GGCCGCCGTG GCTCTCCCAT

281 CGCCATCAAG AAGTTCAAGC AGTCCAAGGA GGGCGACGGT

321 GTCTCGCCCA CCGCCATCAG AGAGATCATG CTTCTGCGTG

361 AGATCAACCA CGAGAATGTT GTCAAGCTCG TCAATGTTCA

401 CATCAACCAC GCCGACATGT CCCTCTACCT CGCCTTCGAT

441 TACGCCGAGC ACGATCTCTA TGAGATTATC AGGCATCACA

481 GAGAGAAGCT TAACCTCCCC ATAAATCCCT ACACAGTCAA

521 ATCTTTGCTC TGGCAACTGC TCAATGGTCT CAACTATCTC

561 CATAGTAACT GGATTATCCA TCGAGATCTC AAGCCTTCTA

601 ATATACTGGT CATGGGAGAA GGAGAAGAAC ATGGAATTAT

641 AAAGATTGCT GATTTTGGAC TCGCTAGGAT ATATCAAGCT

681 CCATTAAAGC CATTAAGTGA TAACGGGGTT GTTGTTACCA

721 TCTGGTATCG GGCTCCAGAG TTGTTACTTG GGGCAAAGCA

761 CTACACAAGT GCTGTTGATA TGTGGGCAGT TGGTTGCATT

801 TTTGCTGAAT TGCTTACACT CAAACCACTG TTCCAAGGTG

841 TTGAAGCCAA AGCTACTCCA AACCCGTTTC AACTTGATCA

881 ACTAGACAAG ATTTTTAAGG TCTTAGGTCA TCCTACCGTT

921 GAGAAATGGC CTACCCTCGC TAATCTTCCA TGCTGGCAAA

961 ACGATCAACA ACACATTCAA GGGCATAAGT ATGAGAACAC

1001 AGGACTTCAT AATATTGTTC ACTTGCCTCA GAAGAGTCCT

1041 GCGTTTGATC TTCTCTCAAA AATGCTCGAG TATGATCCTC

1081 GAAAGCGTAT AACAGCTGCG CAAGCTTTGG AACATGAGTA

1121 CTTTCGAATG GATCCTCTGC CTGGACGGAA TGCACTTTTA

1161 CCATCGCAGG CTGGAGAGAA AATTGTGCAA TATCCTGTGC

1201 GTCCAGTTGA TACCACAACT GATTTTGAAG GAACAACAAG

1241 CCTTCAACCA ACTCAAGCGC CATCAGGGAA CGCAGCTCCT

1281 GGCAACCAGT CTGTGGTACC GAGACCCATT CCGAGGCAAA

1321 TGCAACAACC CATGGTCGGT ATGTCGAGAA TGGGTGGTAC

1361 AAACATGGCG GCCTTTGGTG CAGCTCCGCA AGGAGGCATA

1401 GCTGGGATGA ATCCTGGTAA TATTCCAATG CAGAGGGGCG

1441 CTGGAGGCCA ATCTCATCCG CATCAGTTGA GAAGGAAAGG

1481 TGATCAAGGG ATGGGGATGC AGAACCCCGG TTATCCTACT

1521 CAACAGAAGA GGCGGTTCTG ACCGACTGAA TTTGTAATTG

1561 TATATCTATT TGGTGTGTTA CTTGTGAGCA CGCTTAGCTT

1601 TTGCGGTGGT TGCTCCTAGT CGTACAGTGA GAATTGTATC

1641 TGTTCTGTTG TAATTGAACG CCATCACAAC CAACACCTCT

1681 ACTAGTTAGT TACTAGAGTG ACTACGGAGA CAGGGCCAGG
```

```
1721 TTGCCGATGA TGCCATCACC AATGGAGACA GGCATACCCA

1761 GCCAGAGTTT CGCCAATACT CTGCCCCCTG AACCCAACCA

1801 ATGAATGAAT TGGCATCGTA CGATCTATTT CA
```

For example, a wild type plant can have cdk8 nucleic acids or express CDK8 polypeptides or CDK8-related polypeptides with at least 70%, or at least 75%, or at least 80%, or at least 85%, or at least 90%, or at least 95%, or at least 97%, or at least 98%, or at least 99% sequence identity to any of SEQ ID NOs:53-66. Plant cells from such wild type plants can be mutated, and mutant plants can be generated therefrom as described herein to provide modified jazD cdk8 plants and plant seed with improved plant growth and seed yields.

The mutant cdk8 plant cells, plants, and/or seeds with increased jasmonic acid responses and improved insect resistance can express mutant CDK8 and/or CDK8-related polypeptides that have reduced activity. In some cases, detectable levels of CDK8 proteins are not expressed Such cdk8 mutant plant cells and plant tissues have reduced CDK8 activity can cdk8 nucleic acids or cdk8 polypeptides that have less than 99%, or less than 98%, or less than 95%, or less than 90%, or less than 85%, or less than 75%, or less than 60%, or less than 50%, or less than 40%, or less than 30%, or less than 20% sequence identity to any of SEQ ID NOs: 53-66.

The mutant CDK8 and/or CDK8-related polypeptides can, for example, have mutations in at least one conserved amino acid position, or at least two conserved amino acid positions, or at least three conserved amino acid positions, or at least five conserved amino acid positions, or at least seven conserved amino acid positions, or at least eight conserved amino acid positions, or at least ten conserved amino acid positions, or at least fifteen amino acid positions, or at least twenty conserved amino acid positions, or at least twenty-five amino acid positions. In some cases, an entire conserved CDK8 and/or JAZ-related domain or the entire endogenous Cdk8 and/or Cdk8-related gene or chromosomal segment is deleted or mutated.

The conserved amino acids and/or domains are in some cases mutated by deletion or replacement with amino acids that have dissimilar physical and/or chemical properties. Examples of amino acids with different physical and/or chemical properties that can be employed are shown in Tables 1 and 2.

Plant Modification

Mutations can be introduced into any of the wild type JAZ, JAZ-related, CDK8 or CDK8-related plant genomes by introducing targeting vectors, T-DNA, transposons, nucleic acids encoding TALENS, CRISPR, or ZFN nucleases, and combinations thereof into a recipient plant cell to create a transformed cell. Cells from virtually any dicot or monocot species can be stably modified or transformed, and these cells can be regenerated into transgenic plants, through the application of the techniques disclosed herein. The plant cells, plants, and seeds can therefore be monocotyledons or dicotyledons.

The cell(s) that undergo transformation may be in a suspension cell culture or may be in an intact plant part, such as an immature embryo, or in a specialized plant tissue, such as callus, such as Type I or Type II callus.

Transformation of the cells of the plant tissue source can be conducted by any one of a number of methods available to those of skill in the art. Examples include: Transformation by direct DNA transfer into plant cells by electroporation (U.S. Pat. Nos. 5,384,253 and 5,472,869, Dekeyser et al., The Plant Cell, 2:591602 (1990)); direct DNA transfer to plant cells by PEG precipitation (Hayashimoto et al., Plant Physiol. 93:857 863 (1990)); direct DNA transfer to plant cells by microprojectile bombardment (McCabe et al., Bio/ Technology, 6:923 926 (1988); Gordon Kamm et al., The Plant Cell. 2:603 618 (1990); U.S. Pat. Nos. 5,489,520; 5,538,877; and 5,538,880) and DNA transfer to plant cells via infection with *Agrobacterium*. Methods such as microprojectile bombardment or electroporation can be carried out with "naked" DNA where the expression cassette may be simply carried on any *E. coli* derived plasmid cloning vector. In the case of viral vectors, it is desirable that the system retain replication functions, but lack functions for disease induction.

One method for dicot transformation, for example, involves infection of plant cells with *Agrobacterium tumefaciens* using the leaf disk protocol (Horsch et al., Science 227:1229 1231 (1985). Monocots such as *Zea mays* can be transformed via microprojectile bombardment of embryogenic callus tissue or immature embryos, or by electroporation following partial enzymatic degradation of the cell wall with a pectinase containing enzyme (U.S. Pat. Nos. 5,384,253; and 5,472,869). For example, embryogenic cell lines derived from immature *Zea mays* embryos can be transformed by accelerated particle treatment as described by Gordon Kamm et al. (The Plant Cell. 2:603 618 (1990)) or U.S. Pat. Nos. 5,489,520; 5,538,877 and 5,538,880, cited above. Excised immature embryos can also be used as the target for transformation prior to tissue culture induction, selection and regeneration as described in PCT publication WO 95/06128. Furthermore, methods for transformation of monocotyledonous plants utilizing *Agrobacterium tumefaciens* have been described by Hiei et al. (European Patent 0 604 662, 1994) and Saito et al. (European Patent 0 672 752, 1995).

Methods such as microprojectile bombardment or electroporation can be carried out with "naked" DNA where the expression cassette may be simply carried, for example, on any *E. coli* derived plasmid cloning vector. In the case of viral vectors, it is desirable that the system retain replication functions, but lack functions for disease induction.

The choice of plant tissue source for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent cells. Type I or Type II embryonic maize callus and immature embryos are exemplary *Zea mays* tissue sources. Selection of tissue sources for transformation of monocots is described in detail in in PCT publication WO 95/06128.

The transformation is carried out under conditions directed to the plant tissue of choice. The plant cells or tissue are exposed to the DNA or RNA carrying the targeting vector and/or other nucleic acids for an effective period of time. This may range from a less than one second pulse of electricity for electroporation to a 2-3-day co-cultivation in the presence of plasmid bearing *Agrobacterium* cells. Buffers and media used will also vary with the plant tissue source and transformation protocol. Many transformation protocols employ a feeder layer of suspended culture cells (tobacco or Black Mexican Sweet corn, for example) on the surface of solid media plates, separated by a sterile filter paper disk from the plant cells or tissues being transformed.

Where one wishes to introduce DNA by means of electroporation, it is contemplated that the method of Krzyzek et al. (U.S. Pat. No. 5,384,253) may be advantageous. In this method, certain cell wall degrading enzymes, such as pectin degrading enzymes, are employed to render the target recipient cells more susceptible to transformation by electroporation than untreated cells. Alternatively, recipient cells can be made more susceptible to transformation, by mechanical wounding.

To effect transformation by electroporation, one may employ either friable tissues such as a suspension cell cultures, or embryogenic callus, or alternatively, one may transform immature embryos or other organized tissues directly. The cell walls of the preselected cells or organs can be partially degraded by exposing them to pectin degrading enzymes (pectinases or pectolyases) or mechanically wounding them in a controlled manner. Such cells would then be receptive to DNA uptake by electroporation, which may be carried out at this stage, and transformed cells then identified by a suitable selection or screening protocol dependent on the nature of the newly incorporated DNA.

A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. In an illustrative embodiment, non-embryogenic cells were bombarded with intact cells of the bacteria *E. coli* or *Agrobacterium tumefaciens* containing plasmids with either the β-glucouronidase or bar gene engineered for expression in maize. Bacteria were inactivated by ethanol dehydration prior to bombardment. A low level of transient expression of the β-glucouronidase gene was observed 24-48 hours following DNA delivery. In addition, stable transformants containing the bar gene can be recovered following bombardment with either *E. coli* or *Agrobacterium tumefaciens* cells. It is contemplated that particles may contain DNA rather than be coated with DNA. Hence it is proposed that particles may increase the level of DNA delivery but are not, in and of themselves, necessary to introduce DNA into plant cells.

An advantage of microprojectile bombardment, in addition to being an effective means of reproducibly stably transforming monocots, is that the isolation of protoplasts (Christou et al., PNAS. 84:3962 3966 (1987)), the formation of partially degraded cells, or the susceptibility to *Agrobacterium* infection is not required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with maize cells cultured in suspension (Gordon Kamm et al., The Plant Cell. 2:603 618 (0.1990)). The screen disperses the particles so that they are not delivered to the recipient cells in large aggregates. It is believed that a screen intervening between the projectile apparatus and the cells to be bombarded reduces the size of projectile aggregate and may contribute to a higher frequency of transformation, by reducing damage inflicted on the recipient cells by an aggregated projectile.

For bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth here in one may obtain up to 1000 or more foci of cells transiently expressing a marker gene. The number of cells in a focus which express the exogenous gene product 48 hours post bombardment often range from about 1 to 10 and average about 1 to 3.

In bombardment transformation, one may optimize the prebombardment culturing conditions and the bombardment parameters to yield the maximum numbers of stable transformants. Both the physical and biological parameters for bombardment can influence transformation frequency. Physical factors are those that involve manipulating the DNA/microprojectile precipitate or those that affect the path and velocity of either the macroprojectiles or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmid DNA.

One may wish to adjust various bombardment parameters in small scale studies to fully optimize the conditions and/or to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Execution of such routine adjustments will be known to those of skill in the art.

Examples of plants and/or plant cells that can be modified as described herein include alfalfa (e.g., forage legume alfalfa), algae, avocado, barley, broccoli, Brussels sprouts, cabbage, canola, cassava, cauliflower, cole vegetables, collards, corn, crucifers, grain legumes, grasses (e.g., forage grasses), jatropa, kale, kohlrabi, maize, miscanthus, mustards, nut sedge, oats, oil firewood trees, oilseeds, potato, radish, rape, rapeseed, rice, rutabaga, sorghum, soybean, sugar beets, sugarcane, sunflower, switchgrass, tobacco, tomato, turnips, and wheat. In some embodiments, the plant is a *Brassicaceae* or other *Solanaceae* species. In some embodiments, the plant or cell can be a maize plant or cell. In some embodiments, the plant is not a species of *Arabidopsis*, for example, in some embodiments, the plant is not *Arabidopsis thaliana*.

An exemplary embodiment of methods for identifying transformed cells involves exposing the bombarded cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing.

To use the bar-bialaphos or the EPSPS-glyphosate selective system, bombarded tissue is cultured for about 0-28 days on nonselective medium and subsequently transferred to medium containing from about 1-3 mg/l bialaphos or about 1-3 mM glyphosate, as appropriate. While ranges of about 1-3 mg/l bialaphos or about 1-3 mM glyphosate can be employed, it is proposed that ranges of at least about 0.1-50 mg/l bialaphos or at least about 0.1-50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase is also useful as a screenable marker in the context of the present invention. In the presence of the substrate luciferin, cells expressing luciferase emit light which can be detected on photographic or X-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers may be useful for identification of transformed cells. For example, selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. In an illustrative embodiment embryogenic Type II callus of *Zea mays* L. can be selected with sub-lethal levels of bialaphos. Slowly growing tissue was subsequently screened for expression of the luciferase gene and transformants can be identified.

Regeneration and Seed Production

Cells that survive the exposure to the selective agent, or cells that have been scored positive in a screening assay, are cultured in media that supports regeneration of plants. One example of a growth regulator that can be used for such purposes is dicamba or 2,4-D. However, other growth regulators may be employed, including NAA, NAA+2,4-D or perhaps even picloram. Media improvement in these and like ways can facilitate the growth of cells at specific developmental stages. Tissue can be maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are typically transferred every two weeks on this medium. Shoot development signals the time to transfer to medium lacking growth regulators.

The transformed cells, identified by selection or screening and cultured in an appropriate medium that supports regeneration, can then be allowed to mature into plants. Developing plantlets are transferred to soilless plant growth mix, and hardened, e.g., in an environmentally controlled chamber at about 85% relative humidity, about 600 ppm $CO_2$, and at about 25-250 microeinsteins/sec-$m^2$ of light. Plants can be matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con™. Regenerating plants can be grown at about 19° C. to 28° C. After the regenerating plants have reached the stage of shoot and root development, they may be transferred to a greenhouse for further growth and testing.

Mature plants are then obtained from cell lines that are known to have the mutations. In some embodiments, the regenerated plants are self-pollinated. In addition, pollen obtained from the regenerated plants can be crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to inbred plants in order to introgress the mutations into the genome of the inbred plants. This process is referred to as backcross conversion. When a sufficient number of crosses to the recurrent inbred parent have been completed in order to produce a product of the backcross conversion process that is substantially isogenic with the recurrent inbred parent except for the presence of the introduced, Jaz or Cdk8 mutations, the plant is self-pollinated at least once in order to produce a homozygous backcross converted inbred containing the mutations. Progeny of these plants are true breeding.

Alternatively, seed from transformed mutant plant lines regenerated from transformed tissue cultures is grown in the field and self-pollinated to generate true breeding plants.

Seed from the fertile transgenic plants can then be evaluated for the presence of the desired Jaz or Cdk8 mutation, and/or the expression of the desired mutant protein. Transgenic plant and/or seed tissue can be analyzed using standard methods such as SDS polyacrylamide gel electrophoresis, liquid chromatography (e.g., HPLC) or other means of detecting a mutation.

Once a transgenic plant with a mutant sequence and having improved growth and insect resistance is identified, seeds from such plants can be used to develop true breeding plants. The true breeding plants are used to develop a line of plants with an increase insect resistance relative to wild type, and acceptable growth characteristics while still maintaining other desirable functional agronomic traits. Adding the mutation to other plants can be accomplished by backcrossing with this trait and with plants that do not exhibit this trait and studying the pattern of inheritance in segregating generations. Those plants expressing the target trait (insect resistance, good growth) in a dominant fashion are preferably selected. Back-crossing is carried out by crossing the original fertile transgenic plants with a plant from an inbred line exhibiting desirable functional agronomic characteristics while not necessarily expressing the trait of an increased insect resistance and good plant growth. The resulting progeny are then crossed back to the parent that expresses the increased insect resistance and good plant growth. The progeny from this cross will also segregate so that some of the progeny carry the trait and some do not. This backcrossing is repeated until an inbred line with the desirable functional agronomic traits, and with expression of the trait involving an increase in insect resistance and good plant growth. Such insect resistance and good plant growth can be expressed in a dominant fashion.

The new transgenic plants can also be evaluated for a battery of functional agronomic characteristics such as growth, lodging, kernel hardness, yield, resistance to disease and insect pests, drought resistance, and/or herbicide resistance.

Plants that may be improved by these methods include but are not limited to agricultural plants of all types, oil and/or starch plants (canola, potatoes, lupins, sunflower and cottonseed), forage plants (alfalfa, clover and fescue), grains (maize, wheat, barley, oats, rice, sorghum, millet and rye), grasses (switchgrass, prairie grass, wheat grass, sudangrass, sorghum, straw-producing plants), softwood, hardwood and other woody plants (e.g., those used for paper production such as poplar species, pine species, and eucalyptus). In some embodiments the plant is a gymnosperm. Examples of plants useful for pulp and paper production include most pine species such as loblolly pine. Jack pine, Southern pine, Radiata pine, spruce, Douglas fir and others. Hardwoods that can be modified as described herein include aspen, poplar, eucalyptus, and others. Plants useful for making biofuels and ethanol include corn, grasses (e.g., miscanthus, switchgrass, and the like), as well as trees such as poplar, aspen, willow, and the like. Plants useful for generating dairy forage include legumes such as alfalfa, as well as forage grasses such as bromegrass, and bluestem.

Determination of Stably Transformed Plant Tissues

To confirm the presence of Jaz, and/or Cdk8 mutations in the regenerating plants, seeds or progeny derived from the regenerated plant, a variety of assays may be performed. Such assays include, for example, molecular biological assays available to those of skill in the art, such as Southern and Northern blotting and PCR; biochemical assays, such as detecting the presence of a protein product, e.g., by immunological means (ELISAs and Western blots) or by enzymatic function; plant part assays, such as leaf, seed or root assays; and also, by analyzing the phenotype of the whole regenerated plant.

Whereas DNA analysis techniques may be conducted using DNA isolated from any part of a plant. RNA may only be expressed in particular cells or tissue types and so RNA for analysis can be obtained from those tissues. PCR techniques may also be used for detection and quantification of RNA produced from the introduced Jaz or Cdk8 mutants. For example, PCR also be used to reverse transcribe RNA into DNA, using enzymes such as reverse transcriptase, and then this DNA can be amplified through the use of conventional PCR techniques.

Information about mutations can also be obtained by primer extension or single nucleotide polymorphism (SNP) analysis.

Further information about the nature of the RNA product may be obtained by Northern blotting. This technique will demonstrate the presence of an RNA species and give information about the integrity of that RNA. The presence of some mutations can be detected by Northern blotting. The presence or absence of an RNA species (e.g., a Jaz or cdk8 RNA) can also be determined using dot or slot blot Northern hybridizations. These techniques are modifications of Northern blotting and also demonstrate the presence or absence of an RNA species.

While Southern blotting and PCR may be used to detect the presence of Jaz, and/or cdk8 mutations or the presence of a PIF4 expression cassette, they do not provide information as to whether the preselected DNA segment is being expressed.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange, liquid chromatography or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products, or the absence thereof, that have been separated by electrophoretic techniques. Additional techniques may be employed to absolutely confirm the identity of a mutation such as evaluation by screening for reduced transcription (or no transcription) of Jaz, and/or cdk8 mRNAs, or by amino acid sequencing following purification. The Examples of this application also provide assay procedures for detecting and quantifying insect resistance and plant growth. Other procedures may be additionally used.

The expression of a gene product can also be determined by evaluating the phenotypic results of its expression. These assays also may take many forms including but not limited to analyzing changes in the insect resistance, growth characteristics, or other physiological properties of the plant. Expression of selected DNA segments encoding different amino acids or having different sequences and may be detected by amino acid analysis or sequencing.

The jazD cdk8 plants and seeds described herein can also be identified and characterized phenotypically. For example, the jazD cdk8 plant's vegetative weight or vegetative weight of a jazD cdk8 plant grown from jazD cdk8 plant seeds is within at least about 40%, or at least about 50%, or within at least 60%, or at least about 70% of the average vegetative weight of a wild type plant grown for the same time and under the same conditions as a wild type plant. Similarly, jazD cdk8 plants or plants grown from jazD cdk8 plant seeds have a seed yield that is at least 10%, or at least 20%, or at least 30%, or at least 40% greater than the average seed yield of wild type plants.

The jazD cdk8 plants or plants grown from jazD cdk8 plant seeds have at least 5% less, 10% less, 20% less, 30% less, 40% less, 50% less, 60% less, 70% less, 80% less, 90% less, or 100% less leaf damage from insect feeding than average insect feeding of a wild type plant of the same species grown for the same time under the same conditions.

The jazD cdk8 plants or plants grown from jazD cdk8 plant seeds have at least about 10%, or at least about 20%, or at least about 30%, or at least about 40%, or at least about 50%, or at least about 60%, or at least about 70%, or at least about 80%, or at least about 90% fewer insects or insect larvae than an average number of insects or insect larvae of wild type plants of the same species grown for the same time under the same conditions.

Defense Against Pests

As illustrated herein, loss of function mutations of Jaz and cdk8 genes, such as those provided by loss of function of the JazD cdk8 genes, can improve plant resistance to insects. Plants with such mutations can produce a variety of compounds that can repel, metabolically undermine, or otherwise discourage insects and/or insect larvae from infesting plant tissues. Such compounds are referred to as defense compounds. In some cases, the defense compounds are aliphatic glucosinolates. Examples of defense compounds include:

3MSOP: 3-methylsulphinylpropyl glucosinolate, glucoiberin;
4MSOB: 4-methylsulphinylbutyl glucosinolate, glucoraphanin;
5MSOP: 5-methylsulphinylpentyl glucosinolate, glucoalyssin;
6MSOH: 6-methylsulphinylhexyl glucosinolate, glucohesperin;
7MSOH: 7-methylsulphinylheptyl glucosinolate, glucoibarin;
3MTP: 3-methylthiopropyl glucosinolate, glucoiberverin;
8MSOO: 8-methylsulphinyloctyl glucosinolate, glucohirsutin;
4MTB: 4-methylthiobutyl glucosinolate, glucoerucin;
5MTP: 5-methylthiopentyl glucosinolate, glucoberteroin;
7MTH: 7-methylthioheptyl glucosinolate;
Or a combination thereof.

Mutation of jaz and/or cdk8 genes in plants can lead to increased synthesis of at least one defense compound, at least two defense compounds, at least three defense compounds, at least four defense compound, at least five defense compounds, at least six defense compounds, at least seven defense compound, at least eight defense compounds, or at least nine defense compounds.

Figure 12:
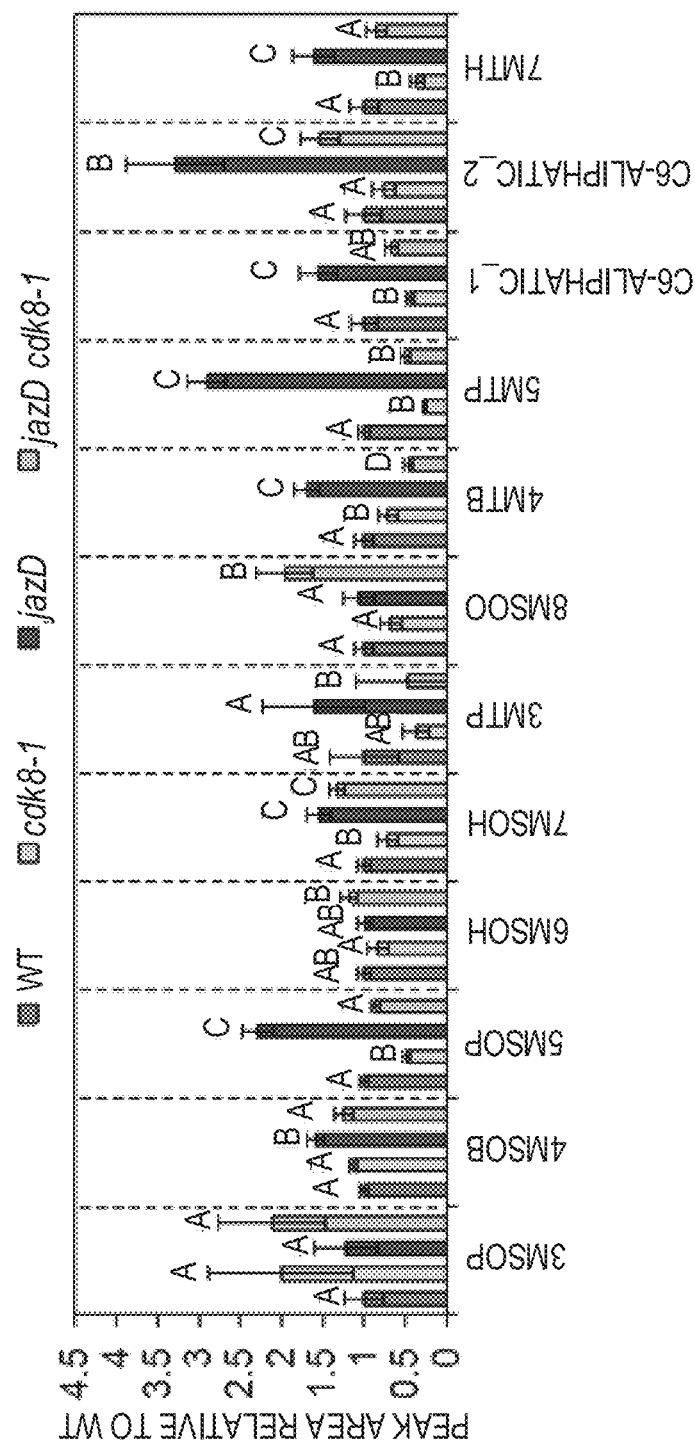
FIG. 12 graphically illustrates that CDK8 loss promotes the production of many aliphatic glucosinolates in jazD cdk8 plants as shown by the aliphatic glucosinolate levels in WT, cdk8, jazD and jazD cdk8 leaves. Aliphatic glucosinolates were extracted from leaves of 23-day-old plants grown under long-day conditions (16-h-light/8-h-dark). Peak area for the indicated compound in the WT sample was set to "1" and the peak area of the same compound in other genotypes was normalized to the WT sample. Abbreviations for the compounds detected were: 3MSOP: 3-methylsulphinylpropyl glucosinolate, glucoiberin: 4MSOB: 4-methylsulphinylbutyl glucosinolate, glucoraphanin; 5MSOP: 5-methylsulphinylpentyl glucosinolate, glucoalyssin; 6MSOH: 6-methylsulphinylhexyl glucosinolate, glucohesperin; 7MSOH: 7-methylsulphinylheptyl glucosinolate, glucoibarin; 3MTP: 3-methylthiopropyl glucosinolate, glucoiberverin; 8MSOO: 8-methylsulphinyloctyl glucosinolate, glucohirsutin; 4MTB: 4-methylthiobutyl glucosinolate, glucoerucin; 5MTP: 5-methylthiopentyl glucosinolate, glucoberteroin; and 7MTH: 7-methylthioheptyl glucosinolate. The data shown are the mean±SD of three biological replicates per genotype. Letters denote significant differences according to Tukey's HSD test (P<0.05).

The defense compounds can be produced by a variety of plant tissues. Examples of plant tissues where the defense compounds can be made include leaves, stems, seeds, or a combination thereof. For example, plant leaves can have increased content of a variety of defense compounds in plants with loss of function JazD cdk8 genes, as illustrated in FIG. 12.

The defense compounds can be at least 2%, at least 3%, at least 4%, at least 5%, at least 7%, at least 10%, at least 13%, at least 15%, at least 17%, at least 20%, at least 25%, at least 30%, at least 40%, at least 50%, at least 70%, at least 80%, at least 90%, or at least 100% greater levels in plants with loss of function Jaz mutations, loss of function cdk8 mutations, or a combination thereof, than in unmodified parental or wild type plants.

Definitions

As used herein, the singular forms "a," "an," and "the" are intended to include the plural forms as well, unless the context clearly indicates otherwise. Also, as used herein, "and/or" refers to, and encompasses, any and all possible combinations of one or more of the associated listed items. Unless otherwise defined, all terms, including technical and scientific terms used in the description, have the same meaning as commonly understood by one of ordinary skill in the art to which this invention pertains.

The term "about", as used herein, can allow for a degree of variability in a value or range, for example, within 10%, within 5%, or within 1% of a stated value or of a stated limit of a range.

The term "heterologous" when used in reference to a nucleic acid or protein refers to a nucleic acid or protein that has been manipulated in some way. For example, a heterologous nucleic acid includes a nucleic acid from one species introduced into another species. A heterologous nucleic acid also includes a nucleic acid that is native to an organism that has been altered in some way (e.g., mutated, added in multiple copies, present in a locus within the genome, expressed from an autonomously replicating vector, linked to a non-native promoter, linked to a mutated promoter, or linked to an enhancer sequence, etc.). Heterologous nucleic acids may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). In some cases, heterologous nucleic acids are distinguished from endogenous plant genes in that the heterologous nucleic acids can be joined to nucleotide sequences comprising regulatory elements such as promoters that are not found naturally associated with the nucleic acid. In another example, the heterologous nucleic acids are associated with portions of the chromosome not found in nature (e.g., genes expressed in loci where the gene is not normally expressed).

The terms "identical" or percent "identity", as used herein, in the context of two or more nucleic acids, or two or more polypeptide sequences, refer to two or more sequences or subsequences that are the same or have a specified percentage of nucleotides or amino acid residues that are the same (e.g., 75% identity, 80% identity, 85% identity, 90% identity, 95% identity, 97% identity, 98% identity, 99% identity, or 100% identity in pairwise comparison). Sequence identity can be determined by comparison and/or alignment of sequences for maximum correspondence over a comparison window, or over a designated region as measured using a sequence comparison algorithm, or by manual alignment and visual inspection. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. A "reference sequence" is a defined sequence used as a basis for a sequence comparison; a reference sequence may be a subset of a larger sequence.

The term "nucleic acid," "nucleic acid segment" or "nucleic acid of interest" refers to any RNA or DNA, where the manipulation of which may be deemed desirable for any reason (e.g., treat or reduce the incidence of disease, confer improved qualities, etc.), by one of ordinary skill in the art. Such nucleic acids include, but are not limited to, coding sequences of structural genes (e.g., disease resistance genes, reporter genes, selection marker genes, oncogenes, drug resistance genes, growth factors, etc.), and noncoding regulatory sequences which do not encode an mRNA or protein product (e.g., promoter sequence, polyadenylation sequence, termination sequence, enhancer sequence, etc.).

As used herein, the term "plant" is used in its broadest sense. It includes, but is not limited to, any species of grass (fodder, ornamental or decorative), crop or cereal, fodder or forage, fruit or vegetable, fruit plant or vegetable plant, herb plant, woody plant, flower plant or tree. It is not meant to limit a plant to any particular structure. It also refers to a unicellular plant (e.g. microalga) and a plurality of plant cells that are largely differentiated into a colony (e.g. volvox) or a structure that is present at any stage of a plant's development. Such structures include, but are not limited to, a seed, a tiller, a sprig, a stolen, a plug, a rhizome, a shoot, a stem, a leaf, a flower petal, a fruit, et cetera.

The term "seed" refers to a ripened ovule, consisting of the embryo and a casing.

Vegetative tissues or vegetative plant parts do not include plant seeds, and instead include non-seed tissues or parts of a plant. The vegetative tissues can include reproductive tissues of a plant, but not the mature seeds.

As used herein, the term "wild-type" when made in reference to a gene refers to a functional gene common throughout an outbred population. As used herein, the term "wild-type" when made in reference to a gene product refers to a functional gene product common throughout an outbred population. A functional wild-type gene is that which is most frequently observed in a population and is thus arbitrarily designated the "normal" or "wild-type" form of the gene.

The following Example illustrate some of the experiments performed and experimental results obtained during the development of the invention. Appendix A may provide further information.

Example 1: Materials and Methods

This Example illustrates some of the materials and methods that were used in the development of the invention.
Plant Material and Growth Conditions The Columbia accession (Col-0) of *A. thaliana* was used as wild type for all experiments. Plants with jazD were constructed by crossing jazQ (Campos et al., Nat. Commun. 7: 12570 (2016)) to other transfer DNA (T-DNA) or transposon insertion mutants obtained from the *Arabidopsis* Biological Research Center (ABRC; Ohio State University). The following jaz-single mutants were combined with jazQ as described in FIGS. 1A-1D, and were named as follows: jaz2-3 (RIKEN_13-5433-1) (Gimenez-Ibanez t al. *New Phytol* 213:1378-1392 (2017)), jaz5-1 (SALK_053775) (Thines et al. *Nature* 448:661-665 (2007)), jaz6-4 (CSHL-ET30) (described herein), jaz7-1 (WiscDsLox7H11) (Thines et al. *Nature* 448:661-665 (2007)), jaz8-V (Thireault et al., *Plant J* 82:669-679 (2015)), and jaz13-1 (GK-193G07) (Thireault et al., *Plant J* 82:669-679 (2015)). As illustrated in FIG. 1D, these jazD mutations eliminate transcription from Jaz1, Jaz2, Jaz3, Jaz4, Jaz, Jaz6, Jaz7, Jaz9, Jaz10 and Jaz13 genes. Although an amplicon appears in the Jaz4 gel, this amplicon is unrelated to Jaz4 and does not indicate that a Jaz4 transcript was expressed.

Figures 1, 1A, 2, 3:
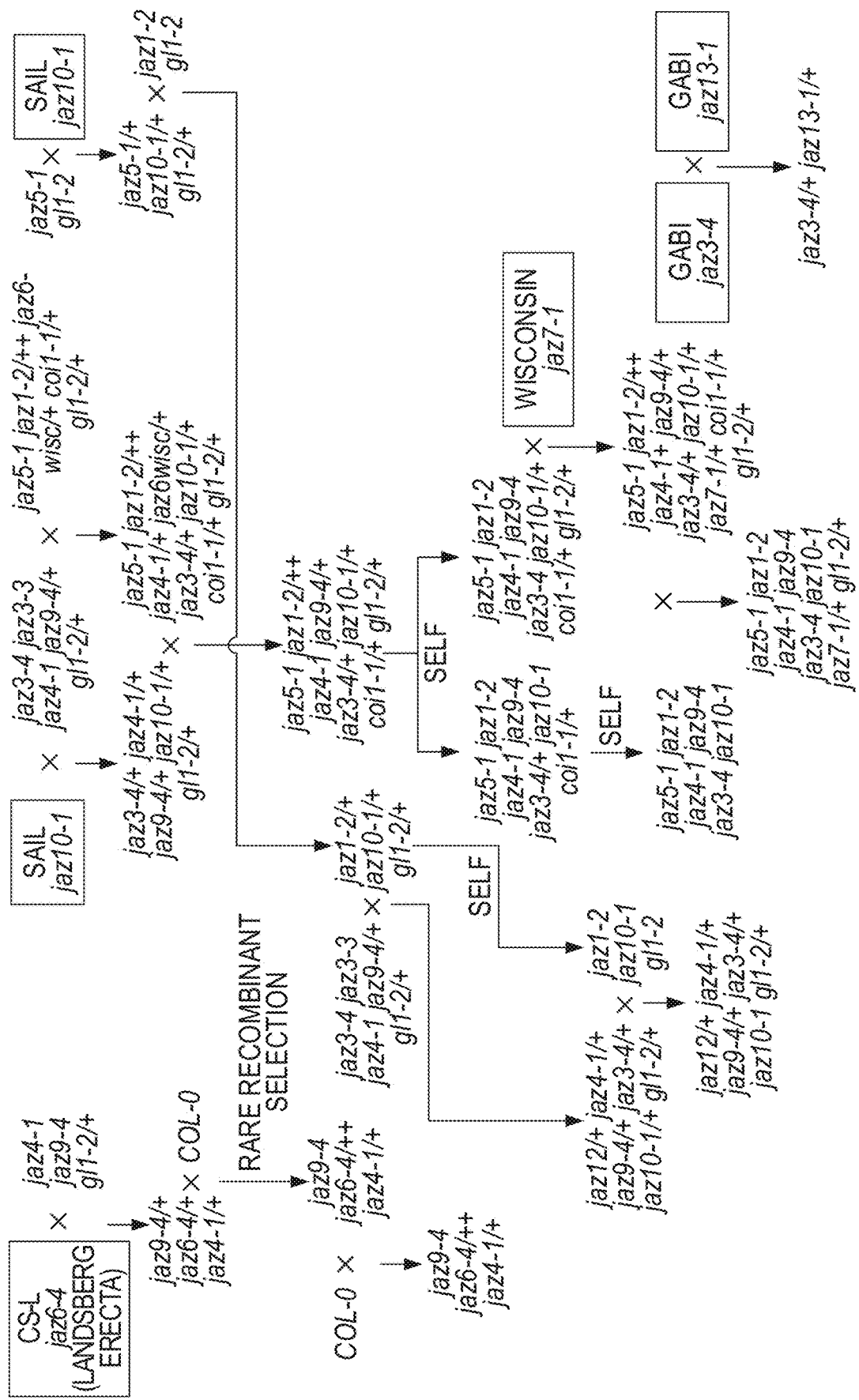
Figures 1, 1A, 2, 3, 4:
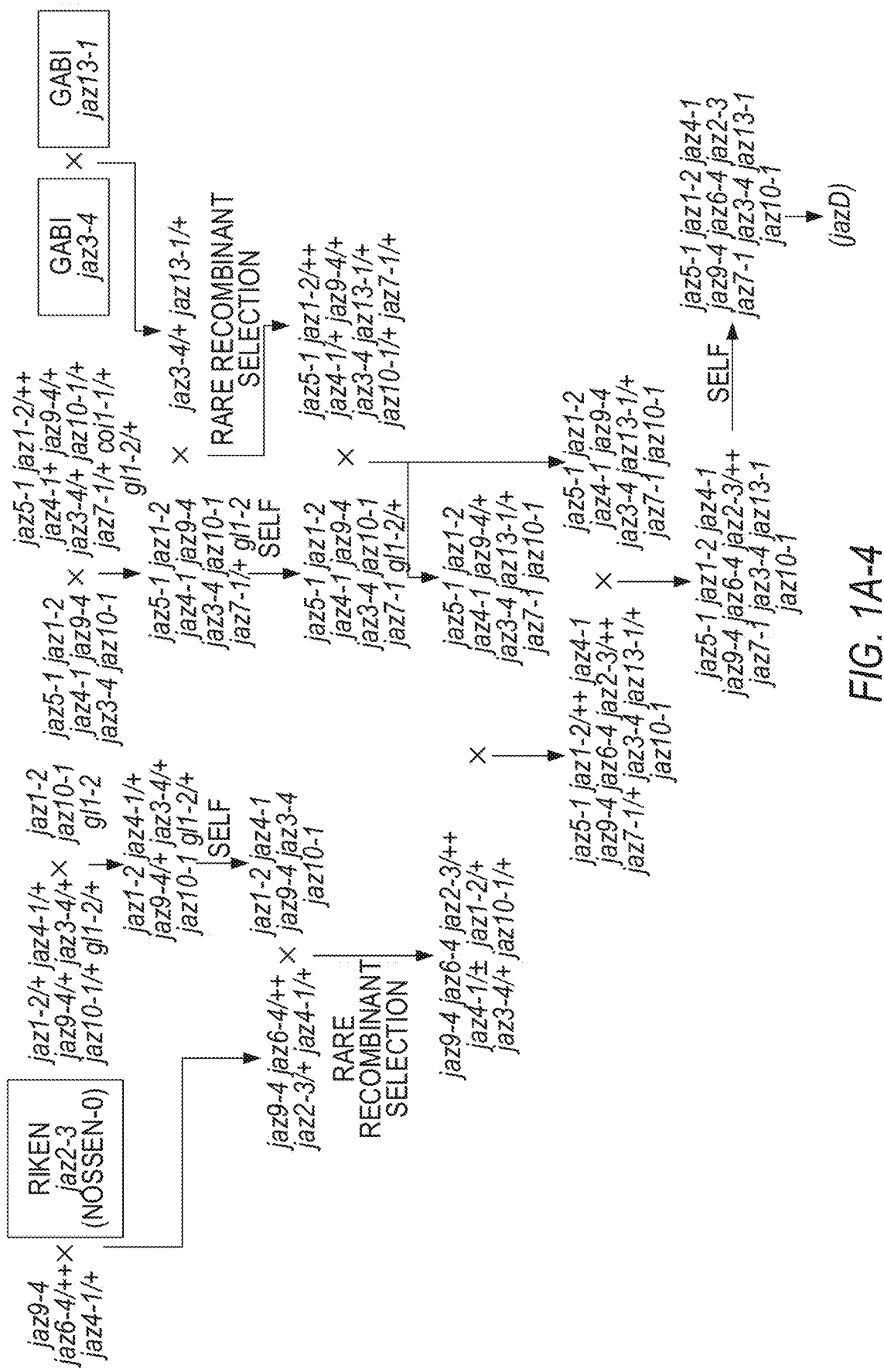

Additional details on jaz-single mutants and the breeding scheme used to obtain jazD are provided in Table 3 and FIG. 1 respectively.

TABLE 3

| Mutants used for construction of jazD and jazU. | | | | | |
| --- | --- | --- | --- | --- | --- |
| Mutant | Original name | Source | Accession | Mutagen | Resistance[1] |
| jaz1-2 | SM_3.22668 | JIC SM | Col-0 | dSpm transposon | Basta (confirmed) |
| jaz2-3 | RIKEN_13-5433-1 | RIKEN | No-0 | Ds transposon | Hygromycin (confirmed) |
| jaz3-4 | GK-097F09 | GABI Kat | Col-0 | T-DNA (pAC161) | Sulfadiazine (confirmed) |

TABLE 3-continued

Mutants used for construction of jazD and jazU.

| Mutant | Original name | Source | Accession | Mutagen | Resistance[1] |
|---|---|---|---|---|---|
| jaz4-1 | SALK_141628 | SALK | Col-0 | T-DNA (pROK2) | Kanamycin (silenced) |
| jaz5-1 | SALK_053775 | SALK | Col-0 | T-DNA (pROK2) | Kanamycin (confirmed) |
| jaz6-4 | CSHL_ET30 | CSHL | Ler | Ds transposon (Enhancer trap GUS) | Kanamycin (confirmed) |
| jaz7-1 | WiscDsLox7H11 | Wisconsin | Col-0 | T-DNA (pWiscDsLox) | Basta (not tested) |
| jaz8-V[2] | N/A | ABRC | Vash-1 | SNP | N/A |
| jaz9-4 | GK_265H05 | GABI kat | Col-0 | T-DNA (pAC161) | Sulfadiazine (confirmed) |
| jaz10-1 | SAIL_92_D08 | SAIL | Col-0 | T-DNA (pCSA110) | Basta (confirmed) GUS |
| jaz13-1 | GK_193G07 | GABI kat | Col-0 | T-DNA (pAC161) | Sulfadiazine (not tested) |

[1]Resistance of the mutant line to the indicated selectable marker was tested and confirmed.
[2]The C-to-A nonsense mutation present in JAZ8 from accession Vash-1 was backcrossed four times to Col-0 to generate a line (#28-6-30) that was used for subsequent genetic crosses (Thireault et al., *Plant J* 82: 669-679 (2015)).
N/A, not applicable.

Efforts were made to reduce chromosomal contributions from other accessions by testing multiple SSLP polymorphic markers over many generations, so that the majority of jazD genome is derived from Col-0 (FIG. 1). Following sowing of seeds in soil, potted plants were covered with a transparent plastic dome for 10 days. Soil-grown plants were maintained under a 16-hour light (100 µE m$^{-2}$ s$^{-1}$) and 8-hour dark photoperiod at 20° C. unless otherwise noted. Immediately after seed harvest, small seeds were eliminated by passing bulk seed through a brass sieve with a 250 µm pore size. Seeds retained after sieving (referred to as "sieved seeds") were dried for two weeks in 1.5 mL Eppendorf tubes containing Drierite desiccant. PCR analysis PCR-based genotyping of jazD and lower-order mutants was performed using primer sets flanking DNA insertion sites and a third primer recognizing the T-DNA border (Table 4).

TABLE 4

Primers used for genotyping

| Gene | Locus | Primer | Sequence (5'-3') |
|---|---|---|---|
| JAZ1 | AT1G19180 | JAZ1_F | ACCGAGACACATTCCCGATT (SEQ ID NO: 67) |
| | | JAZ1_R | CATCAGGCTTGCATGCCATT (SEQ ID NO: 68) |
| | | JAZ1_border | ACGAATAAGAGCGTCCATTTTAGAG (SEQ ID NO: 69) |
| JAZ2 | AT1G74950 | JAZ2_F | TCTTCCTCGTGACAAAACGCA (SEQ ID NO: 70) |
| | | JAZ2_R | CCAAACACAGAACCATCTCCACA (SEQ ID NO: 71) |
| | | JAZ2_border | CCGGATCGTATCGGTTTTCG (SEQ ID NO: 72) |
| JAZ3 | AT3G17860 | JAZ3_F | ACGGTTCCTCTATGCCTCAAGTC (SEQ ID NO: 73) |
| | | JAZ3_R | GTGGAGTGGTCTAAAGCAACCTTC (SEQ ID NO: 74) |
| | | JAZ3_border | ATAACGCTGCGGACATCTACATT (SEQ ID NO: 75) |
| JAZ4 | AT1G48500 | JAZ4_F | TCAGGAAGACAGAGTGTTCCC (SEQ ID NO: 76) |
| | | JAZ4_R | TGCGTTTCTCTAAGAACCGAG (SEQ ID NO: 77) |
| | | JAZ4_border | TTGGGTGATGGTTCACGTAG (SEQ ID NO: 78) |
| JAZ5 | AT1G17380 | JAZ5_F | GCTTATACCGAAACCCGATTCCAG (SEQ ID NO: 79) |
| | | JAZ5_R | GGCTCATTGAGATCAGGAAACCA (SEQ ID NO: 80) |
| | | JAZ5_border | TTGGGTGATGGTTCACGTAG (SEQ ID NO: 81) |

TABLE 4-continued

Primers used for genotyping

| Gene | Locus | Primer | Sequence (5'-3') |
|---|---|---|---|
| JAZ6 | AT1G72450 | JAZ6_F | GACACACATCACTGTCACTTC (SEQ ID NO: 82) |
| | | JAZ6_R | AGTTTCTGAGGTCTCTACCTTC (SEQ ID NO: 83) |
| | | JAZ6_border | CCGTTTTGTATATCCCGTTTCCGT (SEQ ID NO: 84) |
| JAZ7 | AT2G34600 | JAZ7_F | ATGCGACTTGGAACTTCGCC (SEQ ID NO: 85) |
| | | JAZ7_R | GGAGGATCCGAACCGTCTG (SEQ ID NO: 86) |
| | | JAZ7_border | ACGTCCGCAATGTGTTATTA (SEQ ID NO: 87) |
| JAZ8 | AT1G30135 | JAZ8_F | TGTCCTAAGAGTCCGCCGTTGT (SEQ ID NO: 88) |
| | | JAZ8_R | TTTGGAGGATCCGACCCGTTTG (SEQ ID NO: 89) |
| JAZ9 | AT1G70700 | JAZ9_F | TACCGCATAATCATGGTCGTC (SEQ ID NO: 90) |
| | | JAZ9_R | TCATGCTCATTGCATTAGTCG (SEQ ID NO: 91) |
| | | JAZ9_border | CTTTGAAGACGTGGTTGGAACG (SEQ ID NO: 92) |
| JAZ10 | AT15G13220 | JAZ10_F | ATTTCTCGATCGCCGTCGTAGT-3 (SEQ ID NO: 93) |
| | | JAZ10_R | GCCAAAGAGCTTTGGTCTTAGAGTG (SEQ ID NO: 94) |
| | | JAZ10_border | GTCTAAGCGTCAATTTGTTTACACC (SEQ ID NO: 95) |
| JAZ13 | AT3G22275 | JAZ13_F | GCACGTGACCAAATTTGCAGA (SEQ ID NO: 96) |
| | | JAZ13_R | TGAAGAGAGGAGGATGATGAGGA (SEQ ID NO: 97) |
| | | JAZ13_border | AAACCTCCTCGGATTCCATTGC (SEQ ID NO: 98) |

PCR reactions were performed with the following condition: 95° C. for 5 min, followed by 35 cycles of denaturation (30 s at 95° C.), annealing (30 s at 56° C.) and elongation (1.5 min at 72° C.). Final elongation step was performed at 72° C. for 10 min and completed reactions were maintained at 12° C. The jaz8-V mutant was distinguished from wild-type JAZ8 amplicons by digestion with AflII (New England Biolabs). The presence or absence of full-length JAZ transcripts in Col-0, jazQ, and jazD plants was determined by reverse transcription (RT) PCR. RNA was extracted from rosette leaves of soil-grown plants using a RNeasy kit (Qiagen). cDNA was reverse transcribed with a High-Capacity cDNA Reverse Transcription kit (Applied Biosystems, ABI). RT-PCR reactions were performed with primer sets designed to amplify target JAZ genes and the internal control ACTIN1 (At2g37620) by GoTaq Green Master Mix (Promega). Primer sets and additional details of the RT-PCR procedures are provided in Table 5.

TABLE 5

Primers used for RT-PCR

| Gene | Locus | Primer | Sequence (5'-3') | Annealing (° C.) | PCR cycles |
|---|---|---|---|---|---|
| JAZ1 | AT1619180 | JAZ1_RT_F | ATGTCGAGTTCTAT GGAATG (SEQ ID NO: 99) | 52 | 30 |
| | | JAZ1_RT_R | TCATATTTCAGCTGC TAAAC (SEQ ID NO: 100) | | |
| JAZ2 | AT1G74950 | JAZ2_RT_F | ATGTCGAGTTTTTCT GCCGA (SEQ ID NO: 101) | 52 | 30 |
| | | JAZ2_RT_R | TTACCGTGAACTGA GCCAAG (SEQ ID NO: 102) | | |
| JAZ3 | AT3G17860 | JAZ3_RT_F | ATGGAGAGAGATTT TCTCGGG (SEQ ID NO: 103) | 52 | 30 |
| | | JAZ3_RT_R | TTAGGTTGCAGAGC TGAGAGAAG (SEQ ID NO: 104) | | |

TABLE 5-continued

Primers used for RT-PCR

| Gene | Locus | Primer | Sequence (5'-3') | Annealing (° C.) | PCR cycles |
|---|---|---|---|---|---|
| JAZ4 | AT1G48500 | JAZ4_RT_F | ATGGAGAGAGATTT TCTCGGGCTGG (SEQ ID NO: 105) | 64.7 | 40 |
| | | JAZ4_RT_R | TTAGTGCAGATGAT GAGCTGGAGGA (SEQ ID NO: 106) | | |
| JAZ5 | AT1G17380 | JAZ5_RT_F | ATGTCGTCGAGCAA TGAAAA (SEQ ID NO: 107) | 54 | 35 |
| | | JAZ5_RT_R | CTATAGCCTTAGAT CGAGAT (SEQ ID NO: 108) | | |
| JAZ6 | AT1G72450 | JAZ6RT_F | ATGTCAACGGGACA AGCGC (SEQ ID NO: 109) | 54 | 35 |
| | | JAZ6_RT_R | CTAAAGCTTGAGTT CAAGGT (SEQ ID NO: 110) | | |
| JAZ7 | AT2G34600 | JAZ7_RT_F | ATGATCATCATCAT CAAAAACTG (SEQ ID NO: 111) | 58 | 40 |
| | | JAZ7_RT_R | CTATCGGTAACGGT GGTAAG (SEQ ID NO: 112) | | |
| JAZ9 | AT1G70700 | JAZ9_RT_F | ATGGAAAGAGATTT TCTGGG (SEQ ID NO: 113) | 52 | 40 |
| | | JAZ9_RT_R | TTATGTAGGAGAAG TAGAAG (SEQ ID NO: 114) | | |
| JAZ10 | AT5G13220 | JAZ10_RT_F | ATGTCGAAAGCTAC CATAGAAC (SEQ ID NO: 115) | 57 | 40 |
| | | JAZ10_RT_R | GATAGTAAGGAGAT GTTGATACTAATCTCT (SEQ ID NO: 116) | | |
| JAZ13 | AT3G22275 | JAZ13_RT_F | ATGAAGGGTTGCAG CTTAGA (SEQ ID NO: 117) | 56 | 35 |
| | | JAZ13_RT_R | TTAGAAATTATGAA GAGAGGAGG (SEQ ID NO: 118) | | |
| ACTIN1 | AT2G37620 | Actin1_F | ATGGCTGATGGTGA AGACATTCAA (SEQ ID NO: 119) | 67.2 | 40 |
| | | Actin1_R | TCAGAAGCACTTCC TGTGAACAAT (SEQ ID NO: 120) | | |

Growth Measurements

For relative growth rate (RGR) analysis, five plants per genotype were harvested every two days beginning and ending 11 and 29 days, respectively, after seed sowing. Excised shoots were lyophilized for determination of dry weight. Relative growth rate (RGR) was calculated from the slope of the log(dry weight) over the duration of the time course. Leaf area of 23-day-old plants was determined by photographing rosettes from the top with a Nikon D80 camera. The resulting images were used to measure projected leaf area with GIMP software (see website at gimp.org).

Root Elongation Assays

Seeds were surface sterilized with 50% (v/v) bleach for three min, washed 10 times with sterile water and stratified in dark at 4° C. for two days. Seedlings were grown on 0.7% (w/v) agar media containing half-strength Linsmaier and Skoog (LS; Caisson Labs) salts supplemented with 0.8% (w/v) sucrose and the indicated concentration of MeJA (Sigma-Aldrich). Each square Petri plate (Fisher; 100×100× 15 mm) contained five seedlings per genotype. Plates were incubated vertically in a growth chamber maintained at 21° C. for eight days under 16-hour-light (80 µE m$^{-2}$s$^{-1}$)/8-hour-dark conditions. The length of primary roots was measured using ImageJ software (see website at imagej.nih.gov/ij/).

Coronatine Treatment

The eighth true leaf of 40-day-old plants grown under 12-hour-light/12-hour-dark conditions were spotted with 5 µL of sterile water (mock) or a solution containing 50 µM coronatine (Sigma-Aldrich, C8115) prepared in sterile water. Photographs were taken two and four days after treatment.

Insect and Pathogen Assays

Insect feeding assays were performed at 20° C. under a short-day photoperiod of 8-hour light and 16-hour dark. Neonate *Trichoplusia ni* larvae (Benzon Research) were transferred to fully expanded rosette leaves of 9-week-old plants. Four larvae were reared on each of 12 plants for approximately 12 days, after which larval weights were measured (Herde et al. *Methods Mol Biol* 1011:51-61 (2013)). *Botrytis cinerea* bioassays were performed as described previously (Rowe et al. *Mol Plant Microbe Interact* 20:1126-1137 (2007)), with minor modifications. Detached leaves from 10-week-old short-day-grown (8-hour light/16-hour dark) plants were placed in Petri dishes containing filter paper moistened with 10 mL sterile water, with petioles submerged in the water. Each leaflet was inoculated with a single 4 µL droplet of *Botrytis cinereal* spore suspension (5,000 spores/mL in 50% organic grape juice). Petri dishes were sealed with Micropore surgical tape (3M Health Care) and kept under the same conditions used for plant growth. Photographs were taken after five days and lesion area was measured using the ImageJ software (see website at imagej.nih.gov/ij/).

Seed Yield Measurements

Individual plants were grown in 6.5-cm square pots. An inverted plastic cone and plastic tube (Arasystem 360 kit; Arasystem) were fitted to each plant 23 days after seed sowing to collect all seeds from dehiscing siliques. Seeds collected from individual plants were harvested and dried with Drierite desiccant for two weeks, after which total seed mass per plant was measured. Average seed mass was determined by weighing dry seeds in batches of 200 (Jofuku et al., *Proc Natl Acad Sci USA* 102:3117-3122 (2005)). For each plant, the weights of three sample batches were measured and averaged. The silique length and number of seeds per silique were measured by sampling the fully-elongated seventh, ninth and eleventh siliques on the main stem (Roux et al., *Genetics* 166:449-460 (2004)).

Germination Assays

Germination assays were performed on half-strength LS agar plates without sucrose. Unsieved seeds were surface sterilized and stratified in dark at 4° C. for two days. Plates were incubated vertically under continuous light at 21° C. and germination was scored daily for seven days by radicle emergence from the seed coat (Dekkers et al., *Planta* 218: 579-588 (2004)).

RNA-Seq Analysis

Global gene expression profiling was performed on the Illumina HiSeq 2000 platform at the Michigan State University Research Technologies Service Facility (see website at rtsf.natsci.msu.edu/). Rosettes of 23-day-old soil-grown Col-0, jazQ, and jazD plants were harvested for RNA extraction 6 h after the beginning of the light period. Three independent RNA samples (biological replicates) were used for each genotype, with each replicate derived from pooling rosette leaves from 20 plants. Raw sequencing reads were filtered with Illumina quality control tool FASTX-Toolkit (see website at hannonlab.csh1.edu/fastx_toolkit/) and then mapped to TAIR10 gene models by RSEM (version 1.2.25) (Li et al., *BMC Bioinformatics* 12:323 (2011)). mRNA abundances for all *Arabidopsis* genes were expressed as transcripts per million (TPM). The average TPM±s.e.m for all genes is shown in Dataset S1, sheet a. DESeq2 (version 3.3) (Anders. *Genome Biol* 11:R106 (2010)) was used to normalize expected counts from RSEM and to determine differential gene expression by comparing normalized counts in Col-0 to those in mutants. DAVID (version 6.8) (Huang et al., *Nat Protoc* 4:44-57 (2009)) and MapMan (version 3.6.0) (Thimm et al., *The Plant* 37:914-939 (2004)) was used to perform gene ontology (GO) analysis of enriched functional categories. Over-represented and under-represented GO categories among differentially expressed genes were assessed by hypergeometric test with Benjamini & Hochberg's false discovery rate (FDR) correction at P<0.05. Analysis of the induction or repression of metabolic pathways was performed by Kyoto Encyclopedia of Genes and Genomes (KEGG) Mapper (see website at genome.jp/kegg/pathway.html) (Kanehisa & Goto. *Nucleic Acids Res* 28:27-30 (2000)). Data deposition: RNA sequencing data from this study have been deposited in the Gene Expression Omnibus (GEO) database, see website at ncbi.nlm.nih.gov/geo (accession no. GSE116681).

Quantitative Proteomic Analysis

Quantitative proteomic analysis was performed with proteins extracted from leaf tissue of 23-day-old soil-grown Col-0 and jazD plants. Proteins from three biological replicates (20 plants/replicate) of each genotype were extracted with the following extraction buffer: 100 mM Tris-HCl (pH 6.8), 150 mM NaCl, 10% glycerol (v/v), 4% SDS (w/v), 200 mM DTT, and protease inhibitor (Sigma-Aldrich, 1 tablet/10 mL buffer). Protein concentrations were determined by Bradford assay. Trypsin-digested peptides derived from these proteins were derivatized with a tandem mass tag (TMT) labeling kit (ThermoFisher) for quantification by mass spectrometry (MS) performed at the Michigan State University Proteomics Core Facility (see website at rtsf.natsci.msu.edu/proteomics/). Briefly, protein samples were digested with trypsin using the Filter-Aided Sample Preparation (FASP) protocol according to Wisniewski et al. (*Nat Methods* 6:359-362 (2009)). Samples were then labeled with TMTsixple Isobaric Label Reagents (ThermoFisher) according to manufacturer's protocol. After labeling, all six samples were combined and dried by vacuum centrifugation. The combined peptide samples were separated over a pH gradient (pH 3-10) into six fractions using an Agilent OffGel 3100 fractionator (agilent.org) according to manufacturer's protocol. Dried fractions were washed and eluted. Eluted peptides were sprayed into a ThermoFisher Q-Exactive mass spectrometer (thermo.com) using a FlexSpray nano-spray ion source. Survey scans were taken in the Orbitrap (70,000 resolution, determined at m/z 200) and the top ten ions in each survey scan were then subjected to automatic higher energy collision induced dissociation (HCD) with fragment spectra acquired at 35,000 resolution. Conversion of MS/MS spectra to peak lists and quantitation of TMT reporter ions was done using Proteome Discover, v1.4.1.14. Peptide-to-spectrum matching was performed with the Sequest HT and Mascot search algorithms against the TAIR10 protein sequence database appended with common laboratory contaminants (downloaded from the website arabidopsis.org and thegpm.org, respectively). The output from both search algorithms was then combined and analyzed using Scaffold Q+S (version 4.5.3) to probabilistically validate protein identifications and quantification. Assignments validated using the Scaffold 1% FDR confidence filter were considered true.

Gas Exchange Measurements and $^{13}C$ Discrimination Analysis

Plants grown under short-day photoperiod (8 h light/16 h dark) in 'Cone-tainers' (Steuwe and Sons. Tangent, OR, USA) were used for gas exchange analysis. The measurements were performed on LI-6400XT and LI-6800 systems (LI-COR Biosciences, Lincoln, NE USA) as described by Campos et al. (*Nat Commun* 7:12570 (2016)). Daytime respiration was determined from slope-intercept regression analysis of the common intersection of five $CO_2$ response curves (using intercellular $CO_2$ below 10 Pa) measured at decreasing, sub-saturating irradiances (Walker et al., *Plant Cell Environ* 38:2462-2474 (2015)). Leaf tissue was freeze-dried and used for the measurement of the ratio of $^{13}CO_2$ to $^{12}CO_2$ by mass spectrometry at the Stable Isotope Ratio Facility for Environmental Research, University of Utah (Salt Lake City, UT). Isotopic ratios and $CO_2$ partial pressure at Rubisco were calculated as described (Weraduwage et al. *Front Plant Sci* 6:167 (2015); Farquhar et al. *Funct Plant Biol* 9:121-137 (1982); Farquhar et al. *Annu Rev Plant Biol* 40:503-537 (1989)).

Protein, Lipid and Cell Wall Measurements

For protein, lipid and cell wall measurements, leaf tissue was harvested from 23-day-old plants grown under our standard long-day conditions. Excised shoots were lyophilized to determine the dry weight. Total protein was extracted using a Plant Total Protein Extraction Kit (PE0230, Sigma-Aldrich) and quantified by Bradford assay. Lipid extraction, thin-layer chromatography (TLC) of polar and neutral lipids, transesterification, and gas chromatography were performed as described previously (Wang & Benning, J Vis Exp 49:2518 (2011); Wang et al. *Plant Cell* (2018)). For polar lipids, lipid separation was performed by activated ammonium sulfate-impregnated silica gel TLC plates (TLC Silica gel 60, EMD Chemical) with a solvent consisting of acetone, toluene, and water (91:30:7.5 by volume). Lipids were visualized by brief exposure to iodine vapor on TLC plates. Acyl groups of the isolated lipids were then converted to methyl esters, which were subsequently quantified by a gas chromatography. Cell wall was extracted with a solution containing 70% ethanol, chloroform/methanol solution (1:1 v/v) and acetone as described (Foster et al. *J Vis Exp* 37:1837 (2010)). Starch was removed from the extracts using amylase and pullulanase (Sigma-Aldrich). Protein, lipid and cell wall content was normalized to leaf dry weight.

Glucosinolate Measurements

Plants were grown under long-day conditions (16-hour day and 8-hour night) for 23 days. Rosette leaves were harvested and frozen in liquid nitrogen immediately. Two plants were pooled for each sample, with three biological replicates collected per sample. Frozen tissue was homogenized with a TissueLyser II (Qiagen) and glucosinolates were extracted following published procedures (Glauser et al. *Phytochem Anal* 23:520-528 (2012)), with minor modifications. Briefly, 80% methanol (v/v) was added to homogenized tissues and the mixture was vortexed for 5 min. Extracts were then centrifuged at 16,000×g for 5 min and the supernatant was transferred to a 2-mL glass vial (RESTEK). Samples were analyzed in the MSU Mass Spectrometry Facility by ultrahigh pressure liquid chromatography (UPLC) coupled to quadrupole time-of-flight mass spectrometry (QTOFMS) using Waters Xevo G2-XS. Data analysis and processing were performed as described previously (Glauser et al. *Phytochem Anal* 23:520-528 (2012)).

Sucrose Rescue Assays

The effect of exogenous sucrose on leaf biomass and root growth was determined by growing seedlings on square Petri plates (Greiner Bio-One; 120×120×17 mm). In order to control for variation in seed quality, seeds were sieved after drying with desiccant for two weeks (see above). After sterilization and washing, seeds were sown without stratification on 0.7% (w/v) agar media containing half-strength LS salts supplemented with sucrose or sorbitol. Each plate contained ten (for biomass) or five (for root growth) seeds of Col-0 and mutant lines. Plates were placed in the dark at 4° C. for four days and then incubated horizontally (for leaf biomass) or vertically (for root growth) in growth chambers maintained at 21° C. under 16 h at a light intensity of 80 µE $m^{-2}$ $s^{-1}$ and 8-hour dark. ImageJ was used to measure root length after 11 days. Plant biomass and projected leaf area were measured after 16 days.

Example 2: Reduced Growth and Fertility of a JazD Mutant is Associated with Extreme Sensitivity to JA This Example describes the growth and fertility of the jazD mutant plants.

Figure 1B:
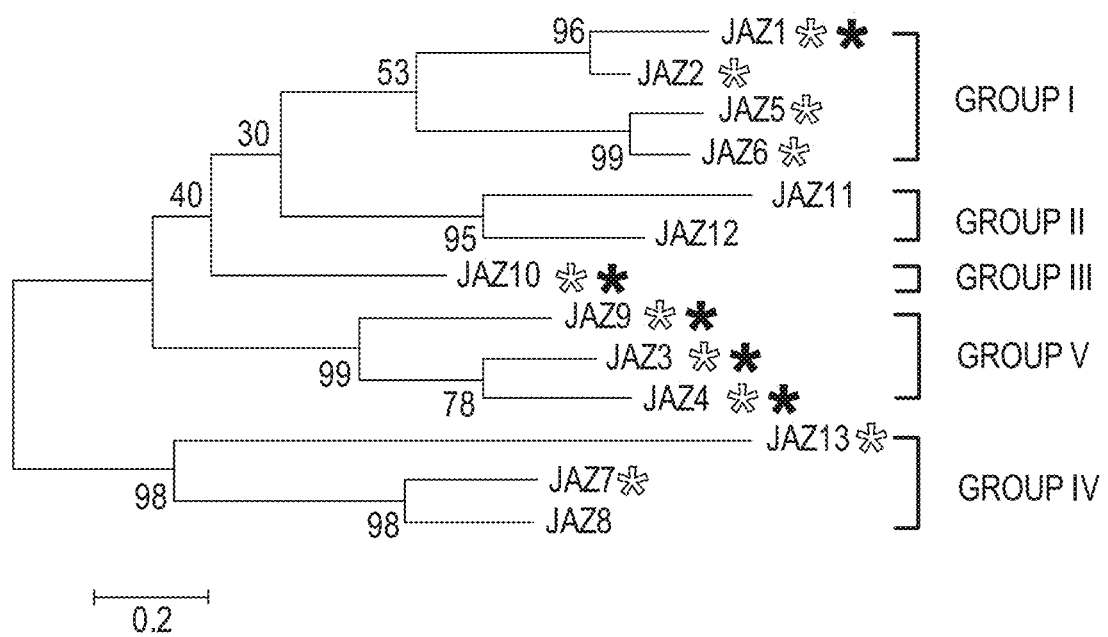
Figure 1C:
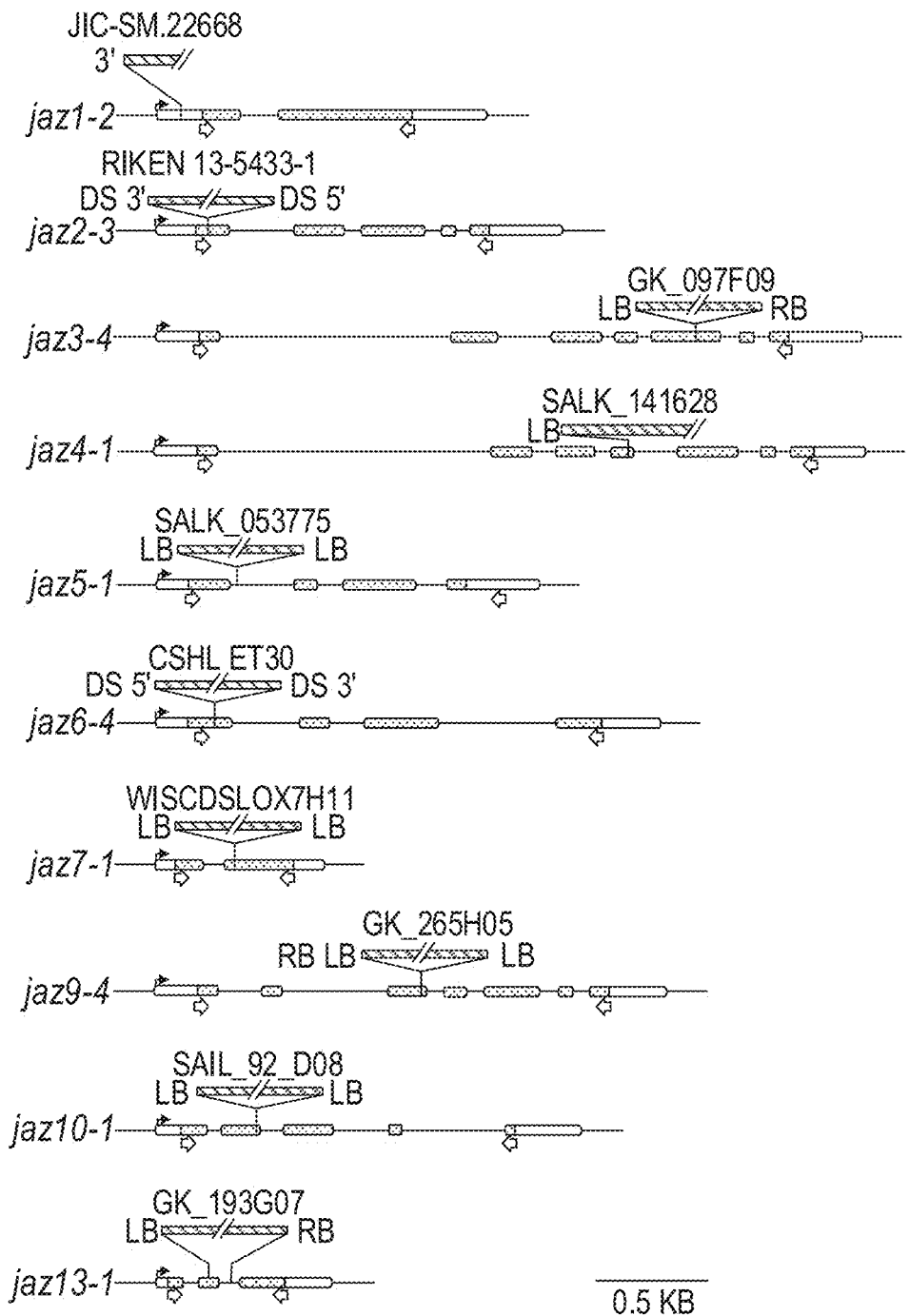
Figure 1D:
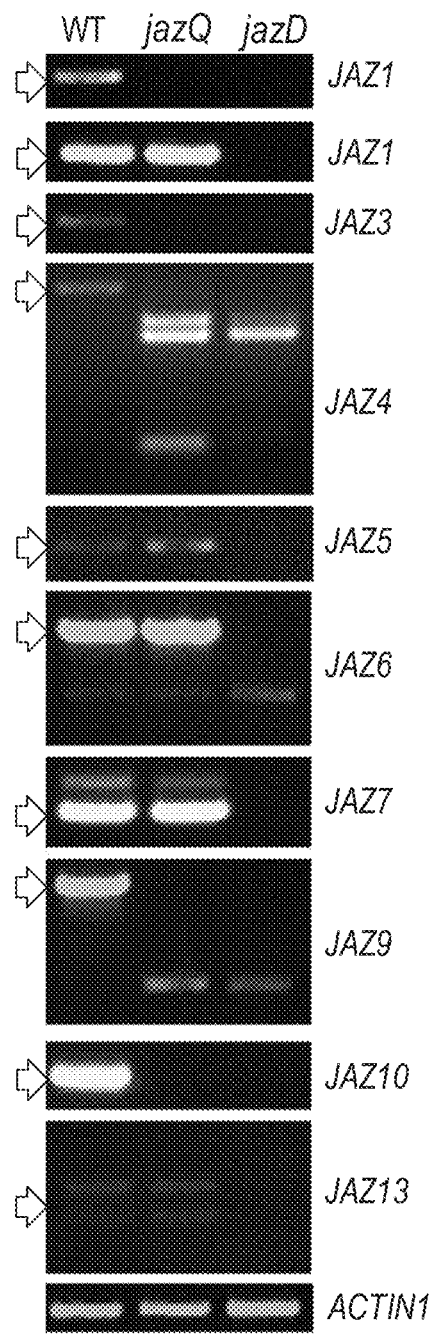

The insertion mutations used to construct a series of higher-order jaz mutants are shown in FIG. 1 with which to interrogate the biological consequences of chronic JAZ deficiency in *Arabidopsis*. The 13-member JAZ family in *Arabidopsis* is comprised of five phylogenetic groups (I-V) that are common to angiosperms (FIG. 1B). The jazQ mutant harbors mutations in the sole member (JAZ10) of group III, all three members of group V (JAZ3. JAZ4, JAZ9), and one member (JAZ1) of the largest group I clade. Building on the jazQ chassis, the inventors used genetic crosses to introduce five additional mutations that target the remaining group I members (JAZ2, JAZ5, JAZ6) and two genes (JAZ7 and JAZ13) within group IV (FIGS. 1B-1D). The resulting homozygous jaz1-jaz7, jaz9, jaz10, jaz13 decuple mutant, referred to hereafter as jazD, thus targets all JAZs except for JAZ8 and the two group II genes (JAZ11 and JAZ12).

Figure 2A:
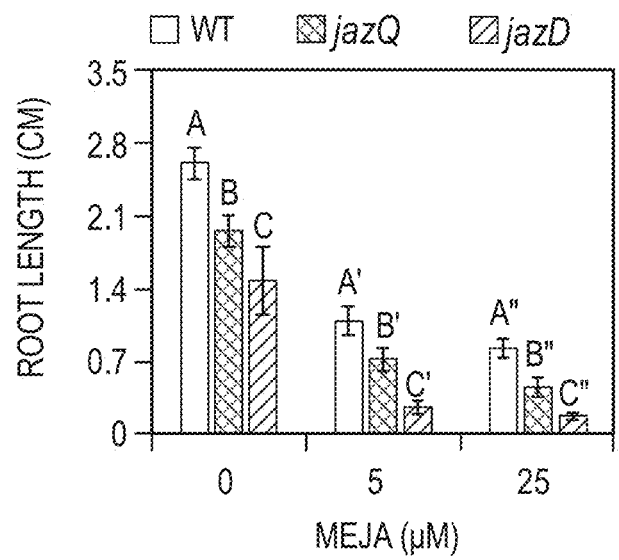
FIGS. 2A-2E illustrate that a jaz decuple mutant (jazD) is highly sensitive to jasmonate (e.g. methyljasmonate, MeJA) and exhibits reduced growth and fertility.
Figure 2B:
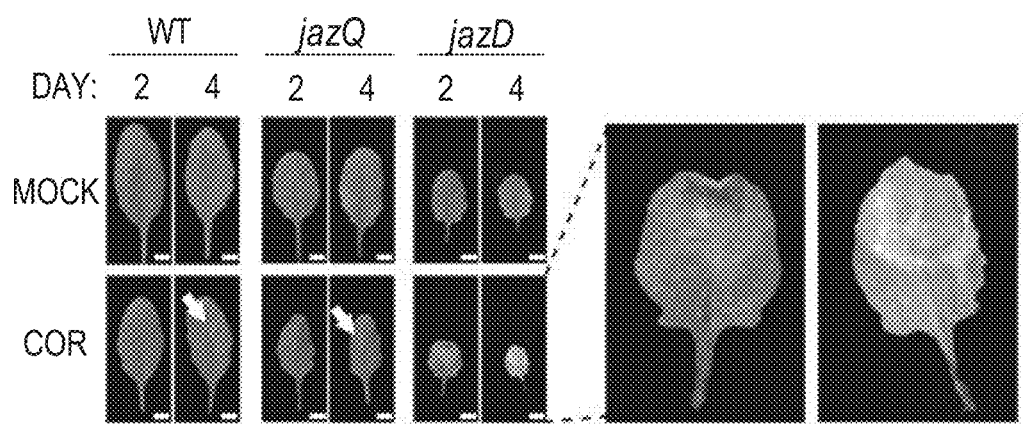

Cultivation of plants in the absence of exogenous jasmonic acid showed that, whereas jazQ roots and leaves grow more slowly than wild type (WT) Col-0, growth of jazD plants was even slower than jazQ (FIGS. 2A-2B). Soil-grown jazD plants displayed less leaf area and shorter petioles than jazQ, and also accumulated more anthocyanins (FIG. 2B). Leaf biomass measurements taken over a 20-day time course confirmed that the relative growth rate (RGR) of jazD rosettes during this developmental stage was significantly less than wild type (FIG. 2C).

The relative growth rate (RGR) of jazQ was comparable to wild type, despite the reduced biomass of jazQ rosettes at later times in development, which may reflect growth changes occurring before the first time point of sampling (11 days after sowing) or the lack of statistical power needed to resolve small differences in RGR that are compounded over time into larger differences in rosette size. Although bulk protein, lipid, and cell wall content of rosette leaves were similar between all three genotypes under the growth conditions employed, the ratio of leaf dry weight (DW) to fresh weight was increased in jazD relative to wild type and jazQ.

The restricted growth of jazD roots and leaves was associated with changes in flowering time under long-day growth conditions. The jazD plants were delayed in their time-to-flowering compared with jazQ but contained a comparable number of leaves at the time of bolting.

The response of jazQ and jazD mutants was next compared to exogenous jasmonic acid. Root growth assays showed that the extent of JAZ deficiency, where jazD has more than jazQ and JazQ has more than wild type, was inversely correlated with root length under a range of MeJA concentrations (FIG. 2A). The growth of jazD roots effectively arrested in the presence of 5 µM MeJA (FIG. 2A).

Shoot responsiveness to the hormone was assessed by treating intact leaves with coronatine (COR), which is a potent agonist of the JA-Ile receptor. Wild type and jazQ leaves exhibited visible accumulation of anthocyanin pigments at the site of COR application (i.e., midvein) within 4 days of the treatment, with no apparent signs of chlorosis (FIG. 2B). In contrast, jazD leaves exhibited visible chlorosis at the site of COR application within 2 days of treatment and, strikingly, near complete loss of chlorophyll and spreading of necrosis-like symptoms throughout the leaf 4 days after treatment, leading to tissue death (FIG. 2B).

These data indicate that progressive loss of JAZ genes in jazQ and jazD results in both quantitative (e.g., root growth inhibition) and qualitative (e.g., COR-induced tissue necrosis) differences in jasmonate responsiveness. These results also indicate that the hypersensitivity of jazD results, at least in part, from loss of JAZ-mediated negative-feedback control of JA responses.

Measurements of reproductive output showed that, whereas the total seed yield of jazQ was only marginally affected, seed production by jazD plummeted to about one-third of wild type levels (Table 6).

TABLE 6

Seed and fruit production in higher-order jaz mutants

| Genotype | Seed yield per plant[†] (mg) | Average seed mass[‡] (μg) | Silique length[§] (cm) | No. seed per silique[§] | No. silique per plant[§] |
|---|---|---|---|---|---|
| WT | 608.3 ± 103.8 | 21.6 ± 1.3 | 1.59 ± 0.07 | 63 ± 11 | 451 ± 77 |
| jazQ | 524.3 ± 98.5 | 17.3 ± 0.9* | 1.70 ± 0.06 | 58 ± 6 | 533 ± 100 |
| jazD | 192.7 ± 70.0* | 16.6 ± 0.7* | 1.45 ± 0.08* | 37 ± 4* | 329 ± 119* |

Data show the mean ± SD of at least 10 plants per genotype.
Asterisks denote significant difference compared with WT plants according to Tukey's HSD test (*P < 0.05).
[†]Seed yield was determined by collecting all seeds from individual WT Col-0 and jaz mutant plants.
[‡]Average seed mass was determined by weighing batches of 200 seeds.
[§]Fully elongated 7th, 9th, and 11th siliques were collected for measurements of silique traits. These traits were used to calculate the estimated number of siliques per plant.

The reduced fecundity of jazD resulted from a combination of decreased average mass per seed and lower total seed number per plant. Mutant plants produced fewer seeds per silique, and the size and number of siliques per plant were reduced as well (Table 4). The reduced size of jazD seeds correlated with a reduction in total fatty acid per seed (FIG. 2D). Analysis of seed fatty acid profiles showed that jazQ and jazD seeds contain less oleic acid (18:1) and more linoleic acid (18:2), indicating that alterations in fatty acid metabolism occur in these jaz mutants during seed development.

Figure 2E:
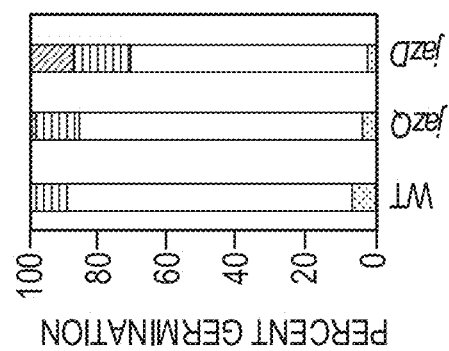
Figure 2D:
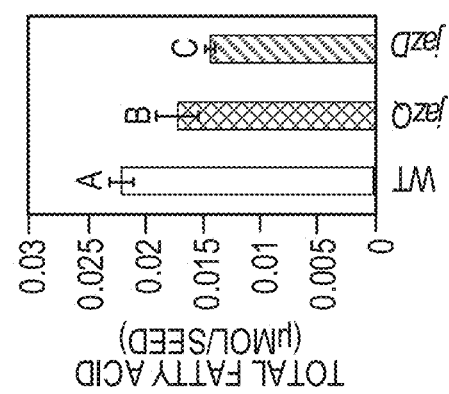
Figure 2C:
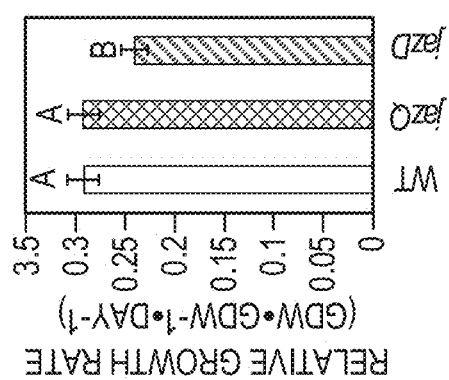

The effect of jazD on seed size and lipid abundance was associated with reduced rates of seed germination (FIG. 2E). These findings indicate that constitutive jasmonic acid responses resulting from JAZ depletion are associated with poor reproductive performance.

Example 3: Constitutive Activation of JA-Mediated and Ethylene-Mediated Defense Pathways in JazD Plants Having established the effects of jazQ and jazD on growth and reproduction, in this Example the inventors assessed how these mutations impact JA-mediated signaling pathways for defense.

Figure 3A:
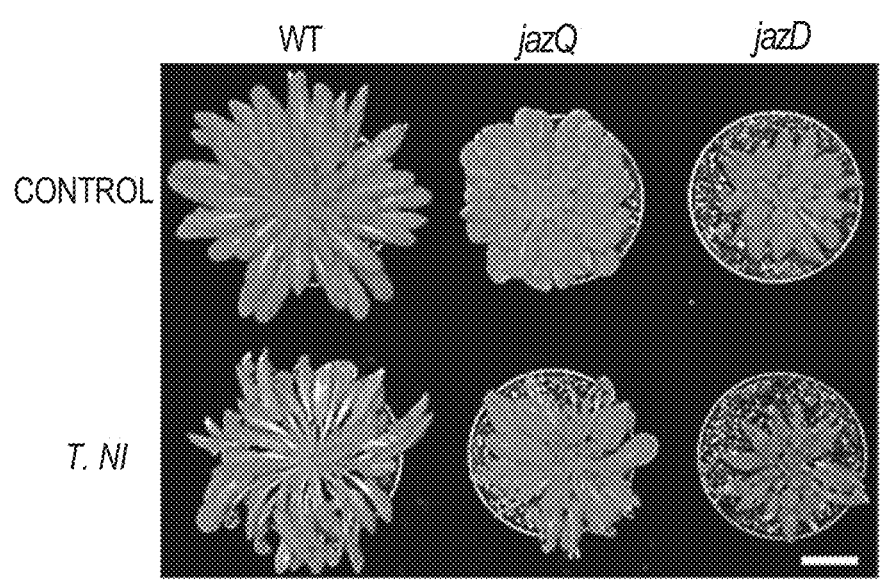

Short-day conditions were used to promote leaf biomass and delay flowering in plants used for insect bioassays. Under such short-day conditions jaz-mediated leaf growth restriction was observed (FIG. 3A). Insect bioassays were performed with the generalist herbivore *Trichoplusia ni*.

Figure 3C:
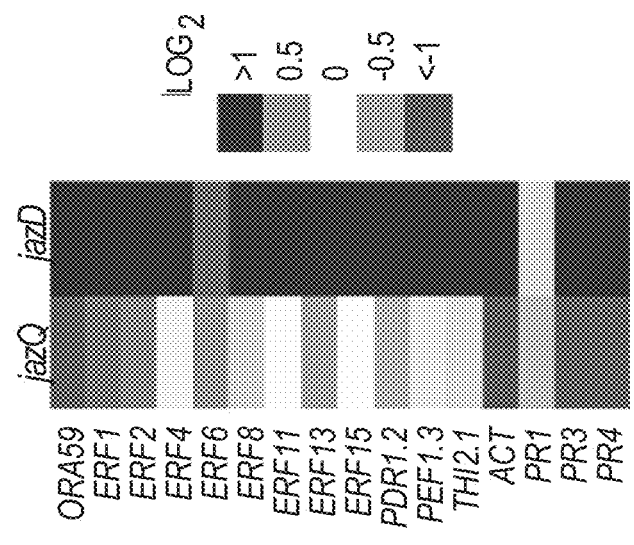
Figure 3B:
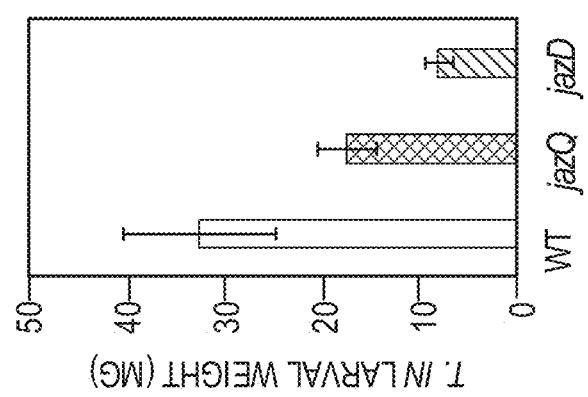

As shown in FIGS. 3A-3B, the strength of host resistance to insect feeding positively correlated with the severity of jaz mutation, where the insect resistance of jazD plants was greater than jazQ plants, and the insect resistance of jazQ plants was greater than that of wild type plants. These results are consistent with a role for JAZ proteins in the negative regulation of defense (FIGS. 3A-3B).

Messenger RNA sequencing (RNA-seq) was used to investigate the molecular basis of the enhanced anti-insect resistance. Global transcript profiles revealed that the total number of differentially expressed genes in jazD leaves (relative to wild type) was more than 10-fold greater than that in jazQ (2,107 for jazD and 186 for jazQ). Among the 186 genes whose expression was statistically different in the jazQ vs. wild type comparison, the majority (59%) of these were also differentially expressed in jazD. Gene Ontology (GO) analysis of 1,290 genes expressed to higher levels in jazD than WT showed that "response to JA/wounding," as well as "defense response," were among the biological processes most statistically over-represented in this comparison. These results, together with analysis of metabolic pathways that are differentially activated in jaz mutants (see below), indicate that the strength of anti-insect resistance correlates with the extent of JAZ deficiency and concomitant reprogramming of gene expression.

Analysis of the RNA-seq data also revealed that ethylene-response genes were highly expressed in jazD but not jazQ. For example, antifungal defense genes controlled by the synergistic action of JA and ethylene were modestly repressed in jazQ but induced in jazD (FIG. 3C). Among these were genes encoding the AP2/ERFs ERF1 and ORA59, which integrate JA and ethylene signals to promote the expression of antimicrobial compounds, including various defensins (PDFs), pathogenesis-related (PR) proteins, and hydroxycinnamic acid amides (HCAAs) (FIG. 3C). Strikingly, several PDF transcripts (e.g., PDF1.2) were among the most abundant of all mRNAs in jazD leaves, with expression levels comparable to that of the most highly expressed photosynthesis transcripts.

Figure 3D:
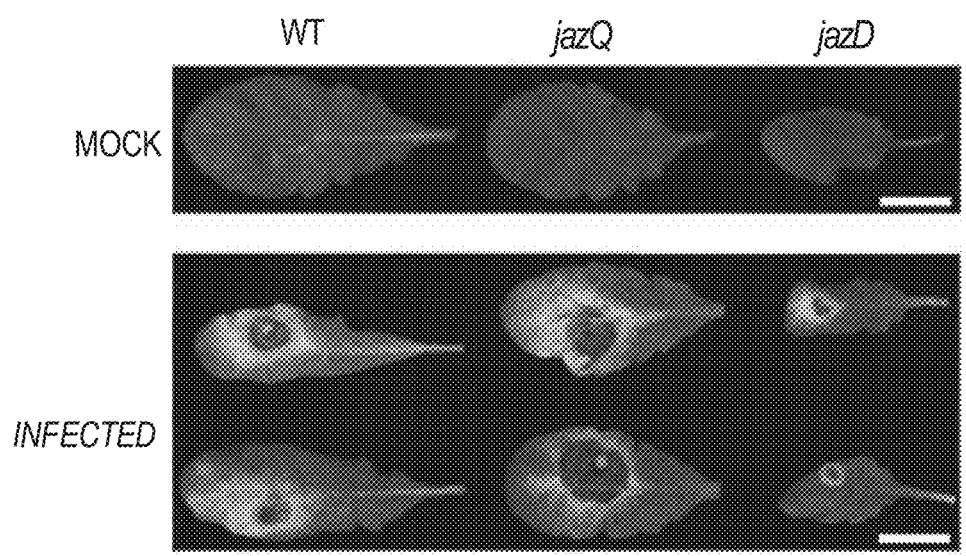

In agreement with the RNA-seq data, jazQ plants were slightly more susceptible than wild type to the necrotrophic pathogen *Botrytis cinerea*, whereas jazD leaves were more resistant to the spread of disease lesions (FIG. 3D-3D). To determine whether jazQ and jazD differentially affect other ethylene responses, the inventors assessed apical hook formation in ethylene-elicited seedlings. Consistent with studies showing that apical hook formation is attenuated by JA signaling (Song et al. Plant Cell 26:263-279 (2014)), FIG. 3F shows that stimulation of hook curvature in response to treatment with the ethylene precursor 1-aminocyclopropane-1-carboxylic acid (ACC) was reduced in jazD but not jazQ seedlings. These data indicate that whereas jazQ moderately activates JA responses and increases resistance to insect feeding, jazD strongly induces both the JA and ethylene branches of immunity to confer robust resistance to insect feeding and infection by *B. cinerea*.

To validate the RNA-seq results and gain additional insight how jazD promotes leaf defense, the inventors used quantitative tandem mass spectrometry to quantify global changes in protein abundance in jazD leaves vs. wild type leaves. Among a total of 4,850 unique proteins identified in both genotypes, 149 accumulated to higher in jazD leaves while 120 proteins accumulated to lower levels in jazD leaves (threshold fold-change>1.2, P<0.05). GO analysis of the 120 down-regulated proteins revealed enrichment of functional categories related to cytokinin response, cold response and various functional domains of photosynthesis (Table 5A-5b).

Table 7A-7 list biological processes in which proteins whose abundance in jaz leaves was increased or decreased in comparison to wild-type Col-0 based on gene ontology (GO) analysis. Enriched functional categories were determined with DAVID (version 6.8) using the hypergeometric test with Benjamini & Hochberg's false discovery rate (FDR) correction.

TABLE 7A

| Upregulated in jazD | | |
|---|---|---|
| GO ID | GO description | P value |
| 0009695 | jasmonic acid biosynthetic process | <0.0001 |
| 0055114 | oxidation-reduction process | <0.0001 |
| 0009611 | response to wounding | <0.0001 |
| 0009651 | response to salt stress | <0.0001 |
| 0009753 | response to jasmonic acid | <0.0001 |
| 0008652 | cellular amino acid biosynthetic process | <0.0001 |

TABLE 7A-continued

Upregulated in jazD

| GO ID | GO description | P value |
|---|---|---|
| 0000162 | tryptophan biosynthetic process | <0.0001 |
| 0050832 | defense response to fungus | <0.0001 |
| 0006952 | defense response | 0.0002 |
| 0019762 | glucosinolate catabolic process | 0.0010 |
| 0006564 | serine biosynthetic process | 0.0113 |
| 0080027 | response to herbivore | 0.0226 |
| 0009414 | response to water deprivation | 0.0336 |

TABLE 7B

Downregulated jazD

| GO ID | GO description | P value |
|---|---|---|
| 0009735 | response to cytokinin | <0.0001 |
| 0015979 | photosynthesis | <0.0001 |
| 0009409 | response to cold | <0.0001 |
| 0010207 | photosystem II assembly | 0.0001 |
| 0019684 | photosynthesis, light reaction | 0.0079 |
| 0042549 | photosystem II stabilization | 0.0239 |
| 0042742 | defense response to bacterium | 0.0257 |

Analysis of proteins that were more abundant in jazD showed there was good agreement with the corresponding mRNA levels determined by RNA-seq; transcripts encoding 78% of these 149 proteins were also induced in jazD plants. As expected, there was strong enrichment in this protein set of GO categories associated with response to JA, herbivore, and fungal attack, among other defense-related processes (Table 7A-7B). For example, the proteomic analysis revealed that jazD coordinately up-regulated the abundance of most JA biosynthetic enzymes, as well as canonical JA marker proteins, such as VSP1 and VSP2.

Leaves from jazD plants exhibited high expression levels of an agmatine coumaroyl transferase (At5g61160) and an associated transporter (At3g23550) involved in the production of antifungal HCAAs. Transcripts encoding the acyl-CoA N-acyltransferase NATA1 (At2g39030), which catalyzes the formation of the defense compound N($\delta$)-acetylornithine, were 50-fold higher in jazD leaves compared with leaves from wild type and jazQ plants. Such expression was accompanied by increased NATA1 protein abundance. Perhaps most striking was the up-regulation in jazD leaves, at both the mRNA and protein levels, of most known structural and enzymatic components of the endoplasmic reticulum (ER)-derived ER body, which is implicated in induced immunity (Nakano et al. Plant J 89: 204-220 (2017); Yamada et al. Plant Cell Physiol 52:2039-2049 (2011)). These findings establish a central role for JAZ proteins as negative regulators of diverse leaf defense traits.

Figures 4A, 4B:
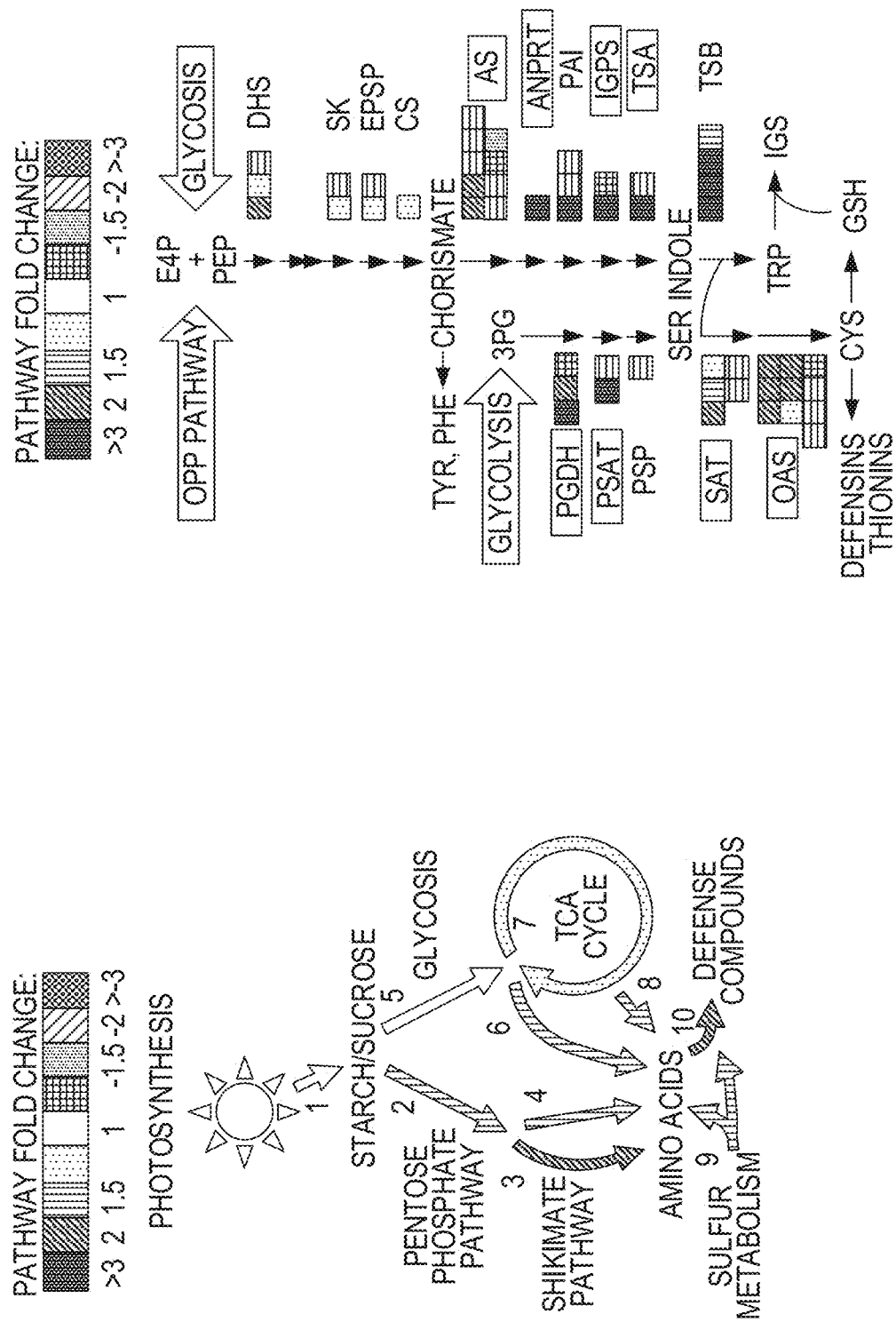
FIGS. 4A-4G illustrate reconfiguration of primary and secondary metabolism in jazD plants.

Example 4: Reprogramming of Primary and Specialized Metabolism in JazD Plants To investigate how the activation of multiple defense pathways influences primary metabolism, RNA-seq and proteomics data were used to infer metabolic pathways that are altered in jazD leaves. Mapping of differentially expressed genes to Kyoto Encyclopedia of Genes and Genomes pathway databases showed that the tricarboxylic acid (TCA) cycle, oxidative pentose phosphate pathway, sulfur assimilation and metabolism, and various amino acid biosynthetic pathways were among the processes most highly induced in jazD, whereas photosynthesis components were generally down-regulated (FIG. 4A).

One prominent example of a metabolic pathway that was upregulated in jazD was the shikimate pathway for the biosynthesis of aromatic amino acids. Trp biosynthetic enzymes involved in the production of indole glucosinolates (IGs) showed particularly high expression at the mRNA and protein levels (FIG. 4B). Consistent with this finding, genes encoding enzymes in the phosphoserine pathway that supplies Ser for the biosynthesis of Trp and Cys were highly up-regulated in jazD, as was the abundance of the corresponding enzymes as determined from proteomics data (FIG. 4B).

Figure 4C:
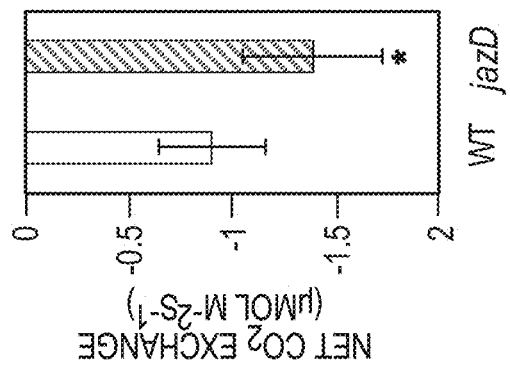

LC-MS analysis of leaf extracts showed that several indole glucosinolates accumulate to high levels in jazD (FIG. 4C), thereby validating the omics data. The inventors also found that pathways involved in sulfur assimilation and cysteine biosynthesis, as well as ascorbate and glutathione metabolic pathways that protect against oxidative stress, were strongly up-regulated in jazD (FIG. 4B). These data indicate that genetic depletion of JAZ proteins recapitulates the transcriptional effects of exogenous JA and demonstrate that JAZ proteins exert control over pathways that operate at the interface of primary and specialized metabolism.

Figure 4D:
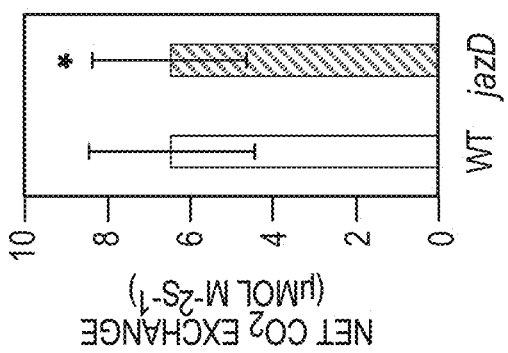
Figure 4E:
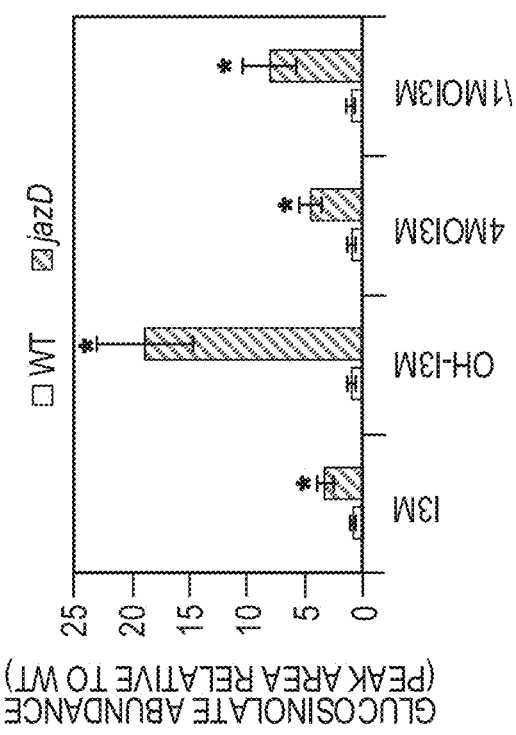
Figure 4F:
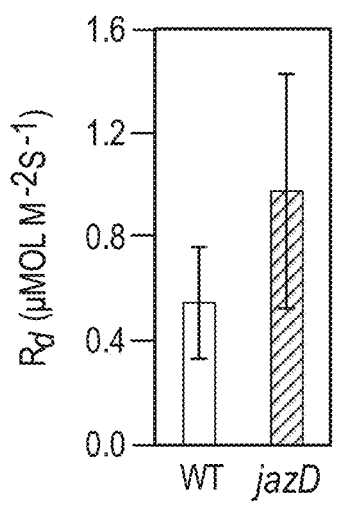
Figure 4G:
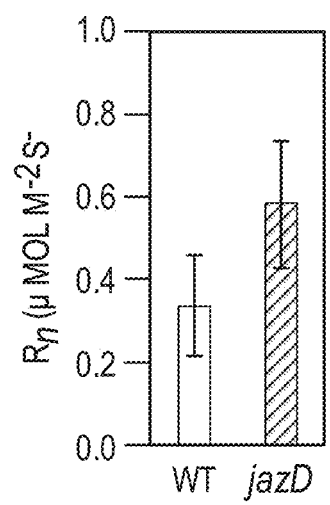

The inventors then addressed the question of whether jazD modulates net carbon assimilation. Despite the down-regulation of photosynthetic mRNAs and proteins in jazD, modeling of photosynthetic parameters derived from gas-exchange data indicated that the leaf area-based photosynthetic rate of jazD plants was comparable to wild type (FIG. 4D). This finding was confirmed by $^3$C isotope discrimination measurements, which showed that the degree of $CO_2$ resistance through mesophyll cells was similar in WT, jazQ, and jazD leaves. In contrast to photosynthesis, the net loss of $CO_2$ from jazD leaves in the dark exceeded that of wild type by about 50% (FIG. 4E). Increased cellular respiration in jazD was confirmed by experiments showing that the mutant had increased respiration in both the day and night portions of the photoperiod (FIGS. 4F-4G). These findings indicate that increased cellular respiration is associated with high-level production of defense compounds.

GO analysis of the 817 down-regulated genes in jazD leaves showed enrichment for growth-related processes, including "response to light stimulus," "cell wall organization," "response to abiotic stimulus," "carbohydrate biosynthetic process," and "lipid biosynthetic process."

Example 4: JazD Plants Exhibit Symptoms of Carbon Starvation

Increased respiration and partitioning of carbon to metabolic defense pathways, in the absence of compensatory changes in photosynthesis, raised the possibility that jazD plants have a carbon deficit.

Figure 5B:
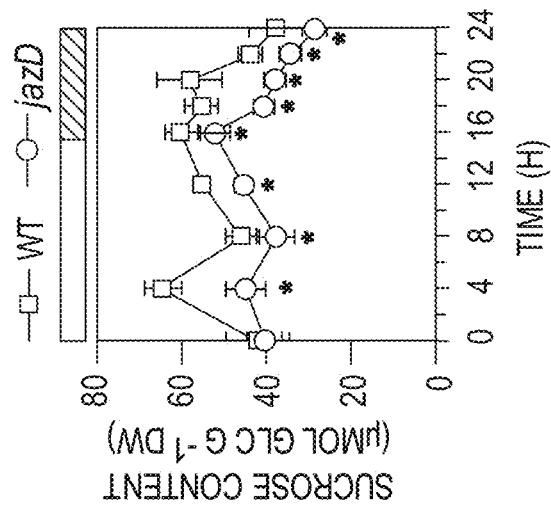
FIGS. 5A-5F illustrate that jazD plants exhibit symptoms of carbon starvation.
Figure 5A:
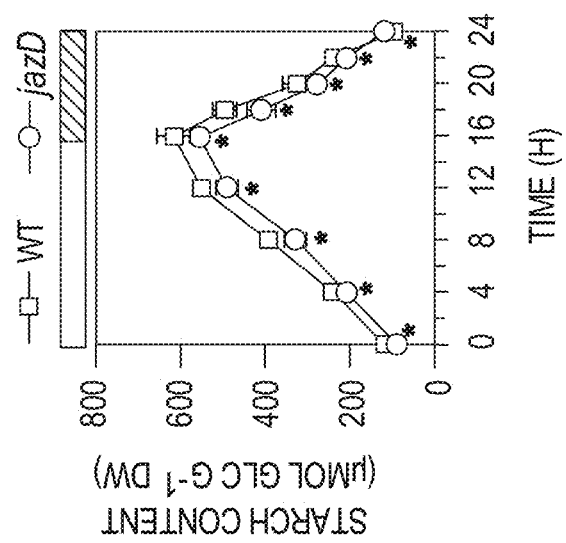

Time-course studies showed that the rates of starch accumulation (wild type: 0.103 μmol Glc g$^{-1}$ dry weight h$^{-1}$; jazD: 0.113 μmol Glc g$^{-1}$ dry weight h$^{-1}$) and degradation (WT: −0.220 g dry weight h$^{-1}$; jazD: −0.186 smol Glc g$^{-1}$ dry weight h$^{-1}$) were comparable between wild type and jazD (FIG. 5A). However, starch levels in jazD leaves were slightly lower than wild type at all times of the diel cycle except at the end of the night, when starch was mostly depleted but modestly elevated in jazD relative to wild type, jazD leaves also had consistently lower sucrose levels (FIG. 5B). The inventors also found that genes involved in starch and sucrose metabolism were generally down-regulated in jazD, including the mRNA and protein abundance of the plastidic starch biosynthetic enzyme phosphoglucomutase (PGM1, At5g51820).

Figures 5C, 5D:
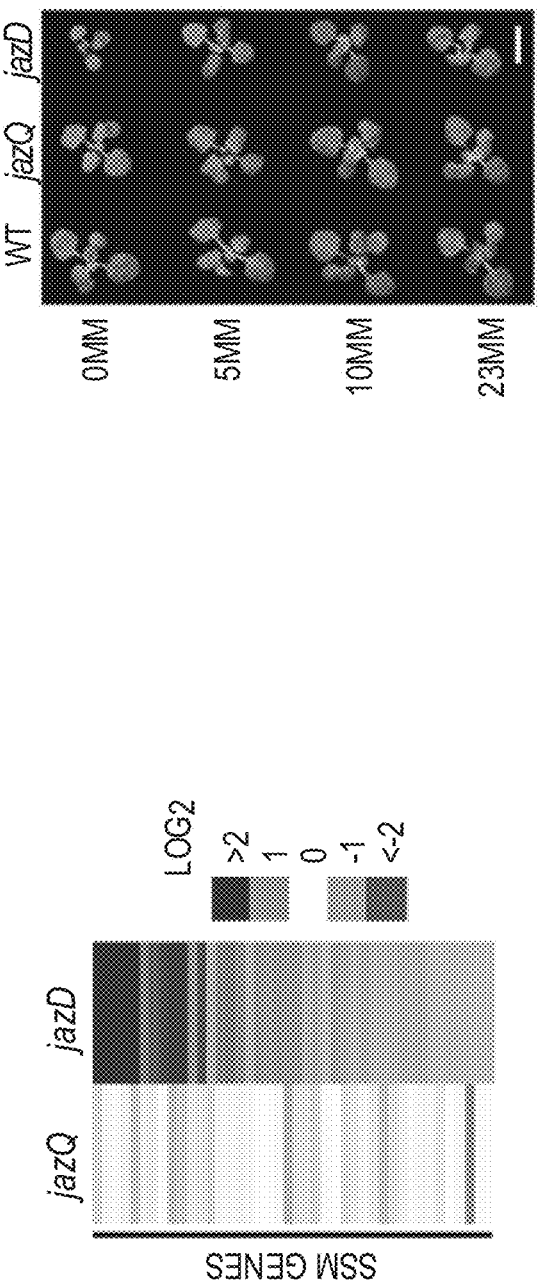

To test whether these changes in central metabolism are associated with carbon deficit, the RNA-seq data was used to query the expression of genes that are induced by conditions (e.g., prolonged darkness) leading to carbon starvation. The inventors found that 42 of 278 (15%) sugar starvation marker (SSM) genes defined by Baena-González et al. (Nature 448:938-942 (2007)), including several DARK INDUCIBLE (DIN) genes that respond to reduced energy status, were expressed to much higher levels in jazD than WT and jazQ (FIG. 5C).

The inventors also examined the expression of EIN3-regulated glutamate dehydrogenases (GDH) that replenish 2-oxoglutarate for the TCA cycle and are considered metabolic markers of carbon deficiency. Both the transcript and protein abundance of GDH1 (At5g18170) and GDH2 (At5g07440) were statistically increased in jazD in comparison with WT, consistent with a carbon deficit in this mutant.

Figures 5E, 5F:
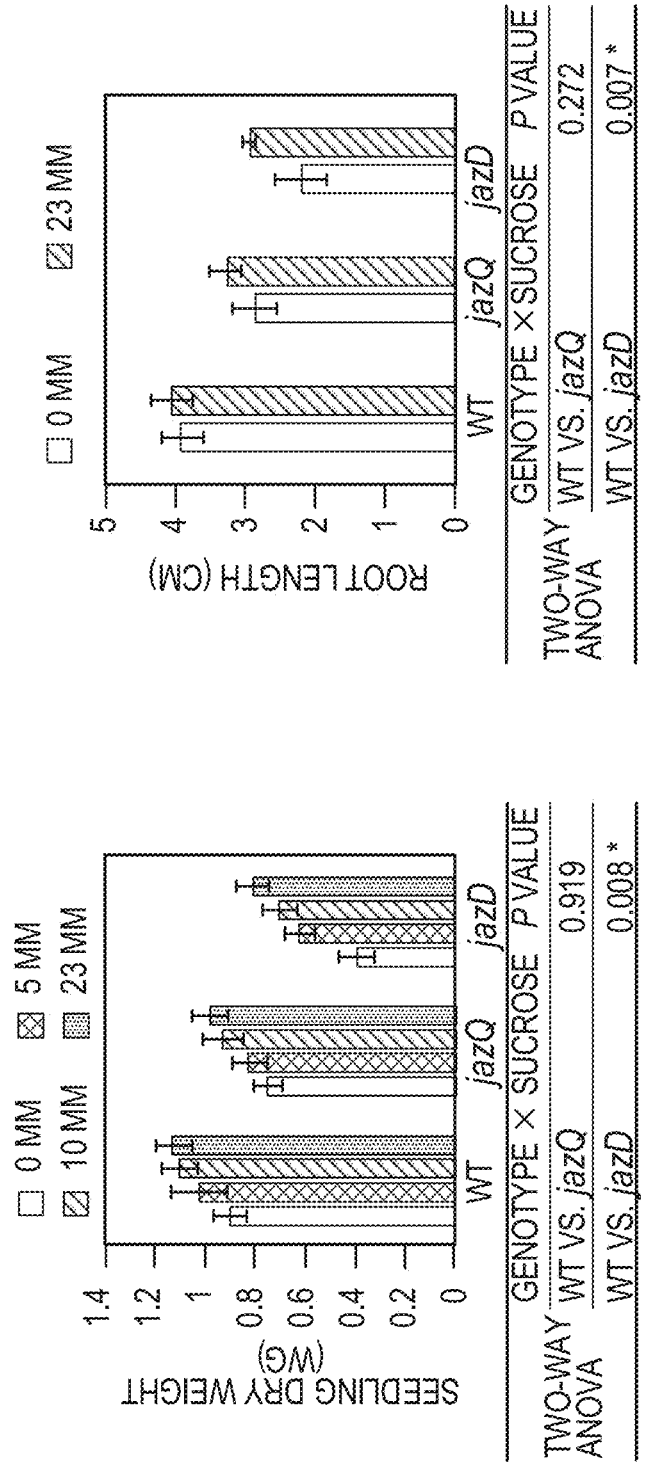

To test the hypothesis that carbon limitation contributes to the slow growth of jaz mutants, the inventors compared the growth of WT, jazQ, and jazD seedlings on agar medium supplemented with sucrose. FIG. 5D-5E show that although exogenous sucrose promotes increased biomass in all genotypes tested, the stimulatory effect on the growth of jazD shoots was statistically greater than that of wild type and jazQ. Exogenous sucrose also enhanced the root growth of jazD in comparison with wild type and jazQ (FIG. 5F). Control experiments with sorbitol showed that the growth-promoting effect of sucrose was not attributed to changes in osmotic strength of the growth medium. These data provide evidence that the reduced growth of jazD but not jazQ results in part from a limitation in carbon supply.

Example 5: A Jaz1-Jaz10 and Jaz13 Undecuple Mutant Produces Few Viable Seeds

The ability of jazD plants to perceive and respond to exogenous jasmonate (JA) suggested that the remaining JAZ proteins in the mutant can actively repress JA-responsive genes. The inventors hypothesized that mutation of these remaining JAZ loci (i.e., JAZ8, JAZ11, and JAZ12) in the jazD background may further enhance the level of growth-defense antagonism. To test this, the inventors focused on JAZ8 because of its established role in repressing JA responses and the availability of a naturally occurring jaz8-null allele (Thireault et al. Plant J 82:669-679 (2015)). The increased expression of JAZ8 in jazD leaves (>15-fold relative to WT) was also consistent with a role in negative-feedback control of JA responses.

Figure 6A:
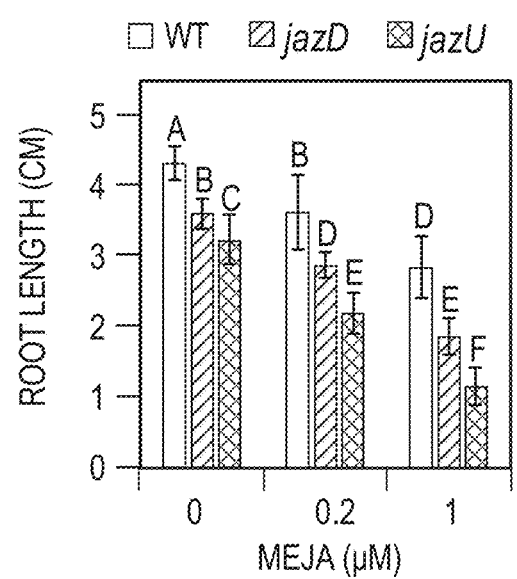
FIGS. 6A-6C illustrate that genetic combination of jaz8 and jazD mutations reduces root lengths and nearly abolishes seed production in the resulting undecuple mutant. The jazD mutations eliminate transcription from Jaz1, Jaz2, Jaz3, Jaz4. Jaz5, Jaz6, Jaz7, Jaz9, Jaz10 and Jaz13 genes, while the jaz undecuple (jazU) mutations are homozygous for mutations in Jaz-Jaz10 and Jaz13. Hence, the jazU plant line has a mutant jaz8 gene whereas the jazD plant line has a wild type Jaz8 gene.
Figures 6B, 6C:
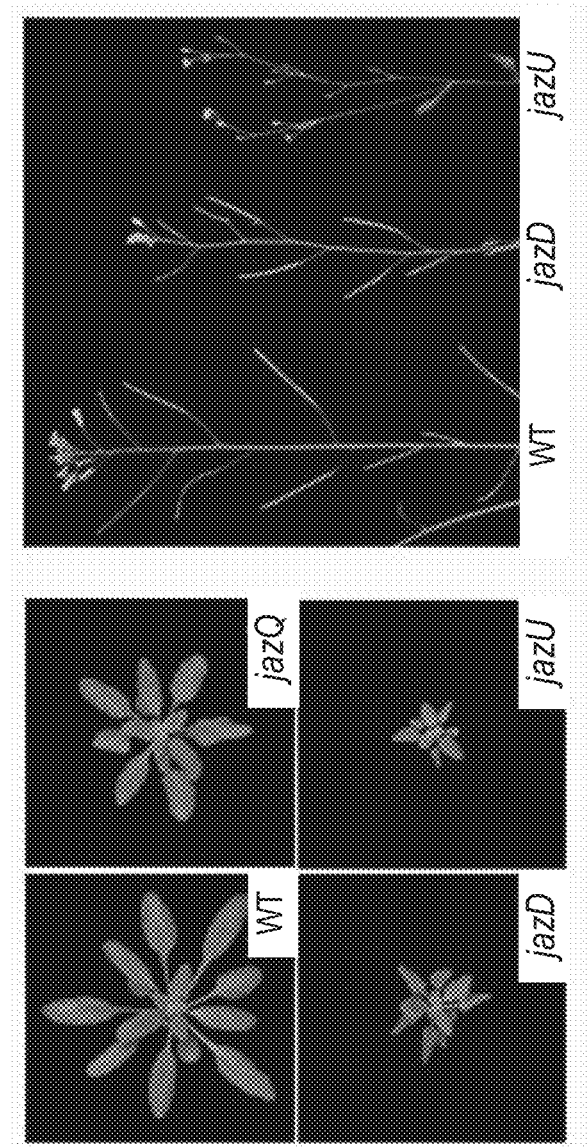

Screening of progeny derived from genetic crosses between jazD and jaz8 resulted in the identification of an undecuple mutant (jazU) homozygous for mutations in JAZ1-JAZ10 and JAZ13. Root growth assays showed that jazU roots were even shorter than jazD in the presence of very low concentrations (e.g., 1 µM) of MeJA (FIG. 7A). When grown on JA-free medium, jazU showed an even stronger constitutive short-root phenotype than jazD (FIG. 6A). Similarly, the rosette morphology of jazU confirmed the progressive effect of JAZ depletion on restriction of rosette growth, including reduced biomass, leaf area, and petiole length (FIG. 6B). Most strikingly, jazU plants exhibited near complete loss of viable seed production (FIG. 6C). Less than 3% of jazU flowers set fruit; although jazU pollen was viable in crosses, among flowers that produced fruit, most senesced and aborted during silique filling. Among the few jazU flowers that did produce seeds, seed set per silique was severely reduced, with recovery of only a few viable seeds per plant. The collective seed-yield phenotype of jazQ, jazD, and jazU supports a key role for JAZ proteins in promoting reproductive vigor.

Example 6: CDK8 Mutation Restores Growth and Seed Yields of Jaz8 Plants

This Example illustrates that cdk8 loss-of-function mutations improve the growth and seed yields of jazD plants.

The inventors used jazD in a genetic suppressor screen to identify 11 independent sjd (suppressor of jazD) mutants in which rosette growth was partially restored while maintaining enhanced production of defense compounds.

Genome sequencing revealed that one suppressor line (sjd56) carries a null mutation in CYLIN-DEPENDENT KINASE 8 (CDK8, also known as CDKE1 and At5G63610)), which encodes a component of the Mediator complex.

Figure 7C:
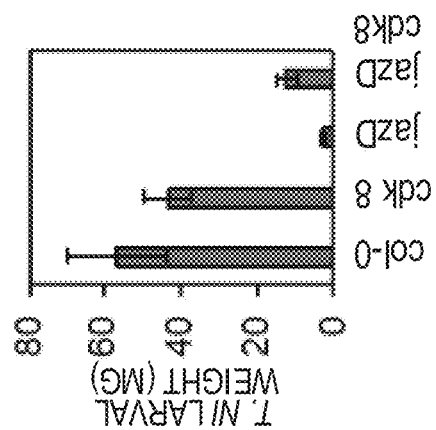
FIGS. 7A-7C illustrate that loss of function of cdk8 restores growth and reproductive output when included in a jazD genetic background while the jazD cdk8 plants maintain anti-insect defenses.
Figure 7B:
Figure 7A:
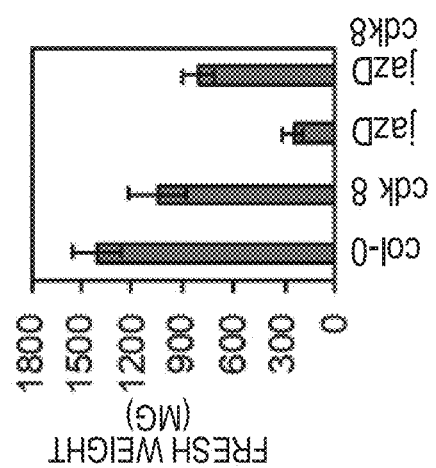

The cdk8 mutation not only partially restores vegetative growth but also fully recovers the low seed yield of jazD, while maintaining robust defense against insect herbivores (FIGS. 7A-7C).

Fifteen sjd56-like F2 plants were generated from a cross between sjd56 and jazD parental lines. Sanger sequencing was performed on the genomes of the F2 progeny, demonstrating that each of the fifteen sjd56-like F2 plants had the C1684T mutation, shown in the nucleic acid segment provided below (SEQ ID NO:121).

```
CCTTCCACAC TGGCAAAATG ATGTTCAACA CATTCAAGCT

CACAAATACG ACAGTGTGGG TCTC
```

The sjd56 C1684T mutation truncates the CDK8 protein by altering a glutamine residue to a stop a codon.

To generate additional jazD plant lines that include the sjd56 CDK8 mutation, jazD (jaz1-SM, jaz2-RK, jaz3-GK, jaz4-1, jaz5-1, jaz6-DT, jaz7-1, jaz9-4, jaz0-1, jaz13-1) plants were crossed with T-DNA insertion CDK8 mutant lines, cdk8-1 or cdk8-2. The progeny of this screen were screened by PCR-genotyping using primer sets flanking DNA insertion sites and a third primer flanking the T-DNA border.

Example 7: Null CDK8 Mutant Exhibits Increased Growth and Similar Defenses as JazD This Example illustrates that jazD plants with a null CDK8 mutation (e.g., sjd56 plants) exhibit increased growth and improved resistance to insects compared to jazD and wild type plants.

Wild type Col-0 (WT), jazD and sjd56 plants were grown under different conditions.

In one experiment, the different plant types were grown under short-day (8-h-light/16-h-dark) conditions, and at 58 days of growth, the rosette fresh weight and projected leaf area of the different plant types was measured.

As shown in FIGS. 8A-8B, the sjd56 plants exhibit greater rosette fresh weight and greater projected leaf area than the jazD plants, but somewhat less rosette fresh weight and less projected leaf area than wild type plants.

In another experiment, wild type Col-0 (WT), jazD and sjd56 plants were grown under long-day (16-h-light/8-h- dark) conditions, and at 23 days of growth anthocyanin levels were measured in the leaves of the different plant types.

Figure 8C:
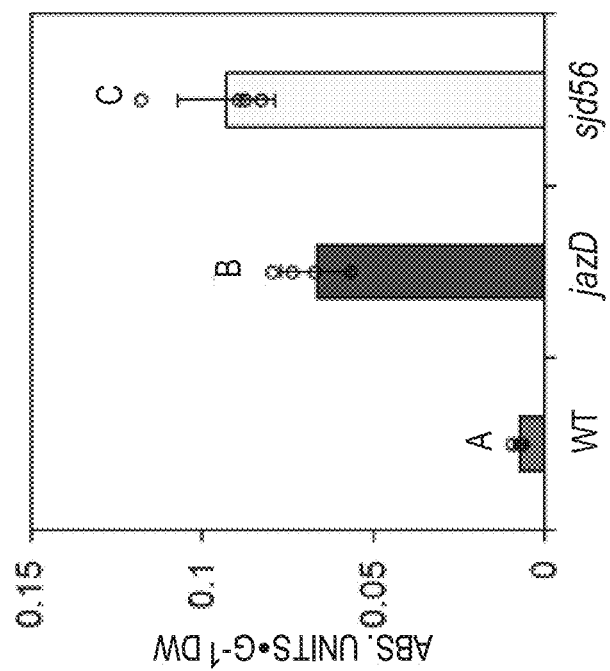

FIG. 8C shows that the anthocyanin levels in leaves of sjd56 plants are significantly greater than in leaves of wild type Col-0 (WT) and jazD plants.

In a third experiment, wild type Col-0 (WT), jazD and sjd56 plants were grown under photoperiods of 16-h-light/8-h-dark for 67 days, and *Trichoplusia ni* (*T. ni*) were allowed to feed on the plants during the last ten days of growth.

Figure 8D:
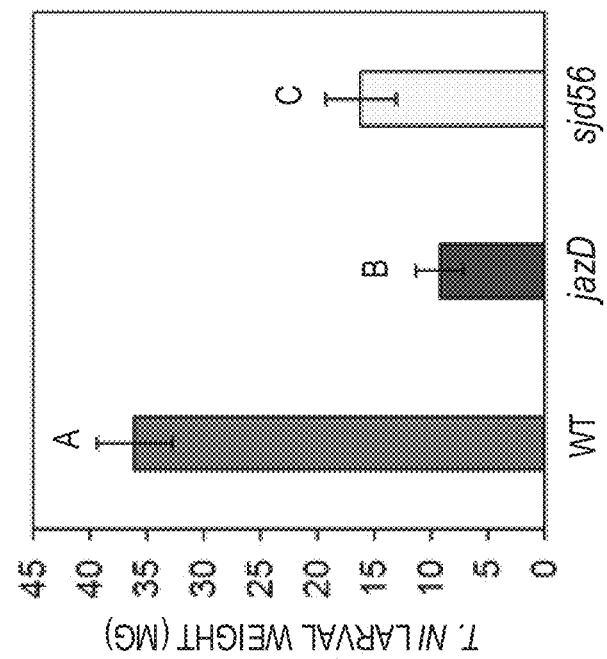

FIG. 8D shows the weight of *Trichoplusia ni* (*T. ni*) after feeding for ten days. As illustrated, substantially more *Trichoplusia ni* (*T. ni*) were present on wild type Col-0 (WT) and even on jazD plants than on the sjd56 plants.

Example 8: Cdk8 Mutations Restore Growth and Reproduction while Delaying Vegetative and Reproductive Transitions of 1azD This Example illustrates that combining cdk8 null mutations overcomes the reduced growth observed in plants with the jazD genetic background.

The growth flowering and seed production of plants with jazD cdk8-1 and jazD cdk8-2 genotypes (generated as described in Example 6) were evaluated.

Figure 9A:
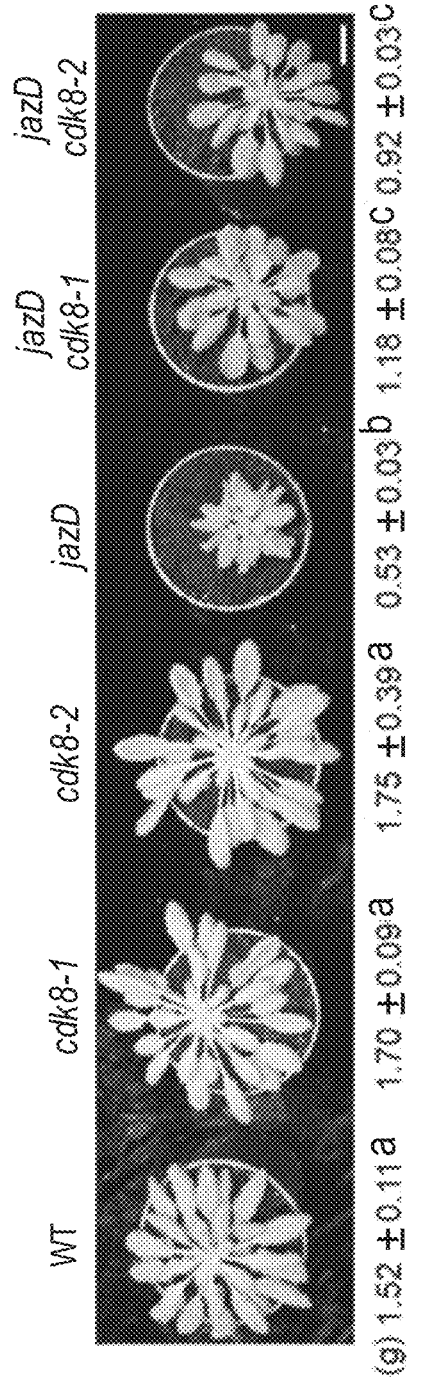
FIGS. 9A-9H illustrate that cdk8 mutations largely restore the growth and reproduction while delaying vegetative and reproductive transitions of jazD.
Figure 9C:
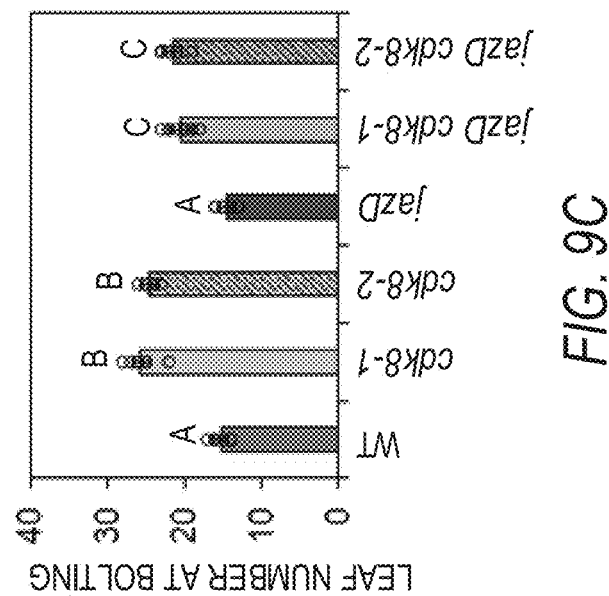
Figure 9B:
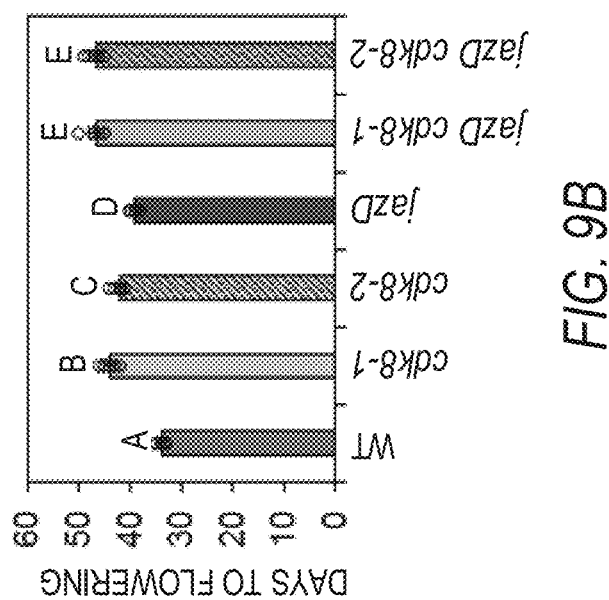

Col-0 (WT), cdk8-1, cdk8-2, jazD, jazD cdk8-1 and jazD cdk8-2 plants were grown under short-day conditions (8-h-light/16-h-dark) for 58 days, and the rosette fresh weights and leaf diameters were then measured. As illustrated in FIGS. 9A and 9G, the rosette fresh weights of jazD cdk8-1 and jazD cdk8-2 plants after 58 days of growth were significantly greater than the rosette fresh weights of jazD plants, approaching the rosette fresh weights of wild type plants. FIG. 9F graphically illustrates that loss of cdk8 increases leaf diameter in jazD plants.

In another experiment, plants were grown under long-day (16-h-light/8-h-dark) conditions in soil. The number of days to flowering and the bolting leaf numbers were then measured. FIG. 9B graphically illustrates that as compared to wild type or jazD plants, the time until the first flowers appear was slightly longer for plants with cdk8 null mutations, including the jazD cdk8-1 and jazD cdk8-2 plants. FIG. 9C shows the number of rosette leaves at the time of bolting is greater for cdk8-1, cdk8-2, jazD cdk8-1 and jazD cdk8-2 plants compared to wild type and jazD plants.

Seed yield and seed mass of WT, cdk8-1, cdk8-2, jazD, jazD cdk8-1 and jazD cdk8-2 plants were also measured. Seed numbers were evaluated by collecting all seeds from individual plants. Average seed mass was determined by weighing batches of 100 seeds.

Figure 9E:
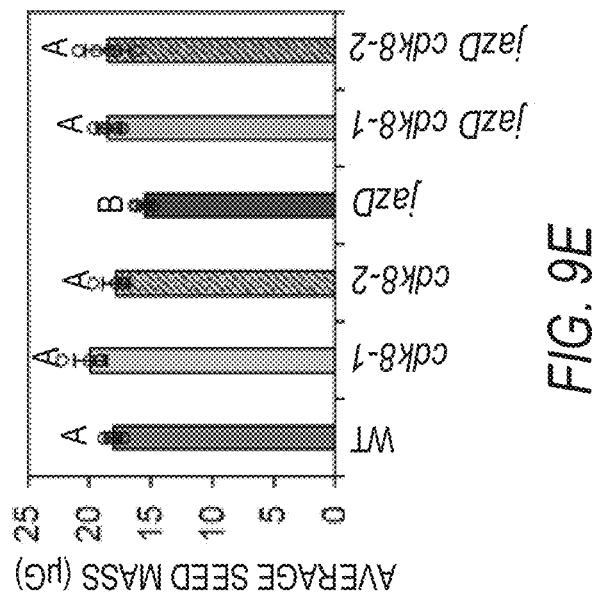
Figure 9D:
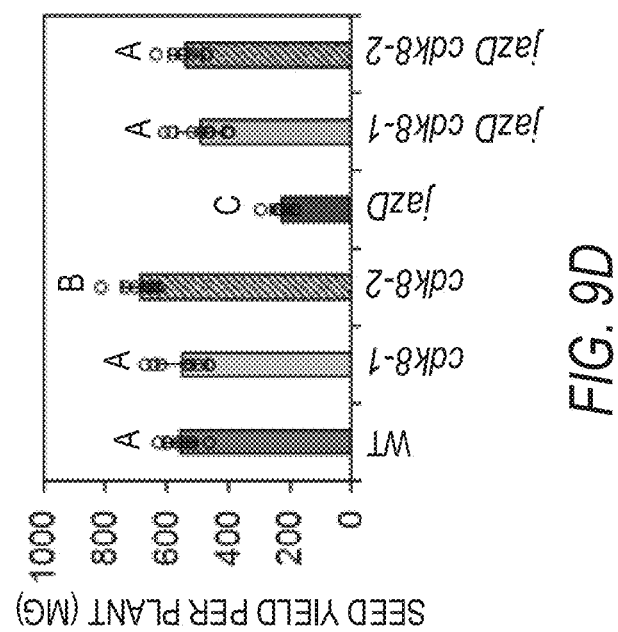
Figure 9G:
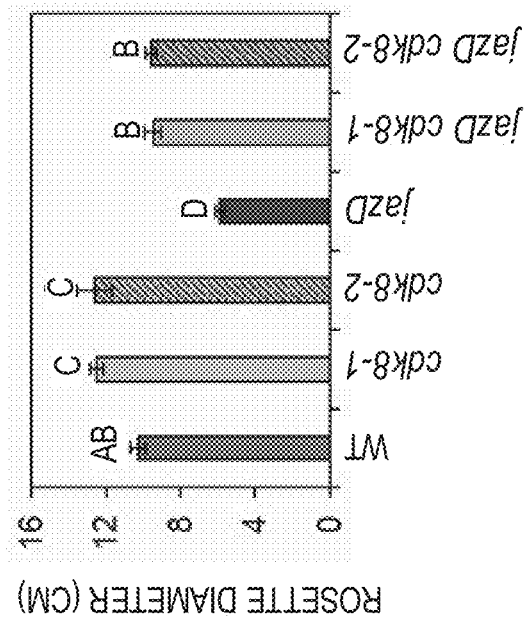
Figure 9F:
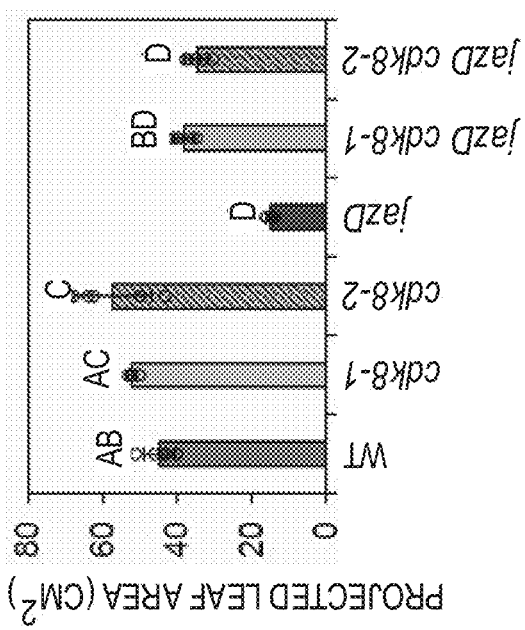

As shown in FIG. 9D-9E, seed yield and seed mass for plants with cdk8 null mutations, including the jazD cdk8-1 and jazD cdk8-2 plants was greater than determined for jazD plants, and was similar to that observed for wild type plants.

Figure 9H:
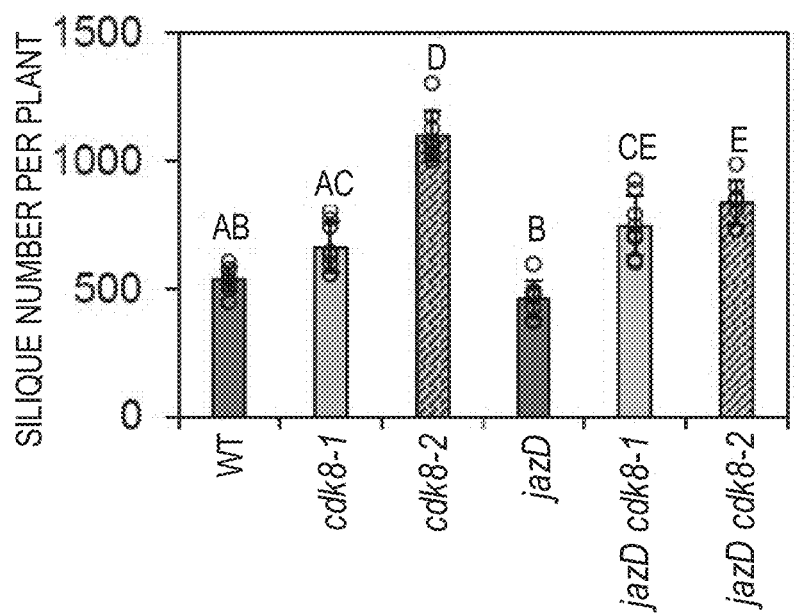

Further studies indicate that although silique length and seeds per silique are about the same for jazD and jazD plants with null cdk8 mutations, the number of siliques per plant is greater for jazD cdk8-1 and jazD cdk8-2 plants than in wild type and jazD plants (FIG. 9H). Hence, loss of cdk8 can positively impact the reproduction of jazD plants.

Example 9: Cdk8 Mutations Partially Recover the Defense Phenotypes of JazD

This Example illustrates the pest resistance provided by combining cdk8 null alleles into jazD plants.

Figure 10A:
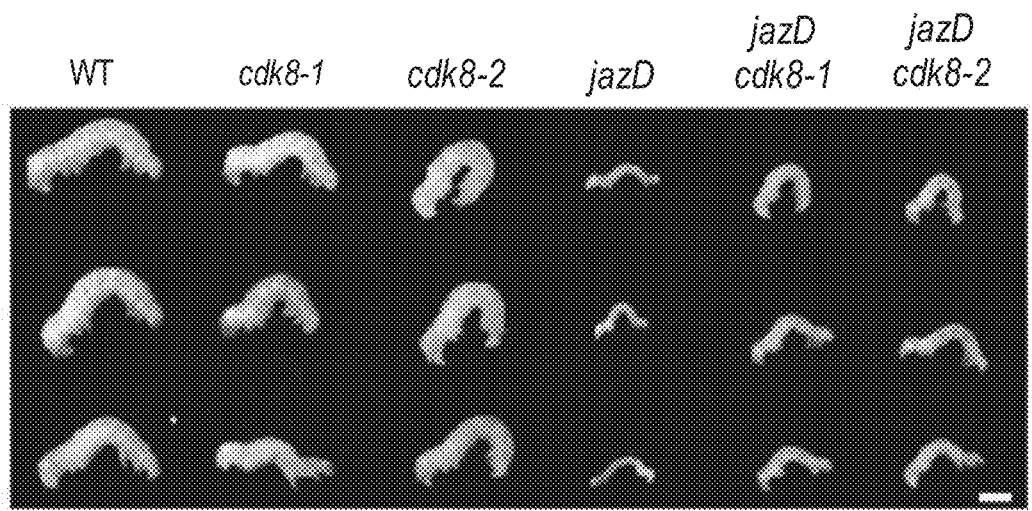
FIGS. 10A-10B shows that cdk8 mutations partially recover the defense phenotypes of jazD.
Figure 10B:
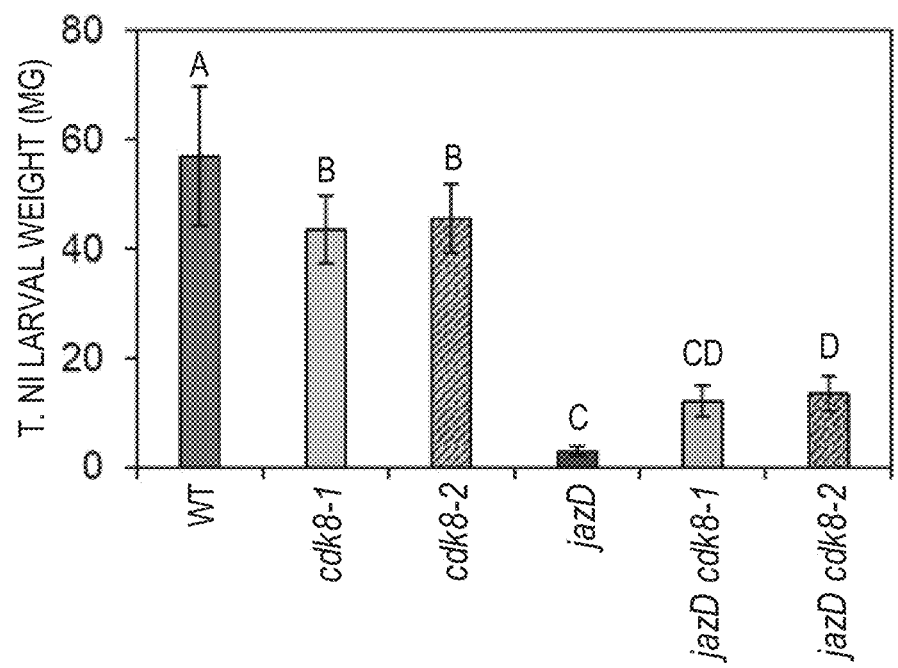

*Trichoplusia ni* (*T. ni*) larvae were allowed to feed on short-day-grown (8-h-light/16-h-dark) WT Col-0 (WT), cdk8-1, cdk8-2, jazD, jazD cdk8-1 and jazD cdk8-2 plants for nine days. FIG. 10A provides images of larvae isolated from the different plant types. As illustrated, larval sizes are significantly smaller when maintained on jazD, jazD cdk8-1 and jazD cdk8-2 plants than larvae maintained on wild type plants. FIG. OB graphically illustrates the weights of larvae isolated from the different plant types. The data show the mean±SD of at least 18 larvae per genotype. As shown in FIG. 10B, larval weights are significantly less when the larvae feed on jazD, jazD cdk8-1 and jazD cdk8-2 plants.

Example 10: The Increased Production of Defense Compounds in JazD is Partially Regulated by CDK8

This Example illustrates production of various plant defense compounds by jazD and jazD cdk8 plants.

Col-0 (WT), cdk8-1, jazD, and jazD cdk8-1 plants were grown under long-day conditions (16-h-light/8-h-dark) in soil. Defense compounds were extracted from leaves of 23-day-old plants grown under long-day conditions (16-h-light/8-h-dark).

Figure 11B:
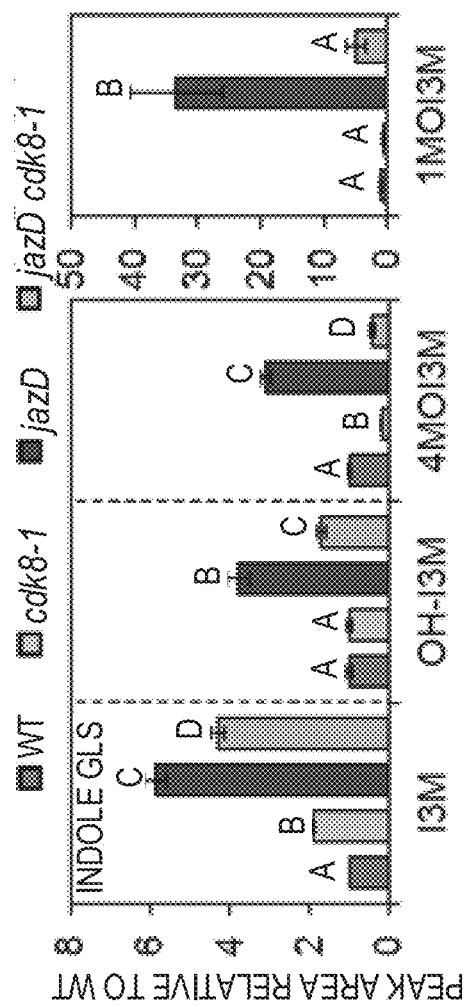
FIGS. 11A-11F illustrate that the increased production of defense compounds in jazD plants is partially regulated by CDK8.
Figure 11A:
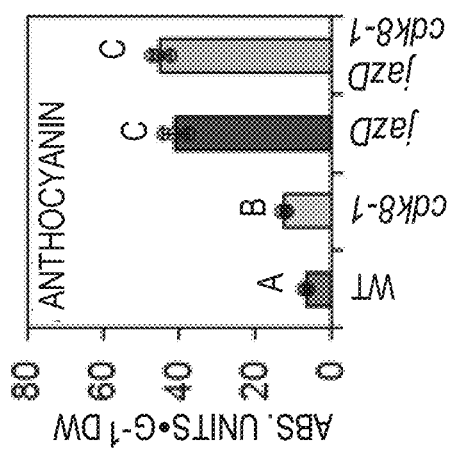
Figure 11D:
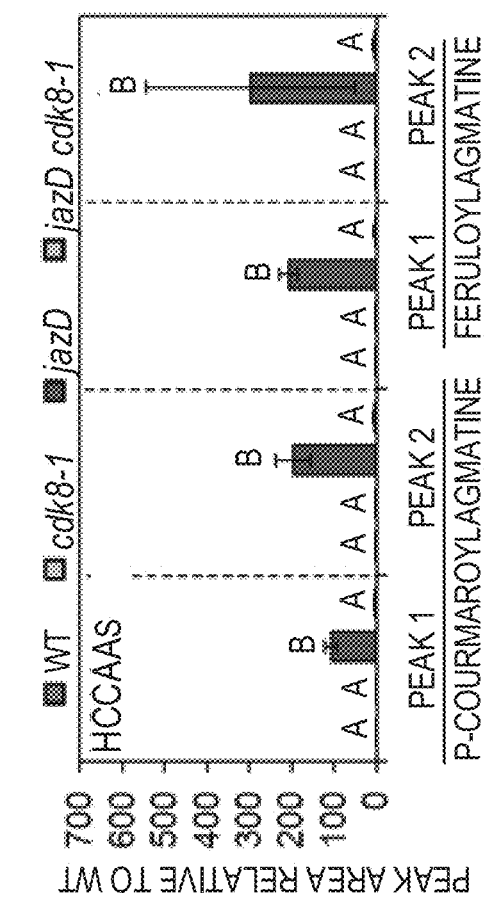
Figure 11C:
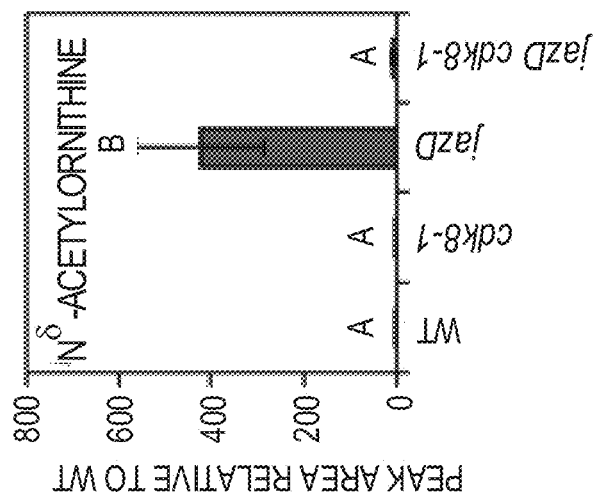
Figure 11F:
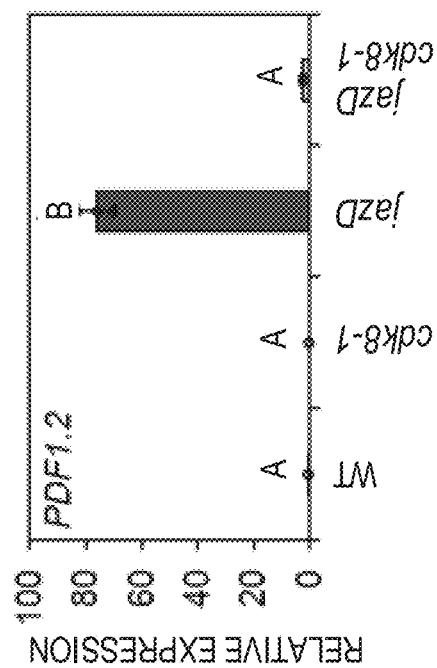

FIG. 11A graphically illustrates anthocyanin levels in leaves of 25-day-old wild type Col-0 (WT), cdk8, jazD and jazD cdk8 plants. FIG. 11B-11D graphically illustrate indole glucosinolates. Nδ-acetylornithine, and hydroxycinnamic acid amides (HCAAs) levels in WT, cdk8, jazD and jazD cdk8 leaves. Comparison of Peak area for the indicated compound in the WT sample was set to "1" and the peak area of the same compound in other genotypes was normalized to the WT sample. Abbreviations: I3M: indol-3-ylmethyl, glucobrassicin; OH-13M: 4-hydroxyindol-3-ylmethyl, hydroxyglucobrassicin; 4MOI3M: 4-methoxyindol-3-ylmethyl, methoxyglucobrassicin; 1MOI3M: 1-methoxyindol-3-ylmethyl, neoglucobrassicin. Data show the mean±SD of three biological replicates per genotype. Letters denote significant differences according to Tukey's HSD test (P<0.05).

In a second experiment. Col-0 (WT), cdk8-1, jazD, and jazD cdk8-1 plants were grown under long-day conditions (16-h-light/8-h-dark) in soil and leaves of 25-day-old were collected for quantitative PCR analysis.

Figure 11E:
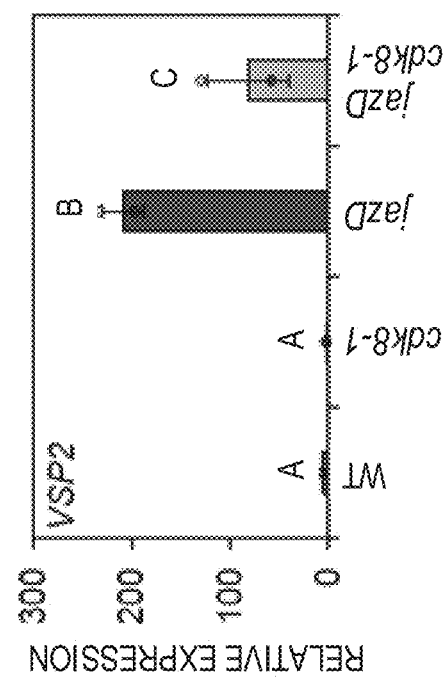

FIG. 11E graphically illustrates relative expression levels of VEGETATIVE STORAGE PROTEIN 2 (VSP2, AT5G24770) while FIG. 1F graphically illustrates relative expression levels of PLANT DEFENSIN 1.2 (PDF1.2, AT5G44420). PP2A (AT1g13320) was used for qPCR normalization. Data show the mean SD of three biological replicates per genotype. Letters denote significant differences according to Tukey's HSD test (P<0.05).

Example 11: Cdk8 Mutations Promotes Production of Aliphatic Glucosinolates in 1azD This Example illustrates some of the compounds generated by leaves of plants of various genotypes, including the from leaves of Col-0, cdk8, jazD and jazD cdk8 plants.

Aliphatic glucosinolates were extracted from leaves of 23-day-old plants grown under long-day conditions (16-h-light/8-h-dark). Peak area for the compound in the wild type (WT) sample was set to "1" and the peak area of the same compound in other genotypes was normalized to the WT sample.

FIG. 12 graphically illustrates aliphatic glucosinolate levels in WT, cdk8, jazD and jazD cdk8 leaves. The compounds detected included:

3MSOP: 3-methylsulphinylpropyl glucosinolate, glucoiberin;
4MSOB: 4-methylsulphinylbutyl glucosinolate, glucoraphanin;
5MSOP: 5-methylsulphinylpentyl glucosinolate, glucoalyssin;
6MSOH: 6-methylsulphinylhexyl glucosinolate, glucohesperin;
7MSOH: 7-methylsulphinylheptyl glucosinolate, glucoibarin;
3MTP: 3-methylthiopropyl glucosinolate, glucoiberverin;
8MSOO: 8-methylsulphinyloctyl glucosinolate, glucohirsutin;
4MTB: 4-methylthiobutyl glucosinolate, glucoerucin;
5MTP: 5-methylthiopentyl glucosinolate, glucoberteroin;
7MTH: 7-methylthioheptyl glucosinolate.

The data shown in FIG. 12 are the mean±SD of three biological replicates per genotype, and the letters denote significant differences according to Tukey's HSD test (P<0.05).

Example 12: Increased Resistance of jazD to 5-Methyl-Tryptophan (5-MT) is Partially Dependent on CDK8

This Example illustrates that loss of cdk8 further reduces jazD root lengths.

Figure 13A:
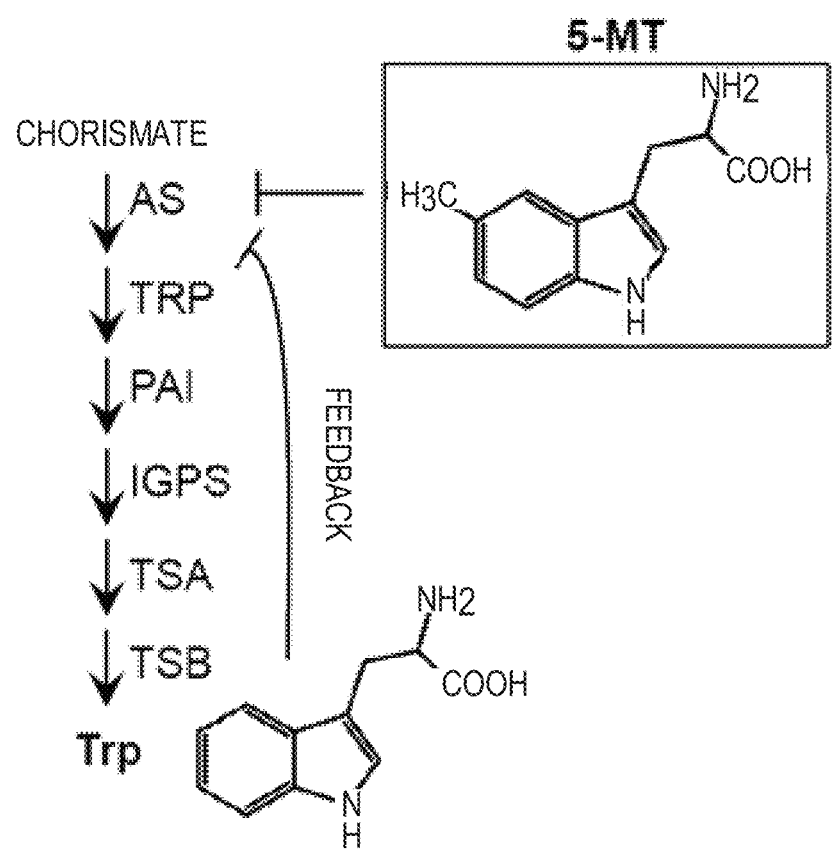
FIGS. 13A-13B illustrate that the increased resistance of jazD to 5-methyl-tryptophan (5-MT) is partially dependent on CDK8.

FIG. 13A is a schematic of tryptophan biosynthesis from chorismate. Tryptophan feedback inhibits the activity of anthranilate synthase (AS). Although 5-methyl-tryptophan (5-MT) inhibits anthranilate synthase activity, it cannot be used for the production of proteins. The abbreviations used in FIG. 13A are: TRP, anthranilate phosphoribosyltransferase; PAIL phosphoribosylanthranilate isomerase; IGPS, indole-3-glycerol-phosphate synthase; TSA, tryptophan synthase alpha subunit; TSB, tryptophan synthase beta subunit.

Figure 13B:
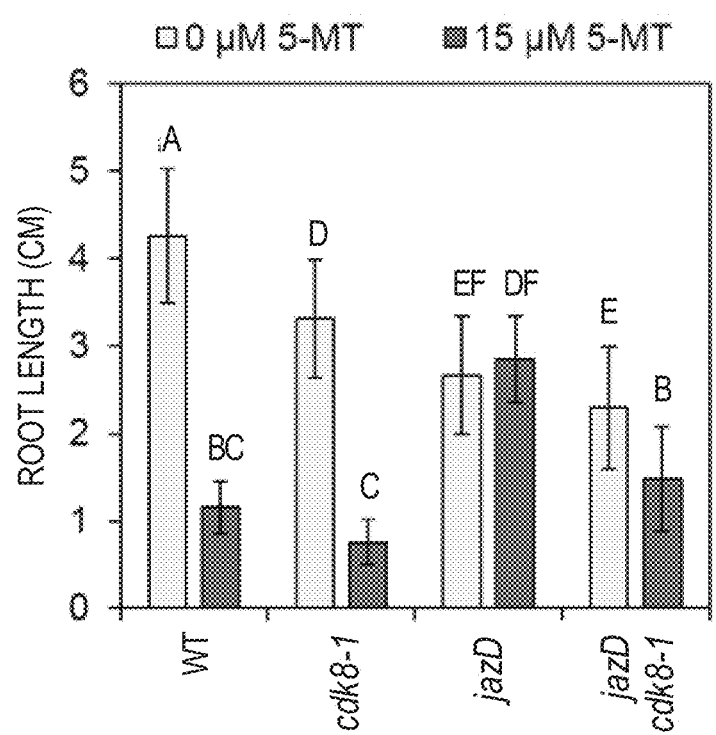

FIG. 13B graphically illustrates root length of WT, cdk8-1, jazD, and jazD cdk8-1 10-day-old seedlings grown on medium supplemented with 0 or 15 µM of 5-methyl-tryptophan (5-MT). The data shown in FIG. 13B are the mean±SD of at least 24 seedlings per genotype at each 5-MT concentration, while the letters denote significant differences according to Tukey's HSD test (P<0.05).

REFERENCES

1. Pieterse C M J, Leon-Reyes A. Van der Ent S. Van Wees S C M (2009) Networking by small-molecule hormones in plant immunity. Nat Chem Biol 5:308-316.
2. Santner A, Calderon-Villalobos L I A, Estelle M (2009) Plant hormones are versatile chemical regulators of plant growth. Nat Chem Biol 5:301-307.
3. Howe G A, Major I T, Koo A J (2018) Modularity in jasmonate signaling for multistress resilience. Annu Rev Plant Biol 69:387-415.
4. Wasternack C, Hause B (2013) Jasmonates: Biosynthesis, perception, signal transduction and action in plant stress response, growth and development. An update to the 2007 review in Annals of Botany. Ann Bot 111:1021-1058.
5. Campos M L, Kang J-H. Howe G A (2014) Jasmonate-triggered plant immunity. J Chem Ecol 40:657-675.
6. Howe G A, Jander G (2008) Plant immunity to insect herbivores. Annu Rev Plant Biol 59:41-66.
7. Wu J, Baldwin I T (2010) New insights into plant responses to the attack from insect herbivores. Annu Rev Genet 44:1-24.
8. Chini A. Gimenez-Ibanez S, Goossens A, Solano R (2016) Redundancy and specificity in jasmonate signalling. Curr Opin Plant Biol 33:147-156.
9. Yan Y. et al. (2007) A downstream mediator in the growth repression limb of the jasmonate pathway. Plant Cell 19:2470-2483.
10. Zhang Y, Turner J G (2008) Wound-induced endogenous jasmonates stunt plant growth by inhibiting mitosis. PLoS One 3:e3699.
11. Havko N E, et al. (2016) Control of carbon assimilation and partitioning by jasmonate: An accounting of growth-defense tradeoffs. Plants (Basel) 5:E7.
12. Major I T, et al. (2017) Regulation of growth-defense balance by the JASMONATE ZIM DOMAIN (JAZ)-MYC transcriptional module. New Phytol 215:1533-1547.
13. Attaran E, et al. (2014) Temporal dynamics of growth and photosynthesis suppression in response to jasmonate signaling. Plant Physiol 165:1302-1314.
14. Bömer M, et al. (Jun. 19, 2018) COI1-dependent jasmonate signalling affects growth, metabolite production and cell wall protein composition in Arabidopsis. Ann Bot, 10.1093/aob/mcy109.
15. Zust T, Agrawal A A (2017) Trade-offs between plant growth and defense against insect herbivory: An emerging mechanistic synthesis. Annu Rev Plant Biol 68:513-534.
16. Karasov T L, Chac E. Herman J J, Bergelson J (2017) Mechanisms to mitigate the tradeoff between growth and defense. Plant Cell 29:666-680.
17. Guo Q. Major I T, Howe G A (2018) Resolution of growth-defense conflict: Mechanistic insights from jasmonate signaling. Curr Opin Plant Biol 44:72-81.
18. Thines B, et al. (2007) JAZ repressor proteins are targets of the SCF (COI1) complex during jasmonate signalling. Nature 448:661-665.
19. Chini A. et al. (2007) The JAZ family of repressors is the missing link in jasmonate signalling. Nature 448:666-671.
20. Kazan K, Manners J M (2013) MYC2: The master in action. Mol Plant 6:686-703.
21. Ferndndez-Calvo P. et al. (0.2011) The *Arabidopsis* bHLH transcription factors MYC3 and MYC4 are targets of JAZ repressors and act additively with MYC2 in the activation of jasmonate responses. Plant Cell 23:701-715.
22. Qi T, Huang H. Song S. Xie D (2015) Regulation of jasmonate-mediated stamen development and seed production by a bHLH-MYB complex in *Arabidopsis*. Plant Cell 27:1620-1633.
23. Figueroa P. Browse J (2015) Male sterility in *Arabidopsis* induced by overexpression of a MYC5-SRDX chimeric repressor. Plant J 81:849-860.
24. Pauwels L, et al. (2010) NINJA connects the co-repressor TOPLESS to jasmonate signalling. Nature 464: 788-791.
25. Shyu C. et al. (2012) JAZ8 lacks a canonical degron and has an EAR motif that mediates transcriptional repression of jasmonate responses in *Arabidopsis*. Plant Cell 24: 536-550.
26. Zhang F, et al. (2015) Structural basis of JAZ repression of MYC transcription factors in jasmonate signalling. Nature 525:269-273.

27. evik V. et al. (2012) MEDIATOR25 acts as an integrative hub for the regulation of jasmonate-responsive gene expression in *Arabidopsis*. Plant Physiol 160:541-555.
28. An C. et al. (2017) Mediator subunit MED25 links the jasmonate receptor to transcriptionally active chromatin. Proc Natl Acad Sci USA 114:E8930-E8939.
29. Katsir L, Schilmiller A L, Staswick P E. He S Y. Howe G A (2008) COI1 is a critical component of a receptor for jasmonate and the bacterial virulence factor coronatine. Proc Natl Acad Sci USA 105:7100-7105.
30. Yan J. et al. (Aug. 7, 2018) Dynamic perception of jasmonates by the F-box protein COI. Mol Plant, 10.1016/j.molp.2018.07.007.
31. Browse J (2009) Jasmonate passes muster: A receptor and targets for the defense hormone. Annu Rev Plant Biol 60:183-205.
32. Thireault C, et al. (2015) Repression of jasmonate signaling by a non-TIFY JAZ protein in *Arabidopsis*. Plant J 82:669-679.
33. Gimenez-Ibanez S, et al. (2017) JAZ2 controls stomata dynamics during bacterial invasion. New Phytol 213:1378-1392.
34. Li R. et al. (2017) Flower-specific jasmonate signaling regulates constitutive floral defenses in wild tobacco. Proc Natl Acad Sci USA 114:E7205-E7214.
35. Campos M L, et al. (2016) Rewiring of jasmonate and phytochrome B signalling uncouples plant growth-defense tradeoffs. Nat Commun 7:12570.
36. Berrocal-Lobo M, Molina A. Solano R (2002) Constitutive expression of ETHYLENERESPONSE-FACTOR in *Arabidopsis* confers resistance to several necrotrophic fungi. Plant J 29:23-32.
37. Pré M. et al. (2008) The AP2/ERF domain transcription factor ORA59 integrates jasmonic acid and ethylene signals in plant defense. Plant Physiol 147:1347-1357.
38. Li J, et al. (2018) Jasmonic acid/ethylene signaling coordinates hydroxycinnamic acid amides biosynthesis through ORA59 transcription factor. Plant J 95:444-457.
39. Song S, et al. (2014) Interaction between MYC2 and ETHYLENE INSENSITIVE3 modulates antagonism between jasmonate and ethylene signaling in *Arabidopsis*. Plant Cell 26:263-279.
40. Muroi A, et al. (2009) Accumulation of hydroxycinnamic acid amides induced by pathogen infection and identification of agmatine coumaroyl transferase in *Arabidopsis thaliana*. Planta 230:517-527.
41. Dobritzsch M. et al. (0.2016) MATE transporter-dependent export of hydroxycinnamic acid amides. Plant Cell 28:583-596.
42. Adio A M. et al. (0.2011) Biosynthesis and defensive function of Nδ-acetylornithine, a jasmonate-induced *Arabidopsis* metabolite. Plant Cell 23:3303-3318.
43. Nakano R T, et al. (2017) PYK10 myrosinase reveals a functional coordination between endoplasmic reticulum bodies and glucosinolates in *Arabidopsis thaliana*. Plant J 89: 204-220.
44. Yamada K. Hara-Nishimura I, Nishimura M (2011) Unique defense strategy by the endoplasmic reticulum body in plants. Plant Cell Physiol 52:2039-2049.
45. Benstein R M, et al. (2013) *Arabidopsis* phosphoglycerate dehydrogenase1 of the phosphoserine pathway is essential for development and required for ammonium assimilation and tryptophan biosynthesis. Plant Cell 25:5011-5029.
46. Kruse C. et al. (2007) Sulfur-enhanced defense: Effects of sulfur metabolism, nitrogen supply, and pathogen lifestyle. Plant Biol (Stuttg) 9:608-619.
47. Sasaki-Sekimoto Y. et al. (2005) Coordinated activation of metabolic pathways for antioxidants and defense compounds by jasmonates and their roles in stress tolerance in *Arabidopsis*. Plant J 44:653-668.
48. Yatusevich R, et al. (2010) Genes of primary sulfate assimilation are part of the glucosinolates biosynthetic network in *Arabidopsis thaliana*. Plant J 62:1-11.
49. Bolton M D (2009) Primary metabolism and plant defense-Fuel for the fire. Mol Plant Microbe Interact 22:487-497.
50. Baena-Gonzilez E. Rolland F. Thevelein J M, Sheen J (2007) A central integrator of transcription networks in plant stress and energy signalling. Nature 448:938-942.
51. Fujiki Y. et al. (2001) Dark-inducible genes from *Arabidopsis thaliana* are associated with leaf senescence and repressed by sugars. Physiol Plant 111:345-352.
52. Gibon Y. et al. (2009) Adjustment of growth, starch turnover, protein content and central metabolism to a decrease of the carbon supply when *Arabidopsis* is grown in very short photoperiods. Plant Cell Environ 32:859-874.
53. Tsai K-J, Lin C-Y, Ting C-Y, Shih M-C (2016) Ethylene-regulated glutamate dehydrogenase fine-tunes metabolism during anoxia reoxygenation. Plant Physiol 172:1548-1562.
54. Miyashita Y. Good A G (2008) NAD(H)-dependent glutamate dehydrogenase is essential for the survival of *Arabidopsis thaliana* during dark-induced carbon starvation. J Exp Bot 59:667-680.
55. Jin J, et al. (2017) Plant TFDB 4.0: Toward a central hub for transcription factors and regulatory interactions in plants. Nucleic Acids Res 45:D1040-D1045.
56. Zhu Z. et al. (2011) Derepression of ethylene-stabilized transcription factors (EIN3/EIL1) mediates jasmonate and ethylene signaling synergy in *Arabidopsis. Proc Nat Acad Sci USA* 108:12539-12544.
57. Solano R, Stepanova A, Chao Q. Ecker J R (1998) Nuclear events in ethylene signaling: A transcriptional cascade mediated by ETHYLENE-INSENSITIVE3 and ETHYLENE-RESPONSEFACTOR. Genes Dev 12:3703-3714.
58. Müller M. Munné-Bosch S (2015) Ethylene response factors: A key regulatory hub in hormone and stress signaling. Plant Physiol 169:32-41.
59. Lorenzo O, Chico J M. Sanchez-Serrano J J, Solano R (2004) JASMONATE-INSENSITIVE encodes a MYC transcription factor essential to discriminate between different jasmonate-regulated defense responses in *Arabidopsis*. Plant Cell 16:1938-1950.
60. Caarls L, et al. (2017) *Arabidopsis* JASMONATE-INDUCED OXYGENASES downregulate plant immunity by hydroxylation and inactivation of the hormone jasmonic acid. Proc Natl Acad Sci USA 114:6388-6393.
61. Smirnova E, et al. (2017) Jasmonic acid oxidase 2 hydroxylates jasmonic acid and represses basal defense and resistance responses against *Botrytis cinerea* infection. Mol Plant 10:1159-1173.
62. Schweizer F. et al. (0.2013) *Arabidopsis* basic helix-loop-helix transcription factors MYC2, MYC3, and MYC4 regulate glucosinolate biosynthesis, insect performance, and feeding behavior. Plant Cell 25:3117-3132.
63. Gigolashvili T, et al. (2007) The transcription factor HIG/MYB51 regulates indolic glucosinolate biosynthesis in *Arabidopsis thaliana*. Plant J 50:886-901.

64. Yang D-L, et al. (2012) Plant hormone jasmonate prioritizes defense overgrowth by interfering with gibberellin signaling cascade. Proc Natl Acad Sci USA 109: E1192-E1200.
65. Hou X, Lee L Y C. Xia K. Yan Y. Yu H (2010) DELLAs modulate jasmonate signaling via competitive binding to JAZs. Dev Cell 19:884-894.
66. Machado R A R, Baldwin I T, Erb M (2017) Herbivory-induced jasmonates constrain plant sugar accumulation and growth by antagonizing gibberellin signaling and not by promoting secondary metabolite production. New Phytol 215:803-812.
67. Agrawal A A (1998) Induced responses to herbivory and increased plant performance. Science 279:1201-1202.
68. Baldwin I T (1998) Jasmonate-induced responses are costly but benefit plants under attack in native populations. Proc Natl Acad Sci USA 95:8113-8118.
69. Farmer E E, Dubugnon L (2009) Detritivorous crustaceans become herbivores on jasmonate-deficient plants. Proc Natl Acad Sci USA 106:935-940.
70. Smith A M. Stitt M (2007) Coordination of carbon supply and plant growth. Plant Cell Environ 30:1126-1149.
71. Bomblies K, Weigel D (2007) Hybrid necrosis: Auto-immunity as a potential gene-flow barrier in plant species. Nat Rev Genet 8:382-393.
72. Qi T et al. (2015) Regulation of jasmonate-induced leaf senescence by antagonism between bHLH subgroup IIIe and IIId factors in *Arabidopsis*. Plant Cell 27:1634-1649.
73. Shan X, et al. (2011) The role of *Arabidopsis* Rubisco activase in jasmonate-induced leaf senescence. Plant Physiol 155:751-764.
74. Ueda J, Kato J (1980) Isolation and identification of a senescence-promoting substance from wormwood (*Artemisia absinthium* L.). Plant Physiol 66:246-249.
75. Orozco-Cárdenas M L, Narváez-Vásquez J, Ryan C A (2001) Hydrogen peroxide acts as a second messenger for the induction of defense genes in tomato plants in response to wounding, systemin, and methyl jasmonate. Plant Cell 13:179-191.
76. Oh Y, Baldwin I T. Gális I (2012) NaJAZh regulates a subset of defense responses against herbivores and spontaneous leaf necrosis in *Nicotiana attenuata* plants. Plant Physiol 159:769-788.
77. Chen Y, et al. (2017) Salt and methyl jasmonate aggravate growth inhibition and senescence in *Arabidopsis* seedlings via the JA signaling pathway. Plant Sci 261:1-9.
78. Machado R A R, et al. (2013) Leaf-herbivore attack reduces carbon reserves and regrowth from the roots via jasmonate and auxin signaling. New Phytol 200: 1234-1246.
79. Sulpice R. et al. (2014) *Arabidopsis* coordinates the diurnal regulation of carbon allocation and growth across a wide range of photoperiods. Mol Plant 7:137-155.
80. Wang K. et al. (2018) Two abscisic acid-responsive plastid lipase genes involved in jasmonic acid biosynthesis in *Arabidopsis thaliana*. Plant Cell 30:1006-1022.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various embodiments of the invention according to the foregoing description in the specification.

Statements:

1. A plant, plant cell, or plant seed comprising at least one endogenous cdk8 loss-of-function mutation in one or more endogenous CDK8 genes and at least one endogenous loss-of-function jaz mutation in one or more endogenous JAZ genes.
2. The plant, plant cell, or plant seed of statement 1, wherein the one or more endogenous JAZ genes is a JAZ1, JAZ2, JAZ3, JAZ4, JAZ, JAZ6, JAZ7, JAZ9, JAZ10, or JAZ13 gene; or wherein the one or more endogenous JAZ genes comprise a combination of two or more JAZ1, JAZ2, JAZ3, JAZ4, JAZ5, JAZ6, JAZ7, JAZ9, JAZ10, or JAZ13 genes.
3. The plant, plant cell, or plant seed of statement 1 or 2, wherein the one or more endogenous JAZ genes is a least one endogenous loss-of-function mutation in each of JAZ1, JAZ2, JAZ3, JAZ4, JAZ5, JAZ6, JAZ7, JAZ9, JAZ10, and JAZ13.
4. The plant, plant cell, or plant seed of statement 1, 2 or 3, wherein endogenous expression of the one or more endogenous JAZ gene, the cdk8 gene, or a combination thereof is reduced by at least 20%, or at least 30%, or at least 40%, or at least 50%, or at least 60%, or at least 70%, or at least 80%, or at least 90%, or at least 95%, or at least 97%, or at least 99% compared to wild type plant cells, plants, and seeds of the same species (that do not have the jaz or cdk8 mutation(s)).
5. The plant, plant cell, or plant seed of statement 1, 2 or 3, wherein endogenous expression of the one or more endogenous JAZ genes or the cdk8 gene, or a combination thereof is undetectable.
6. The plant, plant cell, or plant seed of statement 1-4 or 5, wherein at least one of the plant's, the plant cell's, or the plant seed's endogenous JAZ8, JAZ11, or JAZ12 genes are not modified or mutated.
7. The plant, plant cell, or plant seed of statement 1-5 or 6, wherein the plant's vegetative weight, vegetative weight of a plant generated from the plant cell, or vegetative weight of a plant grown from the plant seed is within at least about 40%, or at least about 50%, or within at least 60%, or at least about 70% of the average vegetative weight of a wild type plant grown for the same time and under the same conditions as a wild type plant.
8. The plant, plant cell, or plant seed of statement 1-6 or 7, wherein the plant, a plant generated from the plant cell, or a plant grown from the plant seed has a rosette weight of about 40% to about 120%, or about 50% to about 110% of the rosette weight of wild type plants grown for the same time and under the same conditions.
9. The plant, plant cell, or plant seed of statement 1-7 or 8, wherein the plant, a plant generated from the plant cell, or a plant grown from the plant seed has a seed yield of at least 10%, or at least 20%, or at least 30%, or at least 40% greater than the average seed yield of wild type plants.
10. The plant, plant cell, or plant seed of statement 1-8 or 9, wherein the plant, a plant generated from the plant cell, or a plant grown from the plant seed has at least 5% less, 10% less, 20% less, 30% less, 40% less, 50% less, 60% less, 70% less, 80% less, 90% less, or 100% less leaf damage from insect feeding than average insect feeding of a wild type plant of the same species grown for the same time under the same conditions.

11. The plant, plant cell, or plant seed of statement 1-9 or 10, wherein the plant, a plant generated from the plant cell, or a plant grown from the plant seed has at least about 10%, or at least about 20%, or at least about 30%, or at least about 40%, or at least about 50%, or at least about 60%, or at least about 70%, or at least about 80%, or at least about 90% fewer insects or insect larvae than an average number of insects or insect larvae of wild type plants of the same species grown for the same time under the same conditions.

12. The plant, plant cell, or plant seed of statement 1-10 or 11, wherein compared to wild type or an unmodified parental plant line, the plant, a plant generated from the plant cell, or a plant grown from the plant seed has higher levels of defense compounds that reduce the incidence or number of insect or insect larvae on the plant.

13. The plant, plant cell, or plant seed of statement 1-11 or 12, wherein compared to wild type or an unmodified parental plant line, leaves of the plant, a plant generated from the plant cell, or a plant grown from the plant seed has higher levels of aliphatic glucosinolates that reduce the incidence or number of insect or insect larvae on the plant.

14. The plant, plant cell, or plant seed of statement 1-12 or 13, wherein compared to wild type or an unmodified parental plant line, the plant, a plant generated from the plant cell, or a plant grown from the plant seed has higher levels of one or more of 3-methylsulphinylpropyl glucosinolate (glucoiberin); 4-methylsulphinylbutyl glucosinolate (glucoraphanin); 5-methylsulphinylpentyl glucosinolate (glucoalyssin): 6-methylsulphinylhexyl glucosinolate (glucohesperin); 7-methylsulphinylheptyl glucosinolate (glucoibarin); 3-methylthiopropyl glucosinolate (glucoiberverin); 8-methylsulphinyloctyl glucosinolate (glucohirsutin); 4-methylthiobutyl glucosinolate (glucoerucin); 5-methylthiopentyl glucosinolate (glucoberteroin); or 7-methylthioheptyl glucosinolate.

15. The plant, plant cell, or plant seed of statement 1-13 or 14, wherein the plant, a plant generated from the plant cell, or a plant grown from the plant seed exhibits resistance to environmental stress compared to a wild type plant of the same species grown for the same time and under the same environmental conditions.

16. The plant, plant cell, or plant seed of statement 4-14, or 15, wherein the wild type plant, wild type plant cell, or wild type plant seed expresses JAZ polypeptides or JAZ-related polypeptides with at least 70%, or at least 75%, or at least 80%, or at least 85%, or at least 90%, or at least 95%, or at least 97%, or at least 98%, or at least 99% sequence identity to any of SEQ ID NO:1, 3, 5, 7, 9, 11, 13, 17, 19, 21-51, or 52.

17. The plant, plant cell, or plant seed of statement 4-15, or 16, wherein the wild type plant, wild type plant cell, or wild type plant seed expresses CDK8 polypeptides or CDK8-related polypeptides with at least 70%, or at least 75%, or at least 80%, or at least 85%, or at least 90%, or at least 95%, or at least 97%, or at least 98%, or at least 99% sequence identity to any of SEQ ID NO: 53, 56, 58, 59, 61, 63, or 65.

18. The plant, plant cell, or plant seed of statement 1-16 or 17, wherein the endogenous loss-of-function mutation of the JAZ1, JAZ2, JAZ3, JAZ4, JAZ5, JAZ6, JAZ7, JAZ9, JAZ10, JAZ3 or cdk8 gene comprises substitution(s) or deletion(s) at chromosomal loci of the JAZ1, JAZ2, JAZ3, JAZ4, JAZ5, JAZ6, JAZ7, JAZ9, JAZ10, JAZ13 or cdk8 gene.

19. The plant, plant cell, or plant seed of statement 1-17 or 18, wherein the endogenous loss-of-function mutation of the JAZ1, JAZ2, JAZ3, JAZ4, JAZ5, JAZ6, JAZ7. JAZ9, JAZ10, JAZ13 or cdk8 gene comprises insertion(s) at chromosomal loci of the JAZ1, JAZ2, JAZ3, JAZ4, JAZ5, JAZ6, JAZ7, JAZ9, JAZ10, JAZ13 or cdk8 gene.

20. The plant, plant cell, or plant seed of statement 1-18 or 19, which is a food crop species (e.g., sugar beets, beets, tomatoes, lettuce, spinach, carrots, peppers, peas, broccoli, beans, asparagus), a legume species (e.g., peas, beans, lentils, peanuts), a fiber-containing plant species, a tree species, flax, a grain species (e.g., maize, wheat, barley, oats, rice, sorghum, millet, and rye), a grass species (e.g., switchgrass, prairie grass, wheat grass, sudangrass, sorghum, straw-producing plants), a woody plant species (e.g., a poplar species, pine species, or *eucalyptus* species), a softwood, a hardwood, an oil and/or starch producing plant species (e.g., canola, potatoes, lupins, sunflower and cottonseed), a forage plant species (e.g., alfalfa, clover, or fescue).

21. The plant, plant cell, or plant seed of statement 1-19 or 20, wherein the one or more endogenous JAZ genes is a combination of two or more, or three or more, or four or more, or five or more, or six or more, or seven or more, or eight or more, or nine or more JAZ1, JAZ2, JAZ3. JAZ4, JAZ5, JAZ6. JAZ7, JAZ9, JAZ10, or JAZ3 genes.

22. A method comprising cultivating the plant, plant cell or plant seed of statement 1-20 or 21 to produce a mature plant.

23. The method of statement 22, further comprising harvesting the mature plant or harvesting seeds, grain, fruit, vegetables, or biomass of the mature plant.

24. The method of statement 22 or 23, wherein the mature plant has less average insect damage or less insect larval and/or less adult insect feeding than a wild plant cultivated for the same time and under similar growing conditions.

25. The method of statements 22, 23 or 24, wherein the mature plant has greater seed yield than a wild plant cultivated for the same time and under similar growing conditions.

26. A method comprising (a) introducing into one or more plant cell(s) at least one chromosomal loss-of-function mutation into one or more endogenous JAZ genes and introducing into the one or more plant cell(s) at least one chromosomal loss-of-function mutation into at least one endogenous cdk8 gene; and (b) generating a plant from the one or more plant cell(s).

27. The method of statement 26, wherein the one or more endogenous JAZ genes is a JAZ1, JAZ2, JAZ3, JAZ4, JAZ5. JAZ6, JAZ7, JAZ9, JAZ10, or JAZ13 gene; or wherein the one or more endogenous JAZ genes comprise a combination of two or more JAZ1, JAZZ JAZ3, JAZ4, JAZ5, JAZ6, JAZ7, JAZ9, JAZ10, or JAZ13 genes.

28. The method of statement 26 or 27, wherein the one or more endogenous JAZ genes has at least 70%, or at least 75%, or at least 80%, or at least 85%, or at least 90%, or at least 95%, or at least 97%, or at least 98%, or at least 99% sequence identity to any of SEQ ID NO:1, 3, 5, 7, 9, 11, 13, 17, 19, 21-51 or 52.

29. The method of statement 26, 27 or 28, wherein the endogenous cdk8 gene has at least 70%, or at least 75%, or at least 80%, or at least 85%, or at least 90%, or at least 95%, or at least 97%, or at least 98%, or at least 99% sequence identity to any of SEQ ID NO: 53, 56, 58, 59, 61, 63, or 65.

30. The method of statement 26-28 or 29, wherein the plant generated from the one or more plant cell(s) comprises a deletion of at least one chromosomal JAZ1, JAZ2, JAZ3, JAZ4, JAZ, JAZ6, JAZ7, JAZ9, JAZ10, or JAZ13 site, a substitution within at least one chromosomal JAZ1, JAZ2, JAZ3, JAZ4, JAZ5, JAZ6, JAZ7, JAZ9, JAZ10, or JAZ13 site, or an insertion into at least one chromosomal JAZ1, JAZ2, JAZ3, JAZ4, JAZ, JAZ6, JAZ7, JAZ9, JAZ10, or JAZ13 site.

31. The method of statement 26-29 or 30, wherein the plant generated from the one or more plant cell(s) comprises a deletion of a chromosomal cdk8 site, a substitution within a chromosomal cdk8 site, or an insertion into a chromosomal cdk8 site.

32. The method of statement 26-30 or 31, wherein the endogenous expression of the JAZ or cdk8 gene in the plant generated from the one or more plant cell(s) is reduced by at least 20%, or at least 30%, or at least 40%, or at least 50%, or at least 60%, or at least 70%, or at least 80%, or at least 90%, or at least 95%, or at least 97%, or at least 99% compared to wild type or parental plants of the same species (that do not have the jazD or cdk8 mutation(s)).

33. The method of statement 26-31 or 32, wherein endogenous expression of the one or more JAZ or cdk8 gene in the plant generated from the one or more plant cell(s) is undetectable.

34. The method of statement 26-32 or 33, wherein endogenous JAZ8. JAZ11, and JAZ12 genes in the plant generated from the one or more plant cell(s) or the progeny thereof are not modified or mutated.

35. The method of statement 26-33 or 34, wherein vegetative weight of plant generated from the one or more plant cell(s) or the progeny thereof is within at least about 40%, or at least about 50%, or within at least 60%, or at least about 70% of the average vegetative weight of a wild type plant grown for the same time and under the same conditions as a wild type plant.

36. The method of statement 26-34 or 35, wherein the plant generated from the one or more plant cell(s) or the progeny thereof has a rosette weight of about 40% to about 120%, or about 50% to about 110% of the rosette weight of wild type plants grown for the same time and under the same conditions.

37. The method of statement 26-35 or 36, wherein the plant generated from the one or more plant cell(s) or the progeny thereof has a seed yield of at least 10%, or at least 20%, or at least 30%, or at least 40% greater than the average seed yield of wild type plants.

38. The method of statement 26-36 or 37, wherein the plant generated from the one or more plant cell(s) or the progeny thereof has at least 5% less, 10% less, 20% less, 30% less, 40% less, 50% less, 60% less, 70% less, 80% less, 90% less, or 100% less leaf damage from insect feeding than average insect feeding of a wild type plant of the same species grown for the same time under the same conditions.

39. The method of statement 26-37 or 38, wherein the plant generated from the one or more plant cell(s) or the progeny thereof has at least about 10%, or at least about 20%, or at least about 30%, or at least about 40%, or at least about 50%, or at least about 60%, or at least about 70%, or at least about 80%, or at least about 90% fewer insects or insect larvae than an average number of insects or insect larvae of wild type plants of the same species grown for the same time under the same conditions.

40. The method of statement 26-38 or 39, wherein the plant generated from the one or more plant cell(s) or the progeny thereof exhibits resistance to environmental stress compared to a wild type plant of the same species under the same environmental conditions.

41. The method of statement 26-39 or 40, wherein the one or more endogenous JAZ genes with the mutation is two or more JAZ genes, or three or more JAZ genes, or four or more JAZ genes, or five or more JAZ genes, or six or more JAZ genes, or seven or more JAZ genes, or eight or more JAZ genes, or nine or more JAZ genes.

The specific plants, seeds, compositions and methods described herein are representative, exemplary and not intended as limitations on the scope of the invention. Other objects, aspects, and embodiments will occur to those skilled in the art upon consideration of this specification and are encompassed within the spirit of the invention as defined by the scope of the claims. It will be readily apparent to one skilled in the art that varying substitutions and modifications may be made to the invention disclosed herein without departing from the scope and spirit of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims and statements of the invention.

The invention illustratively described herein may be practiced in the absence of any element or elements, or limitation or limitations, which is not specifically disclosed herein as essential. The methods and processes illustratively described herein may be practiced in differing orders of steps, and the methods and processes are not necessarily restricted to the orders of steps indicated herein or in the claims.

As used herein and in the appended claims, the singular forms "a." "an," and "the" include plural reference unless the context clearly dictates otherwise. Thus, for example, a reference to "a plant" or "a seed" or "a cell" includes a plurality of such plants, seeds or cells, and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

What is claimed:

1. A plant, plant cell, or plant seed comprising at least one endogenous cdk8 loss-of-function mutation in one or more endogenous cdk8 genes and endogenous loss-of-function jaz mutations in endogenous jaz genes jaz1, jaz2, jaz5, and jaz6, wherein the endogenous cdk8 genes encode an amino acid sequence having at least 90% identity to SEQ ID NO: 53, 56, 58, 59, 61, 63, or 65 the jaz1 gene encodes an amino acid sequence having at least 90% identity to SEQ ID NO: 1, the jaz2 gene encodes an amino acid sequence having at least 90% identity to SEQ ID NO: 3, 26, 27, or 28, the jaz5 gene encodes an amino acid sequence having at least 90% identity to SEQ ID NO: 9, 37, 38, or 39, and the jaz6 gene encodes an amino acid sequence having at least 90% identity to SEQ ID NO: 11, 40, 41, or 42.

2. The plant, plant cell, or plant seed of claim 1, further comprising loss-of-function jaz mutations in one or more of the following endogenous jaz genes jaz3, jaz4, jaz7, jaz9, jaz10, or jaz13, wherein
the jaz3 gene encodes an amino acid sequence having at least 90% identity to SEQ ID NO: 5,
the jaz4 gene encodes an amino acid sequence having at least 90% identity to SEQ ID NO: 7,
the jaz7 gene encodes an amino acid sequence having at least 90% identity to SEQ ID NO: 13,
the jaz9 gene encodes an amino acid sequence having at least 90% identity to SEQ ID NO: 15,
the jaz10 gene encodes an amino acid sequence having at least 90% identity to SEQ ID NO: 17, and
the jaz13 gene encodes an amino acid sequence having at least 90% identity to SEQ ID NO: 19.

3. The plant, plant cell, or plant seed of claim 1, wherein mutation of the endogenous jaz genes reduces endogenous expression of the endogenous jaz gene by at least 50%, or wherein mutation of the one or more endogenous cdk8 genes reduces endogenous expression of the one or more endogenous cdk8 gene by at least 50%.

4. The plant, plant cell, or plant seed of claim 1, wherein mutation of the endogenous jaz genes reduces endogenous expression of the endogenous jaz genes to undetectable levels, or wherein mutation of the one or more endogenous cdk8 genes reduces endogenous expression of the one or more endogenous cdk8 gene to undetectable levels.

5. The plant, plant cell, or plant seed of claim 1, wherein the plant, a plant generated from the plant cell, or a plant grown from the plant seed has a seed yield of at least 10% greater than the average seed yield of wild type plants or of unmodified parental plants.

6. The plant, plant cell, or plant seed of claim 1, wherein the plant, a plant generated from the plant cell, or a plant grown from the plant seed has at least 5% less leaf damage from insect feeding than average damage of insect feeding of a wild type plant of the same species grown for the same time under the same conditions.

7. The plant, plant cell, or plant seed of claim 1, wherein compared to wild type or an unmodified parental plant line, the plant, a plant generated from the plant cell, or a plant grown from the plant seed has higher levels of defense compounds.

8. The plant, plant cell, or plant seed of claim 1, wherein compared to wild type or an unmodified parental plant line, the plant, a plant generated from the plant cell, or a plant grown from the plant seed has higher levels of defense compounds that reduce the incidence or number of insect or insect larvae on the plant, plant generated from the plant cell, or plant grown from the seed.

9. The plant, plant cell, or plant seed of claim 1, wherein compared to wild type or an unmodified parental plant line, the plant, a plant generated from the plant cell, or a plant grown from the plant seed has higher levels of one or more of 3-methylsulphinylpropyl glucosinolate (glucoiberin); 4-methylsulphinylbutyl glucosinolate (glucoraphanin); 5-methyl sulphinylpentyl glucosinolate (glucoalyssin); 6-methylsulphinylhexyl glucosinolate (glucohesperin); 7-methyl sulphinylheptyl glucosinolate (glucoibarin); 3-methylthiopropyl glucosinolate (glucoiberverin); 8-methylsulphinyloctyl glucosinolate (glucohirsutin); 4-methylthiobutyl glucosinolate (glucoerucin); 5-methylthiopentyl glucosinolate (glucoberteroin); or 7-methylthioheptyl glucosinolate.

10. A method comprising cultivating a plant or plant seed comprising at least one endogenous cdk8 loss-of-function mutation in one or more endogenous cdk8 gene(s) and endogenous loss-of-function jaz mutation(s) endogenous jaz genes jaz1, jaz2, jaz5, and jaz6 to produce a mature plant, wherein the endogenous cdk8 gene(s) encode an amino acid sequence having at least 90% identity to SEQ ID NO: 53, 56, 58, 59, 61, 63, or 65, the jaz1 gene encodes an amino acid sequence having at least 90% identity to SEQ ID NO: 1, the jaz2 gene encodes an amino acid sequence having at least 90% identity to SEQ ID NO: 3, 26, 27, or 28, the jaz5 gene encodes an amino acid sequence having at least 90% identity to SEQ ID NO: 9, 37, 38, or 39, and the jaz6 gene encodes an amino acid sequence having at least 90% identity to SEQ ID NO: 11, 40, 41, or 42.

11. The method of claim 10, further comprising harvesting the mature plant or harvesting seeds, grain, fruit, vegetables, forage, or biomass of the mature plant.

12. The method of claim 10, wherein the plant or plant seed further comprises loss-of-function jaz mutations in one or more of the following endogenous jaz genes jaz3, jaz4, jaz7, jaz9, jaz10, or jaz13, wherein
the jaz3 gene encodes an amino acid sequence having at least 90% identity to SEQ ID NO: 5,
the jaz4 gene encodes an amino acid sequence having at least 90% identity to SEQ ID NO: 7,
the jaz7 gene encodes an amino acid sequence having at least 90% identity to SEQ ID NO: 13,
the jaz9 gene encodes an amino acid sequence having at least 90% identity to SEQ ID NO: 15,
the jaz10 gene encodes an amino acid sequence having at least 90% identity to SEQ ID NO: 17, and
the jaz13 gene encodes an amino acid sequence having at least 90% identity to SEQ ID NO: 19.

13. The method of claim 10, wherein mutation of the four or more endogenous jaz genes reduces endogenous expression of the four or more endogenous JAZ gene by at least 50%, or wherein mutation of the one or more endogenous cdk8 genes reduces endogenous expression of the one or more endogenous cdk8 gene by at least 50%.

14. The method of claim 10, wherein mutation of the four or more endogenous jaz genes reduces endogenous expression of the four or more endogenous jaz to undetectable levels, or wherein mutation of the one or more endogenous cdk8 genes reduces endogenous expression of the one or more endogenous cdk8 gene to undetectable levels.

15. The method of claim 10, wherein the mature plant has a seed yield of at least 10% greater than the average seed yield of wild type plants or of unmodified parental plants.

16. The method of claim 10, wherein the mature plant has at least 5% less leaf damage from insect feeding than average leaf damage from insect feeding of wild type plants or of unmodified parental plants of the same species grown for the same time under the same conditions.

17. A method comprising (a) introducing into one or more plant cell(s) at least one chromosomal loss-of-function mutation into at least one endogenous cdk8 gene and into endogenous jaz genes jaz1, jaz2, jaz5, and jaz6, wherein the endogenous cdk8 gene(s) encode an amino acid sequence having at least 90% identity to SEQ ID NO: 53, 56, 58, 59, 61, 63, or 65, the jaz1 gene encodes an amino acid sequence having at least 90% identity to SEQ ID NO: 1, the jaz2 gene encodes an amino acid sequence having at least 90% identity to SEQ ID NO: 3, 26, 27, or 28, the jaz5 gene encodes an amino acid sequence having at least 90% identity to SEQ ID NO: 9, 37, 38, or 39, and the jaz6 gene encodes an amino acid sequence having at least 90% identity to SEQ ID NO: 11, 40, 41, or 42; and (b) generating a plant from the one or more plant cell(s) comprising the at least one chromosomal loss-of-function mutation in the at least one endogenous cdk8 gene and the endogenous jaz genes jaz1, jaz2, jaz5, and jaz6.

18. The method of claim 17, wherein the plant comprises a deletion of at least a portion of four or more endogenous jaz1, jaz2, jaz3, jaz4, jaz5, jaz6, jaz7, jaz9, jaz10, or jaz13 genes and at least one deletion within a cdk8 gene;
a substitution within at least four or more endogenous jaz1, jaz2, jaz3, jaz4, jaz5, jaz6, jaz7, jaz9, jaz10, or jaz13 genes and at least one substitution within a cdk8 gene, or an insertion into at least four or more endogenous jaz1, jaz2, jaz3, jaz4, jaz5, jaz6, jaz7, jaz9, jaz10, or jaz13 genes and at least one substitution within a cdk8 gene.

19. The method of claim 17, wherein mutation of the endogenous jaz1, jaz2, jaz5, and jaz6 genes reduces endogenous expression of the endogenous jaz1, jaz2, jaz5, and jaz6 genes by at least 50%, or wherein mutation of the one or more endogenous cdk8 gene(s) reduces endogenous expression of the one or more endogenous cdk8 gene(s) by at least 50%.

20. The method of claim 17, wherein mutation of the endogenous jaz1, jaz2, jaz5, and jaz6 genes reduces endogenous expression of the endogenous jaz1, jaz2, jaz5, and jaz6 genes to undetectable levels, or wherein mutation of the one or more endogenous cdk8 genes reduces endogenous expression of the one or more endogenous cdk8 gene to undetectable levels.

21. The method of claim 17, wherein the plant has a seed yield of at least 10% greater than the average seed yield of wild type plants or of unmodified parental plants.

22. The method of claim 17, wherein the plant has at least 5% less leaf damage from insect feeding than average insect feeding of a wild type plants or of unmodified parental plants of the same species grown for the same time under the same conditions.

\* \* \* \* \*